(12) United States Patent
Olson et al.

(10) Patent No.: US 7,423,033 B2
(45) Date of Patent: Sep. 9, 2008

(54) HYDROXYALKANOYLAMINOLACTAMS AND RELATED STRUCTURES AS INHIBITORS OF Aβ PROTEIN PRODUCTION

(75) Inventors: Richard E. Olson, Wilmington, DE (US); Hong Liu, Glen Mills, PA (US); Lorin Andrew Thompson, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 12/024,812

(22) Filed: Feb. 1, 2008

(65) Prior Publication Data

US 2008/0132482 A1 Jun. 5, 2008

Related U.S. Application Data

(60) Continuation of application No. 11/522,699, filed on Sep. 18, 2006, now Pat. No. 7,342,008, which is a division of application No. 11/024,377, filed on Dec. 28, 2004, now Pat. No. 7,112,583, and a division of application No. 10/287,117, filed on Nov. 4, 2002, now Pat. No. 6,960,576, and a division of application No. 09/805,645, filed on Mar. 14, 2001, now Pat. No. 6,503,902, which is a continuation-in-part of application No. 09/661,008, filed on Sep. 13, 2000, now abandoned.

(60) Provisional application No. 60/224,388, filed on Aug. 9, 2000, provisional application No. 60/153,511, filed on Sep. 13, 1999.

(51) Int. Cl.
C07D 243/24 (2006.01)
A61K 31/395 (2006.01)

(52) U.S. Cl. ................................. 514/221; 540/509
(58) Field of Classification Search ............ 540/509; 514/221
See application file for complete search history.

(56) References Cited

U.S. PATENT DOCUMENTS

| | | | |
|---|---|---|---|
| 4,666,829 A | 5/1987 | Glenner et al. |
| 5,283,241 A | 2/1994 | Bochis et al. |
| 5,389,631 A | 2/1995 | Claremon |
| 5,532,359 A | 7/1996 | Marsters et al. |
| 5,550,126 A | 8/1996 | Horwell et al. |
| 5,578,629 A | 11/1996 | Ciccarone et al. |
| 5,593,846 A | 1/1997 | Schenk et al. |
| 5,595,990 A | 1/1997 | Baldwin et al. |
| 5,602,145 A | 2/1997 | Samanen |
| 5,618,812 A | 4/1997 | Pineiro et al. |
| 5,672,596 A | 9/1997 | Wyvratt et al. |
| 5,703,129 A | 12/1997 | Felsenstein et al. |
| 5,710,153 A | 1/1998 | Ohmoto et al. |
| 5,710,171 A | 1/1998 | Dinsmore et al. |
| 5,756,528 A | 5/1998 | Anthony et al. |
| 5,763,437 A | 6/1998 | Sato et al. |
| 5,852,010 A | 12/1998 | Graham et al. |
| 5,856,326 A | 1/1999 | Anthony et al. |
| 5,859,012 A | 1/1999 | Dinsmore et al. |
| 5,869,682 A | 2/1999 | DeSolms |
| 5,872,135 A | 2/1999 | DeSolms |
| 5,885,995 A | 3/1999 | Dinsmore |
| 5,891,889 A | 4/1999 | Anthony et al. |
| 5,905,077 A | 5/1999 | Jungheim et al. |
| 5,919,785 A | 7/1999 | Dinsmore et al. |
| 5,936,089 A | 8/1999 | Carpino et al. |
| 5,965,578 A | 10/1999 | Graham et al. |
| 6,503,902 B2 | 1/2003 | Olson et al. |
| 2003/0166636 A1 | 9/2003 | Olson et al. |

FOREIGN PATENT DOCUMENTS

| | | |
|---|---|---|
| DE | 2934355 | 3/1981 |
| EP | 0421802 | 4/1991 |
| EP | 0434360 | 6/1991 |
| EP | 0652009 | 5/1995 |
| EP | 0842944 | 5/1998 |
| WO | WO 9403437 | 2/1994 |
| WO | WO 9405634 | 3/1994 |
| WO | WO 9414776 | 7/1994 |
| WO | WO 9509633 | 4/1995 |
| WO | WO 9617833 | 6/1996 |
| WO | WO 9618602 | 6/1996 |

(Continued)

OTHER PUBLICATIONS

U.S. Appl. No. 09/661,008, filed Sep. 13, 2000, Olson et al.
U.S. Appl. No. 60/153,511, filed Sep. 13 1999, Olson et al.
U.S. Appl. No. 60/224,388, filed Aug. 9, 2000, Olson et al.
H. C. Ardnt, *Synthesis 1979*, pp. 202-204.
M.-C. Bettembourg et al., *Bull. Soc. Chim. Fr. 1963*, pp. 2449-2451.
Bock et al., *J. Med. Chem.*, 1989, 32, pp. 13-16.
Bock et al., *J. Org. Chem 1987*, 52, pp. 3232-3239.

(Continued)

*Primary Examiner*—Bruck Kifle
(74) *Attorney, Agent, or Firm*—Kelly Drye & Warren LLP; Pamela A. Mingo

(57) ABSTRACT

This invention relates to novel lactams having the formula (I):

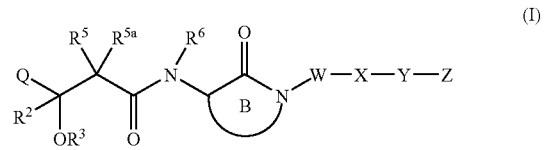

to their pharmaceutical compositions and to their methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

32 Claims, No Drawings

FOREIGN PATENT DOCUMENTS

| | | |
|---|---|---|
| WO | WO 9620918 | 7/1996 |
| WO | WO 9633165 | 10/1996 |
| WO | WO 9639137 | 12/1996 |
| WO | WO 9719053 | 5/1997 |
| WO | WO 9727852 | 8/1997 |
| WO | WO 9736877 | 10/1997 |
| WO | WO 9736879 | 10/1997 |
| WO | WO 9736900 | 10/1997 |
| WO | WO 9738664 | 10/1997 |
| WO | WO 9745412 | 12/1997 |
| WO | WO 9816523 | 4/1998 |
| WO | WO 9822430 | 5/1998 |
| WO | WO 9822433 | 5/1998 |
| WO | WO 9822441 | 5/1998 |
| WO | WO 9822493 | 5/1998 |
| WO | WO 9827053 | 6/1998 |
| WO | WO 9828268 | 7/1998 |
| WO | WO 9828980 | 7/1998 |
| WO | WO 9837079 | 8/1998 |
| WO | WO 9841510 | 9/1998 |
| WO | WO 9844797 | 10/1998 |
| WO | WO 9858915 | 12/1998 |
| WO | WO 9900654 | 1/1999 |
| WO | WO 9903826 | 1/1999 |
| WO | WO 9907730 | 2/1999 |
| WO | WO 9907731 | 2/1999 |
| WO | WO 9917777 | 4/1999 |
| WO | WO 9918951 | 4/1999 |
| WO | WO 9919305 | 4/1999 |
| WO | WO 9932453 | 7/1999 |
| WO | WO 9966934 | 12/1999 |
| WO | WO 9967219 | 12/1999 |
| WO | WO 9967220 | 12/1999 |
| WO | WO 9967221 | 12/1999 |
| WO | WO 0007995 | 2/2000 |
| WO | WO 0038618 | 7/2000 |
| WO | WO 0119797 | 3/2001 |

OTHER PUBLICATIONS

M. Braun, *Synthesis 1989*, p. 856.
Brown et al., *Tetrahedron Letters*, 1971, 8, pp. 667-670.
Castro et al., *J. Med. Chem.*, 1997, 40, pp. 2491-2501.
M. S. Chambers et al., *Bioorg. & Med. Chem. Lett.*, 1993, 3 (10), pp. 1919-1924.
A. R. Chamberlin, *Chem. Rev. 1997*, 97, pp. 2243-2266.
T. Cohen et al., *J. Org. Chem. 1995*, 60, p. 2022.
M. T. Crimmins et al., *J. Am. Chem Soc. 1997*, 119, pp. 7883-7884.
S.G. Davis et al., *Synlett 1995*, p. 700.
D. A. Evans, *J. Org. Chem. 1993*, 58, pp. 2446-2453.
D. A. Evans et al., *Org. Synth 1990*, 68, p. 83-90.
D. A. Evans et al., *Tetrahedron Lett. 1994*, 35 (39), pp. 7171-7172.
A. Furstner et al., *J. Org. Chem. 1994*, 59 (18), pp. 5215-5229.
A. Furstner et al. Tetrahedron 1995,51(3) pp. 773-786.
Glenner and Wong, *Biochem. Biophys. Res. Commun.* 120; pp. 885-890 (1984).
A. K. Ghosh, *J. Am. Chem. Soc. 1996*, 118, pp. 2527-2528.
J. H. Gogerty et al., *J. Med. Chem.*, 1977, 20 (7), p. 952.
T. Imamoto et al. J.Org.Chem. 1984,49,pp. 3904-3912.
J. Jurczak et al., *Synlett 1993*, p. 241.
T.Cohen *J. Org. Chem. 1992*, 57, p. 6.
T. Imamoto*J. Am. Chem. Soc. 1989*,111 pp. 4392-4398.
L.Kruse et al. *J.Med.Chem. 1987*, 30 ,pp. 486-494.
A. S. Kende et al., *Tetrahedron Lett. 1989*, 30 (43), 5821-5824.
P. Kocienski, *Tetrahedron 1990*, 46, pp. 1767-1782.
R. C. Larock, "Comprehensive Organic Transformations," *Wiley-VCH : 1989*, pp. 604-614 and 963-964.
S. V. Ley et al., *Synthesis 1994*, p. 639.
S. Masamune et al., *J. Am. Chem. Soc. 1997*, 119, p. 2586.
T. Mukaiyama et al., *Org. React. 1994*, pp. 1-104.
H. Mulzer et al., *Tetrahedron Lett. 1995*, 36 (42), pp. 7643-7646.
S. Nozaki et al., *Bull. Chem. Soc. Jpn. 1982*, 55, pp. 2165-2168.
M.Hudlicky *Oxidation in Organic Chemistry, ACS*, 1990, pp. 250-264.
M. W. Partridge et al., *J. Chem. Soc. 1964*, p. 3673.
I. Paterson et al., *Org. React. 1997*, 51, pp. 1-200.
G. R. Pettit, *Synthesis 1996*, pp. 719-725.
T. Cohen.*Phosphorus, Sulfur, and Silicon 1993*, 74, p. 1.
"Remington's Pharmeceutical Sciences," *17th ed. Mack Publishing Company*, Easton, PA, 1985, p. 1418.
D. J. Selkoe, "Cell Biology of the amyloid (beta)-protein precursor and the mechanism of Alzheimer's disease," *Annu. Rev. Cell. Biol.* 1994, 10: pp. 373-403.
G. Semple et al., *Bioorg. & Med. Chem. Lett.*, 1996, 6(1), pp. 51-58.
G. Semple et al., *J. Med. Chem.*, 1997, 40, pp. 331-341.
G. Semple et al., Synth.Commun. 1996,26 (4),pp. 721-727.
R.G. Sherrill et al., *J. Org. Chem. 1995*, 60, pp. 730-734.
G. A. Showell et al., *J. Med. Chem.*, 1994, 37, pp. 719-721.
D. Swern, *Synthesis 1981*, pp. 165-185.
T.Cohen *Tetrahedron 1994*, 50, pp. 11569-11584 and 12793-12810.
D. A. Walsh, *Synthesis*, Sep. 1980, p. 677.
M.C. Marcotullio J.Org Chem 1994, 59, pp. 2884.
D.A. Evans. Aldrichimica Acta 1982,15pp. 23-32.
M.Yoon et al. J.Org.Chem.1985, 50, pp. 2443-2450.
S. M. Weinreb, *Tetrahedron Lett. 1981*, 22, pp. 3815-3818.
Dingwall; J. Clinical Invest., 108, Nov. 2001, 1243-1246.
Selkoe; J. Alzheimer's Disease, 3, 2001, p. 75-81.
Tanzi and Parson, "Decoding Darkness, The Search for the Genetic Causes of Alzheimer's Disease", Perseus Publishing, 2000, pp. xvii-xviii.
Olson et al., Current Opinion in Drug Discovery and Development, 4, 2001, p. 390-401.
P. J. Maurer et al, "Total synthesis of a mycobactin; mycobactin S2" Journal of the American Chemical Society, vol. 105, No. 2, 1983, pp. 240-245.
M. Adamczeski et al, Novel sponge-derived amino acids, Journal of the American Chemical Society, Vo. 111, No. 2, 1989, pp. 647-654.
International Search Report PCT/US00/24967 dated Jul. 24, 2001.

HYDROXYALKANOYLAMINOLACTAMS AND RELATED STRUCTURES AS INHIBITORS OF Aβ PROTEIN PRODUCTION

CROSS-REFERENCE TO RELATED APPLICATIONS

This application is a continuation of Ser. No. 11/522,699, filed on Sep. 18, 2006, which is a divisional application of U.S. Ser. No. 11/024,377, filed Dec. 28, 2004 (allowed), and divisional application U.S. Ser. No. 10/287,117, filed Nov. 4, 2002 (U.S. Pat. No. 6,960,576, issued Nov. 1, 2005), and U.S. Ser. No. 09/805,645, filed Mar. 14, 2001 (U.S. Pat. No. 6,503,902, issued Jan. 7, 2003), which is a continuation-in-part of U.S. Ser. No. 09/661,008, filed Sep. 13, 2000 (abandoned), which claims benefit under 35 U.S.C. 119(e) of U.S. Provisional Application Nos. 60/153,511, filed Sep. 13, 1999, and 60/224,388, filed Aug. 9, 2000, which disclosures are incorporated herein by reference in their entirety. Any disclaimer that may have occurred during the prosecution of the above-identified applications are hereby expressly rescinded.

FIELD OF THE INVENTION

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review, Dennis J. Selkoe; Cell Biology of the amyloid (beta)-protein precursor and the mechanism of Alzheimer's disease, Annu Rev Cell Biol, 1994, 10: 373-403)

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Aβ was first purified and a partial amino acid reported in 1984 (Glenner and Wong, Biochem. Biophys. Res. Commun. 120: 885-890). The isolation and sequence data for the first 28 amino acids are described in U.S. Pat. No. 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, α secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or γ secretases could thereby reduce production of Aβ, which, thereby, could reduce or prevent the neurological disorders associated with Aβ protein.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt form or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt form or prodrug form thereof.

These and other objects, which will become apparent during the following detailed description, have been achieved by the inventors' discovery that compounds of Formula (I):

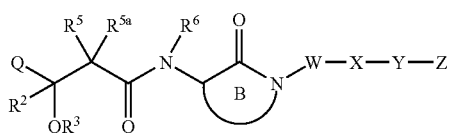

or pharmaceutically acceptable salt form or prodrug forms thereof, wherein Q, $R^2$, $R^3$, $R^5$, $R^{5a}$, $R^6$, B, W, X, Y, and Z are defined below, are effective inhibitors of the production of Aβ.

DETAILED DESCRIPTION OF PREFERRED EMBODIMENTS

Thus, in a first embodiment, the present invention provides a novel compound of Formula (I):

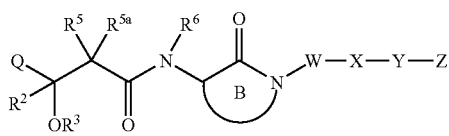

or a pharmaceutically acceptable salt form or prodrug thereof, wherein:

Q is $Q^1$,
  $(C_1-C_3$ alkyl$)$-O-$Q^1$,
  $(C_1-C_3$ alkyl$)$-S-$Q^1$,
  $(C_1-C_3$ alkyl$)$-S(=O)-$Q^1$,
  $(C_1-C_3$ alkyl$)$-S(=O)$_2$-$Q^1$, or
  $(C_1-C_3$ alkyl$)$-N($R^{20}$)-$Q^1$;

$Q^1$ is $C_1-C_9$ alkyl substituted with 0-3 $R^{1a}$;
  $C_2-C_8$ alkenyl substituted with 0-3 $R^{1a}$;
  $C_2-C_8$ alkynyl substituted with 0-3 $R^{1a}$;
  $C_3-C_{10}$ cycloalkyl substituted with 0-3 $R^{1b}$;
  $C_3-C_{10}$ carbocycle substituted with 0-3 $R^{1b}$;
  $C_6-C_{10}$ aryl substituted with 0-3 $R^{1b}$; or
  5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1-C_6$ alkyl, $OR^{14}$, Cl, F, Br, I, $NR^{15}R^{16}$, $CF_3$;
  $C_3-C_{10}$ carbocycle substituted with 0-3 $R^{1b}$;
  $C_6-C_{10}$ aryl substituted with 0-3 $R^{1b}$; and
  5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, $C_1-C_4$ haloalkyl-S—, and $(C_1-C_6$ alkyl$)$-O—C(=O)—;

$R^2$ is H, methyl, ethyl, propyl, or butyl;

$R^3$ is H, $C_1-C_6$ alkyl, —C(=O)($C_1-C_6$ alkyl), —C(=S)($C_1-C_6$ alkyl), or —C(=O)$NR^{21}R^{22}$;

alternatively, $R^2$ and $OR^3$ are combined to form C=O or C=N—OH;

$R^5$ is H, $OR^{14}$;
  $C_1-C_6$ alkyl substituted with 0-3 $R^{5b}$;
  $C_1-C_6$ alkoxy substituted with 0-3 $R^{5b}$;
  $C_2-C_6$ alkenyl substituted with 0-3 $R^{5b}$;
  $C_2-C_6$ alkynyl substituted with 0-3 $R^{5b}$;
  $C_3-C_{10}$ cycloalkyl substituted with 0-3 $R^{5c}$;
  $C_3-C_{10}$ carbocycle substituted with 0-3 $R^{5c}$;
  $C_6-C_{10}$ aryl substituted with 0-3 $R^{5c}$; or
  5 to 10 membered heterocycle containing 1 to 4 heteroatoms selected from nitrogen, oxygen, and sulphur, wherein said 5 to 10 membered heterocycle is substituted with 0-3$R^{5c}$;

$R^{5a}$ is H, $C_1-C_4$ alkyl, or $C_2-C_4$ alkenyl;

alternatively, $R^5$ and $R^{5a}$ may be combined to form a 3-7 membered cycloalkyl ring substituted with 0-3 $R^{5c}$;

optionally the cycloalkyl ring formed by combining $R^5$ and $R^{5a}$ may be benzo fused, wherein the benzo fused ring may be substituted with 0-3 $R^{5c}$;

$R^{5b}$, at each occurrence, is independently selected from:
  H, $C_1-C_6$ alkyl, $CF_3$, $OR^{14}$, Cl, F, Br, I, =O, CN, $NO_2$, $NR^{15}R^{16}$, acetyl, $SCH_3$, $S(=O)CH_3$, $S(=O)_2CH_3$, $C_2-C_6$ alkenyl, $C_2-C_6$ alkynyl, $C_1-C_4$ alkoxy, $C_1-C_4$ haloalkyl, $C_1-C_4$ haloalkoxy, $C_1-C_4$ haloalkyl-S—,
  $C_3-C_{10}$ cycloalkyl substituted with 0-3 $R^{5c}$;
  $C_3-C_{10}$ carbocycle substituted with 0-3 $R^{5c}$;
  $C_6-C_{10}$ aryl substituted with 0-3 $R^{5c}$; and
  5 to 10 membered heterocycle containing 1 to 4 heteroatoms selected from nitrogen, oxygen, and sulphur, wherein said 5 to 10 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^6$ is H or $C_1-C_6$ alkyl;

W is —$(CR^8R^{8a})_p$—;

p is 0, 1, 2, 3, or 4;

$R^8$ and $R^{8a}$, at each occurrence, are independently selected from H, F, $C_1-C_4$ alkyl, $C_2-C_4$ alkenyl, $C_2-C_4$ alkynyl and $C_3-C_8$ cycloalkyl;

X is a bond;
  $C_6-C_{10}$ aryl substituted with 0-3 $R^{Xb}$;
  $C_3-C_{10}$ cycloalkyl substituted with 0-3 $R^{Xb}$;
  $C_3-C_{10}$ carbocycle substituted with 0-3 $R^{Xb}$; or
  5 to 10 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

Y is a bond or —$(CR^9R^{9a})_t$—V—$(CR^9R^{9a})_u$—;

t is 0, 1, 2, or 3;

u is 0, 1, 2, or 3;

$R^9$ and $R^{9a}$, at each occurrence, are independently selected from H, F, $C_1-C_6$ alkyl or $C_3-C_8$ cycloalkyl;

V is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2$$NR^{19b}$—, —C(=O)O—, or —OC(=O)—;

Z is H;
  $C_1-C_8$ alkyl substituted with 0-2 $R^{12}$;
  $C_2-C_4$ alkenyl substituted with 0-2 $R^{12}$;

$C_2$-$C_4$ alkynyl substituted with 0-2 $R^{12}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

Ring B is a 6, 7, or 8 membered lactam,
wherein the lactam is saturated, partially saturated or unsaturated;
wherein each additional lactam carbon is substituted with 0-2 $R^{11}$; and,
optionally, the lactam contains a heteroatom selected from —N=, —NH—, —N($R^{10}$)—, —O—, —S—, —S(=O)—, and —S(=O)$_2$—;

additionally, two $R^{11}$ substituents on adjacent atoms may be combined to form $C_3$-$C_6$ carbocycle fused radical, a benzo fused radical, or a 5 to 6 membered heteroaryl fused radical,
wherein said 5 to 6 membered heteroaryl fused radical comprises 1-2 heteroatoms selected from N, O, and S;
wherein said benzo fused radical or 5 to 6 membered heteroaryl fused radical is substituted with 0-3 $R^{13}$;

$R^{10}$ is H, C(=O)$R^{17}$, C(=O)O$R^{17}$, C(=O)N$R^{18}R^{19}$, S(=O)$_2$N$R^{18}R^{19}$, S(=O)$_2R^{17}$;
$C_1$-$C_6$ alkyl substituted with 0-2 $R^{10a}$;
$C_6$-$C_{10}$ aryl substituted with 0-4 $R^{10b}$;
$C_3$-$C_{10}$ carbocycle substituted with 0-3 $R^{10b}$; or
5 to 10 membered heterocycle containing 1 to 4 heteroatoms selected from nitrogen, oxygen, and sulphur, wherein said 5 to 10 membered heterocycle is optionally substituted with 0-3 $R^{10b}$;

$R^{10a}$, at each occurrence, is independently selected from H, $C_1$-$C_6$ alkyl, O$R^{14}$, Cl, F, Br, I, =O, CN, NO$_2$, N$R^{15}R^{16}$, CF$_3$;
aryl substituted with 0-4 $R^{10b}$;
$C_3$-$C_{10}$ carbocycle substituted with 0-3 $R^{10b}$; or
5 to 10 membered heterocycle containing 1 to 4 heteroatoms selected from nitrogen, oxygen, and sulphur, wherein said 5 to 10 membered heterocycle is optionally substituted with 0-3 $R^{10b}$;

$R^{10b}$, at each occurrence, is independently selected from H, OH, $C_1$-$C_6$ alkyl, $C_1$-$C_4$ alkoxy, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkoxy, $C_1$-$C_4$ alkoxy, $C_1$-$C_4$ haloalkyl, $C_1$-$C_4$ haloalkoxy, and $C_1$-$C_4$ haloalkyl-S—;

$R^{11}$, at each occurrence, is independently selected from H, $C_1$-$C_4$ alkoxy, Cl, F, Br, I, =O, CN, NO$_2$, N$R^{18}R^{19}$, C(=O)$R^{17}$, C(=O)O$R^{17}$, C(=O)N$R^{18}R^{19}$, S(=O)$_2$N$R^{18}R^{19}$, CF$_3$; $C_1$-$C_6$ alkyl substituted with 0-1 $R^{11a}$;
$C_6$-$C_{10}$ aryl substituted with 0-3 $R^{11b}$;
$C_3$-$C_{10}$ carbocycle substituted with 0-3 $R^{11b}$; or
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, O$R^{14}$, Cl, F, Br, I, =O, CN, NO$_2$, N$R^{15}R^{16}$, CF$_3$;
phenyl substituted with 0-3 $R^{11b}$;
$C_3$-$C_{10}$ carbocycle substituted with 0-3 $R^{11b}$; or
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{12}$ at each occurrence, is independently selected from H, OH, Cl, F, Br, I, CN, NO$_2$, N$R^{15}R^{16}$, —C(=O)N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, NO$_2$, N$R^{15}R^{16}$, and CF$_3$;

$R^{14}$, at each occurrence, is independently selected from H, phenyl, benzyl, $C_1$-$C_6$ alkyl, and $C_2$-$C_6$ alkoxyalkyl;

$R^{14a}$ is H, phenyl, benzyl, or $C_1$-$C_6$ alkyl;

$R^{15}$, at each occurrence, is independently selected from H, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

$R^{16}$, at each occurrence, is independently selected from H, OH, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

alternatively, —N$R^{15}R^{16}$ may be a heterocyclic ring selected from the group piperidinyl, morpholinyl, thiomorpholinyl, pyrrolidinyl, homopiperidinyl, piperazinyl, and N-methylpiperazinyl;

$R^{17}$ is H, $C_1$-$C_6$ alkyl, or $C_2$-$C_6$ alkoxyalkyl, aryl substituted by 0-4 $R^{17a}$, or aryl-CH$_2$— wherein said aryl is substituted by 0-4 $R^{17a}$;

$R^{17a}$ is H, methyl, ethyl, propyl, butyl, methoxy, ethoxy, propoxy, butoxy, —OH, F, Cl, Br, I, CF$_3$, OCF$_3$, SCH$_3$, S(=O)CH$_3$, S(=O)$_2$CH$_3$, —NH$_2$, —N(CH$_3$)$_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

alternatively, —N$R^{17}R^{18}$ may be a heterocyclic ring selected from the group piperidinyl, morpholinyl, thiomorpholinyl, pyrrolidinyl, homopiperidinyl, piperazinyl, and N-methylpiperazinyl;

$R^{19}$, at each occurrence, is independently selected from H, OH, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

$R^{19b}$, at each occurrence, is independently selected from H and $C_1$-$C_6$ alkyl;

$R^{20}$ is H, OH, $C_1$-$C_4$ alkyl, phenyl, benzyl, or phenethyl;

$R^{21}$, at each occurrence, is independently selected from H, $C_1$-$C_6$ alkyl, phenyl, benzyl, and phenethyl; and $R^{22}$, at each occurrence, is independently selected from H, $C_1$-$C_6$ alkyl, phenyl, benzyl, and phenethyl.

[1] In another embodiment the present invention provides a compound of Formula (I):

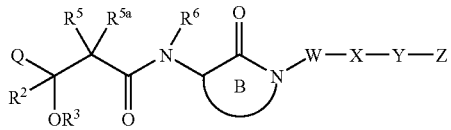

or a pharmaceutically acceptable salt form or prodrug thereof, wherein:

Q is $Q^1$,
($C_1$-$C_3$ alkyl)-O-$Q^1$,
($C_1$-$C_3$ alkyl)-S-$Q^1$,
($C_1$-$C_3$ alkyl)-S(=O)-$Q^1$,
($C_1$-$C_3$ alkyl)-S(=O)$_2$-$Q^1$, or
($C_1$-$C_3$ alkyl)-N($R^{20}$)-$Q^1$;

$Q^1$ is $C_1$-$C_8$ alkyl substituted with 0-3 $R^{1a}$;
$C_2$-$C_8$ alkenyl substituted with 0-3 $R^{1a}$;
$C_2$-$C_8$ alkynyl substituted with 0-3 $R^{1a}$;
$C_3$-$C_{10}$ cycloalkyl substituted with 0-3 $R^{1b}$;
$C_3$-$C_{10}$ carbocycle substituted with 0-3 $R^{1b}$;
$C_6$-$C_{10}$ aryl substituted with 0-3 $R^{1b}$; or
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1$-$C_6$ alkyl, $OR^{14}$, Cl, F, Br, I, $NR^{15}R^{16}$, $CF_3$;
$C_3$-$C_{10}$ carbocycle substituted with 0-3 $R^{1b}$;
$C_6$-$C_{10}$ aryl substituted with 0-3 $R^{1b}$; and
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;

$R^2$ is H, methyl, ethyl, propyl, or butyl;
$R^3$ is H, $C_1$-$C_6$ alkyl, —C(=O)($C_1$-$C_6$ alkyl), —C(=S)($C_1$-$C_6$ alkyl), or —C(=O)$NR^{21}R^{22}$;
alternatively, $R^2$ and $OR^3$ are combined to form C=O or C=N—OH;

$R^5$ is H, $OR^{14}$;
$C_1$-$C_6$ alkyl substituted with 0-3 $R^{5b}$;
$C_1$-$C_6$ alkoxy substituted with 0-3 $R^{5b}$;
$C_2$-$C_6$ alkenyl substituted with 0-3 $R^{5b}$;
$C_2$-$C_6$ alkynyl substituted with 0-3 $R^{5b}$;
$C_3$-$C_{10}$ cycloalkyl substituted with 0-3 $R^{5c}$;
$C_3$-$C_{10}$ carbocycle substituted with 0-3 $R^{5c}$;
$C_6$-$C_{10}$ aryl substituted with 0-3 $R^{5c}$; or
5 to 10 membered heterocycle containing 1 to 4 heteroatoms selected from nitrogen, oxygen, and sulphur, wherein said 5 to 10 membered heterocycle is substituted with 0-3$R^{5c}$;

$R^{5a}$ is H, $C_1$-$C_4$ alkyl, or $C_2$-$C_4$ alkenyl;
alternatively, $R^5$ and $R^{5a}$ may be combined to form a 3-7 membered cycloalkyl ring substituted with 0-3 $R^{5c}$;
optionally the cycloalkyl ring formed by combining $R^5$ and $R^{5a}$ may be benzo fused, wherein the benzo fused ring may be substituted with 0-3 $R^{5c}$;

$R^{5b}$, at each occurrence, is independently selected from:
H, $C_1$-$C_6$ alkyl, $CF_3$, $OR^{14}$, Cl, F, Br, I, =O, CN, $NO_2$, $NR^{15}R^{16}$, acetyl, $SCH_3$, S(=O)$CH_3$, S(=O)$_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, $C_1$-$C_4$ haloalkyl-S—,
$C_3$-$C_{10}$ cycloalkyl substituted with 0-3 $R^{5c}$;
$C_3$-$C_{10}$ carbocycle substituted with 0-3 $R^{5c}$;
$C_6$-$C_{10}$ aryl substituted with 0-3 $R^{5c}$; and
5 to 10 membered heterocycle containing 1 to 4 heteroatoms selected from nitrogen, oxygen, and sulphur, wherein said 5 to 10 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^6$ is H or $C_1$-$C_6$ alkyl;
W is —(CR$^8$R$^{8a}$)$_p$—;
p is 0, 1, 2, 3, or 4;
$R^8$ and $R^{8a}$, at each occurrence, are independently selected from H, F, $C_1$-$C_4$ alkyl, $C_2$-$C_4$ alkenyl, $C_2$-$C_4$ alkynyl and $C_3$-$C_8$ cycloalkyl;

X is a bond;
$C_6$-$C_{10}$ aryl substituted with 0-3 $R^{Xb}$;
$C_3$-$C_{10}$ cycloalkyl substituted with 0-3 $R^{Xb}$;
$C_3$-$C_{10}$ carbocycle substituted with 0-3 $R^{Xb}$; or
5 to 10 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Y is a bond or —(CR$^9$R$^{9a}$)$_t$—V—(CR$^9$R$^{9a}$)$_u$—;
t is 0, 1, 2, or 3;
u is 0, 1, 2, or 3;
$R^9$ and $R^{9a}$, at each occurrence, are independently selected from H, F, $C_1$-$C_6$ alkyl or $C_3$-$C_8$ cycloalkyl;
V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —C(=O)O—, or —OC(=O)—;

Z is H;
$C_1$-$C_8$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

Ring B is a 6, 7, or 8 membered lactam,
wherein the lactam is saturated, partially saturated or unsaturated;
wherein each additional lactam carbon is substituted with 0-2 $R^{11}$; and,
optionally, the lactam contains a heteroatom selected from —N=, —N$^+$(—O$^-$)=, —NH—, —N(R$^{10}$)—, —O—, —S—, —S(=O)—, and —S(=O)$_2$—;
additionally, two $R^{11}$ substituents on adjacent atoms may be combined to form $C_3$-$C_6$ carbocycle fused radical, a benzo fused radical, or a 5 to 6 membered heteroaryl fused radical,
wherein said 5 to 6 membered heteroaryl fused radical comprises 1-2 heteroatoms selected from N, O, and S;

wherein said benzo fused radical or 5 to 6 membered heteroaryl fused radical is substituted with 0-3 $R^{13}$;

$R^{10}$ is H, C(=O)$R^{17}$, C(=O)O$R^{17}$, C(=O)N$R^{18}R^{19}$, S(=O)$_2$N$R^{18}R^{19}$, S(=O)$_2$$R^{17}$;
  $C_1$-$C_6$ alkyl substituted with 0-2 $R^{10a}$;
  $C_6$-$C_{10}$ aryl substituted with 0-4 $R^{10b}$;
  $C_3$-$C_{10}$ carbocycle substituted with 0-3 $R^{10b}$; or
  5 to 10 membered heterocycle containing 1 to 4 heteroatoms selected from nitrogen, oxygen, and sulphur, wherein said 5 to 10 membered heterocycle is optionally substituted with 0-3 $R^{10b}$;

$R^{10a}$, at each occurrence, is independently selected from H, $C_1$-$C_6$ alkyl, O$R^{14}$, Cl, F, Br, I, =O, CN, NO$_2$, N$R^{15}R^{16}$, CF$_3$;
  aryl substituted with 0-4 $R^{10b}$;
  $C_3$-$C_{10}$ carbocycle substituted with 0-3 $R^{10b}$; or
  5 to 10 membered heterocycle containing 1 to 4 heteroatoms selected from nitrogen, oxygen, and sulphur, wherein said 5 to 10 membered heterocycle is optionally substituted with 0-3 $R^{10b}$;

$R^{10b}$, at each occurrence, is independently selected from H, OH, $C_1$-$C_6$ alkyl, $C_1$-$C_4$ alkoxy, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{11}$, at each occurrence, is independently selected from H, $C_1$-$C_4$ alkoxy, Cl, F, Br, I, =O, CN, NO$_2$, N$R^{18}R^{19}$, C(=O)$R^{17}$, C(=O)O$R^{17}$, C(=O)N$R^{18}R^{19}$, S(=O)$_2$N$R^{18}R^{19}$, CF$_3$;
  $C_1$-$C_6$ alkyl substituted with 0-1 $R^{11a}$;
  $C_6$-$C_{10}$ aryl substituted with 0-3 $R^{11b}$;
  $C_3$-$C_{10}$ carbocycle substituted with 0-3 $R^{11b}$; or
  5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, O$R^{14}$, Cl, F, Br, I, =O, CN, NO$_2$, N$R^{15}R^{16}$, CF$_3$;
  phenyl substituted with 0-3 $R^{11b}$;
  $C_3$-$C_{10}$ carbocycle substituted with 0-3 $R^{11b}$; or
  5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, benzyl, benzoyl, C(=O)CH$_3$, t-butoxycarbonyl, and 3,5-dimethyl-isoxazole-S(=O)$_2$—;

$R^{12}$ at each occurrence, is independently selected from H, OH, Cl, F, Br, I, CN, NO$_2$, N$R^{15}R^{16}$, —C(=O)N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
  $C_6$-$C_{10}$ aryl substituted with 0-4 $R^{12b}$;
  $C_3$-$C_{10}$ carbocycle substituted with 0-4 $R^{12b}$; or
  5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, NO$_2$, N$R^{15}R^{16}$, and CF$_3$;

$R^{14}$, at each occurrence, is independently selected from H, phenyl, benzyl, $C_1$-$C_6$ alkyl, and $C_2$-$C_6$ alkoxyalkyl;

$R^{14a}$ is H, phenyl, benzyl, or $C_1$-$C_6$ alkyl;

$R^{15}$, at each occurrence, is independently selected from H, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

$R^{16}$, at each occurrence, is independently selected from H, OH, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

alternatively, —N$R^{15}R^{16}$ may be a heterocyclic ring selected from the group piperidinyl, morpholinyl, thiomorpholinyl, pyrrolidinyl, homopiperidinyl, piperazinyl, and N-methylpiperazinyl;

$R^{17}$ is H, $C_1$-$C_6$ alkyl, or $C_2$-$C_6$ alkoxyalkyl,
  aryl substituted by 0-4 $R^{17a}$, or
  aryl-CH$_2$— wherein said aryl is substituted by 0-4 $R^{17a}$;

$R^{17a}$ is H, methyl, ethyl, propyl, butyl, methoxy, ethoxy, propoxy, butoxy, —OH, F, Cl, Br, I, CF$_3$, OCF$_3$, SCH$_3$, S(=O)CH$_3$, S(=O)$_2$CH$_3$, —NH$_2$, —N(CH$_3$)$_2$, or $C_1$-$C_4$ haloalkyl;

$R^{18}$, at each occurrence, is independently selected from H, is $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

alternatively, —N$R^{18}R^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 $R^{11b}$—;

$R^{19}$, at each occurrence, is independently selected from H, OH, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

$R^{19b}$, at each occurrence, is independently selected from H and $C_1$-$C_6$ alkyl;

$R^{20}$ is H, OH, $C_1$-$C_4$ alkyl, phenyl, benzyl, or phenethyl;

$R^{21}$, at each occurrence, is independently selected from H, $C_1$-$C_6$ alkyl, phenyl, benzyl, and phenethyl; and $R^{22}$, at each occurrence, is independently selected from H, $C_1$-$C_6$ alkyl, phenyl, benzyl, and phenethyl.

[2] In a preferred embodiment the present invention provides a compound of Formula (I) wherein:

Q is $Q^1$,
  ($C_1$-$C_3$ alkyl)-O-$Q^1$,
  ($C_1$-$C_3$ alkyl)-S-$Q^1$,
  ($C_1$-$C_3$ alkyl)-S(=O)-$Q^1$,
  ($C_1$-$C_3$ alkyl)-S(=O)$_2$-$Q^1$, or
  ($C_1$-$C_3$ alkyl)-N($R^{20}$)-$Q^1$;

$Q^1$ is $C_1$-$C_6$ alkyl substituted with 0-3 $R^{1a}$;
  $C_2$-$C_6$ alkenyl substituted with 0-3 $R^{1a}$;
  $C_2$-$C_6$ alkynyl substituted with 0-3 $R^{1a}$;
  $C_3$-$C_{10}$ cycloalkyl substituted with 0-3 $R^{1b}$;
  $C_3$-$C_{10}$ carbocycle substituted with 0-3 $R^{1b}$;
  $C_6$-$C_{10}$ aryl substituted with 0-3 $R^{1b}$; or
  5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1$-$C_6$ alkyl, O$R^{14}$, Cl, F, Br, I, N$R^{15}R^{16}$, CF$_3$;
  $C_3$-$C_{10}$ carbocycle substituted with 0-3 $R^{1b}$;
  $C_6$-$C_{10}$ aryl substituted with 0-3 $R^{1b}$; and 5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;

$R^2$ is H, methyl, ethyl, propyl, or butyl;

$R^3$ is H, $C_1$-$C_4$ alkyl, —C(=O)($C_1$-$C_4$ alkyl), —C(=S)($C_1$-$C_4$ alkyl), or —C(=O)$NR^{21}R^{22}$;

$R^5$ is H, $OR^{14}$;
  $C_1$-$C_6$ alkyl substituted with 0-3 $R^{5b}$;
  $C_1$-$C_6$ alkoxy substituted with 0-3 $R^{5b}$;
  $C_2$-$C_6$ alkenyl substituted with 0-3 $R^{5b}$;
  $C_2$-$C_6$ alkynyl substituted with 0-3 $R^{5b}$;
  $C_3$-$C_{10}$ cycloalkyl substituted with 0-3 $R^{5c}$;
  $C_3$-$C_{10}$ carbocycle substituted with 0-3 $R^{5c}$;
  $C_6$-$C_{10}$ aryl substituted with 0-3 $R^{5c}$; or
  5 to 10 membered heterocycle containing 1 to 4 heteroatoms selected from nitrogen, oxygen, and sulphur, wherein said 5 to 10 membered heterocycle is substituted with 0-3$R^{5c}$;

$R^{5a}$ is H, $C_1$-$C_4$ alkyl, or $C_2$-$C_4$ alkenyl;

alternatively, $R^5$ and $R^{5a}$ may be combined to form a 3-7 membered cycloalkyl ring substituted with 0-3 $R^{5c}$;

$R^{5b}$, at each occurrence, is independently selected from:
  H, $C_1$-$C_6$ alkyl, $CF_3$, $OR^{14}$, Cl, F, Br, I, =O, CN, $NO_2$, $NR^{15}R^{16}$, acetyl, $SCH_3$, $S(=O)CH_3$, $S(=O)_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, and $C_1$-$C_4$ haloalkyl-S—,
  $C_3$-$C_{10}$ cycloalkyl substituted with 0-3 $R^{5c}$;
  $C_3$-$C_{10}$ carbocycle substituted with 0-3 $R^{5c}$;
  $C_6$-$C_{10}$ aryl substituted with 0-3 $R^{5c}$; and
  5 to 10 membered heterocycle containing 1 to 4 heteroatoms selected from nitrogen, oxygen, and sulphur, wherein said 5 to 10 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^6$ is H, methyl, or ethyl;

W is —($CR^8R^{8a}$)$_p$—;

p is 0, 1, or 2;

$R^8$ and $R^{8a}$, at each occurrence, are independently selected from H, F, methyl, and ethyl;

X is a bond;
  phenyl substituted with 0-3 $R^{Xb}$;
  $C_3$-$C_6$ cycloalkyl substituted with 0-3 $R^{Xb}$; or
  5 to 6 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Y is a bond or —($CR^9R^{9a}$)$_t$—V—($CR^9R^{9a}$)$_u$—;

t is 0, 1, or 2;

u is 0, 1, or 2;

$R^9$ and $R^{9a}$, at each occurrence, are independently selected from H, F, methyl, and ethyl;

V is a bond, —C(=O)—, —O—, —S—, —S(=O)—, —S(=O)$_2$—, —N($R^{19}$)—, —C(=O)NH—, —NHC(=O)—, —NHS(=O)$_2$—, or —S(=O)$_2$NH—;

Z is H, halo;

$C_1$-$C_4$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
$C_6$-$C_{10}$ aryl substituted with 0-4 $R^{12b}$;
$C_3$-$C_6$ carbocycle substituted with 0-4 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$;

Ring B is a 7 membered lactam,
  wherein the lactam is saturated, partially saturated or unsaturated;
  wherein each additional lactam carbon is substituted with 0-2 $R^{11}$; and,
  optionally, the lactam contains a heteroatom selected from —N=, —NH—, —N($R^{10}$)—, —O—, —S—, —S(=O)—, and —S(=O)$_2$—;
  additionally, two $R^{11}$ substituents on adjacent atoms may be combined to form $C_3$-$C_6$ carbocycle fused radical, a benzo fused radical, or a 5 to 6 membered heteroaryl fused radical,
    wherein said 5 to 6 membered heteroaryl fused radical comprises 1-2 heteroatoms selected from N, O, and S;
    wherein said benzo fused radical or 5 to 6 membered heteroaryl fused radical is substituted with 0-3 $R^{13}$;

$R^{10}$ is H, C(=O)$R^{17}$, C(=O)$OR^{17}$, C(=O)$NR^{18}R^{19}$, $S(=O)_2NR^{18}R^{19}$, $S(=O)_2R^{17}$;
  $C_1$-$C_6$ alkyl substituted with 0-2 $R^{10a}$;
  $C_6$-$C_{10}$ aryl substituted with 0-4 $R^{10b}$;
  $C_3$-$C_{10}$ carbocycle substituted with 0-3 $R^{10b}$; or
  5 to 10 membered heterocycle containing 1 to 4 heteroatoms selected from nitrogen, oxygen, and sulphur, wherein said 5 to 10 membered heterocycle is optionally substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or aryl substituted with 0-4 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{11}$, at each occurrence, is independently selected from H, $C_1$-$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, $S(=O)_2NR^{18}R^{19}$, $CF_3$;
  $C_1$-$C_6$ alkyl substituted with 0-1 $R^{11a}$;
  $C_6$-$C_{10}$ aryl substituted with 0-3 $R^{11b}$;
  $C_3$-$C_{10}$ carbocycle substituted with 0-3 $R^{11b}$; or
  5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
  phenyl substituted with 0-3 $R^{11b}$;
  $C_3$-$C_{10}$ carbocycle substituted with 0-3 $R^{11b}$; or
  5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{12}$ at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$C_6$-$C_{10}$ aryl substituted with 0-4 $R^{12b}$;

$C_3$-$C_{10}$ carbocycle substituted with 0-4 $R^{12b}$; or 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$-$C_6$ alkyl, and $C_2$-$C_6$ alkoxyalkyl;

$R^{15}$, at each occurrence, is independently selected from H, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

$R^{16}$, at each occurrence, is independently selected from H, OH, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperazinyl;

$R^{17}$ is H, aryl, aryl-$CH_2$—, $C_1$-$C_6$ alkyl, or $C_2$-$C_6$ alkoxyalkyl;

$R^{18}$, at each occurrence, is independently selected from H, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

$R^{19}$, at each occurrence, is independently selected from H, OH, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

alternatively, —$NR^{17}R^{18}$ may be a heterocyclic ring selected from the group piperidinyl, morpholinyl, thiomorpholinyl, pyrrolidinyl, homopiperidinyl, piperazinyl, and N-methylpiperazinyl;

$R^{20}$ is H, OH, $C_1$-$C_4$ alkyl, phenyl, benzyl, or phenethyl;

$R^{21}$, at each occurrence, is independently selected from H, $C_1$-$C_6$ alkyl, phenyl, benzyl, and phenethyl; and $R^{22}$, at each occurrence, is independently selected from H, $C_1$-$C_6$ alkyl, phenyl, benzyl, and phenethyl.

[3] In a preferred embodiment the present invention provides a compound of Formula (I) wherein Ring B is selected from:

wherein each benzo fused radical is substituted with 0-3 $R^{13}$.

[4] In a preferred embodiment the present invention provides a compound of Formula (Ia):

(Ia)

or a pharmaceutically acceptable salt form or prodrug thereof, wherein:

Q is $Q^1$,
($C_1$-$C_3$ alkyl)-O-$Q^1$,
($C_1$-$C_3$ alkyl)-S-$Q^1$,
($C_1$-$C_3$ alkyl)-S(=O)-$Q^1$,
($C_1$-$C_3$ alkyl)-S(=O)$_2$-$Q^1$, or
($C_1$-$C_3$ alkyl)-N($R^{20}$)-$Q^1$;

$Q^1$ is $C_1$-$C_6$ alkyl substituted with 0-3 $R^{1a}$;
$C_2$-$C_6$ alkenyl substituted with 0-3 $R^{1a}$;
$C_2$-$C_6$ alkynyl substituted with 0-3 $R^{1a}$;
$C_3$-$C_{10}$ cycloalkyl substituted with 0-3 $R^{1b}$;
$C_3$-$C_{10}$ carbocycle substituted with 0-3 $R^{1b}$;
$C_6$-$C_{10}$ aryl substituted with 0-3 $R^{1b}$; or 5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1$-$C_6$ alkyl, $OR^{14}$, Cl, F, Br, I, $NR^{15}R^{16}$, $CF_3$;
- $C_3$-$C_{10}$ carbocycle substituted with 0-3 $R^{1b}$;
- $C_6$-$C_{10}$ aryl substituted with 0-3 $R^{1b}$; and
- 5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;

$R^2$ is H, methyl, or ethyl;

$R^5$ is H, $OR^{14}$;
- $C_1$-$C_6$ alkyl substituted with 0-3 $R^{5b}$;
- $C_1$-$C_6$ alkoxy substituted with 0-3 $R^{5b}$;
- $C_2$-$C_6$ alkenyl substituted with 0-3 $R^{5b}$;
- $C_2$-$C_6$ alkynyl substituted with 0-3 $R^{5b}$;
- $C_3$-$C_{10}$ cycloalkyl substituted with 0-3 $R^{5c}$;
- $C_3$-$C_{10}$ carbocycle substituted with 0-3 $R^{5c}$;
- $C_6$-$C_{10}$ aryl substituted with 0-3 $R^{5c}$; or
- 5 to 10 membered heterocycle containing 1 to 4 heteroatoms selected from nitrogen, oxygen, and sulphur, wherein said 5 to 10 membered heterocycle is substituted with 0-3$R^{5c}$;

$R^{5a}$ is H, $C_1$-$C_4$ alkyl, or $C_2$-$C_4$ alkenyl;

alternatively, $R^5$ and $R^{5a}$ may be combined to form a 3-7 membered cycloalkyl ring substituted with 0-3 $R^{5c}$;

$R^{5b}$, at each occurrence, is independently selected from:
- H, $C_1$-$C_6$ alkyl, $CF_3$, $OR^{14}$, Cl, F, Br, I, =O, CN, $NO_2$, $NR^{15}R^{16}$, acetyl, $SCH_3$, $S(=O)CH_3$, $S(=O)_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, and $C_1$-$C_4$ haloalkyl-S—,
- $C_3$-$C_{10}$ cycloalkyl substituted with 0-3 $R^{5c}$;
- $C_3$-$C_{10}$ carbocycle substituted with 0-3 $R^{5c}$;
- $C_6$-$C_{10}$ aryl substituted with 0-3 $R^{5c}$; and
- 5 to 10 membered heterocycle containing 1 to 4 heteroatoms selected from nitrogen, oxygen, and sulphur, wherein said 5 to 10 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

W is —$(CR^8R^{8a})_p$—;

p is 0, 1, or 2;

$R^8$ and $R^{8a}$, at each occurrence, are independently selected from H, F, methyl, and ethyl;

X is a bond;
- phenyl substituted with 0-3 $R^{Xb}$;
- $C_3$-$C_6$ cycloalkyl substituted with 0-3 $R^{Xb}$; or
- 5 to 6 membered heterocycle containing 1 to 3 heteroatoms selected from nitrogen, oxygen, and sulphur, wherein said 5 to 6 membered heterocycle is substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Y is a bond or —$(CR^9R^{9a})_t$—V—$(CR^9R^{9a})_u$—;

t is 0, 1, or 2;
u is 0, 1, or 2;

$R^9$ and $R^{9a}$, at each occurrence, are independently selected from H, F, methyl, and ethyl;

V is a bond, —C(=O)—, —O—, —S—, —S(=O)—, —S(=O)$_2$—, —N($R^{19}$)—, —C(=O)NH—, or —NHC(=O)—;

Z is H, halo;
- $C_1$-$C_4$ alkyl substituted with 0-2 $R^{12}$;
- $C_2$-$C_4$ alkenyl substituted with 0-2 $R^{12}$;
- $C_2$-$C_4$ alkynyl substituted with 0-2 $R^{12}$;
- $C_6$-$C_{10}$ aryl substituted with 0-4 $R^{12b}$;
- $C_3$-$C_6$ carbocycle substituted with 0-4 $R^{12b}$; or
- 5 to 6 membered heterocycle containing 1 to 4 heteroatoms selected from nitrogen, oxygen, and sulphur, wherein said 5 to 6 membered heterocycle is substituted with 0-3 $R^{12b}$;

Ring B is selected from:

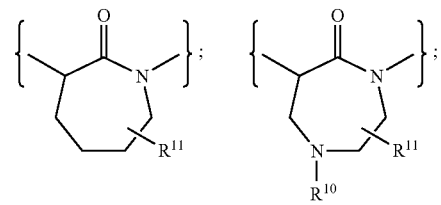

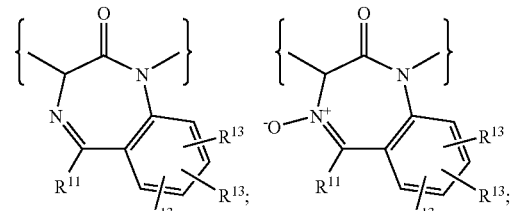

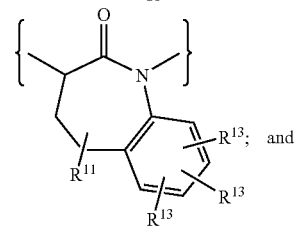

and

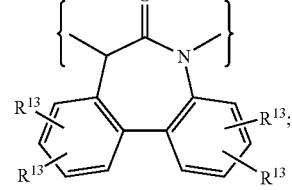

$R^{10}$ is H, C(=O)$R^{17}$, C(=O)O$R^{17}$, C(=O)N$R^{18}R^{19}$, S(=O)$_2$N$R^{18}R^{19}$, S(=O)$_2R^{17}$;
- $C_1$-$C_6$ alkyl substituted with 0-2 $R^{10a}$;
- $C_6$-$C_{10}$ aryl substituted with 0-4 $R^{10b}$;
- $C_3$-$C_{10}$ carbocycle substituted with 0-3 $R^{10b}$; or
- 5 to 10 membered heterocycle containing 1 to 4 heteroatoms selected from nitrogen, oxygen, and sulphur, wherein said 5 to 10 membered heterocycle is optionally substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or aryl substituted with 0-4 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{11}$, at each occurrence, is independently selected from H, $C_1$-$C_4$ alkoxy, Cl, F, Br, I, =O, CN, $NO_2$, $NR^{18}R^{19}$, C(=O)$R^{17}$, C(=O)$OR^{17}$, C(=O)$NR^{18}R^{19}$, $S(=O)_2NR^{18}R^{19}$, $CF_3$;

$C_1$-$C_6$ alkyl substituted with 0-1 $R^{11a}$;
$C_6$-$C_{10}$ aryl substituted with 0-3 $R^{11b}$;
$C_3$-$C_{10}$ carbocycle substituted with 0-3 $R^{11b}$; or
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
phenyl substituted with 0-3 $R^{11b}$;
$C_3$-$C_{10}$ carbocycle substituted with 0-3 $R^{11b}$; or
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, benzyl, benzoyl, C(=O)$CH_3$, t-butoxycarbonyl, and 3,5-dimethyl-isoxazole-$S(=O)_2$—;

$R^{12}$ at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$-$C_6$ alkyl, and $C_2$-$C_6$ alkoxyalkyl;

$R^{15}$, at each occurrence, is independently selected from H, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-$S(=O)_2$—;

$R^{16}$, at each occurrence, is independently selected from H, OH, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-$S(=O)_2$—;

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperazinyl;

$R^{17}$ is H, $C_1$-$C_6$ alkyl, or $C_2$-$C_6$ alkoxyalkyl, aryl substituted by 0-4 $R^{17a}$, or
aryl-$CH_2$— wherein said aryl is substituted by 0-4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(=O)CH_3$, $S(=O)_2CH_3$, —$NH_2$, —$N(CH_3)_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)— and ($C_1$-$C_6$ alkyl)-$S(=O)_2$—;

$R^{19}$, at each occurrence, is independently selected from H, OH, $C_1$-$C_6$ alkyl, phenyl, benzyl, phenethyl, ($C_1$-$C_6$ alkyl)-C(=O)— and ($C_1$-$C_6$ alkyl)-$S(=O)_2$—;

alternatively, —$NR^{18}R^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 $R^{11b}$—; and $R^{20}$ is H, OH, $C_1$-$C_4$ alkyl, phenyl, benzyl, or phenethyl.

[5] In a preferred embodiment the present invention provides a compound of Formula (Ia):

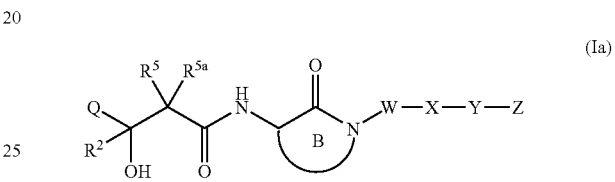

wherein:
Ring B is selected from:

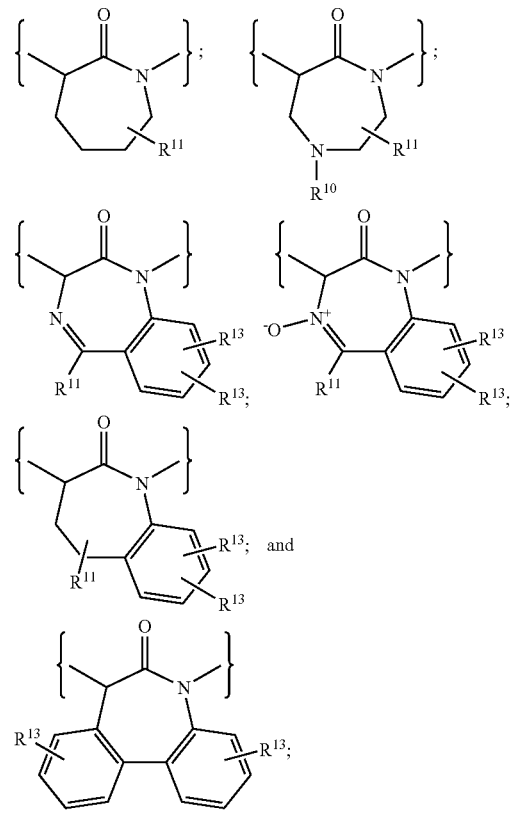

Q is $Q^1$ or ($C_1$-$C_3$ alkyl)-O-$Q^1$;
$Q^1$ is $C_1$-$C_6$ alkyl substituted with 0-3 $R^{1a}$;
$C_2$-$C_6$ alkenyl substituted with 0-3 $R^{1a}$;

$C_2$-$C_6$ alkynyl substituted with 0-3 $R^{1a}$;
$C_3$-$C_{10}$ cycloalkyl substituted with 0-3 $R^{1b}$;
$C_3$-$C_{10}$ carbocycle substituted with 0-3 $R^{1b}$;
$C_6$-$C_{10}$ aryl substituted with 0-3 $R^{1b}$; or
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1$-$C_6$ alkyl, $OR^{14}$, Cl, F, Br, I, $NR^{15}R^{16}$, $CF_3$;
$C_3$-$C_{10}$ carbocycle substituted with 0-3 $R^{1b}$;
$C_6$-$C_{10}$ aryl substituted with 0-3 $R^{1b}$; and
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;

$R^2$ is H, methyl, or ethyl;
$R^5$ is H, $OR^{14}$;
$C_1$-$C_6$ alkyl substituted with 0-3 $R^{5b}$;
$C_2$-$C_6$ alkenyl substituted with 0-3 $R^{5b}$;
$C_2$-$C_6$ alkynyl substituted with 0-3 $R^{5b}$;
$C_3$-$C_6$ cycloalkyl substituted with 0-3 $R^{5c}$;
$C_3$-$C_6$ carbocycle substituted with 0-3 $R^{5c}$;
phenyl substituted with 0-3 $R^{5c}$; or
5 to 7 membered heterocycle containing 1 to 4 heteroatoms selected from nitrogen, oxygen, and sulphur, wherein said 5 to 7 membered heterocycle is substituted with 0-3$R^{5c}$;

$R^{5a}$ is H, $C_1$-$C_4$ alkyl, or $C_2$-$C_4$ alkenyl;
alternatively, $R^5$ and $R^{5a}$ may be combined to form a $C_4$-$C_7$ cycloalkyl ring;

$R^{5b}$, at each occurrence, is independently selected from:
H, $C_1$-$C_6$ alkyl, $CF_3$, $OR^{14}$, Cl, F, Br, I, =O, CN, $NO_2$, $NR^{15}R^{16}$, acetyl, $SCH_3$, $S(=O)CH_3$, $S(=O)_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, and $C_1$-$C_4$ haloalkyl-S—,
$C_3$-$C_{10}$ cycloalkyl substituted with 0-3 $R^{5c}$;
$C_3$-$C_{10}$ carbocycle substituted with 0-3 $R^{5c}$;
$C_6$-$C_{10}$ aryl substituted with 0-3 $R^{5c}$; and
5 to 10 membered heterocycle containing 1 to 4 heteroatoms selected from nitrogen, oxygen, and sulphur, wherein said 5 to 10 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

W is —$(CR^8R^{8a})_p$—;
p is 0, 1, or 2;
$R^8$ and $R^{8a}$, at each occurrence, are independently selected from H, methyl, and ethyl;
X is a bond;
phenyl substituted with 0-3 $R^{Xb}$;
$C_3$-$C_6$ cycloalkyl substituted with 0-3 $R^{Xb}$; or
5 to 6 membered heterocycle containing 1 to 3 heteroatoms selected from nitrogen, oxygen, and sulphur, wherein said 5 to 6 membered heterocycle is substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Y is a bond or —$(CR^9R^{9a})_t$—V—$(CR^9R^{9a})_u$—;
t is 0, 1, or 2;
u is 0, 1, or 2;
$R^9$ and $R^{9a}$, at each occurrence, are independently selected from H, F, methyl, and ethyl;
V is a bond, —C(=O)—, —O—, —S—, —S(=O)—, —S(=O)_2—, —N($R^{19}$)—, —NHC(=O)—, or —C(=O)NH—;
Z is H, F, Cl, Br;
$C_1$-$C_4$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
$C_6$-$C_{10}$ aryl substituted with 0-4 $R^{12b}$;
$C_3$-$C_6$ carbocycle substituted with 0-4 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{10}$ is $C(=O)R^{17}$, $C(=O)NR^{18}R^{19}$, $S(=O)_2R^{17}$;
$C_1$-$C_6$ alkyl substituted with 0-2 $R^{10a}$;
phenyl substituted with 0-3 $R^{10b}$; or
5 to 6 membered heterocycle containing 1 to 4 heteroatoms selected from nitrogen, oxygen, and sulphur, wherein said 5 to 6 membered heterocycle is optionally substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or aryl substituted with 0-3 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{11}$ at each occurrence, is independently selected from H, =O, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$-$C_6$ alkyl substituted with 0-1 $R^{11a}$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$;

$R^{11a}$, at each occurrence, is independently selected from H, $C_1$-$C_4$ alkyl, $OR^{14}$, Cl, F, Br, =O, CN, $NO_2$, $NR^{15}R^{16}$, $CF_3$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$;

$R^{11b}$, at each occurrence, is independently selected from H. OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, benzyl, benzoyl, $C(=O)CH_3$, t-butoxycarbonyl, and 3,5-dimethyl-isoxazole-$S(=O)_2$—;

$R^{12}$ at each occurrence, is independently selected from H, OH, Cl, F, Br, I, CN, $NO_2$, $NR^{15}R^{16}$, —$C(=O)NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$C_6$-$C_{10}$ aryl substituted with 0-4 $R^{12b}$;
$C_3$-$C_{10}$ carbocycle substituted with 0-4 $R^{12b}$; or 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$-$C_6$ alkyl, and $C_2$-$C_6$ alkoxyalkyl;

$R^{15}$, at each occurrence, is independently selected from H, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

$R^{16}$, at each occurrence, is independently selected from H, OH, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperazinyl; and $R^{17}$ is H, $C_1$-$C_6$ alkyl, or $C_2$-$C_6$ alkoxyalkyl, aryl substituted by 0-4 $R^{17a}$, or aryl-$CH_2$— wherein said aryl is substituted by 0-4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(=O)CH_3$, $S(=O)_2CH_3$, —$NH_2$, —$N(CH_3)_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

$R^{19}$, at each occurrence, is independently selected from H, OH, methyl, ethyl, propyl, butyl, phenyl, benzyl, and phenethyl; and alternatively, —$NR^{18}R^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 $R^{11b}$—.

[6] In a preferred embodiment the present invention provides a compound of Formula (Ia) wherein:

Q is $Q^1$;

$Q^1$ is $C_1$-$C_6$ alkyl substituted with 0-3 $R^{1a}$;
$C_2$-$C_6$ alkenyl substituted with 0-3 $R^{1a}$;
$C_2$-$C_6$ alkynyl substituted with 0-3 $R^{1a}$;
$C_3$-$C_{10}$ cycloalkyl substituted with 0-3 $R^{1b}$;
$C_3$-$C_{10}$ carbocycle substituted with 0-3 $R^{1b}$;
$C_6$-$C_{10}$ aryl substituted with 0-3 $R^{1b}$; or
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1$-$C_6$ alkyl, $OR^{14}$, CL, F, Br, I, $NR^{15}R^{16}$, $CF_3$;
$C_3$-$C_{10}$ carbocycle substituted with 0-3 $R^{1b}$;
$C_6$-$C_{10}$ aryl substituted with 0-3 $R^{1b}$; and
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;

$R^2$ is H, methyl, or ethyl;

$R^5$ is H, $OR^{14}$,
$C_1$-$C_6$ alkyl substituted with 0-3 $R^{5b}$;
$C_2$-$C_6$ alkenyl substituted with 0-3 $R^{5b}$; or
$C_2$-$C_6$ alkynyl substituted with 0-3 $R^{5b}$;

$R^{5a}$ is H, methyl, ethyl, propyl, butyl, or $C_2$-$C_4$ alkenyl;

alternatively, $R^5$ and $R^{5a}$ may be combined to form a $C_4$-$C_7$ cycloalkyl ring;

$R^{5b}$, at each occurrence, is independently selected from:
H, methyl, ethyl, propyl, butyl, $CF_3$, $OR^{14}$, Cl, F, Br, I, =O, $NR^{15}R^{16}$,
$C_3$-$C_7$ cycloalkyl substituted with 0-3 $R^{5c}$;
$C_3$-$C_7$ carbocycle substituted with 0-3 $R^{5c}$;
phenyl substituted with 0-3 $R^{5c}$; and
5 to 7 membered heterocycle containing 1 to 4 heteroatoms selected from nitrogen, oxygen, and sulphur, wherein said 5 to 7 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

W is —$(CHR^8)_p$—;

p is 0 or 1;

$R^8$ is H, methyl, or ethyl;

X is a bond;
phenyl substituted with 0-2 $R^{Xb}$;
$C_5$-$C_6$ cycloalkyl substituted with 0-3 $R^{Xb}$; or
5 to 6 membered heterocycle containing 1 to 3 heteroatoms selected from nitrogen, oxygen, and sulphur, wherein said 5 to 6 membered heterocycle is substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Y is a bond, —V—, —$CH_2$—V—, —V—$CH_2$—, or —$CH_2$—V—$CH_2$—;

V is a bond, —C(=O)—, —O—, —S—, —S(=O)—, —S(=O)$_2$—, or —N($R^{19}$)—;

Z is H, F, Cl, Br,
$C_1$-$C_4$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
$C_6$-$C_{10}$ aryl substituted with 0-4 $R^{12b}$;
$C_3$-$C_6$ carbocycle substituted with 0-4 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{10}$ is C(=O)$R^{17}$, C(=O)$NR^{18}R^{19}$, $S(=O)_2R^{17}$;
$C_1$-$C_6$ alkyl substituted with 0-2 $R^{10a}$;
phenyl substituted with 0-3 $R^{10b}$; or
5 to 6 membered heterocycle containing 1 to 4 heteroatoms selected from nitrogen, oxygen, and sulphur, wherein said 5 to 6 membered heterocycle is optionally substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or aryl substituted with 0-3 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{11}$, at each occurrence, is independently selected from H, =O, $NR^{18}R^{19}$, $C(=O)R^{17}$, $C(=O)OR^{17}$, $C(=O)NR^{18}R^{19}$, $S(=O)_2NR^{18}R^{19}$, $CF_3$;

$C_1$-$C_6$ alkyl substituted with 0-1 $R^{11a}$;

phenyl substituted with 0-3 $R^{11b}$;

$C_3$-$C_6$ carbocycle substituted with 0-3 $R^{11b}$; or 5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, =O, $NR^{15}R^{16}$, $CF_3$;

phenyl substituted with 0-3 $R^{11b}$;

$C_3$-$C_6$ carbocycle substituted with 0-3 $R^{11b}$; or 5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, $C_1$-$C_2$ haloalkoxy, benzyl, benzoyl, $C(=O)CH_3$, t-butoxycarbonyl, and 3,5-dimethyl-isoxazole-$S(=O)_2$—;

$R^{12}$ at each occurrence, is independently selected from H, OH, Cl, F, Br, I, CN, $NO_2$, $NR^{15}R^{16}$, —$C(=O)NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$C_6$-$C_{10}$ aryl substituted with 0-4 $R^{12b}$;

$C_3$-$C_{10}$ carbocycle substituted with 0-4 $R^{12b}$; or 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$-$C_4$ alkyl, and $C_2$-$C_4$ alkoxyalkyl;

$R^{15}$, at each occurrence, is independently selected from H, methyl, ethyl, propyl, butyl, phenyl, benzyl, and phenethyl;

$R^{16}$, at each occurrence, is independently selected from H, OH, methyl, ethyl, propyl, butyl, phenyl, benzyl, phenethyl, $CH_3CH_2C(=O)$—, $CH_3C(=O)$—, $CH_3CH_2C(=O)$—, $CH_3C(=O)$—, $CH_3CH_2S(=O)_2$— and $CH_3S(=O)_2$—;

$R^{17}$ is H, $C_1$-$C_4$ alkyl, or $C_2$-$C_4$ alkoxyalkyl;

phenyl substituted by 0-2 $R^{17a}$; or benzyl substituted by 0-2 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(=O)CH_3$, $S(=O)_2CH_3$, —$NH_2$, —$N(CH_3)_2$, or $C_1$-$C_4$ haloalkyl;

$R^{18}$, at each occurrence, is independently selected from H, methyl, ethyl, propyl, butyl, phenyl, benzyl, and phenethyl;

$R^{19}$, at each occurrence, is independently selected from H, OH, methyl, ethyl, propyl, and butyl; and alternatively, —$NR^{18}R^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 $R^{11b}$—.

[7] In a preferred embodiment the present invention provides a compound of Formula (Ia) wherein:

Q is $Q^1$;

$Q^1$ is $C_1$-$C_6$ alkyl substituted with 0-3 $R^{1a}$;

$C_2$-$C_6$ alkenyl substituted with 0-3 $R^{1a}$;

$C_2$-$C_6$ alkynyl substituted with 0-3 $R^{1a}$;

$C_3$-$C_6$ cycloalkyl substituted with 0-3 $R^{1b}$;

phenyl substituted with 0-3 $R^{1b}$; or 5 to 6 membered heterocycle containing 1 to 4 heteroatoms selected from nitrogen, oxygen, and sulphur, wherein said 5 to 6 membered heterocycle is substituted with 0-3 $R^{1b}$;

$R^{1a}$, at each occurrence, is independently selected from H, methyl, ethyl, propyl, butyl, $OR^{14}$, Cl, F, Br, I, $NR^{15}R^{16}$, $CF_3$;

$C_3$-$C_6$ carbocycle substituted with 0-3 $R^{1b}$;

phenyl substituted with 0-3 $R^{1b}$; and 5 to 6 membered heterocycle containing 1 to 4 heteroatoms selected from nitrogen, oxygen, and sulphur, wherein said 5 to 6 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, $C_1$-$C_2$ haloalkoxy, (methyl)$OC(=O)$—, (ethyl)$OC(=O)$—, (propyl)$OC(=O)$—, and (butyl)$OC(=O)$—;

$R^2$ is H or methyl;

$R^5$ is H, $OR^{14}$;

$C_1$-$C_4$ alkyl substituted with 0-1 $R^{5b}$;

$C_2$-$C_4$ alkenyl substituted with 0-1 $R^{5b}$; or $C_2$-$C_4$ alkynyl substituted with 0-1 $R^{5b}$;

$R^{5a}$ is H, methyl, ethyl, propyl, or butyl;

alternatively, $R^5$ and $R^{5a}$ may be combined to form a cyclobutyl, cyclopentyl, cyclohexyl, or cycloheptyl ring;

$R^{5b}$, at each occurrence, is independently selected from:

H, methyl, ethyl, propyl, butyl, $CF_3$, $OR^{14}$, Cl, F, =O, $NR^{15}R^{16}$, $C_3$-$C_7$ cycloalkyl substituted with 0-3 $R^{5c}$;

$C_3$-$C_7$ carbocycle substituted with 0-3 $R^{5c}$;

phenyl substituted with 0-3 $R^{5c}$; and 5 to 7 membered heterocycle containing 1 to 4 heteroatoms selected from nitrogen, oxygen, and sulphur, wherein said 5 to 7 membered heterocycle is substituted with 0-3 $R^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

W is a bond, —$CH_2$—, or —$CH(CH_3)$—;

X is a bond;
  phenyl substituted with 0-1 $R^{Xb}$;
  $C_5$-$C_6$ cycloalkyl substituted with 0-1 $R^{Xb}$; or
  5 to 6 membered heterocycle containing 1 to 3 heteroatoms selected from nitrogen, oxygen, and sulphur, wherein said 5 to 6 membered heterocycle is substituted with 0-1 $R^{Xb}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, and isoxazolyl;
$R^{Xb}$, at each occurrence, is independently selected from H, OH, Cl, F, Br, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
Y is a bond, —V—, —V—$CH_2$—, or —$CH_2$V—;
V is a bond, —C(=O)—, —O—, —S—, —S(=O)—, —S(=O)$_2$—, or —N($R^{19}$)—;
Z is H, F, Cl, Br,
  $C_1$-$C_4$ alkyl substituted with 0-2 $R^{12}$;
  $C_2$-$C_4$ alkenyl substituted with 0-2 $R^{12}$;
  $C_2$-$C_4$ alkynyl substituted with 0-2 $R^{12}$;
  $C_6$-$C_{10}$ aryl substituted with 0-4 $R^{12b}$;
  $C_3$-$C_6$ carbocycle substituted with 0-4 $R^{12b}$; or
  5 to 6 membered heterocycle containing 1 to 4 heteroatoms selected from nitrogen, oxygen, and sulphur, wherein said 5 to 6 membered heterocycle is substituted with 0-3 $R^{12b}$;
$R^{11}$, at each occurrence, is independently selected from:
  H, $NR^{18}R^{19}$, $CF_3$;
  $C_1$-$C_4$ alkyl substituted with 0-1 $R^{11a}$;
  phenyl substituted with 0-3 $R^{11b}$;
  $C_3$-$C_6$ carbocycle substituted with 0-3 $R^{11b}$; or
  5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;
$R^{11a}$, at each occurrence, is independently selected from H, methyl, ethyl, propyl, butyl, methoxy, ethoxy, propoxy, Cl, F, =O, $NR^{15}R^{16}$, $CF_3$;
  phenyl substituted with 0-3 $R^{11b}$;
  $C_3$-$C_6$ carbocycle substituted with 0-3 $R^{11b}$; or
  5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;
$R^{12}$ at each occurrence, is independently selected from H, OH, Cl, F, Br, $NR^{15}R^{16}$, —C(=O)$NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
  phenyl substituted with 0-4 $R^{12b}$;
  $C_3$-$C_6$ carbocycle substituted with 0-4 $R^{12b}$; or
  5 to 6 membered heterocycle containing 1 to 4 heteroatoms selected from nitrogen, oxygen, and sulphur, wherein said 5 to 6 membered heterocycle is substituted with 0-3 $R^{12b}$;
$R^{12b}$, at each occurrence, is independently selected from H, OH, Cl, F, Br, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^{13}$, at each occurrence, is independently selected from H, OH, methyl, ethyl, propyl, butyl, methoxy, ethoxy, propoxy, Cl, F, Br, CN, $NR^{15}R^{16}$, and $CF_3$;
$R^{14}$, at each occurrence, is independently selected from H, phenyl, benzyl, methyl, ethyl, propyl, and butyl;
$R^{15}$, at each occurrence, is independently selected from H, methyl, ethyl, propyl, or butyl;
$R^{16}$, at each occurrence, is independently selected from H, OH, methyl, ethyl, propyl, butyl, phenyl, benzyl, and phenethyl;
$R^{18}$, at each occurrence, is independently selected from H, methyl, ethyl, propyl, butyl, phenyl, benzyl and, phenethyl; and
$R^{19}$, at each occurrence, is independently selected from H, OH, methyl, ethyl, propyl, butyl, phenyl, benzyl and, phenethyl.

[8] In a preferred embodiment the present invention provides a compound of Formula (Ia) wherein:
Q is —$CH_3$, —$CH_2CH_3$, —$CH_2CH_2CH_3$, —$CH_2CH_2CH_2CH_3$, —$CH_2CH_2CH_2CH_2CH_3$, —$CH_2CH_2CH_2CH_2CH_2CH_3$, —$CH(CH_3)_2$, —$CH(CH_3)CH_2CH_3$, —$CH_2CH(CH_3)_2$, —$CH_2C(CH_3)_3$,
  —$CF_3$, —$CH_2CF_3$, —$CH_2CH_2CF_3$, —$CH_2CH_2CH_2CF_3$,
  —CH=$CH_2$, —$CH_2$CH=$CH_2$, —$CH_2$C($CH_3$)=$CH_2$, —$CH_2$CH=C($CH_3$)$_2$, —$CH_2CH_2$CH=$CH_2$, —$CH_2CH_2$C($CH_3$)=$CH_2$, —$CH_2CH_2$CH=C($CH_3$)$_2$,
  cis-$CH_2$CH=CH($CH_3$), cis-$CH_2CH_2$CH=CH($CH_3$), trans —$CH_2$CH=CH($CH_3$), trans-$CH_2CH_2$CH=CH($CH_3$);
  —C≡CH, —$CH_2$C≡CH, —$CH_2$C≡C($CH_3$),
  cyclopropyl-, cyclobutyl-, cyclopentyl-, cyclohexyl-, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—,
  phenyl-, 2-F-phenyl-, 3-F-phenyl-, 4-F-phenyl-, 4-methoxyphenyl-, 4-ethoxyphenyl-, 4-propoxyphenyl-, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—,
  (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—,
  2-furanyl-$CH_2$—, 3-furanyl-$CH_2$—, 2-thienyl-$CH_2$—, 3-thienyl-$CH_2$—, 2-pyridyl-$CH_2$—, 3-pyridyl-$CH_2$—, 4-pyridyl-$CH_2$—, 1-imidazolyl-$CH_2$—, 2-oxazolyl-$CH_2$—, 4-oxazolyl-$CH_2$—, 5-oxazolyl-$CH_2$—, 3-isoxazolyl-$CH_2$—, 4-isoxazolyl-$CH_2$—, 5-isoxazolyl-$CH_2$—,
  phenyl-$CH_2CH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6- diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—;

furanyl-CH₂CH₂—, thienyl-CH₂CH₂—, pyridyl-CH₂CH₂—, 1-imidazolyl-CH₂CH₂—, oxazolyl-CH₂CH₂—, isoxazolyl-CH₂CH₂—, 3,5-dimethylisoxazol-4-yl-CH₂CH₂—, phenyl-propyl-;

benzyl-CH(NH₂)—, benzyl-CH(NHC(=O)—O-tBu)-, benzyloxy-CH₂—, pyrrolidin-2-yl-, or 3-t-butoxycarbonylpyrrolidin-2-yl-;

$R^2$ is H or methyl;

$R^5$ is —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —CH₂C(CH₃)₃,
—CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂,
—CF₃, —CH₂CF₃, —CH₂CH₂CF₃, —CH₂CH₂CH₂CF₃, —CH₂CH₂CH₂CH₂CF₃,
—CH=CH₂, —CH₂CH=CH₂, —CH₂CH₂CH=CH₂, —CH=CHCH₃, cis-CH₂CH=CH(CH₃), trans-CH₂CH=CH(CH₃), trans-CH₂CH=CH(C₆H₅), —CH₂CH=C(CH₃)₂, cis-CH=CHCH₂CH₃, trans-CH₂CH=CHCH₂CH₃, cis-CH₂CH₂CH=CH(CH₃), trans-CH₂CH₂CH=CH(CH₃), trans-CH₂CH=CHCH₂(C₆H₅),
—C≡CH, —CH₂C≡CH, —CH₂C≡C(CH₃), —CH₂C≡C(C₆H₅), —CH₂CH₂C≡CH, —CH₂CH₂C≡C(CH₃), —CH₂CH₂C≡C(C₆H₅), —CH₂CH₂CH₂C≡CH, —CH₂CH₂CH₂C≡C(CH₃), —CH₂CH₂CH₂C≡C(C₆H₅), cyclopropyl-CH₂—, cyclobutyl-CH₂—, cyclopentyl-CH₂—, cyclohexyl-CH₂—, (2-CH₃-cyclopropyl)CH₂—, (3-CH₃-cyclobutyl)CH₂—, cyclopropyl-CH₂CH₂—, cyclobutyl-CH₂CH₂—, cyclopentyl-CH₂CH₂—, cyclohexyl-CH₂CH₂—, (2-CH₃-cyclopropyl)CH₂CH₂—, (3-CH₃-cyclobutyl)CH₂CH₂—, phenyl-CH₂—, (2-F-phenyl)CH₂—, (3-F-phenyl)CH₂—, (4-F-phenyl)CH₂—, (3,5-diF-phenyl)CH₂—, 2-furanyl-CH₂—, 3-furanyl-CH₂—, 2-thienyl-CH₂—, 3-thienyl-CH₂—, 2-pyridyl-CH₂—, 3-pyridyl-CH₂—, 4-pyridyl-CH₂—, 1-imidazolyl-CH₂—, 2-oxazolyl-CH₂—, 4-oxazolyl-CH₂—, 5-oxazolyl-CH₂—, 3-isoxazolyl-CH₂—, 4-isoxazolyl-CH₂—, 5-isoxazolyl-CH₂—, phenyl-CH₂CH₂—, (2-F-phenyl)CH₂CH₂—, (3-F-phenyl)CH₂CH₂—, (4-F-phenyl)CH₂CH₂—, furanyl-CH₂CH₂—, thienyl-CH₂CH₂—, pyridyl-CH₂CH₂—, 1-imidazolyl-CH₂CH₂—, oxazolyl-CH₂CH₂—, isoxazolyl-CH₂CH₂—;

methoxy, ethoxy, propoxy, or butoxy;

$R^{5a}$ is H;

alternatively, $R^5$ and $R^{5a}$ may be combined to form cyclopentyl, cyclohexyl, or cycloheptyl;

W is a bond, —CH₂—, or —CH(CH₃)—;
X is a bond;

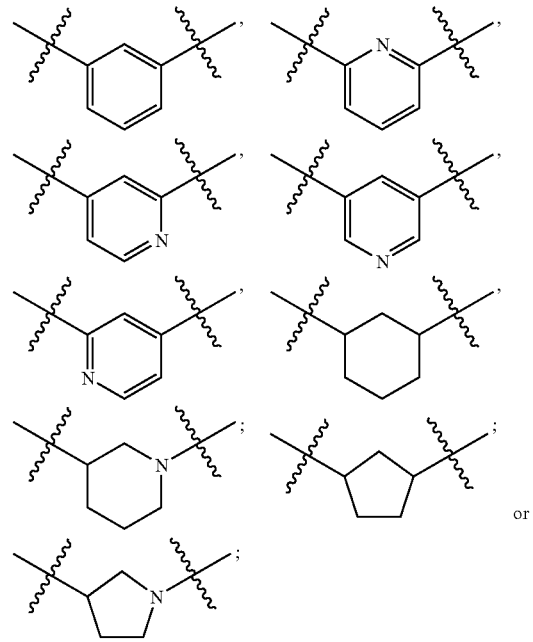

Y is a bond, —CH₂—V—, —V—, or —V—CH₂—;
V is a bond, —C(=O)—, —O—, —S(=O)—, —S(=O)₂—, —NH—, or —N(CH₃)—;
Z is H, F, Cl, Br, methyl, ethyl, n-propyl, i-propyl, n-butyl, i-butyl, s-butyl, t-butyl,
cyclopropyl, cyclobutyl, cyclopentyl, cyclohexyl,
phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl,
furanyl, thienyl, pyridyl, N-oxide-pyridinyl, 2-Me-pyridyl, 3-Me-pyridyl, 4-Me-pyridyl, 1-imidazolyl, oxazolyl, isoxazolyl, 1-benzimidazolyl, morpholino, N-piperidyl,
phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-C₁-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-PhO-phenyl)CH₂—, (3-PhO-phenyl)CH₂—, (4-PhO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl)CH₂—, (pyridyl)CH₂—, (2-Me-pyridyl)CH₂—, (3-Me-pyridyl)CH₂—, (4-Me-pyridyl)CH₂—, (1-imidazolyl)

CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl)CH₂—, (cyclohexyl)CH₂—, (morpholino)CH₂—, (N-piperidinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-piperidinyl)CH₂CH₂—;

$R^{11}$, at each occurrence, is independently selected from H, methyl, ethyl, n-propyl, i-propyl, n-butyl, i-butyl, s-butyl, t-butyl, phenyl, benzyl, phenethyl, cyclopropyl, cyclobutyl, cyclopentyl, cyclohexyl, cycloheptyl, cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, 2-F-phenyl-, 3-F-phenyl, 4-F-phenyl, 4-Cl-phenyl, 4-CH₃-phenyl, 4-MeO-phenyl-, 4-CF₃-phenyl, (4-F-phenyl)CH₂—, (4-Cl-phenyl)CH₂—, (4-CH₃-phenyl)CH₂—, (4-CF₃-phenyl)CH₂—, (4-F-phenyl)CH₂CH₂—, (4-Cl-phenyl)CH₂CH₂—, (4-CH₃-phenyl)CH₂CH₂—, (4-CF₃-phenyl)CH₂CH₂—, pyridin-2-yl-, pyridin-3-yl-, 4-CF₃-pyridin-2-yl-, 4-CH₃-pyridin-2-yl-, thiazol-2-yl-, azapan-1-yl, N,N-dimethylamino, N,N-diethylamino, N,N-dipropylamino, and N,N-dibutylamino; and $R^{13}$, at each occurrence, is independently selected from H, MeO, F, and Cl.

[9] In a preferred embodiment the present invention provides a compound of Formula of Formula (Ic);

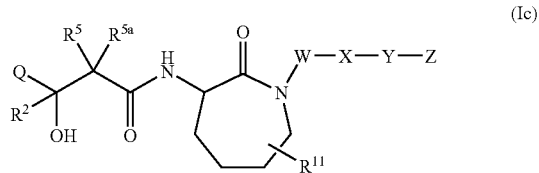

or a pharmaceutically acceptable salt form or prodrug thereof.

[10] In a preferred embodiment the present invention provides a compound of Formula (Id);

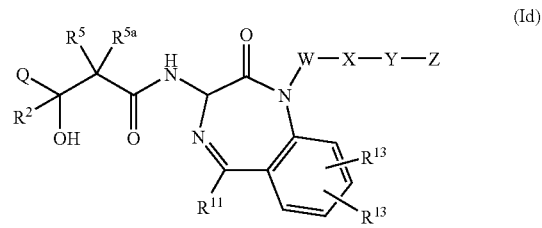

or a pharmaceutically acceptable salt form or prodrug thereof.

[11] In a preferred embodiment the present invention provides a compound of Formula (Ie):

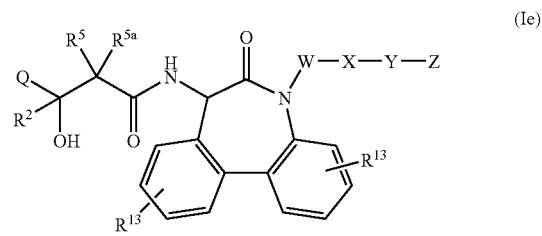

or a pharmaceutically acceptable salt form or prodrug thereof.

[12] In a preferred embodiment the present invention provides a compound selected from:

3-(2(R)-Cyclopentylmethyl-3(S)-hydroxyl-1-oxo-5-phenylpentyl)amino-1-methyl-5-phenyl-2,3-dihydro-1H-1,4-benzodiazepin-2-one;

3-(2(R)-Cyclopentylmethyl-3(S)-hydroxyl-1-oxo-5-phenylpentyl)amino-1-methyl-5-(4-fluoro-phenyl)-2,3-dihydro-1H-1,4-benzodiazepin-2-one;

3-(2(R)-Benzyl-3(S)-hydroxyl-1-oxo-5-phenylpentyl)amino-1-methyl-5-phenyl-2,3-dihydro-1H-1,4-benzodiazepin-2-one;

3-(2(R)-Isopropyl-3(S)-hydroxyl-1-oxo-5-phenylpentyl)amino-1-methyl-5-phenyl-2,3-dihydro-1H-1,4-benzodiazepin-2-one;

3-(2(R)-Cyclopentylmethyl-3(S)-hydroxyl-1-oxo-4-(3,5-difluorophenoxy)butyl)amino-1-methyl-5-phenyl-2,3-dihydro-1H-1,4-benzodiazepin-2-one;

3-(2(R)-Isobutyl-3(S)-hydroxyl-1-oxo-4-(3,5-difluorophenoxy)butyl)amino-1-methyl-5-phenyl-2,3-dihydro-1H-1,4-benzodiazepin-2-one;

3-(2(R)-Cyclopentylmethyl-3(S)-hydroxyl-1-oxo-4-phenoxybutyl)amino-7-chloro-1-methyl-5-phenyl-2,3-dihydro-1H-1,4-benzodiazepin-2-one;

3-(2(R)-Isobutyl-3(S)-hydroxyl-1-oxo-4-phenoxybutyl)amino-7-chloro-1-methyl-5-(4-fluorophenyl)-2,3-dihydro-1H-1,4-benzodiazepin-2-one;

3-(2(R)-Methyl-3(S)-hydroxyl-1-oxo-4-cyclohexyloxybutyl)amino-1-methyl-5-phenyl-2,3-dihydro-1H-1,4-benzodiazepin-2-one;

3-(2(R)-Isobutyl-3(S)-hydroxyl-1-oxo-4-cyclohexyloxybutyl)amino-1-methyl-5-phenyl-2,3-dihydro-1H-1,4-benzodiazepin-2-one;

3-(2(R)-Methyl-3(S)-hydroxyl-1-oxo-4-phenoxybutyl)amino-7-chloro-1-methyl-5-phenyl-2,3-dihydro-1H-1,4-benzodiazepin-2-one;

3-(2(R)-Isobutyl-3(S)-hydroxyl-1-oxo-4-phenoxybutyl)amino-7-chloro-1-methyl-5-phenyl-2,3-dihydro-1H-1,4-benzodiazepin-2-one;
3-(2(R)-Benzyl-3(S)-hydroxyl-1-oxo-4-cyclohexyloxybutyl)amino-7-chloro-1-methyl-5-phenyl-2,3-dihydro-1H-1,4-benzodiazepin-2-one;
3-(2(R)-Cyclopentylmethyl-3(S)-hydroxyl-1-oxo-4-cyclohexyloxybutyl)amino-7-chloro-1-methyl-5-phenyl-2,3-dihydro-1H-1,4-benzodiazepin-2-one;
3-(2(R)-Isobutyl-3(S)-hydroxyl-1-oxo-4-cyclohexyloxybutyl)amino-7-chloro-1-methyl-5-phenyl-2,3-dihydro-1H-1,4-benzodiazepin-2-one;
3-(2(R)-Isopropyl-3(S)-hydroxyl-1-oxo-4-cyclohexyloxybutyl)amino-7-chloro-1-methyl-5-phenyl-2,3-dihydro-1H-1,4-benzodiazepin-2-one;
3-(2(R)-Methoxy-3(S)-hydroxyl-1-oxo-4-(4-trifluoromethylbenzyloxy)butyl)amino-7-chloro-1-methyl-5-phenyl-2,3-dihydro-1H-1,4-benzodiazepin-2-one;
3-(2(R)-Methyl-3(S)-hydroxyl-1-oxo-4-(2,4-difluorobenzyloxy)butyl)amino-7-chloro-1-methyl-5-phenyl-2,3-dihydro-1H-1,4-benzodiazepin-2-one;
3-(2(R)-Vinyl-3(S)-hydroxyl-1-oxo-4-benzyloxybutyl)amino-7-chloro-1-methyl-5-phenyl-2,3-dihydro-1H-1,4-benzodiazepin-2-one;
3-(2(R)-Methyl-3(S)-hydroxyl-1-oxo-4-cyclohexyloxybutyl)amino-7-chloro-1-methyl-5-phenyl-2,3-dihydro-1H-1,4-benzodiazepin-2-one;
3-(2(R)-Isobutyl-3(S)-hydroxyl-1-oxo-5-phenylpentyl)amino-1-methyl-5-phenyl-2,3-dihydro-1H-1,4-benzodiazepin-2-one;
3-(2(R)-Isobutyl-3(S)-hydroxyl-1-oxo-3-cyclopropylpropyl)amino-1-methyl-5-phenyl-2,3-dihydro-1H-1,4-benzodiazepin-2-one;
3-(2(R)-Isobutyl-3(S)-hydroxyl-1-oxo-heptyl)amino-1-methyl-5-phenyl-2,3-dihydro-1H-1,4-benzodiazepin-2-one;
3-(R)-(2(R)-Isobutyl-3(S)-hydroxyl-1-oxo-heptyl)amino-1-methyl-5-phenyl-2,3-dihydro-1H-1,4-benzodiazepin-2-one;
3-(S)-(2(R)-Isobutyl-3(S)-hydroxyl-1-oxo-heptyl)amino-1-methyl-5-phenyl-2,3-dihydro-1H-1,4-benzodiazepin-2-one;
3-(2(R)-Isobutyl-3(S)-hydroxyl-1-oxo-nonyl)amino-1-methyl-5-phenyl-2,3-dihydro-1H-1,4-benzodiazepin-2-one;
3-(2(R)-Isobutyl-3(S)-hydroxyl-1-oxo-hexyl)amino-1-methyl-5-phenyl-2,3-dihydro-1H-1,4-benzodiazepin-2-one;
3-(2(R)-Isobutyl-3(S)-hydroxyl-1-oxo-4-phenylbutyl)amino-1-methyl-5-phenyl-2,3-dihydro-1H-1,4-benzodiazepin-2-one;
3-(2(R)-Methyl-3(S)-hydroxyl-1-oxo-5-phenylpentyl)amino-1-methyl-5-phenyl-2,3-dihydro-1H-1,4-benzodiazepin-2-one;
3-(2(R)-Methyl-3(S)-hydroxyl-1-oxo-6-phenylhexyl)amino-1-methyl-5-phenyl-2,3-dihydro-1H-1,4-benzodiazepin-2-one;
3-(2(R)-Isobutyl-3(S)-hydroxyl-1-oxo-butyl)amino-1-methyl-5-phenyl-2,3-dihydro-1H-1,4-benzodiazepin-2-one;
3-(2(R)-Isobutyl-3(S)-hydroxyl-1-oxo-octyl)amino-1-methyl-5-phenyl-2,3-dihydro-1H-1,4-benzodiazepin-2-one;
3-(2(R)-Methyl-3(S)-hydroxyl-1-oxo-heptyl)amino-1-methyl-5-phenyl-2,3-dihydro-1H-1,4-benzodiazepin-2-one;
3-(2(R)-Methyl-3(S)-hydroxyl-1-oxo-3-phenylpropyl)amino-1-methyl-5-phenyl-2,3-dihydro-1H-1,4-benzodiazepin-2-one;
3-(2(R)-Methyl-3(S)-hydroxyl-1-oxo-5,5-dimethyl-hexyl)amino-1-methyl-5-phenyl-2,3-dihydro-1H-1,4-benzodiazepin-2-one;
3-(2(R)-Methyl-3(S)-hydroxyl-1-oxo-hexyl)amino-1-methyl-5-phenyl-2,3-dihydro-1H-1,4-benzodiazepin-2-one;
3-(2(R)-Methyl-3(S)-hydroxyl-1-oxo-3-(4-propoxyphenyl)propyl)amino-1-methyl-5-phenyl-2,3-dihydro-1H-1,4-benzodiazepin-2-one;
2-(R)-cyclopropylmethyl-3-(S)-hydroxylheptanoic acid (2-oxo-1-(3-phenoxybenzyl)azapan-3-(S)-yl)amide;
2(R)-cyclopropylmethyl-5-(3,5-difluorophenyl)-3-(S)-hydroxypentanoic acid (2-oxo-1-(3-phenoxybenzyl)azapan-3-(S)-yl)amide;
4-cyclopentyl-2-(R)-cyclopropylmethyl-3-(S)-hydroxybutanoic acid(2-oxo-1-(3-phenoxybenzyl)azapan-3-(S)-yl) amide;
2-(R)-cyclopropylmethyl-3-(S)-hydroxyheptanoic acid (1-(5-bromo-3-pyridinyl)methyl-2-oxo-azapan-3-(S)-yl) amide;
3-(2-(R)-cyclopropylmethyl-3-(S)-hydroxyl-1-oxoheptyl)amino-5-(2-fluorophenyl)-1-methyl-2,3-dihydro-1H-1,4-benzodiazepin-2-one;
3-(2-(R)-cyclopropylmethyl-3-(S)-hydroxyl-1-oxoheptyl)amino-5-(azapan-1-yl)-1-methyl-2,3-dihydro-1H-1,4-benzodiazepin-2-one;
3-(2-(R)-cyclopropylmethyl-5-(3,5-difluorophenyl)-3(S)-hydroxyl-1-oxopentyl)amino-1-methyl-5-(pyridin-2-yl)-2,3-dihydro-1H-1,4-benzodiazepin-2-one;
3-(2-(R)-cyclopropylmethyl-3-(S)-hydroxyl-1-oxopentyl)amino-1-methyl-5-(4-chlorophenyl)-2,3-dihydro-1H-1,4-benzodiazepin-2-one;
3-(2-(R)-cyclopropylmethyl-3-(S)-hydroxyl-1-oxoheptyl)amino-5-(4-methoxyphenyl)-1-methyl-2,3-dihydro-1H-1,4-benzodiazepin-2-one;
3-(2-(R)-cyclopropylmethyl-3-(S)-hydroxyl-1-oxoheptyl)amino-5-(4-methoxyphenyl)-1-methyl-2,3-dihydro-1H-1,4-benzodiazepin-2-one;
3-(S)-(4-cyclopentyl-2-(R)-cyclopropylmethyl-3-(S)-hydroxyl-1-oxobutyl)amino-1-methyl-5-phenyl-2,3-dihydro-1H-1,4-benzodiazepin-2-one;
3-(S)-(2-(R)-cyclopropylmethyl-3-(S)-hydroxyl-1-oxohept-6-enyl)amino-1-methyl-5-phenyl-2,3-dihydro-1H-1,4-benzodiazepin-2-one;
3-(2-(R)-cyclopropylmethyl-3-(S)-hydroxyl-1-oxohept-6-enyl)amino-1-methyl-5-(4-trifluoromethyl-phenyl)-2,3-dihydro-1H-1,4-benzodiazepin-2-one;
3-(S)-(2-(R)-cyclopropylmethyl-5-(3,5-dimethylisoxazol-4-yl)-3-(S)-hydroxyl-1-oxopentyl)amino-1-methyl-5-phenyl-2,3-dihydro-1H-1,4-benzodiazepin-2-one;
3-(2-(R)-cyclopropylmethyl-3-(S)-hydroxyl-1-oxoheptyl)amino-7-chloro-1-methyl-5-phenyl-2,3-dihydro-1H-1,4-benzodiazepin-2-one;
3-(2-(R)-cyclopropylmethyl-3-(S)-hydroxyl-1-oxoheptyl)amino-1-methyl-(pyridin-2-yl)-2,3-dihydro-1H-1,4-benzodiazepin-2-one;
3-(2-(R)-cyclopropylmethyl-3-(S)-hydroxyl-1-oxoheptyl)amino-5-(4-fluorophenyl)-1-methyl-2,3-dihydro-1H-1,4-benzodiazepin-2-one;
3-(2-(R)-cyclopropylmethyl-3-(S-hydroxyl-1-oxoheptyl)amino-1-methyl-5-(4-trifluoromethylphenyl)-2,3-dihydro-1H-1,4-benzodiazepin-2-one;
3-(5-cyclopentyl-2-(R)-cyclopropylmethyl-3-(S)-hydroxyl-1-oxopentyl)amino-1-methyl-5-(pyridin-2-yl)-2,3-dihydro-1H-1,4-benzodiazepin-2-one;
3-(2-(R)-iso-butyl-3-(S)-hydroxyl-1-oxoheptyl)amino-1-methyl-5-(4-trifluoromethylphenyl)-2,3-dihydro-1H-1,4-benzodiazepin-2-one;
3-(S)-(2-(R)-cyclopropylmethyl-3-(S)-hydroxyl-1-oxo-5-(thiophen-2-yl)amino-1-methyl-5-phenyl-2,3-dihydro-1H-1,4-benzodiazepin-2-one;

3-(S)-(2-(R)-cyclopropylmethyl-5-(furan-2-yl)3-(S)-hydroxyl-1-oxopentyl)amino-1-methyl-5-phenyl-2,3-dihydro-1H-1,4-benzodiazepin-2-one;
3-(5-cyclopentyl-2-(R)-cyclopropylmethyl-3-(S)-hydroxyl-1-oxopentyl)amino-5-(4-fluorophenyl)-1-methyl-2,3-dihydro-1H-1,4-benzodiazepin-2-one;
3-(S)-(2-(R)-cyclopropylmethyl-5-(3,5-difluorophenyl)-3-(S)-hydroxy-1-oxopentyl)amino-1-methyl-5-phenyl-2,3-dihydro-1H-1,4-benzodiazepin-2-one;
3-(S)-(3-(S)-hydroxyl-2-(R)-(thiophen-2-yl)methyl-1-oxoheptyl)amino-1-methyl-5-phenyl-2,3-dihydro-1H-1,4-benzodiazepin-2-one;
3-(S)-(2-(R)-cyclopropylmethyl-3-(S)-hydroxyl-1-oxoheptyl)amino-7-methyl-5-phenyl-2,3-dihydro-1H-1,4-benzodiazepin-2-one;
3-(2-(R)-cyclopropylmethyl-3-(S)-hydroxyl-1-oxoheptyl)amino-7-methoxy-1-methyl-5-phenyl-2,3-dihydro-1H-1,4-benzodiazepin-2-one;
3-(S)-(2-(R)-cyclobutylmethyl-3-(S)-hydroxyl-1-oxoheptyl)amino-1-methyl-5-phenyl-2,3-dihydro-1H-1,4-benzodiazepin-2-one;
3-(S)-(2-(R)-(3,5-difluorobenzyl)-3-(S)-hydroxyl-1-oxoheptyl)amino-1-methyl-5-phenyl-2,3-dihydro-1H-1,4-benzodiazepin-2-one;
3-(S)-(2-(R)-(furan-2-yl)methyl-3-(S)-hydroxyl-1-oxoheptyl)amino-1-methyl-5-phenyl-2,3-dihydro-1H-1,4-benzodiazepin-2-one;
3-(2-(R)-cyclopropylmethyl-3-(S)-hydroxyl-1-oxo-5-phenylpentyl)amino-1-methyl-5-(pyridin-2-yl)-2,3-dihydro-1H-benzodiazepin-2-one;
3-(2-(R)-iso-butyl-3-(S)-hydroxyl-1-oxoheptyl)amino-5-(4-fluorophenyl)-1-methyl-2,3-dihydro-1H-1,4-benzodiazepin-2-one;
3-(2-(R)-iso-butyl-3-(S)-hydroxyl-1-oxoheptyl)amino-5-(4-fluorophenyl)-1-methyl-2,3-dihydro-1H-1,4-benzodiazepin-2-one;
3-(2-(R)-cyclopropylmethyl-3-(S)-hydroxyl-1-oxo-5-phenylpentyl)amino-1-methyl-5-phenyl-2,3-dihydro-1H-1,4-benzodiazepin-2-one;
3-(2-(R)-cyclopropylmethyl-5-(furan-2-yl)-3-(S)-hydroxyl-1-oxopentyl)amino-1-methyl-5-(4-trifluoromethylphenyl)-2,3-dihydro-1H-1,4-benzodiazepin-2-one;
3-(5-cyclopentyl-2-(R)-cyclopropylmethyl-3-(S)-hydroxyl-1-oxopentyl)amino-1-methyl-5-(4-trifluoromethylphenyl)-2,3-dihydro-1H-1,4-benzodiazepin-2-one;
3-(2-(R)-cyclopropylmethyl-3-(S)-hydroxyl-1-oxooctyl)amino-1-methyl-5-(4-trifluoromethylphenyl)-2,3-dihydro-1H-1,4-benzodiazepin-2-one;
3-(2-(R)-cyclopropylmethyl-3-(S)-hydroxyl-1-oxononyl)amino-1-methyl-5-(4-trifluoromethylphenyl)-2,3-dihydro-1H-1,4-benzodiazepin-2-one;
3-(2-(R)-cyclopropylmethyl-3-(S)-hydroxyl-1-oxoheptyl)amino-1-methyl-5-(4-trifluoromethyl(pyridin-2-yl))-2,3-dihydro-1H-1,4-benzodiazepin-2-one;
3-(2-(R)-cyclobutylmethyl-3-(S)-hydroxyl-1-oxoheptyl)amino-1-methyl-5-(40trifluoromethylphenyl)-2,3-dihydro-1H-1,4-benzodiazepin-2-one;
3-(2-(R)-cyclopentylmethyl-3-(S)-hydroxyl-1-oxoheptyl)amino-1-methyl-5-(4-trifluoromethylphenyl)-2,3-dihydro-1H-1,4-benzodiazepin-2-one;
3-(2-(R)-cyclopropylmethyl-3-(S)-hydroxyl-1-oxoheptyl)amino-1-methyl-5-(4-methyl-2-pyridyl)-2,3-dihydro-1H-1,4-benzodiazepin-2-one;
3-(2-(R)-cyclopropylmethyl-3-(S)-hydroxyl-1-oxoheptyl)amino-1-methyl-5-(4-methyl-2-pyridyl)-2,3-dihydro-1H-1,4-benzodiazepin-2-one;
3-(2-(R)-cyclopropylmethyl-3-(S)-hydroxyl-1-oxobutyl)amino-1-methyl-5-(4-trifluoromethylphenyl)-2,3-dihydro-1H-1,4-benzodiazepin-2-one;
3-(S)-(2-(R)-(3-butenyl)-3-(S)-hydroxyl-1-oxoheptyl)amino-1-methyl-5-phenyl-2,3-dihydro-1H-1,4-benzodiazepin-2-one;
3-(S)-(2-(R)-(3-methylbutyl)3-(S)-hydroxyl-1-oxoheptyl)amino-1-methyl-5-phenyl-2,3-dihydro-1H-1,4-benzodiazepin-2-one;
3-(S)-(2-(R)-ethyl-3-(S)-hydroxyl-1-oxoheptyl)amino-1-methyl-5-phenyl-2,3-dihydro-1H-1,4-benzodiazepin-2-one;
3-(S)-(2-(R)-propyl-3-(S)-hydroxyl-1-oxoheptyl)amino-1-methyl-5-phenyl-2,3-dihydro-1,4-benzodiazepin-2-one;
3-(S)-(2-(R)-butyl-3-(S)-hydroxyl-1-oxoheptyl)amino-1-methyl-5-phenyl-2,3-dihydro-1H-1,4-benzodiazepin-2-one;
3-(4-(S)-amino-3-(R)-hydroxyl-2-(R)-methyl-1-oxo-5-phenylpentyl)amino-7-chloro-5-(2-fluorophenyl)-1-methyl-2,3-dihydro-1H-1,4-benzodiazepin-2-one;
3-(4-(S)-(tert-butoxycarbonylamino-3-(R)-hydroxyl-2-(R)-methyl-1-oxo-5-phenylpentyl)amino-7-chloro-5-(2-fluorophenyl)-1-methyl-2,3-dihydro-1H-1,4-benzodiazepin-2-one;
3-(3-(tert-butoxycarbonylpyrrolidin-2-(R)-yl)-3-(R)-hydroxyl-2-(R)-methyl-1-oxopropyl)amino-7-chloro-5-(2-fluorophenyl)-1-methyl-2,3-dihydro-1H-1,4-benzodiazepin-2-one;
3-(3-(R)-hydroxyl-2-(R)-methyl-1-oxo-3-(pyrrolidin-2-(R)-yl)propyl)-amino-7-chloro-5-(2-fluorophenyl)-1-methyl-2,3-dihydro-1H-1,4-benzodiazepin-2-one;
3-(4-benzyloxy-3-(R)-hydroxyl-2-(R)-iso-propyl-1-oxobutyl-amino-7-chloro-1-methyl-5-phenyl-2,3-dihydro-1H-1,4-benzodiazepin-2-one;
2-(4-(S)-amino-3-(S)-hydroxyl-2-(S)-methyl-1-oxo-5-phenylpentyl)amino-7-chloro-5-(2-fluorophenyl)-1-methyl-2,3-dihydro-1H-1,4-benzodiazepin-2-one;
2-(4-(S)-(tert-butoxycarbonylamino-3-(S)hydroxyl-2-(S)-methyl-1-oxo-5-phenylpentyl)amino-7-chloro-5-(2-fluorophenyl)-1-methyl-2,3-dihydro-1H-1,4-benzodiazepin-2-one;
3-(2-(R)-cyclopropylmethyl-3-(S)-hydroxyl-1-oxoheptyl)amino-1-methyl-5-(thiazol-2-yl)-2,3-dihydro-1H-1,4-benzodiazepin-2-one;
3-(2-(R)-cyclopropylmethyl-3-(S)-hydroxyl-1-oxoheptyl)amino-1-cyclopropylmethyl-5-(thiazol-2-yl)-2,3-dihydro-1H-1,4-benzodiazepin-2-one;
3-(2-(R)-cyclopropylmethyl-3-(S)-hydroxyl-1-oxoheptyl)amino-1-cyclopropylmethyl-5-(4-trifluoromethylphenyl)-2,3-dihydro-1H-1,4-benzodiazepin-2-one;
3-(2-(R)-cyclopropylmethyl-3-(S)-hydroxyl-1-oxoheptyl)amino-1-benzyl-5-(4-trifluoromethylphenyl)-2,3-dihydro-1H-1,4-benzodiazepin-2-one;
3-(2-(R)-cyclopropylmethyl-3-(S)-hydroxyl-1-oxoheptyl)amino-1-(3-phenoxybenzyl)-5-(4-trifluoromethyl-phenyl)-2,3-dihydro-1H-1,4-benzodiazepin-2-one;
3-(2-(R)-cyclopropylmethyl-3-(S)-hydroxyl-1-oxoheptyl)amino-1-(3-pyridinylmethyl)-5-(4-trifluoromethyl-phenyl)-2,3-dihydro-1H-1,4-benzodiazepin-2-one;
3-(2-(S)-cyclopropylmethyl-3-(R)-hydroxyl-1-oxoheptyl)amino-1-methyl-5-(4-trifluoromethyl-phenyl)-2,3-dihydro-1H-1,4-benzodiazepin-2-one;
3-(2-(S)-cyclopropylmethyl-3-(R)-hydroxyl-1-oxoheptyl)amino-1-methyl-5-(4-trifluoromethylphenyl)-2,3-dihydro-1H-1,4-benzodiazepin-2-one;

3-(2-(R)-cyclopropylmethyl-3-(R)-hydroxyl-1-oxoheptyl) amino-1-methyl-5-(4-trifluoromethylphenyl)-2,3-dihydro-1H-1,4-benzodiazepin-2-one;

3-(2-(S)-cyclopropylmethyl-3-(S)-hydroxyl-1-oxoheptyl) amino-1-methyl-5-(4-trifluoromethylphenyl)-2,3-dihydro-1H-1,4-benzodiazepin-2-one;

3-(2-(S)-cyclopropylmethyl-3-(S)-hydroxyl-1-oxoheptyl) amino-1-methyl-5-(4-trifluoromethylphenyl)-2,3-dihydro-1H-1,4-benzodiazepin-2-one;

3-(2-(R)-cyclopropylmethyl-3-(S)-hydroxyl-3-(S)-methyl-1-oxoheptyl)amino-1-methyl-5-(4-trifluoromethyl-phenyl)-2,3-dihydro-1H-1,4-benzodiazepin-2-one;

3-(2-(R)-cyclopropylmethyl-3-(S)-hydroxyl-1-oxoheptyl) amino-1-(3-phenoxybenzyl)-5-methyl-2,3-dihydro-1H-1,4-benzodiazepin-2-one;

3-(2-(R)-cyclopropylmethyl-3-(S)-hydroxyl-1-oxoheptyl) amino-1-benzyl-5-methyl-2,3-dihydro-1H-1,4-benzodiazepin-2-one;

3-(3-(S)-acetoxy-2-(R)-iso-butyl-1-oxoheptyl)amino-5-(4-fluorophenyl)-1-methyl-2,3-dihydro-1H-1,4-benzodiazepin-2-one;

3-(S)-(5-cyclopentyl-2-(R)-cyclopropylmethyl-3-(S)-methoxy-1-oxopentyl)amino-1-methyl-5-phenyl-2,3-dihydro-1H-1,4-benzodiazepin-2-one;

1-(1-hydroxypentyl)cyclohexanecarboxylic acid(5-(4-fluorophenyl)-1-methyl-2-oxo-2,3-dihydro-1H-1,4-benzodiazepin-3-yl)amide;

3-(2-(R)-cyclopropylmethyl-3-(S)-hydroxyl-1-oxoheptyl) amino-5-methyl-5H,7H-dibenzo[b,d]azepin-6-one;

3-(2-(R)-cyclopropylmethyl-3-(S)-hydroxyl-1-oxooctyl) amino-5-methyl-5H,7H-dibenzo[b,d]azepin-6-one;

3-(2-(R)-cyclopropylmethyl-3-(S)-hydroxyl-1-oxononyl) amino-5-methyl-5H,7H-dibenzo[b,d]azepin-6-one;

3-(2-(R)-cyclopropylmethyl-5-(furan-2-yl)-3-(S)-hydroxyl-1-oxopentyl)amino-5-methyl-5H,7H-dibenzo[b,d]azepin-6-one;

2-(R)-cyclopropylmethyl-3-(S)-hydroxyl-heptanoic acid (2-oxo-1-(3-phenylamino-benzyl)azapan-3-(S)-yl)amide;

3-(2-(R)-cyclopropylmethyl-3-(S)-hydroxyl-1-oxoheptyl) amino-5-cyclopentyl-1-methyl-2,3-dihydro-1H-1,4-benzodiazepin-2-one;

3-(2-(R)-cyclopropylmethyl-3-(S)-hydroxyl-1-oxoheptyl) amino-5-benzyl-1-methyl-2,3-dihydro-1H-1,4-benzodiazepin-2-one;

3-(2-(R)-cyclopropylmethyl-3-(S)-hydroxyl-1-oxoheptyl) amino-5-benzyl-1-butyl-2,3-dihydro-1H-1,4-benzodiazepin-2-one;

3-(2-(R)-cyclopropylmethyl-3-(S)-hydroxyl-1-oxoheptyl) amino-5-cycloheptyl-1-methyl-2,3-dihydro-1H-1,4-benzodiazepin-2-one;

3-(2-(R)-cyclopropylmethyl-3-(S)-hydroxyl-1-oxoheptyl) amino-1-benzyl-5-cycloheptyl-2,3-dihydro-1H-1,4-benzodiazepin-2-one;

3-(2-(R)-cyclopropylmethyl-3-(S)-hydroxyl-1-oxoheptyl) amino-1-butyl-5-cycloheptyl-2,3-dihydro-1H-1,4-benzodiazepin-2-one;

3-(2-(R)-cyclopropylmethyl-3-(S)-hydroxyl-1-oxoheptyl) amino-1-(2-pyridinylmethyl)-5-(4-trifluoromethylphenyl)-2,3-dihydro-1H-1,4-benzodiazepin-2-one;

3-(2-(R)-cyclopropylmethyl-3-(S)-hydroxyl-1-oxoheptyl) amino-1-(3-pyridinylmethyl)-5-(2-fluorophenyl)-2,3-dihydro-1H-1,4-benzodiazepin-2-one;

3-(2-(S)-cyclopropylmethyl-3-(S)-hydroxyl-1-oxopentyl) amino-1-(3-pyridinylmethyl)-5-(4-trifluoromethylphenyl)-2,3-dihydro-1H-1,4-benzodiazepin-2-one;

3-(2-1(R)-Cyclopropylmethyl-3-(S)-hydroxyl-1-oxoheptyl) amino-1-methyl-5-(N,N-dibutylamino)-2,3-dihydro-1H-1,4-benzodiazepin-2-one;

3-(2-(R)-Cyclopropylmethyl-3-(S)-hydroxyl-1-oxoheptyl) amino-1-n-butyl-5-t-butyl-2,3-dihydro-1H-1,4-benzodiazepin-2-one;

3-(2-(R)-Cyclopropylmethyl-3-(S)-hydroxyl-1-oxoheptyl) amino-1-(2-oxo-3,3-dimethylbutyl)-5-n-butyl-2,3-dihydro-1H-1,4-benzodiazepin-2-one;

3-(2-(R)-Cyclopropylmethyl-3-(S)-hydroxyl-1-oxoheptyl) amino-1-benzyl-5-t-butyl-2,3-dihydro-1H-1,4-benzodiazepin-2-one;

3-(2-(R)-Cyclopropylmethyl-3-(S)-hydroxyl-1-oxoheptyl) amino-1-(2-picolyl)-5-n-butyl-2,3-dihydro-1H-1,4-benzodiazepin-2-one;

3-(2-(R)-Isobutyl-3-(S)-hydroxyl-1-oxoheptyl)amino-1-methyl-5-homopiperidino-2,3-dihydro-1H-1,4-benzodiazepin-2-one;

3-(2-(R)-cyclopropylmethyl-1,3-dioxoheptyl)amino-1-methyl-5-(4-trifluoromethylphenyl)-2,3-dihydro-1H-1,4-benzodiazepin-2-one; and 1-pentyrylcyclohexanecarboxylic acid (S-(4-fluorophenyl)-1-methyl-2-oxo-2,3-dihydro-1H-1,4-benzodiazepin-3-yl) amide.

[13] In a preferred embodiment the present invention provides a compound of Formula (I) wherein the stereochemistry of carbon 3 in lactam ring B is of the S configuration.

[14] In a preferred embodiment the present invention provides a compound of Formula (I) wherein the stereochemistry of carbon 3 in lactam ring B is of the R configuration.

[15] In a preferred embodiment the present invention provides a compound of Formula (Ib):

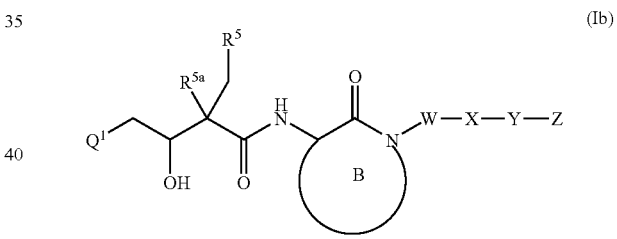

wherein:
Ring B is selected from:

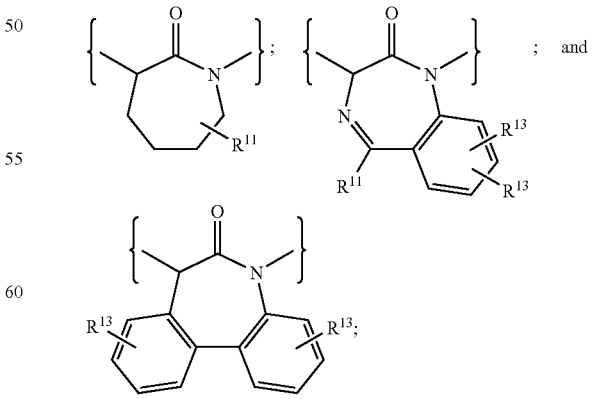

$Q^1$ is $C_1$-$C_6$ alkyl substituted with 0-3 $R^{1a}$;
$C_2$-$C_6$ alkenyl substituted with 0-3 $R^{1a}$;

$C_2$-$C_6$ alkynyl substituted with 0-3 $R^{1a}$;
$C_3$-$C_{10}$ cycloalkyl substituted with 0-3 $R^{1b}$;
$C_3$-$C_{10}$ carbocycle substituted with 0-3 $R^{1b}$;
$C_6$-$C_{10}$ aryl substituted with 0-3 $R^{1b}$; or
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1$-$C_6$ alkyl, $OR^{14}$, Cl, F, Br, I, $NR^{15}R^{16}$, $CF_3$;
$C_3$-$C_{10}$ carbocycle substituted with 0-3 $R^{1b}$;
$C_6$-$C_{10}$ aryl substituted with 0-3 $R^{1b}$; and
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;

$R^5$ is $OR^{14}$;
$C_1$-$C_6$ alkyl substituted with 0-3 $R^{5b}$;
$C_2$-$C_6$ alkenyl substituted with 0-3 $R^{5b}$; or
$C_2$-$C_6$ alkynyl substituted with 0-3 $R^{5b}$;

$R^{5a}$ is H, methyl, ethyl, propyl, butyl, or $C_2$-$C_4$ alkenyl;
alternatively, $R^5$ and $R^{5a}$ may be combined to form a $C_4$-$C_7$ cycloalkyl ring;

$R^{5b}$, at each occurrence, is independently selected from:
H, methyl, ethyl, propyl, butyl, $CF_3$, $OR^{14}$, Cl, F, Br, I, =O, $NR^{15}R^{16}$,
$C_3$-$C_7$ cycloalkyl substituted with 0-3 $R^{5c}$;
$C_3$-$C_7$ carbocycle substituted with 0-3 $R^{5c}$;
phenyl substituted with 0-3 $R^{5c}$; and
5 to 7 membered heterocycle containing 1 to 4 heteroatoms selected from nitrogen, oxygen, and sulphur, wherein said 5 to 7 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

W is —$(CHR^8)_p$—;
p is 0 or 1;
$R^8$ is H, methyl, or ethyl;
X is a bond;
phenyl substituted with 0-2 $R^{Xb}$;
$C_5$-$C_6$ cycloalkyl substituted with 0-3 $R^{Xb}$; or
5 to 6 membered heterocycle containing 1 to 3 heteroatoms selected from nitrogen, oxygen, and sulphur, wherein said 5 to 6 membered heterocycle is substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Y is a bond, —V—, —$CH_2$—V—, —V—$CH_2$—, or —$CH_2$—V—$CH_2$—;
V is a bond, —C(=O)—, —O—, —S—, —S(=O)—, —S(=O)_2—, or —N($R^{19}$)—;
Z is H, F, Cl, Br,
$C_1$-$C_4$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
$C_6$-$C_{10}$ aryl substituted with 0-4 $R^{12b}$;
$C_3$-$C_6$ carbocycle substituted with 0-4 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{11}$, at each occurrence, is independently selected from H, =O, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$-$C_6$ alkyl substituted with 0-1 $R^{11a}$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, =O, $NR^{15}R^{16}$, $CF_3$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

$R^{12}$ at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
$C_6$-$C_{10}$ aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$-$C_4$ alkyl, and $C_2$-$C_4$ alkoxyalkyl;

$R^{15}$, at each occurrence, is independently selected from H, methyl, ethyl, propyl, butyl, phenyl, benzyl, and phenethyl;

$R^{16}$, at each occurrence, is independently selected from H, OH, methyl, ethyl, propyl, butyl, phenyl, benzyl, phenethyl, $CH_3CH_2C(=O)$—, $CH_3C(=O)$—, $CH_3CH_2C(=O)$—, $CH_3OC(=O)$—, $CH_3CH_2S(=O)_2$— and $CH_3S(=O)_2$—;

$R^{17}$ is H, phenyl, benzyl, $C_1$-$C_4$ alkyl, or $C_2$-$C_4$ alkoxyalkyl;

$R^{18}$, at each occurrence, is independently selected from H, methyl, ethyl, propyl, butyl, phenyl, benzyl, and phenethyl; and $R^{19}$, at each occurrence, is independently selected from H, OH, methyl, ethyl, propyl, and butyl.

[16] In a preferred embodiment the present invention provides a compound of Formula (Ib)

$Q^1$ is $C_1$-$C_6$ alkyl substituted with 0-3 $R^{1a}$;
$C_2$-$C_6$ alkenyl substituted with 0-3 $R^{1a}$;
$C_2$-$C_6$ alkynyl substituted with 0-3 $R^{1a}$;
$C_3$-$C_6$ cycloalkyl substituted with 0-3 $R^{1b}$;
phenyl substituted with 0-3 $R^{1b}$; or
5 to 6 membered heterocycle containing 1 to 4 heteroatoms selected from nitrogen, oxygen, and sulphur, wherein said 5 to 6 membered heterocycle is substituted with 0-3 $R^{1b}$;

$R^{1a}$, at each occurrence, is independently selected from H, methyl, ethyl, propyl, butyl, $OR^{14}$, Cl, F, Br, I, $NR^{15}R^{16}$, $CF_3$;
$C_3$-$C_6$ carbocycle substituted with 0-3 $R^{1b}$;
phenyl substituted with 0-3 $R^{1b}$; and
5 to 6 membered heterocycle containing 1 to 4 heteroatoms selected from nitrogen, oxygen, and sulphur, wherein said 5 to 6 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, $C_1$-$C_2$ haloalkoxy, (methyl)OC(=O)—, (ethyl)OC(=O)—, (propyl)OC(=O)—, and (butyl)OC(=O)—;

$R^5$ is $OR^{14}$;
$C_1$-$C_4$ alkyl substituted with 0-1 $R^{5b}$;
$C_2$-$C_4$ alkenyl substituted with 0-1 $R^{5b}$; or
$C_2$-$C_4$ alkynyl substituted with 0-1 $R^{5b}$;

$R^{5a}$ is H, methyl, ethyl, propyl, or butyl;
alternatively, $R^5$ and $R^{5a}$ may be combined to form a cyclobutyl, cyclopentyl, cyclohexyl, or cycloheptyl ring;

$R^{5b}$, at each occurrence, is independently selected from:
H, methyl, ethyl, propyl, butyl, $CF_3$, $OR^{14}$, Cl, F, =O, $NR^{15}R^{16}$,
$C_3$-$C_7$ cycloalkyl substituted with 0-3 $R^{5c}$;
$C_3$-$C_7$ carbocycle substituted with 0-3 $R^{5c}$;
phenyl substituted with 0-3 $R^{5c}$; and
5 to 7 membered heterocycle containing 1 to 4 heteroatoms selected from nitrogen, oxygen, and sulphur, wherein said 5 to 7 membered heterocycle is substituted with 0-3 $R^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

W is a bond, —$CH_2$—, or —$CH(CH_3)$—;
X is a bond;
phenyl substituted with 0-1 $R^{Xb}$;
$C_5$-$C_6$ cycloalkyl substituted with 0-1 $R^{Xb}$; or
5 to 6 membered heterocycle containing 1 to 3 heteroatoms selected from nitrogen, oxygen, and sulphur, wherein said 5 to 6 membered heterocycle is substituted with 0-1 $R^{Xb}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, oxazolyl, and isoxazolyl;

$R^{Xb}$, at each occurrence, is independently selected from H, OH, Cl, F, Br, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

Y is a bond, —V—, —V—$CH_2$—, or —$CH_2$V—;
V is a bond, —C(=O)—, —O—, —S—, —S(=O)—, —$S(=O)_2$—, or —$N(R^{19})$—;

Z is H, F, Cl, Br,
$C_1$-$C_4$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
$C_6$-$C_{10}$ aryl substituted with 0-4 $R^{12b}$;
$C_3$-$C_6$ carbocycle substituted with 0-4 $R^{12b}$; or
5 to 6 membered heterocycle containing to 4 heteroatoms selected from nitrogen, oxygen, and sulphur, wherein said 5 to 6 membered heterocycle is substituted with 0-3 $R^{12b}$;

$R^{11}$, at each occurrence, is independently selected from H, $NR^{18}R^{19}$, $CF_3$;
$C_1$-$C_4$ alkyl substituted with 0-1 $R^{11a}$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, =O, $NR^{15}R^{16}$ $CF_3$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

$R^{12}$ at each occurrence, is independently selected from H, OH, Cl, F, Br, $NR^{15}R^{16}$, —C(=O)$NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
phenyl substituted with 0-4 $R^{12b}$;
$C_3$-$C_6$ carbocycle substituted with 0-4 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{12b}$, at each occurrence, is independently selected from H, OH, Cl, F, Br, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

$R^{13}$, at each occurrence, is independently selected from H, OH, methyl, ethyl, propyl, butyl, methoxy, ethoxy, propoxy, Cl, F, Br, CN, $NR^{15}R^{16}$, and $CF_3$;

$R^{14}$, at each occurrence, is independently selected from H, phenyl, benzyl, methyl, ethyl, propyl, and butyl;

$R^{15}$, at each occurrence, is independently selected from H, methyl, ethyl, propyl, or butyl;

R$^{16}$, at each occurrence, is independently selected from H, OH, methyl, ethyl, propyl, butyl, phenyl, benzyl, and phenethyl;

R$^{18}$, at each occurrence, is independently selected from H, methyl, ethyl, propyl, butyl, phenyl, benzyl and, phenethyl; and R$^{19}$, at each occurrence, is independently selected from H, OH, methyl, ethyl, propyl, butyl, phenyl, benzyl and, phenethyl.

[17] In a preferred embodiment the present invention provides a compound of Formula (Ib) wherein:

Q$^1$ is —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH(CH$_3$)$_2$, —CH(CH$_3$)CH$_2$CH$_3$, —CH$_2$CH(CH$_3$)$_2$, —CH$_2$C(CH$_3$)$_3$,

—CF$_3$, —CH$_2$CF$_3$, —CH$_2$CH$_2$CF$_3$, —CH$_2$CH$_2$CH$_2$CF$_3$, —CH═CH$_2$, —CH$_2$CH═CH$_2$, —CH$_2$C(CH$_3$)═CH$_2$, —CH$_2$CH═C(CH$_3$)$_2$, —CH$_2$CH$_2$CH═CH$_2$, —CH$_2$CH$_2$C(CH$_3$)═CH$_2$, —CH$_2$CH$_2$CH═C(CH$_3$)$_2$, cis-CH$_2$CH═CH(CH$_3$), cis-CH$_2$CH$_2$CH═CH(CH$_3$), trans-CH$_2$CH═CH(CH$_3$), trans-CH$_2$CH$_2$CH═CH(CH$_3$);

—C≡CH, —CH$_2$C≡CH, —CH$_2$C≡C(CH$_3$), cyclopropyl-, cyclobutyl-, cyclopentyl-, cyclohexyl-, cyclopropyl-CH$_2$—, cyclobutyl-CH$_2$—, cyclopentyl-CH$_2$—, cyclohexyl-CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, phenyl-, 2-F-phenyl-, 3-F-phenyl-, 4-F-phenyl-, 4-methoxyphenyl-, 4-ethoxyphenyl-, 4-propoxyphenyl-, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, 2-furanyl-CH$_2$—, 3-furanyl-CH$_2$—, 2-thienyl-CH$_2$—, 3-thienyl-CH$_2$—, 2-pyridyl-CH$_2$—, 3-pyridyl-CH$_2$—, 4-pyridyl-CH$_2$—, 1-imidazolyl-CH$_2$—, 2-oxazolyl-CH$_2$—, 4-oxazolyl-CH$_2$—, 5-oxazolyl-CH$_2$—, 3-isoxazolyl-CH$_2$—, 4-isoxazolyl-CH$_2$—, 5-isoxazolyl-CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—;

furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, isoxazolyl-CH$_2$CH$_2$—, 3,5-dimethylisoxazol-4-yl-CH$_2$CH$_2$—, phenyl-propyl-;

benzyl-CH(NH$_2$)—, benzyl-CH(NHC(═O)—O-tBu)-, benzyloxy-CH$_2$—, pyrrolidin-2-yl-, or 3-t-butoxycarbonylpyrrolidin-2-yl-;

R$^5$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —CH$_2$C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$,

—CF$_3$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$,

—CH═CH$_2$, —CH$_2$CH═CH$_2$, —CH$_2$CH$_2$CH═CH$_2$, —CH═CHCH$_3$, cis-CH$_2$CH═CH(CH$_3$), trans-CH$_2$CH═CH(CH$_3$), trans-CH$_2$CH═CH(C$_6$H$_5$), —CH$_2$CH═C(CH$_3$)$_2$, cis-CH$_2$CH═CHCH$_2$CH$_3$, trans-CH$_2$CH═CHCH$_2$CH$_3$, cis-CH$_2$CH$_2$CH═CH(CH$_3$), trans-CH$_2$CH$_2$CH═CH(CH$_3$), trans-CH$_2$CH═CHCH$_2$(C$_6$H$_5$),

—C≡CH, —CH$_2$C≡CH, —CH$_2$C≡C(CH$_3$), —CH$_2$C≡C(C$_6$H$_5$),

—CH$_2$CH$_2$C≡CH, —CH$_2$CH$_2$C≡C(CH$_3$), —CH$_2$CH$_2$C≡C(C$_6$H$_5$), —CH$_2$CH$_2$CH$_2$C≡CH, —CH$_2$CH$_2$CH$_2$C≡C(CH$_3$), —CH$_2$CH$_2$CH$_2$C≡C(C$_6$H$_5$), cyclopropyl-CH$_2$—, cyclobutyl-CH$_2$—, cyclopentyl-CH$_2$—, cyclohexyl-CH$_2$—, (2-CH$_3$-cyclopropyl)CH$_2$—, (3-CH$_3$-cyclobutyl)CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, (2-CH$_3$-cyclopropyl)CH$_2$CH$_2$—, (3-CH$_3$-cyclobutyl)CH$_2$CH$_2$—, phenyl-CH$_2$—, (2-F-phenyl)CH$_2$—, (3-F-phenyl)CH$_2$—, (4-F-phenyl)CH$_2$—, (3,5-diF-phenyl)CH$_2$—, 2-furanyl-CH$_2$—, 3-furanyl-CH$_2$—, 2-thienyl-CH$_2$—, 3-thienyl-CH$_2$—, 2-pyridyl-CH$_2$—, 3-pyridyl-CH$_2$—, 4-pyridyl-CH$_2$—, 1-imidazolyl-CH$_2$—, 2-oxazolyl-CH$_2$—, 4-oxazolyl-CH$_2$—, 5-oxazolyl-CH$_2$—, 3-isoxazolyl-CH$_2$—, 4-isoxazolyl-CH$_2$—, 5-isoxazolyl-CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, isoxazolyl-CH$_2$CH$_2$—;

methoxy, ethoxy, propoxy, or butoxy;

R$^{5a}$ is H;

alternatively, R$^5$ and R$^{5a}$ may be combined to form cyclopentyl, cyclohexyl, or cycloheptyl;

W is a bond, —CH$_2$—, or —CH(CH$_3$)—;

X is a bond;

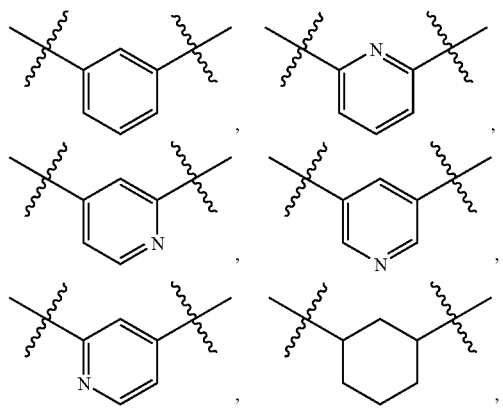

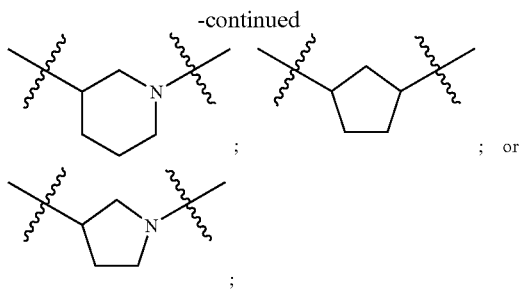

Y is a bond, —CH₂—V—, —V—, or —V—CH₂—;

V is a bond, —C(=O)—, —O—, —S—, —S(=O)—, —S(=O)₂—, —NH—, or —N(CH₃)—;

Z is H, F, Cl, Br, methyl, ethyl, n-propyl, i-propyl, n-butyl, i-butyl, s-butyl, t-butyl, cyclopropyl, cyclobutyl, cyclopentyl, cyclohexyl, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, morpholino, N-piperidyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-PhO-phenyl)CH₂—, (3-PhO-phenyl)CH₂—, (4-PhO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl)CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl)CH₂—, (cyclohexyl)CH₂—, (morpholino)CH₂—, (N-piperidinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-piperidinyl)CH₂CH₂—;

$R^{11}$, at each occurrence, is independently selected from H, methyl, ethyl, n-propyl, i-propyl, n-butyl, i-butyl, s-butyl, t-butyl, phenyl, benzyl, phenethyl, cyclopropyl, cyclobutyl, cyclopentyl, cyclohexyl, cycloheptyl, cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, 2-F-phenyl-, 3-F-phenyl, 4-F-phenyl, 4-Cl-phenyl, 4-CH₃-phenyl, 4-MeO-phenyl-, 4-CF₃-phenyl, (4-F-phenyl)CH₂—, (4-Cl-phenyl)CH₂—, (4-CH₃-phenyl)CH₂—, (4-CF₃-phenyl)CH₂—, (4-F-phenyl)CH₂CH₂—, (4-Cl-phenyl)CH₂CH₂—, (4-CH₃-phenyl)CH₂CH₂—, (4-CF₃-phenyl)CH₂CH₂—, pyridin-2-yl-, pyridin-3-yl-, 4-CF₃-pyridin-2-yl-, 4-CH₃-pyridin-2-yl-, thiazol-2-yl-, azapan-1-yl, N,N-dimethylamino, N,N-diethylamino, N,N-dipropylamino, and N,N-dibutylamino; and $R^{13}$, at each occurrence, is independently selected from H, MeO, F, and Cl.

[18] In a preferred embodiment the present invention provides a compound of Formula (If);

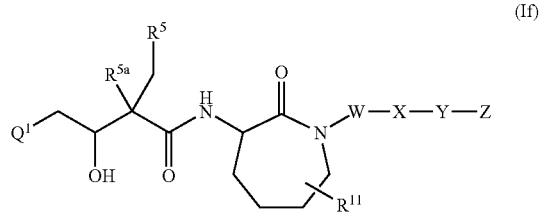

or a pharmaceutically acceptable salt form or prodrug thereof.

[19] In a preferred embodiment the present invention provides a compound of Formula (Ig);

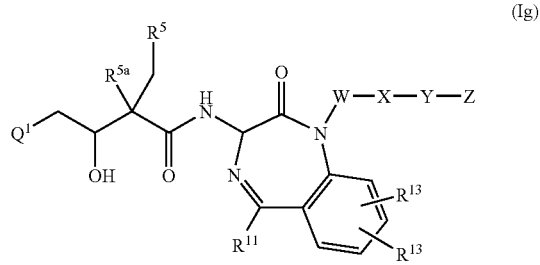

or a pharmaceutically acceptable salt form or prodrug thereof.

[20] In a preferred embodiment the present invention provides a compound of Formula (Ih);

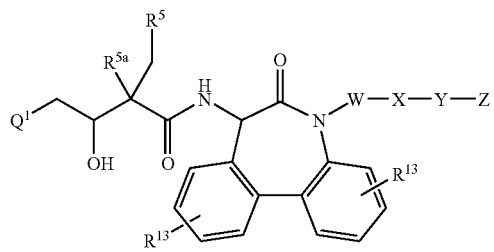

or a pharmaceutically acceptable salt form or prodrug thereof.

[21] In a preferred embodiment the present invention provides a compound of Formula (Ii);

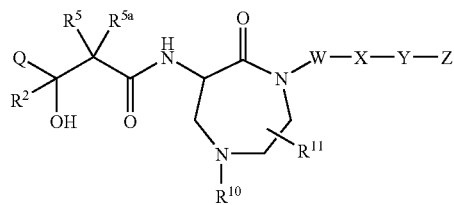

or a pharmaceutically acceptable salt form or prodrug thereof.

[22] In a preferred embodiment the present invention provides a compound of Formula (Ij);

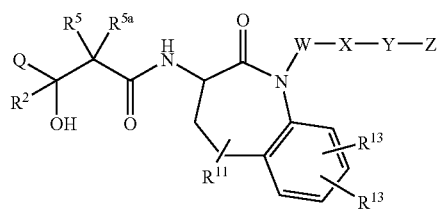

or a pharmaceutically acceptable salt form or prodrug thereof.

[23] In a preferred embodiment the present invention provides a compound of Formula (Ik);

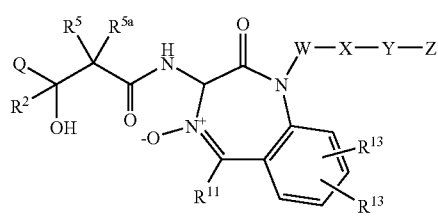

or a pharmaceutically acceptable salt form or prodrug thereof.

[24] In a preferred embodiment the present invention provides a compound selected from:

(2R,3S)—N-[1-butyl-5-(methylethyl)-2-oxo(3H-benzo[f]1,4-diazepin-3-yl)]-2-(cyclopropylmethyl)-3-hydroxyheptanamide;

(2R,3S)-2-(cyclopropylmethyl)-3-hydroxy-N-[5-(methylethyl)-2-oxo-1-benzyl (3H-benzo[f]1,4-diazepin-3-yl)]heptanamide;

(2R,3S)-2-(cyclopropylmethyl)-3-hydroxy-N-{5-methyl-1-[(3-{[(4-methylphenyl)sulfonyl]amino}phenyl)-methyl]-2-oxo(3H-benzo[f]1,4-diazepin-3-yl)}heptanamide;

3-(R,S)-(2-(R)-Cyclopropylmethyl-3-(S)-hydroxyl-1-oxoheptyl)amino-1-methyl-5-t-butyl-2,3-dihydro-1H-1,4-benzodiazepin-2-one;

(2R,3S)-2-(cyclopropylmethyl)-3-hydroxy-N-{1-[(3-{[(4-methylphenyl)sulfonyl]amino}phenyl)methyl]-2-oxo(3H,4H,5H-benzo[f]1,4-diazaperhydroepin-3-yl)}heptanamide;

3-(R,S)-(2-(R)-Cyclopropylmethyl-3-(S)-hydroxyl-1-oxoheptyl)amino-1-methyl-5-piperizinyl-2,3-dihydro-1H-1,4-benzodiazepin-2-one;

7-(R,S)-(2-(R)-Cyclopropylmethyl-3-(S)-hydroxyl-1-oxoheptyl)amino-5-(2-diethylaminoethyl)-6,7-dihydro-5H-dibenzoazepin-6-one;

7-(R,S)-(2-(R)-Cyclopropylmethyl-3-(S)-hydroxyl-1-oxoheptyl)amino-5-(3-hydroxypropyl)-6,7-dihydro-5H-dibenzoazepin-6-one;

3-(R,S)-(2-(R)-Cyclopropylmethyl-3-(S)-hydroxyl-1-oxoheptyl)amino-1-(benzyl-5-(2,2-dimethylpropyl)-2,3-dihydro-1H-1,4-benzodiazepin-2-one;

3-(R,S)-(2-(R)-Cyclopropylmethyl-3-(S)-hydroxyl-1-oxoheptyl)amino-1-n-butyl-5-n-butyl-2,3-dihydro-1H-1,4-benzodiazepin-2-one;

3-(R,S)-(2-(R)-Cyclopropylmethyl-3-(S)-hydroxyl-1-oxoheptyl)amino-1-benzyl-5-n-butyl-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-(3,4-dihydro-1H-isoquinolin-2-yl)-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-(2,2-dimethylpropyl)-2,3-dihydro-1H-1,4-benzodiazepin-2-one;

7-(R,S)-(2-(R)-Cyclopropylmethyl-3-(S)-hydroxyl-1-oxoheptyl)amino-5-n-butyl-6,7-dihydro-5H-dibenzoazepin-6-one;

3-(R,S)-(2-(R)-Cyclopropylmethyl-3-(S)-hydroxyl-1-oxoheptyl)amino-1-(2-ethylbutyl)-5-n-butyl-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-pyrrolidin-1-yl-2,3-dihydro-1H-1,4-benzodiazepin-2-one;

7-(R,S)-(2-(R)-Cyclopropylmethyl-3-(S)-hydroxyl-1-oxoheptyl)amino-5-benzyl-6,7-dihydro-5H-dibenzoazepin-6-one;

3-(R,S)-(2-(R)-Cyclopropylmethyl-3-(S)-hydroxyl-1-oxoheptyl)amino-1-(3-hydroxypropyl)-5-t-butyl-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-ethoxy-2,3-dihydro-1H-1,4-benzodiazepin-2-one;

3-(R,S)-(2-(R)-Cyclopropylmethyl-3-(S)-hydroxyl-1-oxoheptyl)amino-1-butyl-5-(2,2-dimethylpropyl)-2,3-dihydro-1H-1,4-benzodiazepin-2-one;

3-(2-(R)-cyclopropylmethyl-3-(S)-hydroxyl-1-oxoheptyl)amino-1-(2-pyridinylmethyl N-oxide)-5-(4-trifluoromethyl)phenyl-2,3-dihydro-1H-1,4-benzodiazepin-2-one;

3-(2-(R)-cyclopropylmethyl-3-(S)-hydroxyl-1-oxoheptyl)
amino-1-(3-pyridinylmethyl N-oxide)-5-(4-trifluorom-
ethyl)phenyl-2,3-dihydro-1H-1,4-benzodiazepin-2-one;
3-(2-(S)-cyclopropylmethyl-3-(S)-hydroxyl-1-oxopentyl)
amino-1-(3-pyridinylmethyl)-5-phenyl-2,3-dihydro-1H-
1,4-benzodiazepin-2-one;
3-(2-(R)-cyclopropylmethyl-3-(S)-hydroxyl-1-oxoheptyl)
amino-1-(2-(diethylamino)ethyl)-5-(4-trifluorometh-
ylphenyl)-2,3-dihydro-1H-1,4-benzodiazepin-2-one;
3-(2-(R)-cyclopropylmethyl-3-(S)-hydroxyl-1-oxopentyl)
amino-1-(3-pyridinylmethyl N-oxide)-5-phenyl-2,3-dihy-
dro-1H-1,4-benzodiazepin-2-one;
(2R,3S)—N-(8-bromo-1,5-dimethyl-2-oxo-2,3-dihydro-
1H-1,4-benzodiazepin-3-yl)-2-(cyclopropylmethyl)-3-
hydroxyheptanamide;
6-(2-(R)-cyclopropylmethyl-3-(S)-hydroxyl-1-oxoheptyl)
amino-1,4-dibenzyl-hexahydro-5H-1,4-diazepin-5-one;
6-(2-(R)-cyclopropylmethyl-3-(S)-hydroxy-1-oxoheptyl)
amino-4-benzyl-1-[(4-chlorophenyl)sulfonyl]-hexahy-
dro-5H-1,4-diazepin-5-one;
6-(2-(R)-cyclopropylmethyl-3-(S)-hydroxy-1-oxopentyl)
amino-4-benzyl-1-[(4-chlorophenyl)sulfonyl]-hexahy-
dro-5H-1,4-diazepin-5-one;
(2R,3S)-2-(cyclopropylmethyl)-N-(1-{[3-(4-fluorophe-
noxy)phenyl]methyl}-2-oxo(3H,4H,5H-benzo[f]azaper-
hydroepin-3-yl))-3-hydroxyheptanamide;
(2R,3S)-2-(cyclopropylmethyl)-3-hydroxy-N-[2-oxo-1-ben-
zyl(3H,4H,5H-benzo[f]azaperhydroepin-3-yl)]heptana-
mide;
3-(R,S)-(2-(R)-Cyclopropylmethyl-3-(S)-hydroxyl-1-oxo-
heptyl)amino-1-methyl-5-(4-benzylpiperazin-1-yl)-2,3-
dihydro-1H-1,4-benzodiazepin-2-one;
3-(R,S)-(2-(R)-Cyclopropylmethyl-3-(S)-hydroxyl-1-oxo-
heptyl)amino-1-methyl-5-(4-methanesulfonyl-piperazin-
1-yl)-2,3-dihydro-1H-1,4-benzodiazepin-2-one;
3-(R,S)-(2-(R)-Cyclopropylmethyl-3-(S)-hydroxyl-1-oxo-
heptyl)amino-1-methyl-5-(4-methylpiperazin-1-yl)-2,3-
dihydro-1H-1,4-benzodiazepin-2-one;
3-(R,S)-(2-(R)-Cyclopropylmethyl-3-(S)-hydroxyl-1-oxo-
heptyl)amino-1-methyl-5-(4-acetylpiperazin-1-yl)-2,3-
dihydro-1H-1,4-benzodiazepin-2-one;
3-(R,S)-(2-(R)-Cyclopropylmethyl-3-(S)-hydroxyl-1-oxo-
heptyl)amino-1-methyl-5-([4-(3,5-dimethyl-isoxazole-4-
sulfonyl)-piperazin-1-yl]-2,3-dihydro-1H-1,4-benzodiaz-
epin-2-one;
3-(R,S)-(2-(R)-Cyclopropylmethyl-3-(S)-hydroxyl-1-oxo-
heptyl)amino-1-methyl-5-(4-benzoylpiperazin-1-yl)-2,3-
dihydro-1H-1,4-benzodiazepin-2-one;
4-[3-(2-(R)-Cyclopropylmethyl-3-(S)-hydroxy-heptanoy-
lamino)-1-methyl-2-oxo-2,3-dihydro-1H-benzo[e][1,4]
diazepin-5-yl]-piperazine-1-carboxylic acid tert-butyl
ester; and
3-(2-(R)-cyclopropylmethyl-3-(S)-hydroxyl-1-oxoheptyl)
amino-1-(3-pyridinylmethyl N-oxide)-5-(4-trifluorom-
ethyl)phenyl-2,3-dihydro-1H-1,4-benzodiazepin-2-one-
4-N-oxide.

In another preferred embodiment the present invention provides all herein disclosed embodiments with the proviso that when $R^5$ and $R^{5a}$ are not simultaneously H.

In another preferred embodiment the present invention provides all herein disclosed embodiments with the proviso that when Q is a 9 membered benzofused heterocyclic group substituted by 0, 1, or 2 $R^{1a}$, then $R^3$ is H.

In another preferred embodiment the present invention provides all herein disclosed embodiments with the proviso that when —WXYZ is a tertiary butyl group and $R^5$ is either $C_1$-$C_4$ alkyl or $C_2$ alkenyl, then Q is not phenyl substituted by 0, 1 or 2 $R^{1a}$.

In another preferred embodiment the present invention provides all herein disclosed embodiments with the proviso that when $R^5$ is $C_1$-$C_3$ alkyl, then Q is not phenyl substituted by 0, 1 or 2 $R^{1a}$.

In another preferred embodiment the present invention provides all herein disclosed embodiments with the proviso that the moiety:

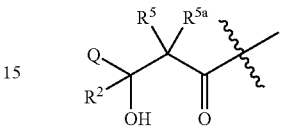

of Formula (I), et seq., is not a $C_1$-$C_8$ alkyl, $C_2$-$C_8$ alkenyl, $C_2$-$C_8$ alkynyl, $C_3$-$C_{10}$ cycloalkyl-$C_1$-$C_4$ alkyl, $C_3$-$C_{10}$ cycloalkyl, $C_1$-$C_4$ alkyl-O—$C_1$-$C_4$ alkyl, $C_1$-$C_4$ alkyl-S—$C_1$-$C_4$ alkyl, $C_2$-$C_4$ alkyl-$NR^{20}$—$C_2$-$C_4$ alkyl, $C_2$-$C_4$ alkyl-$C_6$-$C_{10}$ aryl, $C_2$-$C_4$ alkyl-$C_6$-$C_{10}$ cycloalkyl, $C_2$-$C_8$ alkenyl, $C_6$-$C_{10}$ aryl-$C_1$-$C_4$ alkyl, $C_6$-$C_{10}$ aryl-$C_2$-$C_4$-alkynyl, indol-3-yl-$C_1$-$C_3$ alkyl, and imidazol-4-yl-$C_1$-$C_3$ alkyl; where the alkyl group is substituted with OH.

In another preferred embodiment the present invention provides all herein disclosed embodiments with the proviso that the moiety:

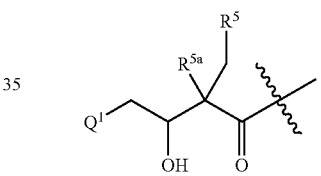

of Formula (I), et seq., is not a $C_1$-$C_8$ alkyl, $C_2$-$C_8$ alkenyl, $C_2$-$C_8$ alkynyl, $C_3$-$C_{10}$ cycloalkyl-$C_1$-$C_4$ alkyl, $C_3$-$C_{10}$ cycloalkyl, $C_1$-$C_4$ alkyl-O—$C_1$-$C_4$ alkyl, $C_1$-$C_4$ alkyl-S—$C_1$-$C_4$ alkyl, $C_2$-$C_4$ alkyl-$NR^{20}$—$C_2$-$C_4$ alkyl, $C_2$-$C_4$ alkyl-$C_6$-$C_{10}$ aryl, $C_2$-$C_4$ alkyl-$C_6$-$C_{10}$ cycloalkyl, $C_2$-$C_8$ alkenyl, $C_6$-$C_{10}$ aryl-$C_1$-$C_4$ alkyl, $C_6$-$C_{10}$ aryl-$C_2$-$C_4$-alkynyl, indol-3-yl-$C_1$-$C_3$ alkyl, and imidazol-4-yl-$C_1$-$C_3$ alkyl; where the alkyl group is substituted with OH.

In a second embodiment, the present invention provides a pharmaceutical composition comprising a compound of Formula (I) and a pharmaceutically acceptable carrier.

In a third embodiment, the present invention provides a method for the treatment of a neurological disorder associated with β-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for inhibiting γ-secretase activity for the treatment of a physiological disorder associated with inhibiting γ-secretase activity comprising administering to a host in need of such inhibition a therapeutically effective amount of a compound of Formula (I) that inhibits γ-secretase activity.

In a preferred embodiment the physiological disorder associated with inhibiting γ-secretase activity is Alzheimer's Disease.

In a fifth embodiment, the present invention provides a compound of Formula (I) for use in therapy.

In a preferred embodiment the present invention provides a compound of Formula (I) for use in therapy of Alzheimer's Disease.

In a sixth embodiment, the present invention provides for the use of a compound of Formula (I) for the manufacture of a medicament for the treatment of Alzheimer's Disease.

Definitions

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is:

```
 1
Asp Ala Glu Phe Arg His Asp Ser Gly Tyr

11
Glu Val His His Gln Lys Leu Val Phe Phe

21
Ala Glu Asp Val Gly Ser Asn Lys Gly Ala

31
Ile Ile Gly Leu Met Val Gly Gly Val Val

41
Ile Ala Thr
```

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted" as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^{1a}$, $R^{4a}$, $R^{13}$ etc.) occurs more than one time in any constituent or formula for a compound, its definition at each occurrence is independent of its definition at every other occurrence. Thus, for example, if a group is shown to be substituted with 0-3 $R^{1a}$, then said group may optionally be substituted with up to three $R^{1a}$ groups and $R^{1a}$ at each occurrence is selected independently from the definition of $R^{1a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group is "$C_1$-$C_4$ alkyl" wherein methyl, ethyl, n-propyl, i-propyl, n-butyl, and i-butyl, are specifically preferred. As used herein, "$C_1$-$C_3$ alkyl", whether a terminal substituent or a alkylene group linking two substituents, is understood to specifically include both branched and straight-chain methyl, ethyl, and propyl.

As used herein, "alkenyl" or "alkenylene" is intended to include hydrocarbon chains of either a straight or branched configuration and one or more unsaturated carbon-carbon bonds which may occur in any stable point along the chain. Examples of "$C_2$-$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$-$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred example of "$C_3$-$C_{10}$ carbocycle" or "$C_3$-$C_6$ carbocycle" is $C_3$-$C_6$ cycloalkyl, specifically cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms, preferably 1, 2, or 3 heteroatoms, independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, homopiperidinyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, purinyl, pyranyl, pyrazinyl, pyrazolidinyl, pyrazolinyl, pyrazolyl, pyridazinyl, pyridooxazole, pyridoimidazole, pyridothiazole, pyridinyl, N-oxide-pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, N-oxide-pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 7 membered heterocycles include, but are not limited to, pyridinyl, N-oxide-pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, tetrazolyl; more preferred 5 to 7 membered heterocycles include, but are not limited to, pyridinyl, N-oxide-pyridinyl, pyrimidinyl, triazinyl, furanyl, thienyl, thiazolyl, piperazinyl, piperidinyl, homopiperidinyl, pyrazolyl, imidazolyl, and tetrazolyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, N-oxide-pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$-$C_{10}$ aryl" or aromatic residue, is intended to mean an aromatic moiety containing the specified number of carbon atoms; for example phenyl, pyridinyl or naphthyl. Unless otherwise specified, "aryl" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The phrase "additional lactam carbons", as used herein, is intended to denote the number of optional carbon atoms in the lactam ring B of Formula (I). Formula (I*):

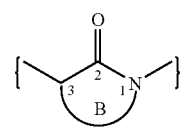

(I*)

represents the lactam ring B of Formula (I). Additional lactam carbons are carbons in lactam ring B other than the carbons numbered 2 and 3 in the backbone of the formula. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. Examples of lactam ring B include:

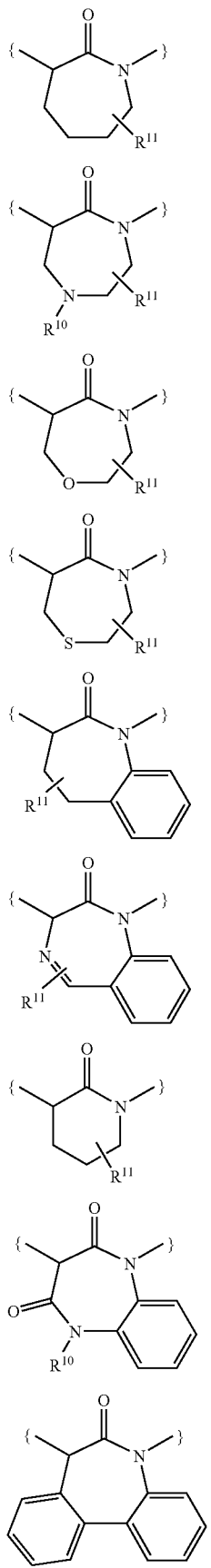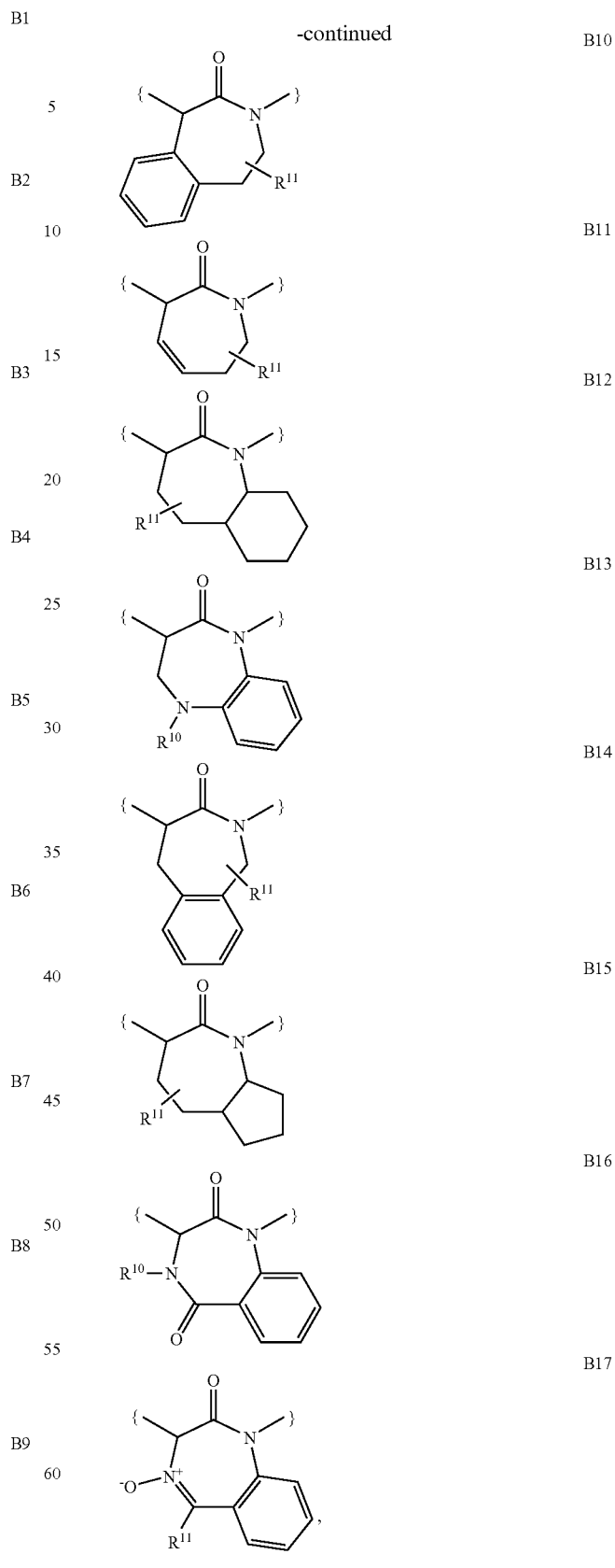
but are not intended to limit the invention. Preferred examples of lactam ring B are B1, B2, B5, B6, B8, B9, B13, and B16;

more preferred examples of lactam ring B are B1, B6, B8, B9, and B13. Preferred examples of substituent $R^{10}$ or $R^{11}$ on lactam B are methyl, ethyl, phenyl, 4-fluorophenyl, 4-chlorophenyl, 4-trifluorophenyl, (4-fluorophenyl)methyl, (4-chlorophenyl)methyl, and (4-trifluorophenyl)methyl. Preferred examples of substituent $R^{13}$ on fused rings of lactam B are methyl, fluoro, and chloro.

The compounds herein described may have asymmetric centers. One enantiomer of a compound of Formula (I) may display superior biological activity over the opposite enantiomer. For example carbon 3 of lactam ring B Formula (I") may exist in either an S or R configuration. Thus, an R or S configuration at carbon 3 in Formula (I") is considered part of the invention. An example of such configuration includes,

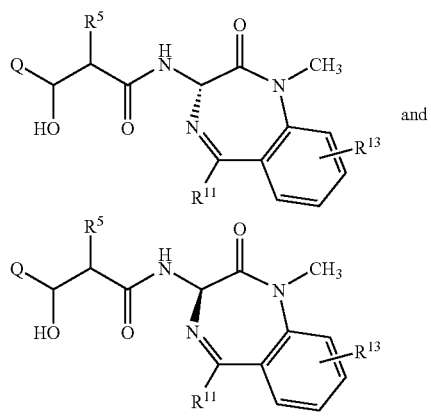

but is not intended to be limited to this example of ring B. When required, separation of the racemic material can be achieved by methods known in the art. Additionally, the carbon atoms to which the OH and $R^5$ are attached may describe chiral carbons which may display superior biological activity over the opposite enantiomer. For example, where Q and $R^5$ are not H, then the configuration of the two centers may be described as (2R,3R), (2R,3S), (2S,3R), or (2S,3S). All configurations are considered part of the invention; however, the (2R,3S) and the (2S,3R) are preferred and the (2R,3S) is more preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lis of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Scheme 1

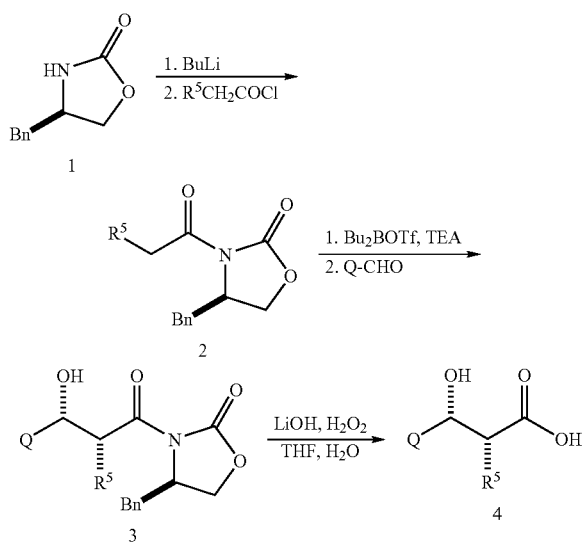

Aldol derivatives can be prepared by the procedure of Evans (D. A. Evans et al, *Org. Synth.* 1990, 68, 83-90), which is outlined in Scheme 1 where acylation of an oxazolidinone with an acid chloride provides structure 2. Asymmetric aldol reaction to form 3 followed by cleavage of the chiral auxiliary yielding β-hydroxycarboxylic acid 4. Additional examples are found in D. A. Evans *Aldrichimica Acta* 1982, 15, 23-32. Alternative syntheses of structures 4 can be accomplished by the methods of Crimmins (M. T. Crimmins et al, *J. Am. Chem. Soc.* 1997, 119, 7883-7884), Paterson (I. Paterson et al, *Org. React.* 1997, 51, 1-200) and Mukaiyama (T. Mukaiyama et al, *Org. React.* 1994, 1-104). Anti-aldols may be synthesized according to: (a) A. K. Ghosh, J. Am. Chem. Soc. 1996, 118, 2527-2528, or (b) S. Masamune et al., J. Am. Chem. Soc. 1997, 119, 2586.

Scheme 2

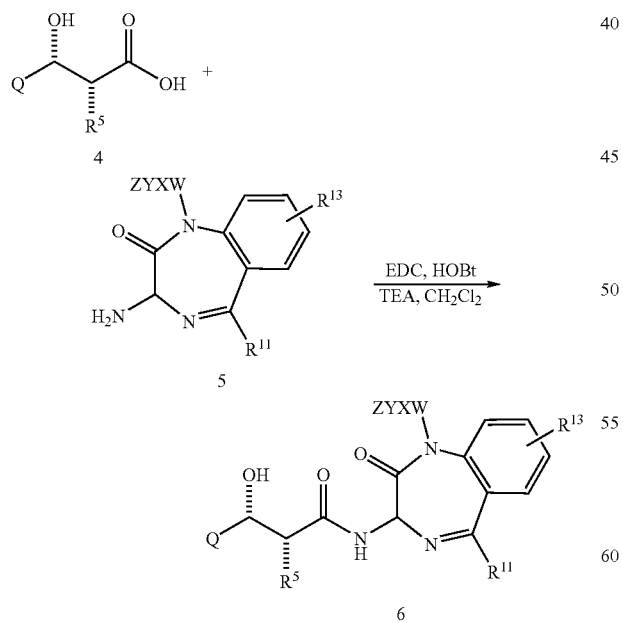

Carboxylic acids of formula 4 can be coupled to an appropriate lactam intermediate using methods commonly used in peptide syntheses, such as DCC, EDC, CDI, BOP, PyBOP, HATU, HBTU and phenyl ester mediated coupling, as described in A. R. Chamberlin, *Chem. Rev.* 1997, 97, 2243-2266. Compound 6 is synthesized, as illustrated in Scheme 2, by coupling acid 4 with 3-amino-1,4-benzodiazepin-2-one 5 under the catalysis of EDC and HOBt providing the final compound 6 (S. Nozaki et al, *Bull. Chem. Soc. Jpn.* 1982, 55, 2165-2168).

Similarly, Schemes 2a and 2b illustrate synthesis of bis-benzodiazepine and lactam compounds of the present invention:

Scheme 2a

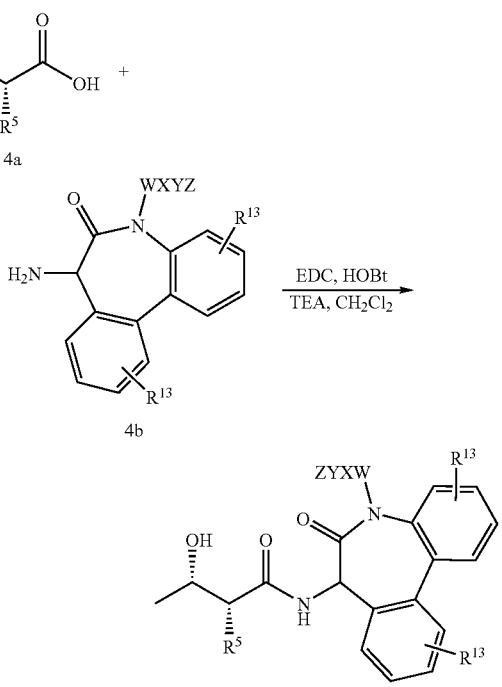

Scheme 2b

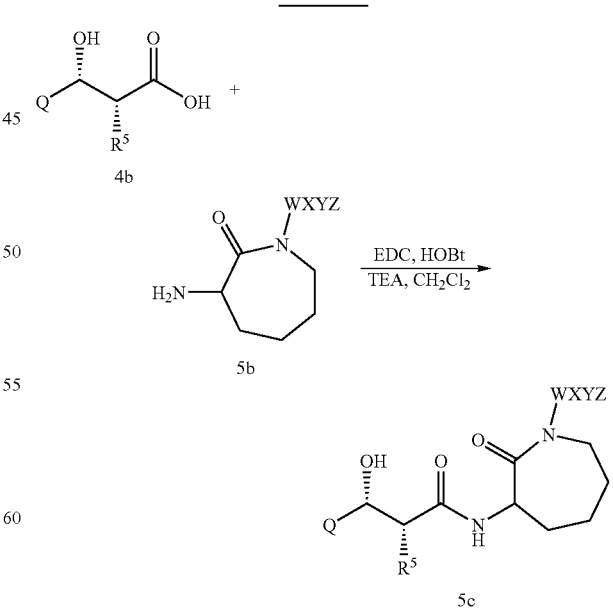

Methods for the synthesis of lactam intermediates as contemplated by the present invention useful in the synthesis of compounds of Formula (I), including amino benzodiazepinones, dibenzo azepinones and other related heterocycles, are known in the art and are disclosed in a number of references including PCT publication number WO 98/28268, WO 99/66934, WO 00/07995, and WO 00/38618, which are hereby incorporated by reference. Additional references include Bock, et al, J. Org. Chem., 1987, 52, 3232-3239; Sherrill et al, J. Org. Chem., 1995, 60, 730-734; and Walsh, D. A., Synthesis, September 1980, p. 677; and Brown, et al., Tetrahedron Letters, 1971, 8, 667-670.

Synthetic approaches to aminobenzodiazepines are widely described in the literature and well known to one skilled in the art. The typical methods are illustrated, but are not limited to, the following references. See (a) M. G. Bock et al., *J. Org. Chem.*, 1987, 52, 3232; (b) R. G. Sherrill et al., *J. Org. Chem.*, 1995, 60, 734; (c) M. G. Bock et al., *J. Med. Chem.*, 1989, 32, 13-16; (d) J. L. Castro et al., *J. Med. Chem.*, 1997, 40, 2491-2501; (e) M. S. Chambers et al., *Bioorg. & Med. Chem. Lett.*, 1993, 3 (10), 1919-1924; (f) J. H. Gogerty et al., *J. Med. Chem.*, 1977, 20 (7), 952; (g) G. Semple et al., *Bioorg. & Med. Chem. Lett.*, 1996, 6(1), 51-54; (h) G. Semple et al., *J. Med. Chem.*, 1997, 40, 331-341; (i) G. Semple et al., *Bioorg. & Med. Chem. Lett.*, 1996, 6 (1), 55-58; (j) G. Semple et al., *Synth. Commun.*, 1996, 26 (4), 721-727; and (k) G. A. Showell et al., *J. Med. Chem.*, 1994, 37, 719-721. For general synthetic descriptions of 2-aminobenzophenone with various substitutions used in the preparation of benzodiazepines, see D. A. Walsh, *Synthesis* 1980, 677.

Scheme 3

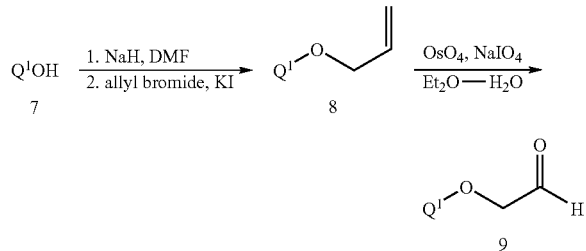

The preparation of aldehyde Q-CHO with general structure of 9 is shown in Scheme 3 (H. C. Arndt, *Synthesis* 1979, 202-204). Allyl ether 8 can be made from the action of an alkoxide generated in DMF with allyl bromide, which is converted to α-alkoxy- or aryloxyaldehyde 9 using a two-phase osmium tetraoxide oxidation.

Scheme 4

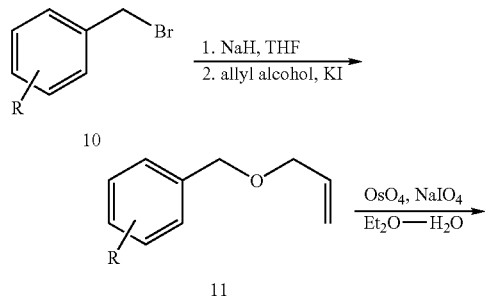

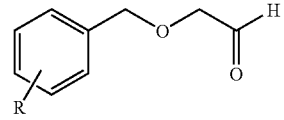

As shown in Scheme 4, aldehyde Q-CHO of general structure 12 can be prepared in the same fashion from the corresponding allyl benzyl ether, which is readily available according to the procedure described by P. Kocienski (P. Kocienski *Tetrahedron* 1990, 46, 1767-1782).

The aldehydes used in Scheme 1 are either commercially available, prepared from commercially available or readily accessible alcohols, or prepared from commercially available or readily accessible carboxylic acids. For preparation of other non-commercially available aldehydes from commercially available or readily accessible alcohols by oxidation of the corresponding alcohols, see (a) S. V. Ley et al *Synthesis* 1994, 639; (b) D. Swern, *Synthesis* 1981, 165-185; and (c) R. C. Larock, *Comprehensive Organic Transformations*, Wiley-VCH: 1989; pp 604-614. For preparation of other non-commercially available aldehydes from commercially available or readily accessible carboxylic acids by reducing the corresponding Weinreb amides or reduction of carboxylic acid derivatives, see (a) S. M. Weinreb et al. *Tetrahedron Lett.* 1981, 22, 3815-3818; (b) M. Braun, *Synthesis* 1989, 856; and (c) D. A. Evans, *J. Org. Chem.* 1993, 58, 2446-2453.

Aminoaldehydes used in the synthesis of the compounds of the invention may be prepared by oxidation of corresponding amino alcohols or reduction of corresponding amino acids; see (a) J. Jurczak et al., *Synlett* 1993, 241; and (b) S. G. Davis et al., *Synlett* 1995, 700.

Sulfur containing aldehydes used in the synthesis of compounds of the invention may be made by conjugate addition of a thiol to α,β-unsaturated aldehydes or reaction of a thiol with a halosubstituted aldehyde. See T. Cohen et al., *J. Org. Chem.* 1995, 60, 2022; *Tetrahedron* 1994, 50, 12793-12810; *J. Org. Chem.* 1992, 57, 6; *Phosphorus, Sulfur, and Silicon* 1993, 74, 1; and *Tetrahedron* 1994, 50, 11569-11584.

Sulfoxides and sulfones are prepared from the corresponding sulfide by oxidation. See M. Hudlicky, *Oxidations in Organic Chemistry*, ACS, 1990; pp 250-264.

The acid chlorides used in Scheme 1 are either commercially available or prepared from commercially available or readily accessible carboxylic acids by the action of oxalyl chloride or thionyl chloride. See R. C. Larock, *Comprehensive Organic Transformations*, Wiley-VCH: 1989; pp 963-964.

EXAMPLES

Chemical abbreviations used in the Examples are defined as follows: "DMPU" for 1,3-dimethyl-3,4,5,6-tetrahydro-2 (1H)-pyrimidone; "TBTU" for O-(1H-benzotriazol-1-yl)-N, N,N',N'-tetramethyluronium tetrafluoroborate; "BOP" for benzotriazol-1-yloxytris-dimethylamino)-phosphonium hexafluorophosphate; "Bu₂BOTf" for dibutylboron triflate; "EDC" for 1-[3-(dimethylamine)propyl]-3-ethylcarbodiimide hydrochloride; "HOBt" for 1-hydroxybenzotriazole; "TPAP" for tetrapropylammonium perruthenate; "NMO" for 4-methylmorpholine N-oxide; and "TEA" for triethylamine.

"HPLC" is an abbreviation used herein for high pressure liquid chromatography. Compounds of the present invention are generally purified by HPLC using conditions known to one skilled in the art. However, unless otherwise indicated, the following conditions are generally applicable. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). Alternatively, reverse-phase HPLC can be carried out using a Vydac C-18 column with gradient elution from 10% to 90% acetonitrile in water.

Example 1

3-(2(R)-Cyclopentylmethyl-3 (S)-hydroxyl-1-oxo-5-phenylpentyl)amino-1-methyl-5-phenyl-2,3-dihydro-1H-1,4-benzodiazepin-2-one (R)-3-(3-cyclopentyl-1-oxopropyl)-4-(phenylmethyl)-2-oxazolidinone (2)

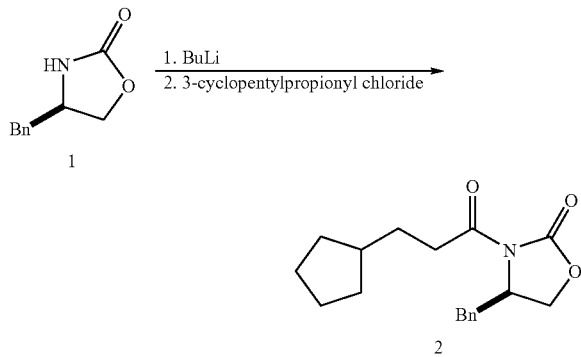

A dry round bottom flask was charged with of (R)-4-(phenylmethyl)-2-oxazolidinone (1, 17.7 g, 0.100 mol). Anhydrous tetrahydrofuran (300 mL) was then added, and the solution was cooled to −78° C. A solution of butyllithium (42.0 mL, 0.105 mol, 2.50 M in hexane) was added to the reaction flask over a 10-min period. After a few minutes, 3-Cyclopentylpropionyl chloride (16.8 mL, 0.110 mol) was added. The resulting solution was stirred for 30 min at −78° C., then allowed to warm to ambient temperature over a 30-min period. Excess 3-cyclopentylpropionyl chloride was quenched by the addition of 60 mL of saturated aqueous ammonium chloride. The bulk of the tetrahydrofuran and hexane was removed on a rotary evaporator, and the slurry was extricated with two 80 mL portion of dichloromethane. The combined organic layers were washed with 75 mL of 1 M sodium hydroxide and 75 mL of brine, dried over anhydrous magnesium sulfate, and filtered. The solvent was removed under reduced pressure. The residue was triturated with hexane to provide 16.5 g of desired product 2 as a white solid. $^1$H NMR (300 MHz, CDCl$_3$) δ 7.18-7.40 (5 H, m), 4.67 (1 H, m), 4.12-4.22 (2 H, m), 3.30 (1 H, dd, J=13.4, 3.1 Hz), 2.84-3.06 (2 H, m), 2.76 (1 H, dd, J=13.4, 9.6 Hz), 1.42-1.96 (9 H, m), 1.15 (2 H, br, m).

3-(2(R)-cyclopentylmethyl-3(S)-hydroxyl-5-phenyl-1-oxopentyl)-4(R)-(phenylmethyl)-2-oxazolidinone (3)

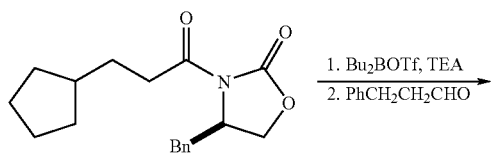

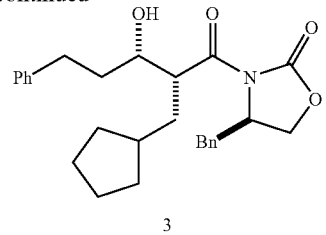

To a solution of acyloxazolidinone 2 (1.57 g, 5.00 mmol) in 20 mL of dichloromethane, cooled to −78° C. under nitrogen atmosphere, dibutylboron triflate (1.40 mL, 5.50 mmol) was added dropwise, followed by the addition of triethylamine. The mixture was warmed slowly to 0° C. and was stirred at 0° C. for an additional hour. The resultant boryl enolate solution was then cooled to −78° C., and 3-phenylpropanal (0.80 mL, 5.5 mmol) was added over a 5-min period time. The solution was stirred for 1 h at −78° C., then for 1 h at 0° C. The reaction mixture was quenched by the addition of 4 mL of a pH 7 aqueous phosphate buffer and 12 mL of methanol. To this cloudy solution was added 8 mL of methanol and 10 mL of 30% aqueous hydrogen peroxide at such a rate as to keep the internal temperature below 10° C. After the solution was stirred for one additional hour, the volatile material was removed in a rotary evaporator. The resulting slurry was extracted with three 20 mL portions of diethyl ether. The combined organic layers was washed with 20 mL of 5% aqueous sodium bicarbonate and 20 mL of brine, dried over anhydrous magnesium sulfate, filtered and concentrated under reduced pressure. Purification by flash column chromatography (25% ethyl acetate-hexane) provided 1.11 g (56%) of aldol 3 as a colorless oil. $^1$H NMR (300 MHz, CDCl$_3$) δ 7.15-7.38 (m, 10 H), 4.72 (m, 1 H), 4.12-4.28 (m, 3 H), 3.85 (m, 1 H), 3.34 (1 H, dd, J=13.4, 3.1 Hz), 2.80-2.95 (1 H, m), 2.60-2.78 (2 H, m), 1.95-2.05 (1 H, m), 1.40-1.90 (10 H, m), 1.10 (2 H, m).

2(R)-cyclopentylmethyl-3 (S)-hydroxyl-5-phenyl-pentanoic acid (4)

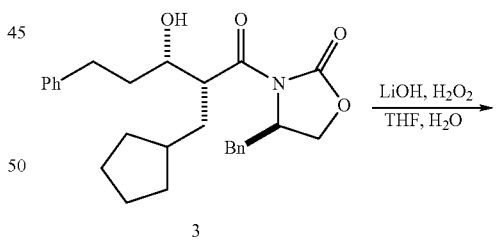

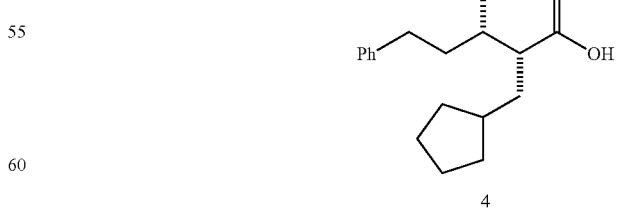

Acyloxazolidinone 3 (226 mg, 0.500 mmol) was dissolved in 3 mL of THF and 1 mL of distilled water. The resulting solution was cooled to 0° C. To this solution was added 30% aqueous hydrogen peroxide (0.40 mL, 4.0 mmol), followed by a solution of lithium hydroxide (19 mg, 0.80 mmol) in 0.5 mL of distilled water. After the solution was stirred for 16 h, sodium sulfite (567 mg, 4.50 mmol) in 3 mL of distilled water was added. The bulk of tetrahydrofuran was removed under reduced pressure, and the resulting mixture (pH 12~13) was extracted with three 20 mL portion of methylene chloride to remove the oxazolidinone auxiliary. The aqueous layer was cooled in an ice bath and acidified to pH 1 with 6 M aqueous hydrochloric acid. The resulting cloudy solution was extracted with five portion of 30 mL ethyl acetate. The combined organic layers are dried over anhydrous magnesium sulfate, filtered and concentrated under reduced pressure to yield 230 mg (81%) of the desired acid 4 as a white solid. $^1$H NMR (300 MHz, CDCl$_3$) δ 7.18-7.35 (5 H, m), 3.87 (1 H, m), 2.81-2.87 (1 H, m), 2.60-2.76 (1 H, m); 2.54-2.60 (1 H, m), 1.00-1.95 (m, 13 H).

3-(2(R)-Cyclopentylmethyl-3 (S)-hydroxyl-1-oxo-5-phenylpentyl)amino-1-methyl-5-phenyl-2,3-dihydro-1H-1,4-benzodiazepin-2-one (6)

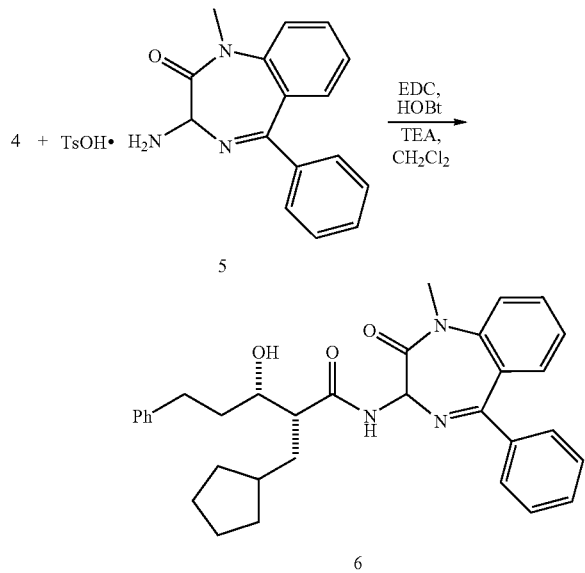

A mixture of acid 4 (250 mg, 0.900 mmol) and 3-amino-1-methyl-5-phenyl-2,3-dihydro-1H-1,4-benzodiazepin-2-one p-toluenesulfonate salt (364 mg, 0.820 mmol) in 4 mL of methylene chloride was stirred at 0° C. 1-Hydroxy-benzotriazole hydrate (133 mg, 0.980 mmol), 1-[3-(dimethylamine) propyl]-3-ethylcarbodiimide hydrochloride (314 mg, 1.64 mmol) and triethylamine (0.51 mL, 3.7 mmol) were added sequentially. After the mixture was stirred for 16 h, 30 mL of ethyl acetate was added. The organic layer was washed with 1 M HCl (15 mL), 5% NaHCO$_3$ (30 mL) and brine (30 mL), dried over anhydrous magnesium sulfate and concentrated under reduced pressure. Purification by chromatotron (30% ethyl acetate-hexane) afforded two diastereomers A and B. A: 120 mg (25%); $^1$H NMR (300 MHz, CDCl$_3$) δ 7.20-7.70 (15H, m), 5.54 (1H, d, J=8.0 Hz), 4.02 (1H, m), 3.48 (3H, s), 2.83-3.00 (1H, m), 2.62-2.74 (1H, m), 2.40-2.48 (1H, m), 1.00-2.00 (13H, m); MS (ESI): 524 (M+H), 546 (M+Na), 522 (M−H), 558 (M+Cl). B: 120 mg (25%); $^1$H NMR (300 MHz, CDCl$_3$) δ 7.60 (1H, d, J=6.9 Hz), 7.20-7.45 (14H, m), 5.56 (1H, d, J=8.4 Hz), 3.84 (1H, m), 3.48 (3H, s), 2.83-3.00 (1H, m), 2.62-2.74 (1H, m), 2.50-2.60 (1H, m), 1.00-1.95 (13H, m); MS (ESI): 524 (M+H), 546 (M+Na), 522 (M−H).

Examples 2-135

The general procedure for Example 1 was followed using the corresponding acid chloride, aldehyde, and substituted benzodiazepine, azepane or bisbenzodiazepine. Starting materials were either commercially available or prepared by methods known to one skilled in the art.

Example 2

3-(2(R)-Cyclopentylmethyl-3(S)-hydroxyl-1-oxo-5-phenylpentyl)amino-1-methyl-5-(4-fluoro-phenyl)-2,3-dihydro-1H-1,4-benzodiazepin-2-one. MS (ESI): 542 (M+H); 564 (M+Na), 540 (M−H). Chromatography Note b and Note c.

Example 3

3-(2(R)-Benzyl-3(S)-hydroxyl-1-oxo-5-phenylpentyl) amino-1-methyl-5-phenyl-2,3-dihydro-1H-1,4-benzodiazepin-2-one. MS (ESI): 532 (M+H), 530 (M−H). Chromatography Note a.

Example 4

3-(2(R)-Isopropyl-3(S)-hydroxyl-1-oxo-5-phenylpentyl) amino-1-methyl-5-phenyl-2,3-dihydro-1H-1,4-benzodiazepin-2-one. MS (ESI): 484 (M+H), 506 (M+Na), 482 (M−H). Chromatography Note u and Note v.

Example 5

3-(2(R)-Cyclopentylmethyl-3(S)-hydroxyl-1-oxo-4-(3,5-difluorophenoxy)butyl)amino-1-methyl-5-phenyl-2,3-dihydro-1H-1,4-benzodiazepin-2-one. MS (ESI): 562 (M+H), 596 (M+Cl). Chromatography Note a.

Example 6

3-(2(R)-Isobutyl-3(S)-hydroxyl-1-oxo-4-(3,5-difluorophenoxy)butyl)amino-1-methyl-5-phenyl-2,3-dihydro-1H-1,4-benzodiazepin-2-one. MS (ESI): 536 (M+H), 558 (M+Na), 534 (M−H), 570 (M+Cl). Chromatography Note u and Note v.

Example 7

3-(2(R)-Cyclopentylmethyl-3(S)-hydroxyl-1-oxo-4-phenoxybutyl)amino-7-chloro-1-methyl-5-phenyl-2,3-dihydro-1H-1,4-benzodiazepin-2-one. MS (ESI): 560 (M+H), 582 (M+Na), 558 (M−H). Chromatography Note u and Note v.

Example 8

3-(2(R)-Isobutyl-3(S)-hydroxyl-1-oxo-4-phenoxybutyl) amino-7-chloro-1-methyl-5-(4-fluorophenyl)-2,3-dihydro-1H-1,4-benzodiazepin-2-one. MS (ESI): 552 (M+H), 574 (M+Na), 550 (M−H). Chromatography Note v.

Example 9

3-(2(R)-Methyl-3(S)-hydroxyl-1-oxo-4-cyclohexyloxybutyl)amino-1-methyl-5-phenyl-2,3-dihydro-1H-1,4-benzodiazepin-2-one. MS (ESI): 464 (M+H), 462 (M+Cl). Chromatography Note a.

Example 10

3-(2(R)-Isobutyl-3(S)-hydroxyl-1-oxo-4-cyclohexyloxybutyl)amino-1-methyl-5-phenyl-2,3-dihydro-1H-1,4-benzodiazepin-2-one. MS (ESI): 506 (M+H), 504 (M−H). Chromatography Note u and Note v.

Example 11

3-(2(R)-Methyl-3(S)-hydroxyl-1-oxo-4-phenoxybutyl)-amino-7-chloro-1-methyl-5-phenyl-2,3-dihydro-1H-1,4-benzodiazepin-2-one. MS (ESI): 492 (M+H), 514 (M+Na), 490 (M−H). Chromatography Note u and Note v.

Example 12

3-(2(R)-Isobutyl-3(S)-hydroxyl-1-oxo-4-phenoxybutyl)amino-7-chloro-1-methyl-5-phenyl-2,3-dihydro-1H-1,4-benzodiazepin-2-one. MS (ESI): 534 (M+H), 532 (M−H). Chromatography Note v.

Example 13

3-(2(R)-Benzyl-3(S)-hydroxyl-1-oxo-4-cyclohexyloxybutyl)amino-7-chloro-1-methyl-5-phenyl-2,3-dihydro-1H-1,4-benzodiazepin-2-one. MS (ESI): 574 (M+H), 572 (M+Cl). Chromatography Note u and Note v.

Example 14

3-(2(R)-Cyclopentylmethyl-3(S)-hydroxyl-1-oxo-4-cyclohexyloxybutyl)amino-7-chloro-1-methyl-5-phenyl-2,3-dihydro-1H-1,4-benzodiazepin-2-one. MS (ESI): 566 (M+H), 588 (M+Na), 564 (M−H). Chromatography Note u and Note v.

Example 15

3-(2(R)-Isobutyl-3(S)-hydroxyl-1-oxo-4-cyclohexyloxybutyl)amino-7-chloro-1-methyl-5-phenyl-2,3-dihydro-1H-1,4-benzodiazepin-2-one. MS (ESI): 540 (M+H), 562 (M+Na), 538 (M−H). Chromatography Note u and Note v.

Example 16

3-(2(R)-Isopropyl-3(S)-hydroxyl-1-oxo-4-cyclohexyloxybutyl)amino-7-chloro-1-methyl-5-phenyl-2,3-dihydro-1H-1,4-benzodiazepin-2-one. MS (ESI): 526 (M+H), 548 (M+Na), 524 (M−H). Chromatography Note v.

Example 17

3-(2(R)-Methoxy-3(S)-hydroxyl-1-oxo-4-(4-trifluoromethylbenzyloxy)butyl)amino-7-chloro-1-methyl-5-phenyl-2,3-dihydro-1H-1,4-benzodiazepin-2-one. MS (ESI): 590 (M+H), 612 (M+Na), 588 (M+Cl). Chromatography Note u and Note v.

Example 18

3-(2(R)-Methyl-3(S)-hydroxyl-1-oxo-4-(2,4-difluorobenzyloxy)butyl)amino-7-chloro-1-methyl-5-phenyl-2,3-dihydro-1H-1,4-benzodiazepin-2-one. MS (ESI): 542 (M+H), 564 (M+Na), 540 (M−H). Chromatography Note u and Note v.

Example 20

3-(2(R)-Vinyl-3(S)-hydroxyl-1-oxo-4-benzyloxybutyl)amino-7-chloro-1-methyl-5-phenyl-2,3-dihydro-1H-1,4-benzodiazepin-2-one. MS (ESI): 536 (M+H), 558 (M+Na), 534 (M−H). Chromatography Note a.

Example 21

3-(2(R)-Methyl-3(S)-hydroxyl-1-oxo-4-cyclohexyloxybutyl)amino-7-chloro-1-methyl-5-phenyl-2,3-dihydro-1H-1,4-benzodiazepin-2-one. MS (ESI): 498 (M+H), 520 (M+Na), 496 (M+Cl). Chromatography Note u and Note v.

Example 23

3-(2(R)-Isobutyl-3(S)-hydroxyl-1-oxo-5-phenylpentyl)amino-1-methyl-5-phenyl-2,3-dihydro-1H-1,4-benzodiazepin-2-one. MS (ESI): 498 (M+H).

Example 24

3-(2(R)-Isobutyl-3(S)-hydroxyl-1-oxo-3-cyclopropylpropyl)amino-1-methyl-5-phenyl-2,3-dihydro-1H-1,4-benzodiazepin-2-one. MS (ESI): 434 (M+H).

Example 25a 3-(2(R)-Isobutyl-3(S)-hydroxyl-1-oxo-heptyl)amino-1-methyl-5-phenyl-2,3-dihydro-1H-1,4-benzodiazepin-2-one. MS (ESI): 450 (M+H).

Example 25b 3-(R)-(2(R)-Isobutyl-3(S)-hydroxyl-1-oxo-heptyl)amino-1-methyl-5-phenyl-2,3-dihydro-1H-1,4-benzodiazepin-2-one. MS (ESI): 450 (M+H).

Example 25c 3-(S)-(2(R)-Isobutyl-3(S)-hydroxyl-1-oxo-heptyl)amino-1-methyl-5-phenyl-2,3-dihydro-1H-1,4-benzodiazepin-2-one. MS (ESI): 450 (M+H).

Example 26

3-(2(R)-Isobutyl-3(S)-hydroxyl-1-oxo-nonyl)amino-1-methyl-5-phenyl-2,3-dihydro-1H-1,4-benzodiazepin-2-one. MS (ESI): 478 (M+H).

Example 27

3-(2(R)-Isobutyl-3(S)-hydroxyl-1-oxo-hexyl)amino-1-methyl-5-phenyl-2,3-dihydro-1H-1,4-benzodiazepin-2-one. MS (ESI): 436 (M+H).

Example 28

3-(2(R)-Isobutyl-3(S)-hydroxyl-1-oxo-4-phenylbutyl)amino-1-methyl-5-phenyl-2,3-dihydro-1H-1,4-benzodiazepin-2-one. MS (ESI): 484 (M+H).

Example 29

3-(2(R)-Methyl-3(S)-hydroxyl-1-oxo-5-phenylpentyl)amino-1-methyl-5-phenyl-2,3-dihydro-1H-1,4-benzodiazepin-2-one. MS (ESI): 442 (M+H).

Example 30

3-(2(R)-Methyl-3(S)-hydroxyl-1-oxo-6-phenylhexyl) amino-1-methyl-5-phenyl-2,3-dihydro-1H-1,4-benzodiazepin-2-one. MS (ESI): 470 (M+H).

Example 31

3-(2(R)-Isobutyl-3 (S)-hydroxyl-1-oxo-butyl)amino-1-methyl-5-phenyl-2,3-dihydro-1H-1,4-benzodiazepin-2-one. MS (ESI): 408 (M+H).

Example 32

3-(2(R)-Isobutyl-3 (S)-hydroxyl-1-oxo-octyl)amino-1-methyl-5-phenyl-2,3-dihydro-1H-1,4-benzodiazepin-2-one. MS (ESI): 464 (M+H).

Example 33

3-(2(R)-Methyl-3(S)-hydroxyl-1-oxo-heptyl)amino-1-methyl-5-phenyl-2,3-dihydro-1H-1,4-benzodiazepin-2-one. MS (ESI): 408 (M+H).

Example 34

3-(2(R)-Methyl-3 (S)-hydroxyl-1-oxo-3-phenylpropyl) amino-1-methyl-5-phenyl-2,3-dihydro-1H-1,4-benzodiazepin-2-one. MS (ESI): 428 (M+H).

Example 35

3-(2(R)-Methyl-3(S)-hydroxyl-1-oxo-5,5-dimethyl-hexyl)amino-1-methyl-5-phenyl-2,3-dihydro-1H-1,4-benzodiazepin-2-one. MS (ESI): 422 (M+H).

Example 36

3-(2(R)-Methyl-3(S)-hydroxyl-1-oxo-hexyl)amino-1-methyl-5-phenyl-2,3-dihydro-1H-1,4-benzodiazepin-2-one. MS (ESI): 394 (M+H).

Example 37

3-(2(R)-Methyl-3(S)-hydroxyl-1-oxo-3-(4-propoxyphenyl)propyl)amino-1-methyl-5-phenyl-2,3-dihydro-1H-1,4-benzodiazepin-2-one. MS (ESI): 486 (M+H).

Example 38

2-(R)-cyclopropylmethyl-3-(S)-hydroxylheptanoic acid (2-oxo-1-(3-phenoxybenzyl)azapan-3-(S)-yl) amide. MS (ESI): 493 (M+H), 491 (M−H), 527 (M+Cl).

Example 39

2(R)-cyclopropylmethyl-5-(3,5-difluorophenyl)-3-(S)-hydroxypentanoic acid (2-oxo-1-(3-phenoxybenzyl)azapan-3-(S)-yl)amide. MS (ESI): 577 (M+H), 575 (M−H), 599 (M+Na).

Example 40

4-cyclopentyl-2-(R)-cyclopropylmethyl-3-(S)-hydroxybutanoic acid (2-oxo-1-(3-phenoxybenzyl)azapan-3-(S)-yl) amide. MS (ESI): 519 (M+H), 541 (M+Na), 517 (M−H).

Example 41

2-(R)-cyclopropylmethyl-3-(S)-hydroxyheptanoic acid (1-(5-bromo-3-pyridinyl)methyl-2-oxo-azapan-3-(S)-yl) amide. MS (ESI): 480 (M($^{79}$Br)+H), 482 (M($^{81}$Br+H), 478 (M($^{79}$Br)+H), 480 (M($^{81}$Br)−H).

Example 42

3-(2-(R)-cyclopropylmethyl-3-(S)-hydroxyl-1-oxoheptyl)amino-5-(2-fluorophenyl)-1-methyl-2,3-dihydro-1H-1,4-benzodiazepin-2-one. MS (ESI): 466 (M+H), 488 (M+Na), 464 (M−H). Chromatography Note b and Note c.

Example 43

3-(2-(R)-cyclopropylmethyl-3-(S)-hydroxyl-1-oxoheptyl)amino-5-(azapan-1-yl)-1-methyl-2,3-dihydro-1H-1,4-benzodiazepin-2-one. MS (ESI): 469 (M+H), 491 (M+Na), 467 (M−H). Chromatography Note b and Note c.

Example 44

3-(2-(R)-cyclopropylmethyl-5-(3,5-difluorophenyl)-3(S)-hydroxyl-1-oxopentyl)amino-1-methyl-5-(pyridin-2-yl)-2,3-dihydro-1H-1,4-benzodiazepin-2-one. MS (ESI): 533 (M+H), 555 (M+Na), 531 (M−H). Chromatography Note b and Note c.

The 3-(3,5-difluorophenyl)propanal used in the aldol reaction was prepared from trans-3,5-difluorocinnamic acid by: (1) hydrogenation to 3-(3,5-difluorophenyl)propionic acid (L. Kruse et al J. Med. Chem. 1987, 30, 486-494); (2) formation of Weinreb amide (M. Braun Synthesis 1989, 856); and (3) reduction to aldehyde (D. A. Evans J. Org. Chem. 1993, 58, 2446-2453).

Example 45

3-(2-(R)-cyclopropylmethyl-3-(S)-hydroxyl-1-oxopentyl)amino-1-methyl-5-(4-chlorophenyl)-2,3-dihydro-1H-1,4-benzodiazepin-2-one. MS (ESI): 482 (M+H), 504 (M+Na), 480 (M−H). Chromatography Note i and Note k.

Example 46

3-(2-(R)-cyclopropylmethyl-3-(S)-hydroxyl-1-oxoheptyl)amino-5-(4-methoxyphenyl)1-methyl-2,3-dihydro-1H-1,4-benzodiazepin-2-one. MS (ESI): 466 (M+H), 488 (M+Na), 464 (M−H). Chromatography Note b and Note c.

Example 47

3-(2-(R)-cyclopropylmethyl-3-(S)-hydroxyl-1-oxoheptyl)amino-5-(4-methoxyphenyl)-1-methyl-2,3-dihydro-1H-1,4-benzodiazepin-2-one. MS (ESI): 479 (M+H), 500 (M+Na), 476 (M−H). Chromatography Note m.

Example 48

3-(S)-(4-cyclopentyl-2-(R)-cyclopropylmethyl-3-(S)-hydroxyl-1-oxobutyl)amino-1-methyl-5-phenyl-2,3-dihydro-1H-1,4-benzodiazepin-2-one. MS (ESI): 474 (M+H), 496 (M+Na), 472 (M−H).

Example 49

3-(S)-(2-(R)-cyclopropylmethyl-3-(S)-hydroxyl-1-oxo-hept-6-enyl)amino-1-methyl-5-phenyl-2,3-dihydro-1H-1,4-benzodiazepin-2-one. MS (ESI): 446 (M+H), 468 (M+Na), 444 (M−H).

Example 50

3-(2-(R)-cyclopropylmethyl-3-(S)-hydroxyl-1-oxohept-6-enyl)amino-1-methyl-5-(4-trifluoromethyl-phenyl)-2,3-dihydro-1H-1,4-benzodiazepin-2-one. MS (ESI): 514 (M+H). Chromatography Note i.

Example 51

3-(S)-(2-(R)-cyclopropylmethyl-5-(3,5-dimethylisoxazol-4-yl)-3-(S)-hydroxyl-1-oxopentyl)amino-1-methyl-5-phenyl-2,3-dihydro-1H-1,4-benzodiazepin-2-one. MS (ESI): 515 (M+H), 537 (M+Na), 513 (M−H).

The 3-(3,5-dimethyl-4-isoxazole)propanal used in the aldol reaction was prepared from: (1) methyl 3-(3,5-dimethyl-4-isoxazole)propionate (M. C. Marcotullio J. Org. Chem 1994, 59, 2884); (2) DIBAL-H reduction to alcohol (N. M. Yoon et al J. Org. Chem. 1985, 50, 2443-2450); and (3) TPAP/NMO oxidation to aldehyde (S. V. Ley et al Synthesis 1994, 639).

Example 52

3-(2-(R)-cyclopropylmethyl-3-(S)-hydroxyl-1-oxoheptyl)amino-7-chloro-1-methyl-5-phenyl-2,3-dihydro-1H-1,4-benzodiazepin-2-one. MS (ESI): 482 (M+H), 504 (M+Na), 480 (M−H). Chromatography Note n and Note o.

Example 53

3-(2-(R)-cyclopropylmethyl-3-(S)-hydroxyl-1-oxoheptyl)amino-1-methyl-(pyridin-2-yl)-2,3-dihydro-1H-1,4 benzodiazepin-2-one. MS (ESI): 449 (M+H), 471 (M+Na), 447 (M−H). Chromatography Note b and Note c.

Example 54

3-(2-(R)-cyclopropylmethyl-3-(S)-hydroxyl-1-oxoheptyl)amino-5-(4-fluorophenyl)-1-methyl-2,3-dihydro-1H,1,4-benzodiazepin-2-one. MS (ESI): 466 (M+H), 500 (M+Cl). Chromatography Note h.

Example 55

3-(2-(R)-cyclopropylmethyl-3-(S)-hydroxyl-1-oxoheptyl)amino-1-methyl-5-(4-trifluoromethylphenyl)-2,3-dihydro-1H-1,4-benzodiazepin-2-one. MS (ESI): 516 (M+H), 514 (M−H), 550 (M+Cl). Chromatography Note i.

The 3-cyclopropyl propionic acid, which was converted to 3-cyclopropyl propionyl chloride used in the aldol reaction, was prepared according to: A. Donetti J. Med. Chem. 1972, 15, (6), 590-592.

Example 56

3-(5-cyclopentyl-2-(R)-cyclopropylmethyl-3-(S)-hydroxyl-1-oxopentyl)amino-1-methyl-5-(pyridin-2-yl)-2,3-dihydro-1H-1,4-benzodiazepin-2-one. MS (ESI): 489 (M+H), 511 (M+Na), 487 (M−H). Chromatography Note b and Note c.

Example 57

3-(2-(R)-iso-butyl-3-(S)-hydroxyl-1-oxoheptyl)amino-1-methyl-5-(4-trifluoromethylphenyl)-2,3dihydro-1H-1,4-benzodiazepin-2-one. MS (ESI): 518 (M+H), 540 (M+Na), 516 (M−H). Chromatography Note b and Note c.

Example 58

3-(S)-(2-(R)-cyclopropylmethyl-3-(S)-hydroxyl-1-oxo-5-(thiophen-2-yl)amino-1-methyl-5-phenyl-2,3-dihydro-1H-1,4-benzodiazepin-2-one. MS (ESI): 502 (M+H), 524 (M+Na), 500 (M−H).

Example 59

3-(S)-(2-(R)-cyclopropylmethyl-5-(furan-2-yl)3-(S)-hydroxyl-1-oxopentyl)amino-1-methyl-5-phenyl-2,3-dihydro-1H-1,4-benzodiazepin-2-one. MS (ESI): 486 (M+H), 508 (M+Na), 484 (M−H).

Example 60

3-(5-cyclopentyl-2-(R)-cyclopropylmethyl-3-(S)-hydroxyl-1-oxopentyl)amino-5-(4-fluorophenyl)-1-methyl-2,3-dihydro-1H-1,4-benzodiazepin-2-one. MS (ESI): 506 (M+H), 528 (M+Na), 504 (M−H). Chromatography Note h.

Example 61

3-(S)-(2-(R)-cyclopropylmethyl-5-(3,5-difluorophenyl)-3-(S)-hydroxy-1-oxopentyl)amino-1-methyl-5-phenyl-2,3-dihydro-1H-1,4-benzodiazepin-2-one. MS (ESI): 532 (M+H), 554 (M+Na), 530 (M−H).

Example 62

3-(S)-(3-(S)-hydroxyl-2-(R)-(thiophen-2-yl)methyl-1-oxoheptyl)amino-1-methyl-5-phenyl-2,3-dihydro-1H-1,4-benzodiazepin-2-one. MS (ESI): 448 (M+H), 470 (M+Na), 446 (M−H).

Example 63

3-(S)-(2-(R)-cyclopropylmethyl-3-(S)-hydroxyl-1-oxoheptyl)amino-7-methyl-5-phenyl-2,3-dihydro-1H-1,4-benzodiazepin-2-one. MS (ESI): 490 (M+H), 512 (M+Na), 488 (M−H).

Example 64

3-(2-(R)-cyclopropylmethyl-3-(S)-hydroxyl-1-oxoheptyl)amino-7-methoxy-1-methyl-5-phenyl-2,3-dihydro-1H-1,4-benzodiazepin-2-one. MS (ESI): 478 (M+H), 500 (M+Na), 476 (M−H). Chromatography Note l.

Example 65

3-(S)-(2-(R)-cyclobutylmethyl-3-(S)-hydroxyl-1-oxoheptyl)amino-1-methyl-5-phenyl-2,3-dihydro-1H-1,4-benzodiazepin-2-one. MS (ESI): 462 (M+H), 484 (M+Na).

The 3-cyclobutyl propionic acid, which was converted to 3-cyclobutyl propionyl chloride used in the aldol reaction, was prepared according to: A. Donetti J. Med. Chem. 1972, 15, (6), 590-592.

Example 66

3-(S)-(2-(R)-(3,5-difluorobenzyl)-3-(S)-hydroxyl-1-oxoheptyl)amino-1-methyl-5-phenyl-2,3-dihydro-1H-1,4-benzodiazepin-2-one. MS (ESI): 520 (M+H), 518 (M−H).

Example 67

3-(S)-(2-(R)-(furan-2-yl)methyl-3-(S)-hydroxyl-1-oxoheptyl)amino-1-methyl-5-phenyl-2,3-dihydro-1H-1,4-benzodiazepin-2-one. MS (ESI): 474 (M+H), 472 (M−H).

Example 68

3-(2-(R)-cyclopropylmethyl-3-(S)-hydroxyl-1-oxo-5-phenylpentyl)amino-1-methyl-5-(pyridin-2-yl)-2,3-dihydro-1H-benzodiazepin-2-one. MS (ESI): 514 (M+H), 536 (M+Na), 512 (M−H). Chromatography Note h.

Example 69

3-(2-(R)-iso-butyl-3-(S)-hydroxyl-1-oxoheptyl)amino-5-(4-fluorophenyl)-1-methyl-2,3-dihydro-1H-1,4-benzodiazepin-2-one. MS (ESI): 497 (M+H), 519 (M+Na), 495 (M−H). Chromatography Note b and Note c.

Example 70

3-(2-(R)-iso-butyl-3-(S)-hydroxyl-1-oxoheptyl)amino-5-(4-fluorophenyl)-1-methyl-2,3-dihydro-1H-1,4-benzodiazepin-2-one. MS (ESI): 468 (M+H), 502 (M+Cl). Chromatography Note h.

Example 71

3-(2-(R)-cyclopropylmethyl-3-(S)-hydroxyl-1-oxo-5-phenylpentyl)amino-1-methyl-5-phenyl-2,3-dihydro-1H-1,4-benzodiazepin-2-one. MS (ESI): 421 (M+H), 443 (M+Na), 419 (M−H). Chromatography Note b and Note c.

Example 72

3-(2-(R)-cyclopropylmethyl-5-(furan-2-yl)-3-(S)-hydroxyl-1-oxopentyl)amino-1-methyl-5-(4-trifluoromethylphenyl)-2,3-dihydro-1H-1,4-benzodiazepin-2-one. MS (ESI): 554 (M+H), 576 (M+Na), 552 (M−H). Chromatography Note i.

Example 73

3-(5-cyclopentyl-2-(R)-cyclopropylmethyl-3-(S)-hydroxyl-1-oxopentyl)amino-1-methyl-5-(4-trifluoromethylphenyl)-2,3-dihydro-1H-1,4-benzodiazepin-2-one. MS (ESI): 542 (M+H), 564 (M+Na), 540 (M−H). Chromatography Note i.

Example 74

3-(2-(R)-cyclopropylmethyl-3-(S)-hydroxyl-1-oxooctyl)amino-1-methyl-5-(4-trifluoromethylphenyl)-2,3-dihydro-1H-1,4-benzodiazepin-2-one. MS (ESI): 530 (M+H), 552 (M+Na), 528 (M−H). Chromatography Note i.

Example 75

3-(2-(R)-cyclopropylmethyl-3-(S)-hydroxyl-1-oxononyl)amino-1-methyl-5-(4-trifluoromethylphenyl)-2,3-dihydro-1H-1,4-benzodiazepin-2-one. MS (ESI): 544 (M+H), 566 (M+Na), 542 (M−H). Chromatography Note i.

Example 76

3-(2-(R)-cyclopropylmethyl-3-(S)-hydroxyl-1-oxoheptyl)amino-1-methyl-5-(4-trifluoromethyl(pyridin-2-yl))-2,3-dihydro-1H-1,4-benzodiazepin-2-one. MS (ESI): 517 (M+H), 539 (M+Na), 515 (M−H). Chromatography Note i.

Example 77

3-(2-(R)-cyclobutylmethyl-3-(S)-hydroxyl-1-oxoheptyl)amino-1-methyl-5-(4-trifluoromethylphenyl)-2,3-dihydro-1H-1,4-benzodiazepin-2-one. MS (ESI): 530 (M+H), 552 (M+Na), 528 (M−H). Chromatography Note i.

Example 78

3-(2-(R)-cyclopentylmethyl-3-(S)-hydroxyl-1-oxoheptyl)amino-1-methyl-5-(4-trifluoromethylphenyl)-2,3-dihydro-1H-1,4-benzodiazepin-2-one. MS (ESI): 544 (M+H), 542 (M−H), 578 (M+Cl). Chromatography Note i.

Example 79

3-(2-(R)-cyclopropylmethyl-3-(S)-hydroxyl-1-oxoheptyl)amino-1-methyl-5-(4-methyl-2-pyridyl)-2,3-dihydro-1H-1,4-benzodiazepin-2-one. MS (ESI): 463 (M+H). Chromatography Note cc.

Example 80

3-(2-(R)-cyclopropylmethyl-3-(S)-hydroxyl-1-oxoheptyl)amino-1-methyl-5-(4-methyl-2-pyridyl)-2,3-dihydro-1H-1,4-benzodiazepin-2-one. MS (ESI): 463 (M+H). Chromatography Note dd.

Example 81

3-(2-(R)-cyclopropylmethyl-3-(S)-hydroxyl-1-oxobutyl)amino-1-methyl-5-(4-trifluoromethylphenyl)-2,3-dihydro-1H-1,4-benzodiazepin-2-one. MS (ESI): 474 (M+H). Chromatography Note i.

Example 82

3-(S)-(2-(R)-(3-butenyl)-3-(S)-hydroxyl-1-oxoheptyl)amino-1-methyl-5-phenyl-2,3-dihydro-1H-1,4-benzodiazepin-2-one. MS (ESI): 448 (M+H).

Example 83

3-(S)-(2-(R)-(3-methylbutyl)3-(S)-hydroxyl-1-oxoheptyl)amino-1-methyl-5-phenyl-2,3-dihydro-1H-1,4-benzodiazepin-2-one. MS (ESI): 464 (M+H).

Example 84

3-(S)-(2-(R)-ethyl-3-(S)-hydroxyl-1-oxoheptyl)amino-1-methyl-5-phenyl-2,3-dihydro-1H-1,4-benzodiazepin-2-one. MS (ESI): 422 (M+H).

Example 85

3-(S)-(2-(R)-propyl-3-(S)-hydroxyl-1-oxoheptyl)amino-1-methyl-5-phenyl-2,3-dihydro-1,4-benzodiazepin-2-one. MS (ESI): 436 (M+H).

Example 86

3-(S)-(2-(R)-butyl-3-(S)-hydroxyl-1-oxoheptyl)amino-1-methyl-5-phenyl-2,3-dihydro-1H-1,4-benzodiazepin-2-one. MS (ESI): 450 (M+H).

Example 87

3-(4-(S)-amino-3-(R)-hydroxyl-2-(R)-methyl-1-oxo-5-phenylpentyl)amino-7-chloro-5-(2-fluorophenyl)-1-methyl-2,3-dihydro-1H-1,4-benzodiazepin-2-one. MS (ESI): 523 (M+H), 521 (M−H). Chromatography Note x.

Example 88

3-(4-(S)-(tert-butoxycarbonylamino-3-(R)-hydroxyl-2-(R)-methyl-1-oxo-5-phenylpentyl)amino-7-chloro-5-(2-fluorophenyl)-1-methyl-2,3-dihydro-1H-1,4-benzodiazepin-2-one. MS (ESI): 645 (M+H), 621 (M−H). Chromatography Note a and Note u.

Example 89

3-(3-(tert-butoxycarbonylpyrrolidin-2-(R)-yl)-3-(R)-hydroxyl-2-(R)-methyl-1-oxopropyl)amino-7-chloro-5-(2-fluorophenyl)-1-methyl-2,3-dihydro-1H-1,4-benzodiazepin-2-one. MS (ESI): 523 (M+H), 521 (M−H). Chromatography Note u and Note v.

Example 90

3-(3-(R)-hydroxyl-2-(R)-methyl-1-oxo-3-(pyrrolidin-2-(R)-yl)propyl)-amino-7-chloro-5-(2-fluorophenyl)-1-methyl-2,3-dihydro-1H-1,4-benzodiazepin-2-one. MS (ESI): 473 (M+H), 471 (M−H). Chromatography Note y and Note z.

Example 91

3-(4-benzyloxy-3-(R)-hydroxyl-2-(R)-iso-propyl-1-oxobutyl-amino-7-chloro-1-methyl-5-phenyl-2,3-dihydro-1H-1,4-benzodiazepin-2-one. MS (ESI): 534 (M+H), 556 (M+Na), 532 (M−H). Chromatography Note u and Note v.

Example 92

2-(4-(S)-amino-3-(S)-hydroxyl-2-(S)-methyl-1-oxo-5-phenylpentyl)amino-7-chloro-5-(2-fluorophenyl)-1-methyl-2,3-dihydro-1H-1,4-benzodiazepin-2-one. MS (ESI): 523 (M+H), 521 (M−H). Chromatography Note w.

Example 93

2-(4-(S)-(tert-butoxycarbonylamino-3-(S)hydroxyl-2-(S)-methyl-1-oxo-5-phenylpentyl)amino-7-chloro-5-(2-fluorophenyl)-1-methyl-2,3-dihydro-1H-1,4-benzodiazepin-2-one. MS (ESI): 645 (M+Na), 621 (M−H). Chromatography Note a and Note v.

Example 94

3-(2-(R)-cyclopropylmethyl-3-(S)-hydroxyl-1-oxoheptyl)amino-1-methyl-5-(thiazol-2-yl)-2,3-dihydro-1H-1,4-benzodiazepin-2-one. MS (ESI): 455 (M+H), 477 (M+Na), 453 (M−H). Chromatography Note b and Note c.

The benzodiazepine was made from 2-aminophenyl-2'thiazolylketone (see A. Furstner et al., *Tetrahedron* 1995, 51 (3), 773-786) following the synthetic sequence from: R. G. Sherrill et al., *J. Org. Chem.* 1995, 60, 734.

Example 95

3-(2-(R)-cyclopropylmethyl-3-(S)-hydroxyl-1-oxoheptyl)amino-1-cyclopropylmethyl-5-(thiazol-2-yl)-2,3-dihydro-1H-1,4-benzodiazepin-2-one. MS (ESI): 495 (M+H), 517 (M+Na), 493 (M−H). Chromatography Note c.

The benzodiazepine was made from 2-aminophenyl-2'thiazolylketone (see A. Furstner et al., *Tetrahedron* 1995, 51 (3), 773-786) following the synthetic sequence from: R. G. Sherrill et al., *J. Org. Chem.* 1995, 60, 734.

Example 96

3-(2-(R)-cyclopropylmethyl-3-(S)-hydroxyl-1-oxoheptyl)amino-1-cyclopropylmethyl-5-(4-trifluoromethylphenyl)-2,3-dihydro-1H-1,4-benzodiazepin-2-one. MS (ESI): 556 (M+H), 578 (M+Na), 554 (M−H). Chromatography Note j and Note p.

Example 97

3-(2-(R)-cyclopropylmethyl-3-(S)-hydroxyl-1-oxoheptyl)amino-1-benzyl-5-(4-trifluoromethylphenyl)-2,3-dihydro-1H-1,4-benzodiazepin-2-one. MS (ESI): 592 (M+H), 614 (M+Na), 590 (M−H). Chromatography Note b and Note c.

Example 98

3-(2-(R)-cyclopropylmethyl-3-(S)-hydroxyl-1-oxoheptyl)amino-1-(3-phenoxybenzyl)-5-(4-trifluoromethyl-phenyl)-2,3-dihydro-1H-1,4-benzodiazepin-2-one. MS (ESI): 684 (M+H), 706 (M+Na), 682 (M−H). Chromatography Note q and Note r.

Example 99

3-(2-(R)-cyclopropylmethyl-3-(S)-hydroxyl-1-oxoheptyl)amino-1-(3-pyridinylmethyl)-5-(4-trifluoromethyl-phenyl)-2,3-dihydro-1H-1,4-benzodiazepin-2-one. MS (ESI): 593 (M+H), 615 (M+Na), 519 (M−H). Chromatography Note q and Note r.

Example 100

3-(2-(S)-cyclopropylmethyl-3-(R)-hydroxyl-1-oxoheptyl)amino-1-methyl-5-(4-trifluoromethyl-phenyl)-2,3-dihydro-1H-1,4-benzodiazepin-2-one. MS (ESI): 516 (M+H), 538 (M+Na), 514 (M−H). Chromatography Note i.

The syn-aldol was made according to Scheme 1, except that (S)-4-(phenylmethyl)-2-oxazolidinone was used instead of the (R)-isomer shown in Scheme 1.

Example 101

3-(2-(S)-cyclopropylmethyl-3-(R)-hydroxyl-1-oxoheptyl)amino-1-methyl-5-(4-trifluoromethylphenyl)-2,3-dihydro-1H-1,4-benzodiazepin-2-one. MS (ESI): 516 (M+H), 538 (M+Na), 514 (M−H). Chromatography Note k.

The syn-aldol was made according to Scheme 1, except that (S)-4-(phenylmethyl)-2-oxazolidinone was used instead of the (R)-isomer shown in Scheme 1.

Example 102

3-(2-(R)-cyclopropylmethyl-3-(R)-hydroxyl-1-oxoheptyl)amino-1-methyl-5-(4-trifluoromethylphenyl)-2,3-dihydro-1H-1,4-benzodiazepin-2-one. MS (ESI): 516 (M+H), 538 (M+Na), 514 (M−H). Chromatography Note i.

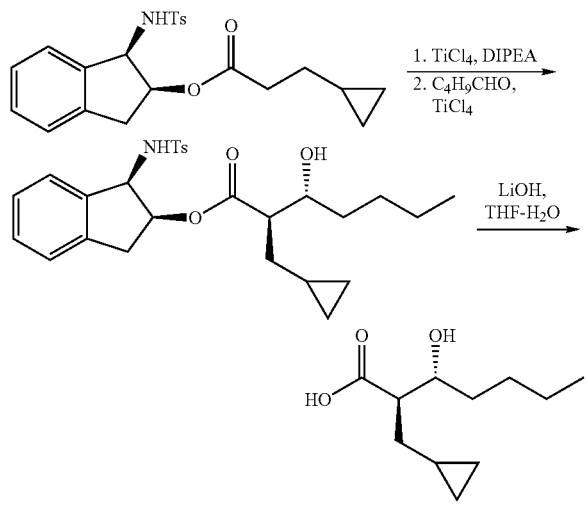

The anti-aldols were made by the method described in: A. K. Ghosh, *J. Am. Chem. Soc.* 1996, 118, 2527-2528. The carboxylic acid shown was coupled with the corresponding benzodiazepine following a procedure analogous to the procedure of the last step in Example 1.

Example 103

3-(2-(S)-cyclopropylmethyl-3-(S)-hydroxyl-1-oxoheptyl)amino-1-methyl-5-(4-trifluoromethylphenyl)-2,3-dihydro-1H-1,4-benzodiazepin-2-one. MS (ESI): 516 (M+H), 538 (M+Na), 514 (M−H). Chromatography Note i.

Followed the synthetic sequence of Example 102, except the opposite enantiomer of the chiral auxiliary was used.

Example 104

3-(2-(S)-cyclopropylmethyl-3-(S)-hydroxyl-1-oxoheptyl)amino-1-methyl-5-(4-trifluoromethylphenyl)-2,3-dihydro-1H-1,4-benzodiazepin-2-one. MS (ESI): 516 (M+H), 514 (M−H). Chromatography Note k.

Followed the synthetic sequence of Example 102, except the opposite enantiomer of the chiral auxiliary was used.

Example 105

3-(2-(R)-cyclopropylmethyl-3-(S)-hydroxyl-3-(S)-methyl-1-oxoheptyl)amino-1-methyl-5-(4-trifluoromethylphenyl)-2,3-dihydro-1H-1,4-benzodiazepin-2-one. MS (ESI): 530 (M+H), 552 (M+Na), 528 (M−H). Chromatography Note i.

Addition of a methyl group to Example 135 was performed with an organocerium reagent generated from methylmagnesium bromide and cerium trichloride according to: T. Imamoto et al (a) *J. Org. Chem.* 1984, 49, 3904-3912, and (b) *J. Am. Chem. Soc.* 1989, 111, 4392-4398.

Example 106

3-(2-(R)-cyclopropylmethyl-3-(S)-hydroxyl-1-oxoheptyl)amino-1-(3-phenoxybenzyl)-5-methyl-2,3-dihydro-1H-1,4-benzodiazepin-2-one. MS (ESI): 554 (M+H). Chromatography Note aa and Note bb.

Example 107

3-(2-(R)-cyclopropylmethyl-3-(S)-hydroxyl-1-oxoheptyl)amino-1-benzyl-5-methyl-2,3-dihydro-1H-1,4-benzodiazepin-2-one. MS (ESI): 462 (M+H). Chromatography Note b and Note c.

Example 108

3-(3-(S)-acetoxy-2-(R)-iso-butyl-1-oxoheptyl)amino-5-(4-fluorophenyl)-1-methyl-2,3-dihydro-1H-1,4-benzodiazepin-2-one. MS (ESI): 510 (M+H), 532 (M+Na), 508 (M−H). Chromatography Note h.

Example 109

3-(S)-(5-cyclopentyl-2-(R)-cyclopropylmethyl-3-(S)-methoxy-1-oxopentyl)amino-1-methyl-5-phenyl-2,3-dihydro-1H-1,4-benzodiazepin-2-one. MS (ESI): 502 (M+H), 524 (M+Na).

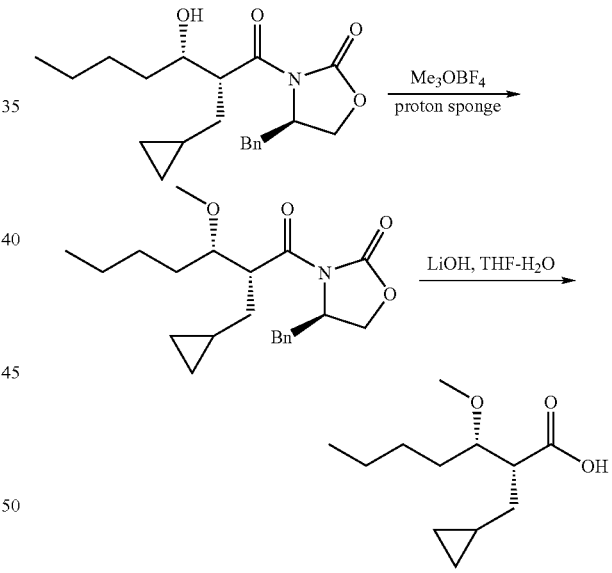

Methylation of the corresponding aldol was carried out according to: (a) D. A. Evans et al., *Tetrahedron Lett.* 1994, 35 (39), 7171-7172; (b) G. R. Pettit, *Synthesis* 1996, 719-725. The carboxylic acid shown was then coupled with the corresponding benzodiazepine following a procedure analogous to the procedure of the last step in Example 1.

Example 113

1-(1-hydroxypentyl)cyclohexanecarboxylic acid(5-(4-fluorophenyl)-1-methyl-2-oxo-2,3-dihydro-1H-1,4-benzodiazepin-3-yl)amide. MS (ESI): 480 (M+H), 502 (M+Na), 478 (M−H). Chromatography Note t and Note h.

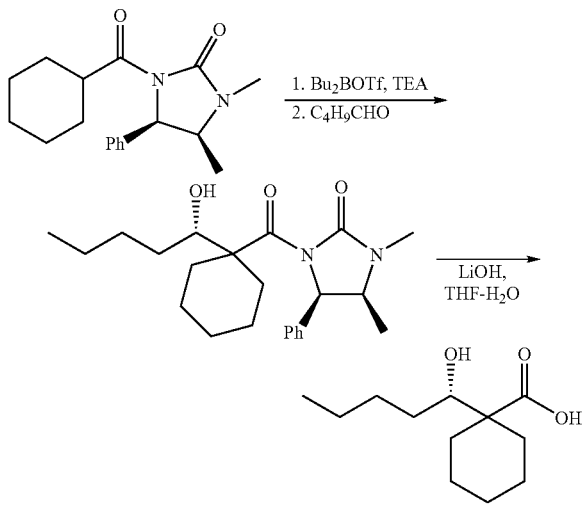

The corresponding aldol was made according to (a) A. S. Kende et al., *Tetrahedron Lett.* 1989, 30 (43), 5821-5824; (b) H. Mulzer et al., *Tetrahedron Lett.* 1995, 36 (42), 7643-7646. The carboxylic acid shown was coupled with benzodiazepine following a procedure analogous to the procedure of the last step in Example 1.

Example 114

3-(2-(R)-cyclopropylmethyl-3-(S)-hydroxyl-1-oxoheptyl)amino-5-methyl-5H,7H-dibenzo[b,d]azepin-6-one. MS (ESI): 421 (M+H), 443 (M+Na), 419 (M–H). Chromatography Note s.

Example 115

3-(2-(R)-cyclopropylmethyl-3-(S)-hydroxyl-1-oxooctyl)amino-5-methyl-5H,7H-dibenzo[b,d]azepin-6-one. MS (ESI): 435 (M+H), 457 (M+Na), 433 (M–H). Chromatography Note s.

Example 116

3-(2-(R)-cyclopropylmethyl-3-(S)-hydroxyl-1-oxononyl)amino-5-methyl-5H,7H-dibenzo[b,d]azepin-6-one. MS (ESI): 449 (M+H), 471 (M+Na), 447 (M–H). Chromatography Note s.

Example 117

3-(2-(R)-cyclopropylmethyl-5-(furan-2-yl)-3-(S)-hydroxyl-1-oxopentyl)amino-5-methyl-5H,7H-dibenzo[b,d]azepin-6-one. MS (ESI): 459 (M+H), 481 (M+Na), 457 (M–H). Chromatography Note s.

Example 118

2-(R)-cyclopropylmethyl-3-(S)-hydroxyl-heptanoic acid (2-oxo-1-(3-phenylamino-benzyl)azapan-3-(S)-yl) amide. MS (ESI): 492 (M+H), 514 (M+Na), 490 (M–H).

Step 1: [2-Oxo-1-(3-phenylamino-benzyl)-azepan-3-yl]-carbamic acid tert-butyl ester: In a 100 ml round bottomed flask Binap, (S)-(–)2,2'-Bis(diphenylphosphino)-1,1'-binaphthyl, (0.210 g, 0.3375 mmol) dissolved in 15 mL toluene was stirred at 80° C. for 1 minute. To the flask cooled to room temperature under inert atmosphere Pd(OAC)$_2$ (0.050 g, 0.225 mmol) was added and the solution was stirred at room temperature for 2 minutes. To the reaction mixture [1-(3-Iodo-benzyl)-2-oxo-azepan-3-yl]-carbamic acid tert-butyl ester (1.0 g, 2.25 mmol) dissolved in 15 mL toluene, aniline (1.047 g, 11.25 mmol) and Sodium tert-butoxide (0.259 g, 2.70 mmol) were added and the solution was stirred at 80° C. for 18 h. The reaction was cooled to room temperature, diluted with 200 mL of water, and extracted twice with 100 mL of ethyl acetate. The organic layer was dried with anhydrous sodium sulfate, filtered and concentrated to an oil. The oil was purified on flash silica gel column using 10-30% ethyl acetate in hexanes as eluent to yield 0.562 g (61%). MS (ESI) M+H=432.5

Step 2: 3-Amino-1-(3-phenylamino-benzyl)-azepan-2-one, trifluoroacetic acid salt: In a 25 mL round bottomed flask the ester from Step 1 above (0.025 g, 0.06 mmol) was dissolved in 10 mL of 50% TFA/CH$_2$Cl$_2$ and was stirred at room temperature for 1 h. The solvent was concentrated to an oil and dried under high vacuum to yield 0.025 g (100%). MS (ESI) M+H=310.4

Step 3: 2-Cyclopropylmethyl-3-hydroxy-heptanoic acid [2-oxo-1-(3-phenylamino-benzyl)-azepan-3-yl]-amide: In a 25 mL round bottomed flask 2-Cyclopropylmethyl-3-hydroxy-heptanoic acid (0.0125 g, 0.061 mmol) was dissolved in 1 mL DMF. To the reaction mixture HATU, O-(7-Azabenzotriazol-1-yl)-N, N,N',N'-tetramethyluronium hexafluorophosphate, (0.029 g, 0.0734 mmol) and N-Methyl morpholine (0.018 g, 0.018 mmol) were added and the reaction solution was stirred at room temperature for 10 minutes. To the reaction mixture the compound from Step 2 above (0.025 g, 0.06 mmol) dissolved in 1 mL of DMF was added and the reaction solution was stirred at room temperature for 18 h. The solution was diluted with 50 mL of water and extracted twice with 20 mL of ethyl acetate. The combined organic layers were dried with anhydrous Sodium sulfate, filtered, and concentrated to an oil. The oil was purified on a flash silica gel column using 20-40% ethyl acetate in hexanes as eluent to yield 6.0 mg (20%). MS (ESI) M+H=492.6

Example 119

3-(2-(R)-cyclopropylmethyl-3-(S)-hydroxyl-1-oxoheptyl)amino-5-cyclopentyl-1-methyl-2,3-dihydro-1H-1,4-benzodiazepin-2-one. MS (ESI): 440 (M+H). Chromatography Note a.

Synthesis of 2-aminophenyl cyclopentylmethanone: To a solution of anthranilonitrile (15.0 g) in diethyl ether (600 mL) was added a solution of 2.0 M cyclopentylmagnesium bromide in diethyl ether (159 mL) at 0° C. under nitrogen. The mixture was stirred at room temperature overnight (20 hours). 500 ml of 5 N HCl in H$_2$O was added very slowly at 0° C. The mixture was stirred at room temperature for 1 hour. The aqueous layer was neutralized with 50% NaOH/H$_2$O to pH=12. 2×500 mL of ethyl acetate was used to extract the aqueous layer. The combined organic layers were dried over Na$_2$SO$_4$. The solvent was removed to give the crude product 22.5 g (93.6% yield). H$^1$NMR (CDCl$_3$): δ6.62-7.82 (m, 4H), 3.64-3.78 (m, 1H), 1.50-1.96 (m, 8H).

The 2-aminophenyl cyclopentylmethanone was converted to benzodiazepine following: R. G. Sherrill et al *J. Org. Chem.* 1995, 60, 734.

Example 120

3-(2-(R)-cyclopropylmethyl-3-(S)-hydroxyl-1-oxoheptyl)amino-5-benzyl-1-methyl-2,3-dihydro-1H-1,4-benzodiazepin-2-one. MS (ESI): 462 (M+H), 460 (M−H). Chromatography Note b and Note c.

The benzodiazepine was made from 1-(2-aminophenyl)-2-phenylethanone (see M. W. Partridge et al., *J. Chem. Soc.* 1964, 3673) following the synthetic sequence from: R. G. Sherrill, *J. Org. Chem.* 1995, 60, 734.

Example 121

3-(2-(R)-cyclopropylmethyl-3-(S)-hydroxyl-1-oxoheptyl)amino-5-benzyl-1-butyl-2,3-dihydro-1H-1,4-benzodiazepin-2-one. MS (ESI): 504 (M+H), 502 (M−H). Chromatography Note b and Note c.

Example 122

3-(2-(R)-cyclopropylmethyl-3-(S)-hydroxyl-1-oxoheptyl)amino-5-cycloheptyl-1-methyl-2,3-dihydro-1H-1,4-benzodiazepin-2-one. MS (ESI): 468 (M+H), 466 (M−H). Chromatography Note b and Note c.

Example 123

3-(2-(R)-cyclopropylmethyl-3-(S)-hydroxyl-1-oxoheptyl)amino-1-benzyl-5-cycloheptyl-2,3-dihydro-1H-1,4-benzodiazepin-2-one. MS (ESI): 544 (M+H), 542 (M−H). Chromatography Note a.

Example 124

3-(2-(R)-cyclopropylmethyl-3-(S)-hydroxyl-1-oxoheptyl)amino-1-butyl-5-cycloheptyl-2,3-dihydro-1H-1,4-benzodiazepin-2-one. MS (ESI): 510 (M+H), 508 (M−H). Chromatography Note b and Note c.

Example 125

3-(2-(R)-cyclopropylmethyl-3-(S)-hydroxyl-1-oxoheptyl)amino-1-(2-pyridinylmethyl)-5-(4-trifluoromethylphenyl)-2,3-dihydro-1H-1,4-benzodiazepin-2-one. MS (ESI): 593 (M+H), 615 (M+Na), 591 (M−H). Chromatography Note a.

Example 126

3-(2-(R)-cyclopropylmethyl-3-(S)-hydroxyl-1-oxoheptyl)amino-1-(3-pyridinylmethyl)-5-(2-fluorophenyl)-2,3-dihydro-1H-1,4-benzodiazepin-2-one. MS (ESI): 543 (M+H), 541 (M−H). Chromatography Note d and Note e.

Example 127

3-(2-(S)-cyclopropylmethyl-3-(S)-hydroxyl-1-oxopentyl)amino-1-(3-pyridinylmethyl)-5-(4-trifluoromethylphenyl)-2,3-dihydro-1H-1,4-benzodiazepin-2-one. MS (ESI): 565 (M+H), 563 (M−H). Chromatography Note f and Note g.

Example 128

3-(2-1(R)-Cyclopropylmethyl-3-(S)-hydroxyl-1-oxoheptyl)amino-1-methyl-5-(N,N-dibutylamino)-2,3-dihydro-1H-1,4-benzodiazepin-2-one. MS (ESI): 499 (M+H). Chromatography Note a.

Example 129

3-(2-(R)-Cyclopropylmethyl-3-(S)-hydroxyl-1-oxoheptyl)amino-1-n-butyl-5-t-butyl-2,3-dihydro-1H-1,4-benzodiazepin-2-one. MS (ESI): 470 (M+H). Chromatography Note b and Note c.

The benzodiazepine can be made from 2-amino-pivalophenone (A. Furstner et al., *J. Org. Chem.* 1994, 59 (18), 5215-5229; M. C. Bettembourg et al., *Bull. Soc. Chim. Fr.* 1963, 2449-2451) following the synthetic sequence from: R. G. Sherrill et al., *J. Org. Chem.* 1995, 60, 734.

Example 130

3-(2-(R)-Cyclopropylmethyl-3-(S)-hydroxyl-1-oxoheptyl)amino-1-(2-oxo-3,3-dimethylbutyl)-5-n-butyl-2,3-dihydro-1H-1,4-benzodiazepin-2-one. MS (ESI): 512 (M+H). Chromatography Note b.

Example 131

3-(2-(R)-Cyclopropylmethyl-3-(S)-hydroxyl-1-oxoheptyl)amino-1-benzyl-5-t-butyl-2,3-dihydro-1H-1,4-benzodiazepin-2-one. MS (ESI): 504 (M+H). Chromatography Note a.

The benzodiazepine can be made from 2-amino-pivalophenone (A. Furstner et al., *J. Org. Chem.* 1994, 59 (18), 5215-5229; M.-C. Bettembourg et al., *Bull. Soc. Chim. Fr.* 1963, 2449-2451) following the synthetic sequence from: R. G. Sherrill et al., *J. Org. Chem.* 1995, 60, 734.

Example 132

3-(2-(R)-Cyclopropylmethyl-3-(S)-hydroxyl-1-oxoheptyl)amino-1-(2-picolyl)-5-n-butyl-2,3-dihydro-1H-1,4-benzodiazepin-2-one. MS (ESI): 505 (M+H). Chromatography Note b and Note c.

Example 133

3-(2-(R)-Isobutyl-3-(S)-hydroxyl-1-oxoheptyl)amino-1-methyl-5-homopiperidino-2,3-dihydro-1H-1,4-benzodiazepin-2-one. MS (ESI): 471 (M+H). Chromatography Note b and Note c.

Example 135

3-(2-(R)-cyclopropylmethyl-1,3-dioxoheptyl)amino-1-methyl-5-(4-trifluoromethylphenyl)-2,3-dihydro-1H-1,4-benzodiazepin-2-one. MS (ESI): 514 (M+H), 536 (M+Na), 512 (M−H). Chromatography Note i.

Example 55 was oxidized to the dicarbonyl compound by TPAP/NMO, see S. V. Ley et al., *Synthesis* 1994, 639.

Example 136

1-pentyrylcyclohexanecarboxylic acid (5-(4-fluorophenyl)-1-methyl-2-oxo-2,3-dihydro-1H-1,4-benzodiazepin-3-yl)amide. MS (ESI): 478 (M+H), 500 (M+Na), 476 (M−H). Chromatography Note h.

Example 137

(2R,3S)—N-[1-butyl-5-(methylethyl)-2-oxo(3H-benzo[f] 1,4-diazepin-3-yl)]-2-(cyclopropylmethyl)-3-hydroxyheptanamide. MS (ESI): 456 (M+H).

Example 138

(2R,3S)-2-(cyclopropylmethyl)-3-hydroxy-N-[5-(methylethyl)-2-oxo-1-benzyl(3H-benzo[f]1,4-diazepin-3-yl)]heptanamide. MS (ESI): 490 (M+H).

Example 139

(2R,3S)-2-(cyclopropylmethyl)-3-hydroxy-N-{5-methyl-1-[(3-{[(4-methylphenyl)sulfonyl]amino}phenyl)-methyl]-2-oxo(3H-benzo[f]1,4-diazepin-3-yl)}heptanamide. MS (ESI): 631 (M+H).

Example 140

3-(R,S)-(2-(R)-Cyclopropylmethyl-3-(S)-hydroxyl-1-oxoheptyl)amino-1-methyl-5-t-butyl-2,3-dihydro-1H-1,4-benzodiazepin-2-one. MS (ESI): 428 (M+H).

Example 141

(2R,3S)-2-(cyclopropylmethyl)-3-hydroxy-N-{1-[(3-{[(4-methylphenyl)sulfonyl]amino}phenyl)methyl]-2-oxo(3H,4H,5H-benzo[f]1,4-diazaperhydroepin-3-yl)}heptanamide. MS (ESI): 570 (M+H).

Example 142

3-(R,S)-(2-(R)-Cyclopropylmethyl-3-(S)-hydroxyl-1-oxoheptyl)amino-1-methyl-5-piperizinyl-2,3-dihydro-1H-1,4-benzodiazepin-2-one. MS (ESI): 456 (M+H).

Example 143

7-(R,S)-(2-(R)-Cyclopropylmethyl-3-(S)-hydroxyl-1-oxoheptyl)amino-5-(2-diethylaminoethyl)-6,7-dihydro-5H-dibenzoazepin-6-one. MS (ESI): 506 (M+H).

Example 144

7-(R,S)-(2-(R)-Cyclopropylmethyl-3-(S)-hydroxyl-1-oxoheptyl)amino-5-(3-hydroxypropyl)-6,7-dihydro-5H-dibenzoazepin-6-one. MS (ESI): 465 (M+H).

Example 145

3-(R,S)-(2-(R)-Cyclopropylmethyl-3-(S)-hydroxyl-1-oxoheptyl)amino-1-(benzyl-5-(2,2-dimethylpropyl)-2,3-dihydro-1H-1,4-benzodiazepin-2-one. MS (ESI): 518 (M+H).

Example 146

3-(R,S)-(2-(R)-Cyclopropylmethyl-3-(S)-hydroxyl-1-oxoheptyl)amino-1-n-butyl-5-n-butyl-2,3-dihydro-1H-1,4-benzodiazepin-2-one. MS (ESI): 506 (M+H).

Example 147

3-(R,S)-(2-(R)-Cyclopropylmethyl-3-(S)-hydroxyl-1-oxoheptyl)amino-1-benzyl-5-n-butyl-2,3-dihydro-1H-1,4-benzodiazepin-2-one. MS (ESI): 504 (M+H).

Example 148

3-(R,S)-(2-(R)-Cyclopropylmethyl-3-(S)-hydroxyl-1-oxoheptyl)amino-1-methyl-5-(3,4-dihydro-1H-isoquinolin-2-yl)-2,3-dihydro-1H-1,4-benzodiazepin-2-one. MS (ESI): 503 (M+H).

Example 149

3-(R,S)-(2-(R)-Cyclopropylmethyl-3-(S)-hydroxyl-1-oxoheptyl)amino-1-methyl-5-(2,2-dimethylpropyl)-2,3-dihydro-1H-1,4-benzodiazepin-2-one. MS (ESI): 442 (M+H).

Example 150

7-(R,S)-(2-(R)-Cyclopropylmethyl-3-(S)-hydroxyl-1-oxoheptyl)amino-5-n-butyl-6,7-dihydro-5H-dibenzoazepin-6-one. MS (ESI): 442 (M+H).

Example 151

3-(R,S)-(2-(R)-Cyclopropylmethyl-3-(S)-hydroxyl-1-oxoheptyl)amino-1-(2-ethylbutyl)-5-n-butyl-2,3-dihydro-1H-1,4-benzodiazepin-2-one. MS (ESI): 498 (M+H).

Example 152

3-(R,S)-(2-(R)-Cyclopropylmethyl-3-(S)-hydroxyl-1-oxoheptyl)amino-1-methyl-5-pyrrolidin-1-yl-2,3-dihydro-1H-1,4-benzodiazepin-2-one. MS (ESI): 441 (M+H).

Example 153

7-(R,S)-(2-(R)-Cyclopropylmethyl-3-(S)-hydroxyl-1-oxoheptyl)amino-5-benzyl-6,7-dihydro-5H-dibenzoazepin-6-one. MS (ESI): 497 (M+H).

Example 154

3-(R,S)-(2-(R)-Cyclopropylmethyl-3-(S)-hydroxyl-1-oxoheptyl)amino-1-(3-hydroxypropyl)-5-t-butyl-2,3-dihydro-1H-1,4-benzodiazepin-2-one. MS (ESI): 472 (M+H).

Example 155

3-(R,S)-(2-(R)-Cyclopropylmethyl-3-(S)-hydroxyl-1-oxoheptyl)amino-1-methyl-5-ethoxy-2,3-dihydro-1H-1,4-benzodiazepin-2-one. MS (ESI): 416 (M+H).

Example 156

3-(R,S)-(2-(R)-Cyclopropylmethyl-3-(S)-hydroxyl-1-oxoheptyl)amino-1-butyl-5-(2,2-dimethylpropyl)-2,3-dihydro-1H-1,4-benzodiazepin-2-one. MS (ESI): 484 (M+H).

Example 157

3-(2-(R)-cyclopropylmethyl-3-(S)-hydroxyl-1-oxoheptyl)amino-1-(2-pyridinylmethyl N-oxide)-5-(4-trifluoromethyl)phenyl-2,3-dihydro-1H-1,4-benzodiazepin-2-one. MS (ESI): 609 (M+H).

Example 158

3-(2-(R)-cyclopropylmethyl-3-(S)-hydroxyl-1-oxoheptyl)amino-1-(3-pyridinylmethyl N-oxide)-5-(4-trifluoromethyl)phenyl-2,3-dihydro-1H-1,4-benzodiazepin-2-one. MS (ESI): 609 (M+H).

Example 159

3-(2-(S)-cyclopropylmethyl-3-(S)-hydroxyl-1-oxopentyl)amino-1-(3-pyridinylmethyl)-5-phenyl-2,3-dihydro-1H-1,4-benzodiazepin-2-one. MS (ESI): 497 (M+H).

Example 160

3-(2-(R)-cyclopropylmethyl-3-(S)-hydroxyl-1-oxoheptyl)amino-1-(2-(diethylamino)ethyl)-5-(4-trifluoromethylphenyl)-2,3-dihydro-1H-1,4-benzodiazepin-2-one. MS (ESI): 601 (M+H).

Example 161

3-(2-(R)-cyclopropylmethyl-3-(S)-hydroxyl-1-oxopentyl)amino-1-(3-pyridinylmethyl N-oxide)-5-phenyl-2,3-dihydro-1H-1,4-benzodiazepin-2-one. MS (ESI): 513 (M+H).

Example 159 (28 mg, 0.056 mmol) and m-CPBA (12.6 mg, 0.056 mmol) were dissolved in methylene chloride (1 mL) and stirred at room temperature for 20 h. The reaction mixture was concentrated and purified on silica gel (3% methanol/methylene chloride) to afford example 161 (28 mg, 100%) as a white solid. MS m/z 513.5 (M+H).

Example 162

(2R,3S)—N-(8-bromo-1,5-dimethyl-2-oxo-2,3-dihydro-1H-1,4-benzodiazepin-3-yl)-2-(cyclopropylmethyl)-3-hydroxyheptanamide Step A: Preparation of 1-(2-amino-4-bromophenyl)ethanone (162a)

Under an argon atmosphere a solution of 3-bromoaniline (31.3 g, 181.8 mmol) and acetonitrile (75 g, 1.818 mol) in anhydrous toluene (120 ml) was added dropwise to boron trichloride (23.4 g, 200 mmol) in (200 ml) hexanes under cooling in an ice bath and stirring over 2.5 hours. After the addition was completed, aluminum chloride (26.6 g, 200 mmol) was added portion wise over 30 minutes. The mixture was allowed to warm to ambient temperature and then heated at reflux for 16 hours with stirring. A 3N HCl solution (100 ml) was added dropwise to the reaction mixture under stirring at 10° C. After the addition was complete, the mixture was heated at reflux for 3.5 hours. The reaction mixture was then cooled to room temperature, and the layers separated. The aqueous layer was extracted with chloroform (3×250 ml). Organic layers were combined, dried over magnesium sulfate, filtered, and the filtrate concentrated to give the title compound 162a (9.58 g, 25%). $^1$H NMR (CDCl$_3$, 300 MHz): δ 7.54 (d, 1H, J=8.8 Hz), 6.83 (d, 1H, J=1.9 Hz), 6.75 (dd, 1H, J=8.4, 1.8 Hz), 2.54 (s, 3H) ppm.

Step B: Preparation of benzyl 8-bromo-5-methyl-2-oxo-2,3-dihydro-1H-1,4-benzodiazepin-3-ylcarbamate (162b)

Under an argon atmosphere 1H-1,2,3-benzotriazol-1-yl{[(benzyloxy)carbonyl]amino}acetic acid (6.71 g, 20.6 mmol) was suspended in anhydrous methylene chloride (92 ml) and cooled to 0° C. in an ice bath. Oxalyl chloride (2.61 g, 20.6 mmol) was added dropwise to the suspension, followed by N,N-dimethylformamide (38 ml) added dropwise. After the addition the reaction was stirred at 0° C. in an ice bath for 30 minutes, until no more gas evolved. Then 1-(2-amino-4-bromophenyl)ethanone (4.0 g, 18.7 mmol) and 4-methylmorpholine (2.84 g, 28.0 mmol) were added dropwise in anhydrous methylene chloride (60 ml) under stirring in an ice bath. The reaction mixture was then allowed to warm to room temperature and stirred over night. Reaction was quenched with water (200 ml), then extracted with ethyl acetate (3×250 ml). The organic layers were combined, dried over magnesium sulfate, filtered, and the filtrate was concentrated to give a residue. This residue was dissolved in tetrahydrofuran (120 ml) and methyl-alcohol (35 ml) and then ammonia gas was bubbled through for 2.5 hours. The reaction was then concentrated to a very viscous light brown oil. The oil was dissolved in acetic acid (120 ml) and ammonium acetate (4.3 g, 56.1 mmol) was added in one portion and stirred for 12 hours. The reaction was diluted with water (100 ml) and then basified to pH=10 with 25% sodium hydroxide under stirring in an ice bath. The aqueous solution was then extracted with ethyl acetate (3×500 ml) and the organic layers combined, dried over magnesium sulfate, filtered and the filtrate concentrated to give a residue. The residue was purified to silica gel column chromatography eluting with 40% ethyl acetate in hexanes to give the title compound 162b (4 g, 53%). $^1$H NMR (CDCl$_3$, 300 MHz): δ 9.90 (s-br, 1H), 7.42-7.31 (m, 6H), 7.12 (d, 1H, 1.5 Hz), 7.06-7.03 (m, 1H), 5.18-5.08 (m, 3H), 2.50 (s, 3H) ppm.

Step C: Preparation of benzyl 8-bromo-1,5-dimethyl-2-oxo-2,3-dihydro-1H-1,4-benzodiazepin-3-ylcarbamate (162c)

162b (2.0 g, 4.98 mmol) was dissolved in anhydrous N,N-dimethylformamide (10 ml), to this was added potassium carbonate (1.72 g, 12.44 mmol) and iodomethane (0.847 g, 5.97 mmol) and the reaction was sealed in a pressure flask and stirred for 12 hours at room temperature. The reaction was diluted with water and ethyl acetate (20/70 ml). The aqueous solution was then extracted with ethyl acetate (3×20 ml). The organic layers combined, washed with water (1×100 ml), dried over magnesium sulfate, filtered and the filtrate concentrated to give the title compound 162a (1.58 g, 77.596). $^1$H NMR (CDCl$_3$, 300 MHz): δ 7.43-7.28 (m, 7H), 6.68 (d, 1H, J=8.1 Hz), 5.15-5.05 (m, 3H), 3.38 (s, 3H), 2.45 (d, 3H, 1.5 Hz) ppm.

Step D: Preparation of 3-amino-8-bromo-1,5-dimethyl-1,3-dihydro-2H-1,4-benzodiazepin-2-one (162d)

162c (0.831 g, 2.00 mmol) was dissolved in anhydrous anisole (16 ml) and then methane sulfonic acid (3.84 g, 40 mmol) was added in one portion, and then the reaction was heated to 40° C. for 30 minutes with stirring. The reaction was cooled to 0° C. in an ice bath then basified to pH=10 with concentrated ammonium hydroxide. The aqueous solution was then extracted with chloroform (3×50 ml) and the organic layers combined, dried over magnesium sulfate, filtered and the filtrate concentrated to give a residue. The residue was purified to silica gel column chromatography eluting with 10% methyl alcohol in chloroform to give the title compound 162d (0.463 g, 82%). $^1$H NMR (CDCl$_3$, 300 MHz): δ 7.32-7.23 (m, 3H), 4.12 (d, 1H, J=1.1 Hz), 3.27 (s, 3H), 2.30 (d, 3H, J=1.5 Hz) ppm.

Step E: Preparation of (2R,3S)—N-(8-bromo-1,5-dimethyl-2-oxo-2,3-dihydro-1H-1,4-benzodiazepin-3-yl)-2-(cyclopropylmethyl)-3-hydroxyheptanamide (Example 162)

Under an argon atmosphere (2S,3R)-2-(cyclopropylmethyl)-3-hydroxyheptanoic acid (0.75 g, 3.74 mmol) and O-(7-azabenzotriazol-1-yl)-N,N,N',N'-tetramethyluronium hexafluorophosphate were dissolved in anhydrous N,N-dimethylformamide (3 ml) and stirred for 10 minutes. Then 1d (0.862 g, 3.06 mmol) and N,N-diisopropylethylamine (0.809 g, 6.24 mmol) in N,N-dimethylformamide (3 ml) were added and reaction was stirred at room temperature under argon for 12 hours. Reaction was quenched with water (20 ml), then extracted with ethyl acetate (3×25 ml). The organic layers were combined, dried over magnesium sulfate, filtered, and the filtrate was concentrated to give a residue. The residue was purified by silica gel column chromatography eluting with 50% ethyl acetate in hexanes to give the title compound Example 162 (1.31 g, 92%). $^1$H NMR (CDCl$_3$, 300 MHz): δ 7.46-7.40 (m, 3H), 5.36 (t, 1H, J=5.7 Hz), 3.94-3.81 (m, 1H), 3.41 (s, 3H), 2.46-2.41 (m, 3H), 1.86-1.81 (m, 1H), 1.62-1.21 (m, 8H), 0.90 (t, 2H, J=6.8 Hz), 0.80-0.773 (m, 1H), 0.494-0.400 (m, 1H), 0.116-0.001 (m, 3H) ppm.

Example 163

6-(2-(R)-cyclopropylmethyl-3-(S)-hydroxyl-1-oxoheptyl)amino-1,4-dibenzyl-hexahydro-5H-1,4-diazepin-5-one

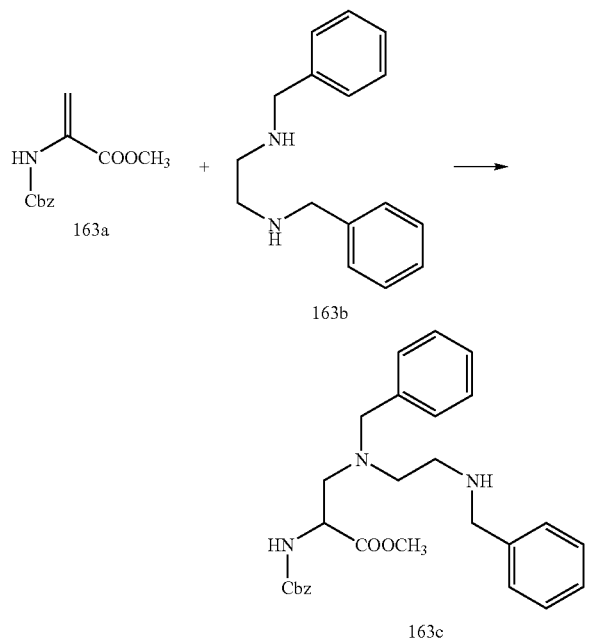

N-Cbz-Dehydroalanine methyl ester (163a) (4.70 g, 0.02 mol) and 1,4-dibenzylethylenediamine (163b) (24.00 g, 0.1 mol) were stirred for 48 h at ambient temperature. The reaction mixture was subjected to flash column chromatography on silica gel, using 5% methanol/methylene chloride, to give 163c (3.84 g, 40%) as a colorless oil. MS m/z 476.2 (MH$^+$).

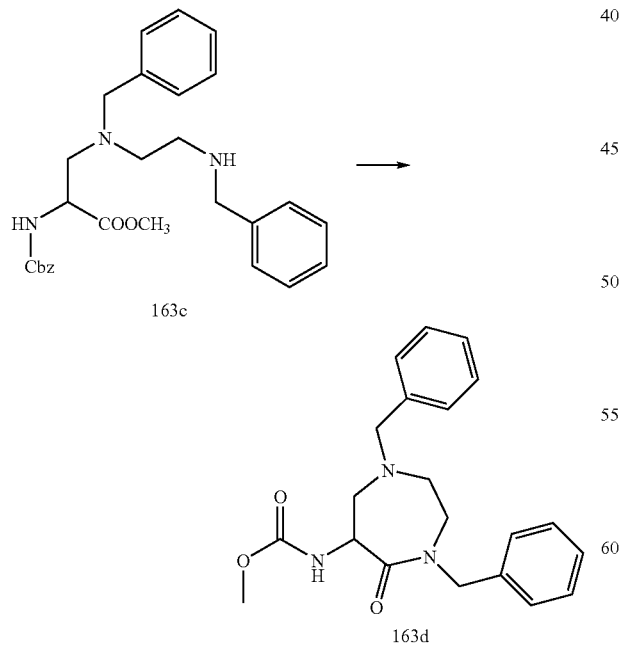

To a solution of 163c (1.7 g, 3.6 mmol) in dry toluene (35 mL) was added NaOCH$_3$ (1.94 g, 9.0 mmol, 25% in methanol). The reaction mixture was refluxed for 2 h, and then cooled to room temperature. The reaction mixture was diluted with ethyl acetate (50 mL), washed with water, brine, and dried (MgSO$_4$). After evaporation of the solvent, the residue was purified on silica gel (2% methanol/methylene chloride) to afford 163d (342 mg, 26%) as a colorless oil. MS m/z 368.5 (M+H).

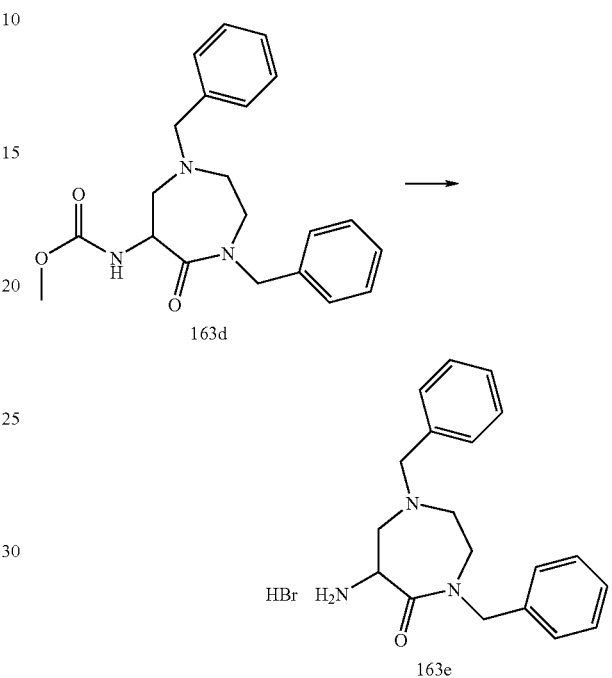

163d (342 mg, 0.93 mmol) was dissolved in HBr/HOAc (5 mL, 30%) and stirred for 20 h at ambient temperature. The reaction mixture was then diluted with ether (50 mL). The precipitate was filtered under nitrogen atmosphere, thoroughly washed with ether, and dried under high vacuum overnight to give a white solid 163e (340 mg, 100%). MS m/z 391.2 (M+H), 310.2 (M+H—HBr).

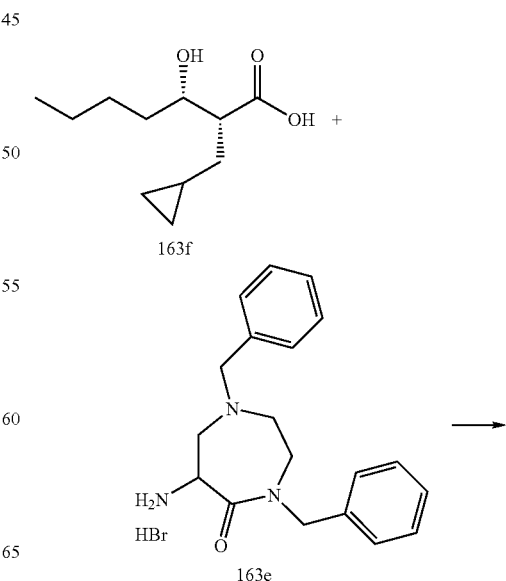

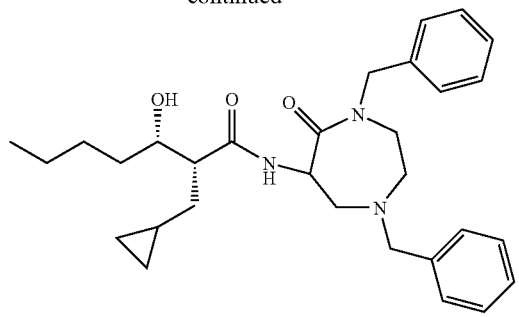

Example 163

163e (78 mg, 0.20 mmol), 163f (40 mg, 0.20 mmol), and HATU (91 mg, 0.24 mmol) were dissolved in DMF (1 mL), diisopropylethylamine (0.12 mL, 0.70 mmol) was added. After being stirred for 24 h at ambient temperature, the reaction mixture was diluted with ethyl acetate, washed with water and brine, dried ($Na_2SO_4$). After evaporation of the solvent, the residue was purified on silica gel (50% ethyl acetate/hexane) to afford Example 163 (28 mg, 29%) as a white solid. $^1$H NMR (300 MHz, $CDCl_3$) δ: –0.05-0.1 (m, 2H), 0.3-0.5 (m, 2H), 0.5-0.7 (m, 1H), 0.89 (t, J=6.6 Hz, 3H), 1.22-1.55 (m, 7H), 1.6-1.8 (m, 1H), 1.9-2.1 (m, 1H), 2.25-2.40 (m, 2H), 2.65-2.80 (m, 1H), 3.08-3.21 (m, 2H), 3.45-3.85 (m, 4H), 4.55-4.70 (m, 2H), 4.85-5.0 (m, 1H), 7.19 (d, J=1.8 Hz, 1H), 7.18-7.38 (m, 10H); MS m/z 492.6 (M+H).

Example 164

6-(2-(R)-cyclopropylmethyl-3-(S)-hydroxy-1-oxoheptyl) amino-4-benzyl-1-[(4-chlorophenyl)sulfonyl]- - -hexahydro-5H-1,4-diazepin-5-one

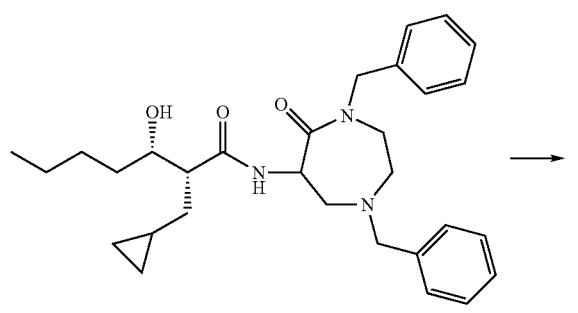

Example 163

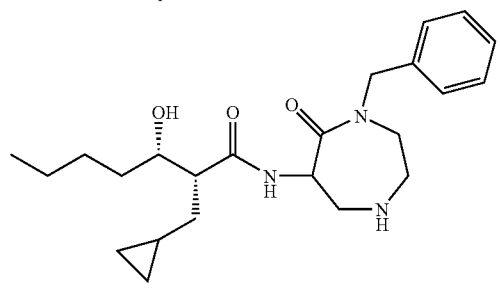

164a

To a solution of Example 163 (85 mg, 0.17 mmol) in THF (1 mL) and $CH_3OH$ (1 mL) was added $H_2O$ (0.5 mL), hydrochloric acid (conc. 0.1 mL), and 10% Pd/C (20 mg). The reaction flask was evacuated and then filled with $H_2$. This process was repeated three times, and the reaction mixture was stirred under hydrogen atmosphere for 24 h at room temperature. The reaction mixture was made basic with saturated $Na_2CO_3$, filtered through a pad of celite, and washed with ethyl acetate (100 mL). The filtrate was evaporated to give 164a (70 mg, 103%) as a colorless oil. MS m/z 402.4 (M+H).

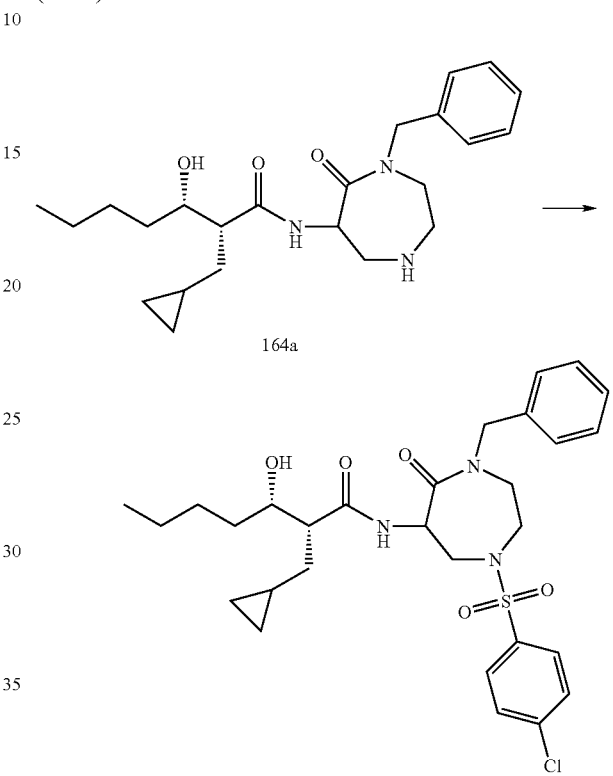

164a

Example 164

To a solution of 164a (68 mg, 0.17 mmol) in pyridine (1 mL) was added p-chlorobenzenesulfonyl chloride (43 mg, 0.2 mmol), and the reaction mixture was stirred overnight at room temperature. Pyridine was removed via rotovap. The residue was dissolved in ethyl acetate (20 mL), washed with water, 1 N HCl, $Na_2CO_3$ (sat'd), brine, and dried ($Na_2SO_4$). After evaporation of the solvent, the residue was purified on silica gel (2% methanol/methylene chloride) to afford Example 164 (94 mg, 96%) as a white solid. $^1$H NMR (300 MHz, $CDCl_3$) δ: –0.1-0.15 (m, 2H), 0.3-0.45 (m, 2H), 0.5-0.65 (m, 1H), 0.78-0.89 (m, 3H), 1.15-1.52 (m, 7H), 1.55-1.70 (m, 1H), 2.25-2.35 (m, 1H), 2.40-2.55 (m, 1H), 2.56-2.68 (m, 1H), 3.15-3.28 (m, 1H), 3.32-3.48 (m, 1H), 3.50-3.85 (m, 3H), 4.02-4.18 (m, 1H), 4.42-4.75 (m, 3H), 7.05-7.15 (m, 2H), 7.18-7.25 (m, 3H), 7.42 (d, J=8.4 Hz, 2H), 7.70-7.75 (m, 2H); MS m/z 576.1 (M+H).

Example 165

6-(2-(R)-cyclopropylmethyl-3-(S)-hydroxy-1-oxopentyl) amino-4-benzyl-1-[(4-chlorophenyl)sulfonyl]- -hexahydro-5H-1,4-diazepin-5-one. $^1$H NMR (300 MHz, $CDCl_3$) δ: –0.1-0.17 (m, 2H), 0.3-0.45 (m, 2H), 0.5-0.65 (m, 1H), 0.82-0.95 (m, 3H), 1.28-1.70 (m, 5H), 2.25-2.35 (m, 1H), 2.40-2.55 (m, 1H), 2.58-2.80 (m, 2H), 3.15-3.25 (m, 1H), 3.32-3.45 (m, 1H), 3.62-3.78 (m, 2H), 4.02-4.18 (m, 1H), 4.42-4.75 (m,

Example 166

(2R,3S)-2-(cyclopropylmethyl)-N-(1-{[3-(4-fluorophenoxy)phenyl]methyl}-2-oxo(3H,4H,5H-benzo[f]azaperhydroepin-3-yl))-3-hydroxyheptanamide. MS (ESI): 559 (M+H).

Example 167

(2R,3S)-2-(cyclopropylmethyl)-3-hydroxy-N-[2-oxo-1-benzyl (3H, 4H, 5H-benzo[f]azaperhydroepin-3-yl)]heptanamide. MS (ESI): 449 (M+H).

Example 168

3-(R,S)-(2-(R)-Cyclopropylmethyl-3-(S)-hydroxyl-1-oxoheptyl)amino-1-methyl-5-(4-benzylpiperazin-1-yl)-2,3-dihydro-1H-1,4-benzodiazepin-2-one. MS (ESI): 546 (M+H).

Example 169

3-(R,S)-(2-(R)-Cyclopropylmethyl-3-(S)-hydroxyl-1-oxoheptyl)amino-1-methyl-5-(4-methanesulfonyl-piperazin-1-yl)-2,3-dihydro-1H-1,4-benzodiazepin-2-one. MS (ESI): 534 (M+H).

Example 170

3-(R,S)-(2-(R)-Cyclopropylmethyl-3-(S)-hydroxyl-1-oxoheptyl)amino-1-methyl-5-(4-methylpiperazin-1-yl)-2,3-dihydro-1H-1,4-benzodiazepin-2-one. MS (ESI): 470 (M+H).

Example 171

3-(R,S)-(2-(R)-Cyclopropylmethyl-3-(S)-hydroxyl-1-oxoheptyl)amino-1-methyl-5-(4-acetylpiperazin-1-yl)-2,3-dihydro-1H-1,4-benzodiazepin-2-one. MS (ESI): 498 (M+H).

Example 172

3-(R,S)-(2-(R)-Cyclopropylmethyl-3-(S)-hydroxyl-1-oxoheptyl)amino-1-methyl-5-([4-(3,5-dimethyl-isoxazole-4-sulfonyl)-piperazin-1-yl]-2,3-dihydro-1H-1,4-benzodiazepin-2-one. MS (ESI): 615 (M+H).

Example 173

3-(R,S)-(2-(R)-Cyclopropylmethyl-3-(S)-hydroxyl-1-oxoheptyl)amino-1-methyl-5-(4-benzoylpiperazin-1-yl)-2,3-dihydro-1H-1,4-benzodiazepin-2-one. MS (ESI): 560 (M+H).

Example 174

4-[3-(2-(R)-Cyclopropylmethyl-3-(S)-hydroxy-heptanoylamino)-1-methyl-2-oxo-2,3-dihydro-1H-benzo[e][1,4]diazepin-5-yl]-piperazine-1-carboxylic acid tert-butyl ester. MS (ESI): 556 (M+H).

Example 175

3-(2-(R)-cyclopropylmethyl-3-(S)-hydroxyl-1-oxoheptyl)amino-1-(3-pyridinylmethyl N-oxide)-5-(4-trifluoromethyl)phenyl-2,3-dihydro-1H-1,4-benzodiazepin-2-one-4-N-oxide. MS (ESI): 625.6 (M+H).

Chromatography Notes:

Note a: epimeric mixture at BZD.
Note b: $1^{st}$ eluting peak on CHIRALPAK AD chiral column with 10-35% i-PrOH/hexane.
Note c: $2^{nd}$ eluting peak on CHIRALPAK AD chiral column with 10-35% i-PrOH/hexane.
Note d: $1^{st}$ eluting peak on CHIRALCEL OD chiral column with 2/200/800 ratio of MeOH/i-PrOH/Hexane.
Note e: $2^{nd}$ eluting peak on CHIRALCEL OD chiral column with 2/200/800 ratio of MeOH/i-PrOH/Hexane.
Note f: $1^{st}$ eluting peak on silica gel column with 2% MeOH/$CH_2Cl_2$.
Note g: $2^{nd}$ eluting peak on silica gel column with 2% MeOH/$CH_2Cl_2$.
Note k: made from BZD-amine which in Cbz protected form was the $2^{nd}$ eluting peak on CHIRALPAK AD column with acetonitrile.
Note m: made from BZD-amine which in Cbz protected form was the $1^{st}$ eluting peak on CHIRALPAK AS with methanol.
Note n: made from BZD-amine which was the $1^{st}$ eluting peak on CHIRALPAK AS with 0.1% diethylamine/methanol.
Note o: made from BZD-amine which was the $2^{nd}$ eluting peak on CHIRALPAK AS with 0.1% diethylamine/methanol.
Note h: made from BZD-amine which was the $1^{st}$ eluting peak on CHIRALPAK AD column with 0.1% diethylamine/MeOH.
Note i: made from BZD-amine which in Cbz protected form was the $1^{st}$ eluting peak on CHIRALPAK AD column with acetonitrile.
Note l: made from BZD-amine which in Cbz protected was the $1^{st}$ eluting peak on CHIRALCEL OJ with 1:4 of hexane/ethanol.
Note j: $1^{st}$ eluting peak on CHIRALPAK AD column with acetonitrile/water.
Note p: $2^{nd}$ eluting peak on CHIRALPAK AD column with acetonitrile/water.
Note q: $1^{st}$ eluting peak on CHIRALCEL OD with 10% i-propanol/hexane.
Note r: $2^{nd}$ eluting peak on CHIRALCEL OD with 10% i-propanol/hexane.
Note s: made from bisbenazapine amine which was the $1^{st}$ peak on CHIRALCEL OD with 20% i-PrOH/hexane with diethylamine.
Note t: made from BZD-amine which was the $2^{nd}$ eluting peak on CHIRALPAK AD column with 0.1% diethylamine/MeOH.
Note w: derived from Example 93 by treatment with TFA.
Note x: derived from Example 88 by treatment with TFA.
Note u: $2^{nd}$ eluting peak on silica gel column with 30-80% EtOAc/hexane.
Note v: $1^{st}$ eluting peak on silica gel column with 30-80% EtOAc/hexane.
Note y: derived from Example 89 by treatment with TFA.
Note z: derived from Example 89 by treatment with TFA.
Note aa: $1^{st}$ eluting peak on CHIRALPAK AD with 20:80 of water/MeCN.
Note bb: $2^{nd}$ eluting peak on CHIRALPAK AD with 20:80 of water/MeCN.

Note cc: made from BZD-amine which in Cbz protected form was the 2nd eluting peak on CHIRALCEL OD column with 1/300/700 ratio of diethylamine/EtOH/CO$_2$.

Note dd: made from BZD-amine which in Cbz protected form was the 1st eluting peak on CHIRALCEL OD column with 1/300/700 ratio of diethylamine/EtOH/CO$_2$.

Tables 1-8 below provide representative Examples of the compounds of Formula (I) of the present invention.

TABLE 1

| Ex. # | Q | R$^5$ | R$^{11}$ | R$^{13}$ | Mass (M + H) |
|---|---|---|---|---|---|
| 1 | phenethyl | cyclopentyl-methyl | phenyl | H | 524 |
| 2 | phenethyl | cyclopentyl-methyl | 4-F-phenyl | H | 542 |
| 3 | phenethyl | benzyl | phenyl | H | 532 |
| 4 | phenethyl | i-propyl | phenyl | H | 484 |
| 5 | 3,5-diF-phenoxymethyl | cyclopentyl-methyl | phenyl | H | 562 |
| 6 | 3,5-diF-phenoxymethyl | i-butyl | phenyl | H | 536 |
| 7 | phenoxymethyl | cyclopentyl-methyl | phenyl | Cl | 560 |
| 8 | phenoxymethyl | i-butyl | 2-F-phenyl | Cl | 552 |
| 9 | cyclohexyl-oxymethyl | methyl | phenyl | H | 464 |
| 10 | cyclohexyl-oxymethyl | i-butyl | phenyl | H | 506 |
| 11 | phenoxymethyl | methyl | phenyl | Cl | 492 |
| 12 | phenoxymethyl | i-butyl | phenyl | Cl | 534 |
| 13 | cyclohexyl-oxymethyl | benzyl | phenyl | Cl | 574 |
| 14 | cyclohexyl-oxymethyl | cyclopentyl-methyl | phenyl | Cl | 566 |
| 15 | cyclohexyl-oxymethyl | i-butyl | phenyl | Cl | 540 |
| 16 | cyclohexyl-oxymethyl | i-propyl | phenyl | Cl | 526 |
| 17 | 4-CF$_3$-benzyl-oxymethyl | methoxy | phenyl | Cl | 590 |
| 18 | 2,4-diF-benzyl-oxymethyl | methyl | phenyl | Cl | 542 |
| 20 | benzyloxymethyl | vinyl | phenyl | Cl | 536 |
| 21 | cyclohexyl-oxymethyl | methyl | phenyl | Cl | 498 |
| 23 | phenethyl | i-butyl | phenyl | H | 498 |
| 24 | cyclopropyl | i-butyl | phenyl | H | 434 |
| 25a | n-butyl | i-butyl | phenyl | H | 450 |
| 25b | n-butyl | i-butyl | phenyl | H | 450 |
| 25c | n-butyl | i-butyl | phenyl | H | 450 |
| 26 | n-hexyl | i-butyl | phenyl | H | 478 |
| 27 | n-propyl | i-butyl | phenyl | H | 436 |
| 28 | benzyl | i-butyl | phenyl | H | 484 |
| 29 | phenethyl | methyl | phenyl | H | 442 |
| 30 | phenpropyl | methyl | phenyl | H | 470 |
| 31 | methyl | i-butyl | phenyl | H | 408 |
| 32 | n-pentyl | i-butyl | phenyl | H | 464 |
| 33 | n-butyl | methyl | phenyl | H | 408 |
| 34 | phenyl | methyl | phenyl | H | 428 |
| 35 | 2,2-dimethyl-propyl | methyl | phenyl | H | 422 |
| 36 | n-propyl | methyl | phenyl | H | 394 |
| 37 | 4-propoxyphenyl | methyl | phenyl | H | 486 |

25a: the chiral carbon of the benzodiazepine ring is racemic.
25b: the chiral carbon of the benzodiazepine ring is (R).
25c: the chiral carbon of the benzodiazepine ring is (S).

TABLE 2

| Ex. # | Q | Z—Y—X—W— |
|---|---|---|
| 38 | n-butyl | 3-phenoxybenzyl |
| 39 | 3,5-diF-phenethyl | 3-phenoxybenzyl |
| 40 | cyclopentylmethyl | 3-phenoxybenzyl |
| 41 | n-butyl | 5-bromo-3-pyridinyl |
| 118 | n-butyl | 3-(phenyl)amino-benzyl |
| 141 | n-butyl | 3-{[(4-Me-phenyl)sulfonyl]-amino}phenyl)methyl |

TABLE 3

| Ex. # | Q | R$^5$ | R$^{11}$ | R$^{13}$ |
|---|---|---|---|---|
| 42 | n-butyl | cyclopropylmethyl | 2-F-phenyl | H |
| 43 | n-butyl | cyclopropylmethyl | azapan-1-yl | H |
| 44 | 3,5-diF-phenethyl | cyclopropylmethyl | pyridin-2-yl | H |
| 45 | n-butyl | cyclopropylmethyl | 4-Cl-phenyl | H |
| 46 | n-butyl | cyclopropylmethyl | 3-F-phenyl | H |
| 47 | n-butyl | cyclopropylmethyl | 4-MeO-phenyl | H |
| 48 | cyclopentyl methyl | cyclopropylmethyl | phenyl | H |
| 49 | but-3-enyl | cyclopropylmethyl | phenyl | H |
| 50 | but-3-enyl | cyclopropylmethyl | 4-CF$_3$-phenyl | H |
| 51 | 2-(3,5-dimethyl isoxazol-4-yl)-ethyl | cyclopropylmethyl | phenyl | H |
| 52 | n-butyl | cyclopropylmethyl | phenyl | Cl |
| 53 | n-butyl | cyclopropylmethyl | pyridin-2-yl | H |
| 54 | n-butyl | cyclopropylmethyl | 4-F-phenyl | H |
| 55 | n-butyl | cyclopropylmethyl | 4-CF$_3$-phenyl | H |
| 56 | 2-cyclopentyl-ethyl | cyclopropylmethyl | pyridin-2-yl | H |
| 57 | n-butyl | i-butyl | 4-CF$_3$-phenyl | H |
| 58 | 2-(thiophen-2-yl)-ethyl | cyclopropylmethyl | phenyl | H |
| 59 | 2-(furan-2-yl)-ethyl | cyclopropylmethyl | phenyl | H |
| 60 | 2-cyclopentyl-ethyl | cyclopropylmethyl | 4-F-phenyl | H |
| 61 | 3,5-diF-phenethyl | cyclopropylmethyl | phenyl | H |
| 62 | n-butyl | cyclopropylmethyl | phenyl | H |
| 63 | n-butyl | thiophen-2-yl-methyl | phenyl | H |
| 64 | n-butyl | cyclopropylmethyl | phenyl | MeO |
| 65 | n-butyl | cyclobutylmethyl | phenyl | H |
| 66 | n-butyl | 3,5-diF-phenyl-methyl | phenyl | H |
| 67 | n-butyl | furan-2-yl-methyl | phenyl | H |
| 68 | phenethyl | cyclopropylmethyl | 4-F-phenyl | H |
| 69 | phenethyl | cyclopropylmethyl | pyridin-2-yl | H |

TABLE 3-continued

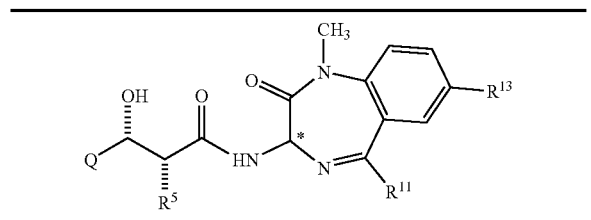

| Ex. # | Q | R⁵ | R¹¹ | R¹³ |
|---|---|---|---|---|
| 70 | n-butyl | i-butyl | 4-F-phenyl | H |
| 71 | phenethyl | cyclopropylmethyl | phenyl | H |
| 72 | 2-furan-2-yl-ethyl | cyclopropylmethyl | 4-CF₃-phenyl | H |
| 73 | 2-cyclopentyl-ethyl | cyclopropylmethyl | 4-CF₃-phenyl | H |
| 74 | n-pentyl | cyclopropylmethyl | 4-CF₃-phenyl | H |
| 75 | n-hexyl | cyclopropylmethyl | 4-CF₃-phenyl | H |
| 76 | n-butyl | cyclopropylmethyl | 4-CF₃-pyridin-2-yl | H |
| 77 | n-butyl | cyclobutylmethyl | 4-CF₃-phenyl | H |
| 78 | n-butyl | cyclopentylmethyl | 4-CF₃-phenyl | H |
| 79 | n-butyl | cyclopropylmethyl | 4-methyl-pyridin-2-yl | H |
| 80 | n-butyl | cyclopropylmethyl | 4-methyl-pyridin-2-yl | H |
| 81 | methyl | cyclopentylmethyl | 4-CF₃-phenyl | H |
| 82 | n-butyl | but-3-enyl | phenyl | H |
| 83 | n-butyl | 3-methyl-butyl | phenyl | H |
| 84 | n-butyl | ethyl | phenyl | H |
| 85 | n-butyl | propyl | phenyl | H |
| 86 | n-butyl | n-butyl | phenyl | H |
| 87 | 1-(S)-amino-phenethyl | methyl | 2-F-phenyl | Cl |
| 88 | 1-(S)-(BOC-NH)-phenethyl | methyl | 2-F-phenyl | Cl |
| 89 | N-BOC-pyrrolidin-2-(R)-yl | methyl | 2-F-phenyl | Cl |
| 90 | pyrrolidin-2-(R)-yl | methyl | 2-F-phenyl | Cl |
| 91 | benzyloxy-methyl | i-propyl | phenyl | Cl |
| 119 | n-butyl | cyclopropylmethyl | cyclopentyl | H |
| 120 | n-butyl | cyclopropylmethyl | beazyl | H |
| 122 | n-butyl | cyclopropylmethyl | cycloheptyl | H |
| 128 | n-butyl | cyclopropylmethyl | N,N-dibutyl-amino | H |
| 133 | n-butyl | i-butyl | homopiperidino | H |
| 134 | n-butyl | i-butyl | spiro-cyclo-pentyl | H |

TABLE 4

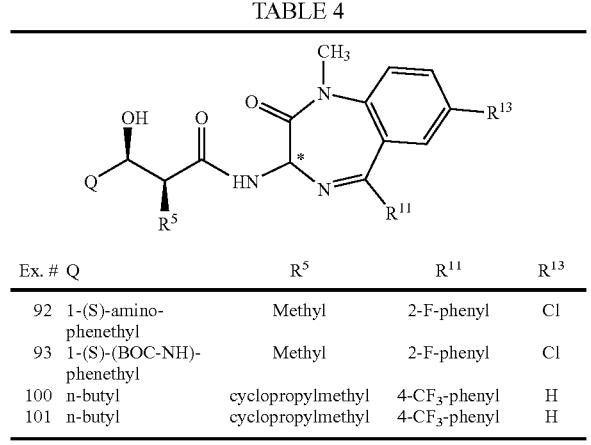

| Ex. # | Q | R⁵ | R¹¹ | R¹³ |
|---|---|---|---|---|
| 92 | 1-(S)-amino-phenethyl | Methyl | 2-F-phenyl | Cl |
| 93 | 1-(S)-(BOC-NH)-phenethyl | Methyl | 2-F-phenyl | Cl |
| 100 | n-butyl | cyclopropylmethyl | 4-CF₃-phenyl | H |
| 101 | n-butyl | cyclopropylmethyl | 4-CF₃-phenyl | H |

TABLE 5A

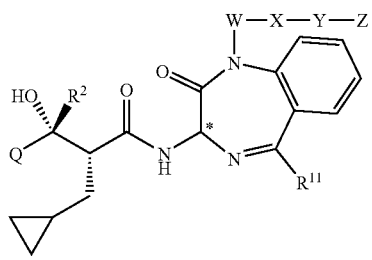

| Ex. # | Q | R² | Z—Y—X—W— | R¹¹ |
|---|---|---|---|---|
| 94 | n-butyl | H | methyl | thiazol-2-yl |
| 95 | n-butyl | H | cyclopropylmethyl | thiazol-2-yl |
| 96 | n-butyl | H | cyclopropylmethyl | 4-CF₃-phenyl |
| 97 | n-butyl | H | benzyl | 4-CF₃-phenyl |
| 98 | n-butyl | H | 3-phenoxy-benzyl | 4-CF₃-phenyl |
| 99 | n-butyl | H | 3-pyridinyl-methyl | 4-CF₃-phenyl |
| 105 | n-butyl | Me | methyl | 4-CF₃-phenyl |
| 106 | n-butyl | H | 3-phenoxy-benzyl | methyl |
| 107 | n-butyl | H | benzyl | methyl |
| 121 | n-butyl | H | n-butyl | benzyl |
| 123 | n-butyl | H | benzyl | cycloheptyl |
| 124 | n-butyl | H | n-butyl | cycloheptyl |
| 125 | n-butyl | H | 2-pyridinyl-methyl | 4-CF₃-phenyl |
| 126 | n-butyl | H | 3-pyridinyl-methyl | 2-F-phenyl |
| 129 | n-butyl | H | n-butyl | t-butyl |
| 130 | n-butyl | H | 2-oxo-3,3-dimethylbutyl | n-butyl |
| 131 | n-butyl | H | benzyl | t-butyl |
| 132 | n-butyl | H | 2-pyridinyl-methyl | n-butyl |
| 137 | n-butyl | H | n-butyl | i-propyl |
| 138 | n-butyl | H | benzyl | i-propyl |
| 139 | n-butyl | H | 3-{[(4-Me-phenyl)sulfonyl]amino}-phenyl)methyl | methyl |
| 140 | n-butyl | H | methyl | t-butyl |
| 145 | n-butyl | H | benzyl | 2,2-dimethylpropyl |
| 146 | n-butyl | H | n-butyl | n-butyl |
| 147 | n-butyl | H | benzyl | n-butyl |
| 148 | n-butyl | H | methyl | 3,4-dihydro-1H-isoquinolin-2-yl |
| 149 | n-butyl | H | methyl | 2,2-dimethylpropyl |
| 151 | n-butyl | H | 2-ethylbutyl | n-butyl |
| 152 | n-butyl | H | methyl | 1-pyrrolidinyl |
| 154 | n-butyl | H | 3-hydroxypropyl | t-butyl |
| 155 | n-butyl | H | methyl | ethoxy |
| 156 | n-butyl | H | n-butyl | 2,2-dimethylpropyl |
| 157 | n-butyl | H | N-oxide-2-pyridinylmethyl | 4-CF₃-phenyl |
| 158 | n-butyl | H | N-oxide-3-pyridinylmethyl | 4-CF₃-phenyl |
| 159 | ethyl | H | 3-pyridinylmethyl | 4-CF₃-phenyl |
| 160 | n-butyl | H | 2-(diethylamino)ethyl | 4-CF₃-phenyl |
| 161 | ethyl | H | N-oxide-3-pyridinylmethyl | phenyl |

TABLE 5B

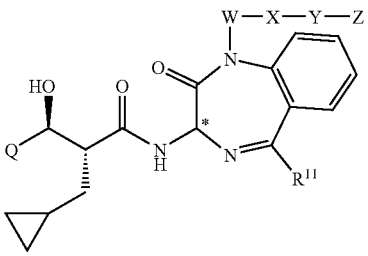

| Ex. # | Q | R² | Z—Y—X—W— | R—11 |
|---|---|---|---|---|
| 102 | n-butyl | H | methyl | 4-CF₃-phenyl |

TABLE 5C

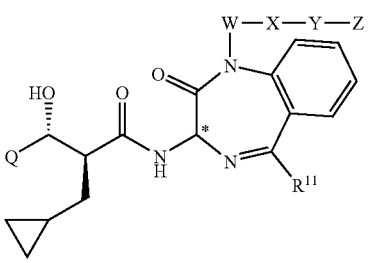

| Ex. # | Q | R² | Z—Y—X—W— | R¹¹ |
|---|---|---|---|---|
| 103 | n-butyl | H | methyl | 4-CF₃-phenyl |
| 104 | n-butyl | H | methyl | 4-CF₃-phenyl |
| 127 | ethyl | H | 3-pyridinyl-methyl | 4-CF₃-phenyl |

TABLE 5D

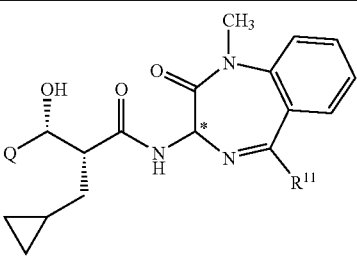

| Ex. # | Q | R¹¹ |
|---|---|---|
| 142 | n-butyl | 1-piperazinyl |
| 168 | n-butyl | 4-benzylpiperazin-1-yl |
| 169 | n-butyl | 4-methanesulfonyl-piperazin-1-yl |
| 170 | n-butyl | 4-methylpiperazin-1-yl |
| 171 | n-butyl | 4-acetylpiperazin-1-yl |
| 172 | n-butyl | 4-(3,5-dimethyl-isoxazole-4-sulfonyl)-piperazin-1-yl |
| 173 | n-butyl | 4-benzoylpiperazin-1-yl |
| 174 | n-butyl | 4-(t-butoxycarbonyl)-piperazin-1-yl |

TABLE 6

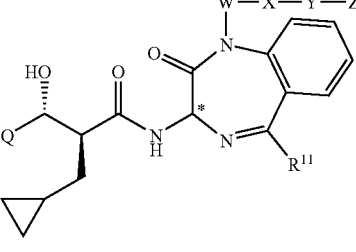

| Ex. # | R³ | Q | R⁵/R⁵ᵃ | R¹¹ | R¹³ |
|---|---|---|---|---|---|
| 108 | acetyl | n-butyl | R⁵ = i-butyl<br>R⁵ᵃ = H | 4-F-phenyl | H |
| 109 | methyl | 2-cyclopentyl ethyl | R⁵ = cyclopropyl methyl<br>R⁵ᵃ = H | phenyl | H |
| 113 | H | n-butyl | CR⁵R⁵ᵃ = 1,1-cyclohexyl | 4-F-phenyl | H |
| 162 | H | n-butyl | R⁵ = cyclopropyl methyl<br>R⁵ᵃ = H | methyl | Br |

TABLE 7

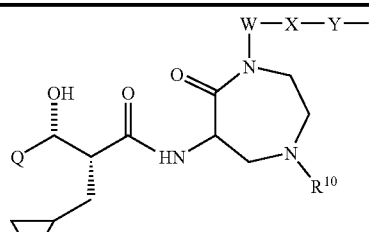

| Ex. # | Q | Z—Y—X—W— | R¹⁰ |
|---|---|---|---|
| 163 | n-butyl | benzyl | benzyl |
| 164 | n-butyl | benzyl | (4-chlorophenyl)sulfonyl |
| 165 | ethyl | benzyl | (4-chlorophenyl)sulfonyl |

TABLE 8

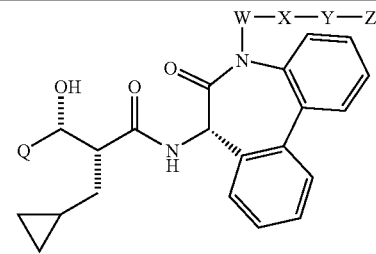

| Ex. # | Q | Z—Y—X—W— |
|---|---|---|
| 114 | n-butyl | methyl |
| 115 | n-pentyl | methyl |
| 116 | n-hexyl | methyl |
| 117 | 2-(furan-2-yl)-ethyl | methyl |
| 143 | n-butyl | 2-diethylaminoethyl |
| 144 | n-butyl | 3-hydroxypropyl |
| 150 | n-butyl | n-butyl |
| 153 | n-butyl | benzyl |

TABLE 9

W—X—Y—Z structure with OH, Q, cyclopropyl, and benzazepinone moieties

| Ex. # | Q | Z—Y—X—W— |
|---|---|---|
| 166 | n-butyl | (4-fluorophenoxy)benzyl |
| 167 | n-butyl | benzyl |

TABLE 10

W—X—Y—Z structure with OH, Q, cyclopropyl, N-oxide and R[11] substituent

| Ex. # | Q | Z—Y—X—W— | R[11] |
|---|---|---|---|
| 175 | n-butyl | N-oxide-3-pyridinylmethyl | 4-CF$_3$-phenyl |

UTILITY

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β amyloid precursor protein. Compounds that inhibit β or γsecretase activity, either directly or indirectly, control the production of Aβ. Such inhibition of β or γsecretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including PCT publication number WO 98/22493, EPO publication number 0652009, U.S. Pat. Nos. 5,703,129 and 5,593,846; all hereby incorporated by reference.

The compounds of the present invention have utility for the prevention and treatment of disorders involving Aβ production, such as cerebrovascular disorders.

Compounds of the present invention have been shown to inhibit Aβ production, as determined by the secretase inhibition assay described below.

Compounds of the present invention have been shown to inhibit Aβ production, utilizing the C-terminus β amyloid precursor protein accumulation assay described below.

Compounds of Formula (I) are expected to possess γ-secretase inhibitory activity. The γ-secretase inhibitory activity of the compounds of the present invention is demonstrated using assays for such activity, for example, using the assay described below. Compounds of the present invention have been shown to inhibit the activity of γ-secretase, as determined by the Aβ immunoprecipitation assay.

Compounds provided by this invention should also be useful as standards and reagents in determining the ability of a potential pharmaceutical to inhibit A, production. These would be provided in commercial kits comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetate.

A compound is considered to be active if it has an IC$_{50}$ or K$_i$ value of less than about 100 μM for the inhibition of Aβ production.

β Amyloid Precursor Protein Accumulation Assay

A novel assay to evaluate the accumulation of Aβ protein was developed to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation. Briefly, N 9 cells are grown to confluency in 6-well plates and washed twice with 1× Hank's buffered salt solution. The cells are starved in methionine/cysteine deficient media for 30 min, followed by replacement with fresh deficient media containing 150 uCi S35 Translabel (Amersham). Test compounds dissolved in DMSO (final concentration 1%) are added together with the addition of radiolabel. The cells are incubated for 4 h at 37° C. in a tissue culture incubator.

At the end of the incubation period, the conditioned medium is harvested and pre-cleared by the addition of 5 μl normal mouse serum and 50 ul of protein A Sepharose (Pharmacia), mixed by end-over-end rotation for 30 minutes at 4° C., followed by a brief centrifugation in a microfuge. The supernatant is then harvested and transferred to fresh tubes containing 5 ug of a monoclonal antibody (clone 1101.1; directed against an internal peptide sequence in Aβ) and 50 μl protein A Sepharose. After incubation overnight at 4° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli, 1970) and boiled for 3 minutes. The supernatant is then fractionated on either 10-20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound blocks Aβ accumulation in the conditioned medium, and is therefore considered active, with an IC$_{50}$ less than 100 μM.

C-Terminus β Amyloid Precursor Protein Accumulation Assay

The effect of test compounds on the accumulation of C-terminal fragments is determined by immunoprecipitation of APP and fragments thereof from cell lysates. N 9 cells are metabolically labeled as above in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% NaN$_3$). Again, lysates are precleared with 5 ul normal rabbit serum/ 50 ul protein A Sepharose, followed by the addition of BC-1 antiserum (15 µl) and 50 µl protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound stimulates C-terminal fragment accumulation in the cell lysates, and is therefore considered active, with an IC$_{50}$ less than 100 µM.

Aβ Immunoprecipitation Assay

This immunoprecipitation assay is specific for γ secretase (i.e., proteolytic activity required to generate the C-terminal end of Aβ either by direct cleavage or generating a C-terminal extended species which is subsequently further proteolyzed). N 9 cells are pulse labeled in the presence of a reported γ secretase inhibitor (MDL 28170) for 1 h, followed by washing to remove radiolabel and MDL 28170. The media is replaced and test compounds are added. The cells are chased for increasing periods of times and Aβ is isolated from the conditioned medium and C-terminal fragments from cell lysates (see above). The test compounds are characterized whether a stabilization of C-terminal fragments is observed and whether Aβ is generated from these accumulated precursor. A typical test compound prevents the generation of Aβ out of accumulated C-terminal fragments and is considered active with an IC$_{50}$ less than 100 µM.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing

What is claimed is:

1. A process for preparing a compound of formula (I)

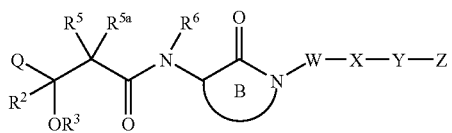

(I)

or a stereoisomer or pharmaceutically acceptable salt forms thereof, comprising a scheme of synthetic steps, wherein an oxazolidinone is acylated with an acid chloride ($R^5R^{5a}CH_2COCl$) followed by an asymmetric aldol reaction forming a chiral auxiliary structure, which upon cleavage forms a beta hydroxycarboxylic acid product

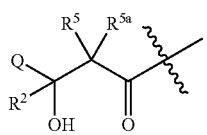

which can be coupled with a lactam ring structure B selected from:

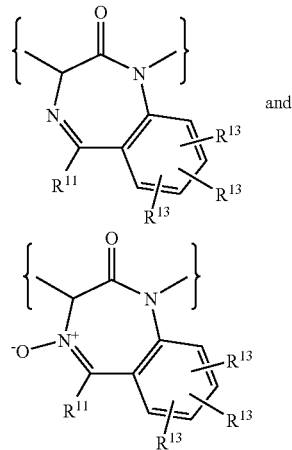

wherein:
Q is $Q^1$,
-($C_1$-$C_3$ alkylene)-O-$Q^1$,
-($C_1$-$C_3$ alkylene)-S-$Q^1$,
-($C_1$-$C_3$ alkylene)-S(=O)-$Q^1$,
-($C_1$-$C_3$ alkylene)-S(=O)$_2$-$Q^1$, or
-($C_1$-$C_3$ alkylene)-N($R^{20}$)-$Q^1$;

$Q^1$ is $C_1$-$C_8$ alkyl substituted with 0-3 $R^{1a}$;
$C_2$-$C_8$ alkenyl substituted with 0-3 $R^{1a}$;
$C_2$-$C_8$ alkynyl substituted with 0-3 $R^{1a}$;
$C_3$-$C_{10}$ cycloalkyl substituted with 0-3 $R^{1b}$;
$C_3$-$C_{10}$ carbocycle substituted with 0-3 $R^{1b}$;
aryl substituted with 0-3 $R^{1b}$; or
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1$-$C_6$ alkyl, $OR^{14}$, Cl, F, Br, I, $NR^{15}R^{16}$, $CF_3$;
$C_3$-$C_{10}$ carbocycle substituted with 0-3 $R^{1b}$;
aryl substituted with 0-3 $R^{1b}$; and
5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S— and ($C_1$-$C_6$ alkyl)-O—C(=O)—;

$R^2$ is H, methyl, ethyl, propyl, or butyl;
$R^3$ is H;
$R^5$ is H, $OR^{14}$;
$C_1$-$C_6$ alkyl substituted with 0-3 $R^{5b}$;
$C_1$-$C_6$ alkoxy substituted with 0-3 $R^{5b}$;
$C_2$-$C_6$ alkenyl substituted with 0-3 $R^{5b}$;
$C_2$-$C_6$ alkynyl substituted with 0-3 $R^{5b}$;
$C_3$-$C_{10}$ cycloalkyl substituted with 0-3 $R^{5c}$;
$C_3$-$C_{10}$ carbocycle substituted with 0-3 $R^{5c}$;
aryl substituted with 0-3 $R^{5c}$; or
5 to 10 membered heterocycle containing 1 to 4 heteroatoms selected from nitrogen, oxygen, and sulphur, wherein said 5 to 10 membered heterocycle is substituted with 0-3$R^{5c}$;

$R^{5a}$ is H, $C_1$-$C_4$ alkyl, or $C_2$-$C_4$ alkenyl;

alternatively, $R^5$ and $R^{5a}$ may be combined to form a 3-7 membered cycloalkyl ring substituted with 0-3 $R^{5c}$; optionally the cycloalkyl ring formed by combining $R^5$ and $R^{5a}$ may be benzo fused, wherein the benzo fused ring may be substituted with 0-3 $R^{5c}$;

$R^{5b}$, at each occurrence, is independently selected from:
  H, $C_1$-$C_6$ alkyl, $CF_3$, $OR^{14}$, Cl, F, Br, I, =O, CN, $NO_2$, $NR^{15}R^{16}$, acetyl, $SCH_3$, $S(=O)CH_3$, $S(=O)_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, $C_1$-$C_4$ haloalkyl-S—,
  $C_3$-$C_{10}$ cycloalkyl substituted with 0-3 $R^{5c}$;
  $C_3$-$C_{10}$ carbocycle substituted with 0-3 $R^{5c}$;
  aryl substituted with 0-3 $R^{5c}$; and
  5 to 7 membered heterocycle containing 1 to 4 heteroatoms selected from nitrogen, oxygen, and sulphur, wherein said 5 to 7 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^6$ is H or $C_1$-$C_6$ alkyl;

W is —$(CR^8R^{8a})_p$—;

p is 0, 1, 2, 3, or 4;

$R^8$ and $R^{8a}$, at each occurrence, are independently selected from H, F, $C_1$-$C_4$ alkyl, $C_2$-$C_4$ alkenyl, $C_2$-$C_4$ alkynyl and $C_3$-$C_8$ cycloalkyl;

X is a bond;
  aryl substituted with 0-3 $R^{Xb}$;
  $C_3$-$C_{10}$ cycloalkyl substituted with 0-3 $R^{Xb}$;
  $C_3$-$C_{10}$ carbocycle substituted with 0-3 $R^{Xb}$; or
  5 to 10 membered heterocycle substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Y is a bond or —$(CR^9R^{9a})_t$—V—$(CR^9R^{9a})_u$—;

t is 0, 1, 2, or 3;

u is 0, 1, 2, or 3;

$R^9$ and $R^{9a}$, at each occurrence, are independently selected from H, F, $C_1$-$C_6$ alkyl or $C_3$-$C_8$ cycloalkyl;

V is a bond, —C(=O)—, —O—, —S—, —S(=O)—, —S(=O)$_2$—, —N($R^{19}$)—, —C(=O)$NR^{19b}$—, —$NR^{19b}$C(=O)—, —$NR^{19b}$S(=O)$_2$—, —S(=O)$_2$$NR^{19b}$—, —C(=O)O—, or —OC(=O)—;

Z is H;
  $C_1$-$C_8$ alkyl substituted with 0-2 $R^{12}$;
  $C_2$-$C_4$ alkenyl substituted with 0-2 $R^{12}$;
  $C_2$-$C_4$ alkynyl substituted with 0-2 $R^{12}$;
  aryl substituted with 0-4 $R^{12b}$;
  $C_3$-$C_{10}$ carbocycle substituted with 0-4 $R^{12b}$; or
  5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{11}$ is selected from H,
  $C_1$-$C_4$ alkoxy, Cl, F, Br, I, CN, $NO_2$, $NR^{18}R^{19}$, C(=O)$R^{17}$, C(=O)$OR^{17}$, C(=O)$NR^{18}R^{19}$, S(=O)$_2$$NR^{18}R^{19}$, $CF_3$;
  $C_1$-$C_6$ alkyl substituted with 0-1 $R^{11a}$;
  aryl substituted with 0-3 $R^{11b}$;
  $C_3$-$C_{10}$ carbocycle substituted with 0-3 $R^{11b}$; or
  5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
  phenyl substituted with 0-3 $R^{11b}$;
  $C_3$-$C_{10}$ carbocycle substituted with 0-3 $R^{11b}$; or
  5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, benzyl, benzoyl, C(=O)$CH_3$, t-butoxycarbonyl, and 3,5-dimethyl-isoxazole-S(=O)$_2$—;

$R^{12}$ at each occurrence is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
  aryl substituted with 0-4 $R^{12b}$;
  $C_3$-$C_{10}$ carbocycle substituted with 0-4 $R^{12b}$; or
  5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$-$C_6$ alkyl, and $C_2$-$C_6$ alkoxyalkyl;

$R^{14a}$ is H, phenyl, benzyl, or $C_1$-$C_6$ alkyl;

$R^{15}$, at each occurrence, is independently selected from H, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

$R^{16}$, at each occurrence, is independently selected from H, OH, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperazinyl;

$R^{17}$ is H, $C_1$-$C_6$ alkyl, or $C_2$-$C_6$ alkoxyalkyl,
  aryl substituted by 0-4 $R^{17a}$, or
  aryl-$CH_2$— wherein said aryl is substituted by 0-4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(=O)CH_3$, $S(=O)_2CH_3$, —$NH_2$, —$N(CH_3)_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

alternatively, —$NR^{18}R^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 $R^{11b}$;

$R^{19}$, at each occurrence, is independently selected from H, OH, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

$R^{19b}$, at each occurrence, is independently selected from H and $C_1$-$C_6$ alkyl;

$R^{20}$ is H, OH, $C_1$-$C_4$ alkyl, phenyl, benzyl, or phenethyl;

$R^{21}$, at each occurrence, is independently selected from H, $C_1$-$C_6$ alkyl, phenyl, benzyl, and phenethyl; and $R^{22}$, at each occurrence, is independently selected from H, $C_1$-$C_6$ alkyl, phenyl, benzyl, and phenethyl.

2. A process according to claim 1, for preparing a compound of formula (Id)

or stereoisomer or pharmaceutically acceptable salt forms thereof, wherein:

Q is $Q^1$ or ($C_1$-$C_3$ alkyl)-O-$Q^1$;

$Q^1$ is $C_1$-$C_6$ alkyl substituted with 0-3 $R^{1a}$;
  $C_2$-$C_6$ alkenyl substituted with 0-3 $R^{1a}$;
  $C_2$-$C_6$ alkynyl substituted with 0-3 $R^{1a}$;
  $C_3$-$C_{10}$ cycloalkyl substituted with 0-3 $R^{1b}$;
  $C_3$-$C_{10}$ carbocycle substituted with 0-3 $R^{1b}$;
  aryl substituted with 0-3 $R^{1b}$; or
  5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1a}$, at each occurrence, is independently selected from H, $C_1$-$C_6$ alkyl, $OR^{14}$, Cl, F, Br, I, $NR^{15}R^{16}$, $CF_3$;
  $C_3$-$C_{10}$ carbocycle substituted with 0-3 $R^{1b}$;
  $C_6$-$C_{10}$ aryl substituted with 0-3 $R^{1b}$; and
  5 to 10 membered heterocycle containing 1 to 4 heteroatoms selected from nitrogen, oxygen, and sulphur, wherein said 5 to 10 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;

$R^2$ is H, methyl, or ethyl;

$R^5$ is H, $OR^{14}$;
  $C_1$-$C_6$ alkyl substituted with 0-3 $R^{5b}$;
  $C_2$-$C_6$ alkenyl substituted with 0-3 $R^{5b}$;
  $C_2$-$C_6$ alkynyl substituted with 0-3 $R^{5b}$;
  $C_3$-$C_6$ cycloalkyl substituted with 0-3 $R^{5c}$;
  $C_3$-$C_6$ carbocycle substituted with 0-3 $R^{5c}$;
  phenyl substituted with 0-3 $R^{5c}$; or
  5 to 7 membered heterocycle containing 1 to 4 heteroatoms selected from nitrogen, oxygen, and sulphur, wherein said 5 to 7 membered heterocycle is substituted with 0-3$R^{5c}$;

$R^{5a}$ is H, $C_1$-$C_4$ alkyl, or $C_2$-$C_4$ alkenyl;

alternatively, $R^5$ and $R^{5a}$ may be combined to form a $C_4$-$C_7$ cycloalkyl ring;

$R^{5b}$, at each occurrence, is independently selected from:
  H, $C_1$-$C_6$ alkyl, $CF_3$, $OR^{14}$, Cl, F, Br, I, =O, CN, $NO_2$, $NR^{15}R^{16}$, acetyl, $SCH_3$, $S(=O)CH_3$, $S(=O)_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, and $C_1$-$C_4$ haloalkyl-S—,
  $C_3$-$C_{10}$ cycloalkyl substituted with 0-3 $R^{5c}$;
  $C_3$-$C_{10}$ carbocycle substituted with 0-3 $R^{5c}$;
  $C_6$-$C_{10}$ aryl substituted with 0-3 $R^{5c}$; and
  5 to 10 membered heterocycle containing 1 to 4 heteroatoms selected from nitrogen, oxygen, and sulphur, wherein said 5 to 10 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

W is —$(CR^8R^{8a})_p$—;

p is 0, 1, or 2;

$R^8$ and $R^{8a}$, at each occurrence, are independently selected from H, methyl, and ethyl;

X is a bond;
  phenyl substituted with 0-3 $R^{Xb}$;
  $C_3$-$C_6$ cycloalkyl substituted with 0-3 $R^{Xb}$; or
  5 to 6 membered heterocycle containing 1 to 3 heteroatoms selected from nitrogen, oxygen, and sulphur, wherein said 5 to 6 membered heterocycle is substituted with 0-2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

Y is a bond or —$(CR^9R^{9a})_t$—V—$(CR^9R^{9a})_u$—;

t is 0, 1, or 2;

u is 0, 1, or 2;

$R^9$ and $R^{9a}$, at each occurrence, are independently selected from H, F, methyl, and ethyl;

V is a bond, —C(=O)—, —O—, —S—, —S(=O)—, —S(=O)$_2$—, —N($R^{19}$)—, —NHC(=O)—, or —C(=O)NH—;

Z is H, F, Cl, Br;
  $C_1$-$C_4$ alkyl substituted with 0-2 $R^{12}$;
  $C_2$-$C_4$ alkenyl substituted with 0-2 $R^{12}$;
  $C_2$-$C_4$ alkynyl substituted with 0-2 $R^{12}$;
  aryl substituted with 0-4 $R^{12b}$;
  $C_3$-$C_6$ carbocycle substituted with 0-4 $R^{12b}$; or
  5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{10}$ is $C(=O)R^{17}$, $C(=O)NR^{18}R^{19}$, $S(=O)_2R^{17}$;
  $C_1$-$C_6$ alkyl substituted with 0-2 $R^{10a}$;
  phenyl substituted with 0-3 $R^{10b}$; or
  5 to 6 membered heterocycle containing 1 to 4 heteroatoms selected from nitrogen, oxygen, and sulphur, wherein said 5 to 6 membered heterocycle is optionally substituted with 0-3 $R^{10b}$;

$R^{10a}$, at each occurrence, is independently selected from H, $C_1$-$C_6$ alkyl, $OR^{14}$, Cl, F, Br, I, =O, CN, $NO_2$, $NR^{15}R^{16}$, $CF_3$, or aryl substituted with 0-3 $R^{10b}$;

$R^{10b}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, $CF_3$, acetyl, $SCH_3$, $S(=O)CH_3$, $S(=O)_2$ CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

R$^{11}$, at each occurrence, is independently selected from H, =O, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;

C$_1$-C$_6$ alkyl substituted with 0-1 R$^{11a}$;

phenyl substituted with 0-3 R$^{11b}$;

C$_3$-C$_6$ carbocycle substituted with 0-3 R$^{11b}$; or 5 to 7 membered heterocycle containing 1 to 4 heteroatoms selected from nitrogen, oxygen, and sulphur, wherein said 5 to 7 membered heterocycle is substituted with 0-3 R$^{11b}$;

R$^{11a}$, at each occurrence, is independently selected from H, C$_1$-C$_4$ alkyl, OR$^{14}$, Cl, F, Br, =O, CN, NO$_2$, NR$^{15}$R$^{16}$, CF$_3$;

phenyl substituted with 0-3 R$^{11b}$;

C$_3$-C$_6$ carbocycle substituted with 0-3 R$^{11b}$; or 5 to 7 membered heterocycle containing 1 to 4 heteroatoms selected from nitrogen, oxygen, and sulphur, wherein said 5 to 7 membered heterocycle is substituted with 0-3 R$^{11b}$;

R$^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, C$_1$-C$_4$ haloalkyl-S—, benzyl, benzoyl, C(=O)CH$_3$, t-butoxycarbonyl, and 3,5-dimethyl-isoxazole-S(=O)$_2$—;

R$^{12}$ at each occurrence, is independently selected from H, OH, Cl, F, BR, I, CN, NR$^{15}$R$^{16}$, —C(=O)NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

aryl substituted with 0-4 R$^{12b}$;

C$_3$-C$_{10}$ carbocycle substituted with 0-4 R$^{12b}$;

5 to 10 membered heterocycle containing 1 to 4 heteroatoms selected from nitrogen, oxygen, and sulphur, wherein said 5 to 10 membered heterocycle is substituted with 0-3 R$^{12b}$;

R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

R$^{13}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, and CF$_3$;

R$^{14}$, at each occurrence, is independently selected from H, phenyl, benzyl, C$_1$-C$_6$ alkyl, and C$_2$-C$_6$ alkoxyalkyl;

R$^{15}$, at each occurrence, is independently selected from H, C$_1$-C$_6$ alkyl, phenyl, benzyl, phenethyl, (C$_1$-C$_6$ alkyl)-C(=O)—, (C$_1$-C$_6$ alkyl)-O—C(=O)— and (C$_1$-C$_6$ alkyl)-S(=O)$_2$—;

R$^{16}$, at each occurrence, is independently selected from H, OH, C$_1$-C$_6$ alkyl, phenyl, benzyl, phenethyl, (C$_1$-C$_6$ alkyl)-C(=O)—, (C$_1$-C$_6$ alkyl)-O—C(=O)— and (C$_1$-C$_6$ alkyl)-S(=O)$_2$—;

alternatively, —NR$^{15}$R$^{16}$ may be a heterocyclic ring selected from the group piperidinyl, morpholinyl, thiomorpholinyl, pyrrolidinyl, homopiperidinyl, piperazinyl, and N-methylpiperazinyl; and R$^{17}$ is H, C$_1$-C$_6$ alkyl, or C$_2$-C$_6$ alkoxyalkyl, aryl substituted by 0-4 R$^{17a}$, or aryl-CH$_2$— wherein said aryl is substituted by 0-4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(=O)CH$_3$, S(=O)$_2$CH$_3$, —NH$_2$, —N(CH$_3$)$_2$, or C$_1$-C$_4$ haloalkyl;

R$^{18}$, at each occurrence, is independently selected from H, C$_1$-C$_6$ alkyl, phenyl, benzyl, phenethyl, (C$_1$-C$_6$ alkyl)-C(=O)— and (C$_1$-C$_6$ alkyl)-S(=O)$_2$—;

R$^{19}$, at each occurrence, is independently selected from H, OH, methyl, ethyl, propyl, butyl, phenyl, benzyl, and phenethyl; and alternatively, —NR$^{18}$R$^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 R$^{11b}$—.

3. A process according to claim 1, for preparing a compound of formula (Id)

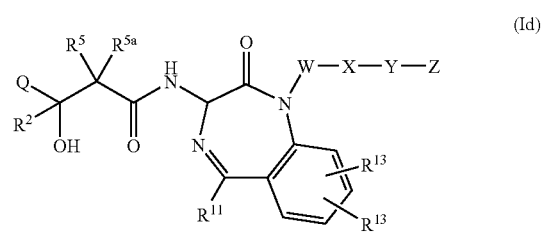

(Id)

or a stereoisomer or pharmaceutically acceptable salt forms thereof, wherein:

Q is Q$^1$;

Q$^1$ is C$_1$-C$_6$ alkyl substituted with 0-3 R$^{1a}$;

C$_2$-C$_6$ alkenyl substituted with 0-3 R$^{1a}$;

C$_2$-C$_6$ alkynyl substituted with 0-3 R$^{1a}$;

C$_3$-C$_{10}$ cycloalkyl substituted with 0-3 R$^{1b}$;

C$_3$-C$_{10}$ carbocycle substituted with 0-3 R$^{1b}$;

aryl substituted with 0-3 R$^{1b}$; or 5 to 10 membered heterocycle containing 1 to 4 heteroatoms selected from nitrogen, oxygen, and sulphur, wherein said 5 to 10 membered heterocycle is substituted with 0-3 R$^{1b}$;

R$^{1a}$, at each occurrence, is independently selected from H, C$_1$-C$_6$ alkyl, OR$^{14}$, Cl, F, Br, I, NR$^{15}$R$^{16}$, CF$_3$;

C$_3$-C$_{10}$ carbocycle substituted with 0-3 R$^{1b}$;

aryl substituted with 0-3 R$^{1b}$; and 5 to 10 membered heterocycle containing 1 to 4 heteroatoms selected from nitrogen, oxygen, and sulphur, wherein said 5 to 10 membered heterocycle is substituted with 0-3 R$^{1b}$;

R$^{1b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, C$_1$-C$_4$ haloalkyl-S—, and (C$_1$-C$_6$ alkyl)-O—C(=O)—;

R$^2$ is H, methyl, or ethyl;

R$^5$ is H, OR$^{14}$;

C$_1$-C$_6$ alkyl substituted with 0-3 R$^{5b}$;

C$_2$-C$_6$ alkenyl substituted with 0-3 R$^{5b}$; or

C$_2$-C$_6$ alkynyl substituted with 0-3 R$^{5b}$;

R$^{5a}$ is H, methyl, ethyl, propyl, butyl, or C$_2$-C$_4$ alkenyl;

alternatively, R$^5$ and R$^{5a}$ may be combined to form a C$_4$-C$_7$ cycloalkyl ring;

R$^{5b}$, at each occurrence, is independently selected from:

H, methyl, ethyl, propyl, butyl, CF$_3$, OR$^{14}$, Cl, F, Br, I, =O, NR$^{15}$R$^{16}$;

C$_3$-C$_7$ cycloalkyl substituted with 0-3 R$^{5c}$;

C$_3$-C$_7$ carbocycle substituted with 0-3 R$^{5c}$;

phenyl substituted with 0-3 R$^{5c}$; and 5 to 7 membered heterocycle containing 1 to 4 heteroatoms selected from nitrogen, oxygen, and sulphur, wherein said 5 to 7 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_4$ alkyl, $C_1$-$C_3$ alkoxy, $C_1$-$C_2$ haloalkyl, and $C_1$-$C_2$ haloalkoxy;

W is a bond;
X is a bond;

Y is a bond;
Z is H,
$C_1$-$C_4$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
aryl substituted with 0-4 $R^{12b}$;
5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{11}$ is selected from
H, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$-$C_6$ alkyl substituted with 0-1 $R^{11a}$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, =O, $NR^{15}R^{16}$, $CF_3$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, $C_1$-$C_2$ haloalkoxy, benzyl, benzoyl, $C(=O)CH_3$, t-butoxycarbonyl, and 3,5-dimethyl-isoxazole-$S(=O)_2$—;

$R^{12}$ at each occurrence, is independently selected from H, OH, Cl, F, Br, I, CN, $NO_2$, $NR^{15}R^{16}$, —$C(=O)NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$-$C_4$ alkyl, and $C_2$-$C_4$ alkoxyalkyl;

$R^{15}$, at each occurrence, is independently selected from H, methyl, ethyl, propyl, butyl, phenyl, benzyl, and phenethyl;

$R^{16}$, at each occurrence, is independently selected from H, OH, methyl, ethyl, propyl, butyl, phenyl, benzyl, phenethyl, $CH_3CH_2C(=O)$—, $CH_3C(=O)$—, $CH_3CH_2OC(=O)$—, $CH_3OC(=O)$—, $CH_3CH_2S(=O)_2$— and $CH_3S(=O)_2$—;

$R^{17}$ is H, $C_1$-$C_4$ alkyl, or $C_2$-$C_4$ alkoxyalkyl;
phenyl substituted by 0-2 $R^{17a}$; or
benzyl substituted by 0-2 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(=O)CH_3$, $S(=O)_2CH_3$, —$NH_2$, —$N(CH_3)_2$, or $C_1$-$C_4$ haloalkyl;

$R^{18}$, at each occurrence, is independently selected from H, methyl, ethyl, propyl, butyl, phenyl, benzyl, and phenethyl;

$R^{19}$, at each occurrence, is independently selected from H, OH, methyl, ethyl, propyl, and butyl; and alternatively, —$NR^{18}R^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 $R^{11b}$—.

4. A process according to claim 1, for preparing a compound of formula (Id)

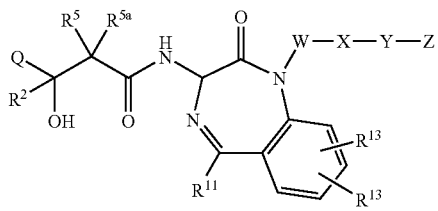

(Id)

or a stereoisomer or pharmaceutically acceptable forms thereof,
wherein:
Q is $Q^1$,
$Q^1$ is $C_1$-$C_6$ alkyl substituted with 0-3 $R^{1a}$;
  $C_2$-$C_6$ alkenyl substituted with 0-3 $R^{1a}$;
  $C_2$-$C_6$ alkynyl substituted with 0-3 $R^{1a}$;
  $C_3$-$C_6$ cycloalkyl substituted with 0-3 $R^{1b}$;
  phenyl substituted with 0-3 $R^{1b}$; or
  5 to 6 membered heterocycle containing 1 to 4 heteroatoms selected from nitrogen, oxygen, and sulphur, wherein said 5 to 6 membered heterocycle is substituted with 0-3 $R^{1b}$;
$R^{1a}$, at each occurrence, is independently selected from
  H, methyl, ethyl, propyl, butyl, $OR^{14}$, Cl, F, Br, I, $NR^{15}R^{16}$, $CF_3$;
  $C_3$-$C_6$ carbocycle substituted with 0-3 $R^{1b}$;
  phenyl substituted with 0-3 $R^{1b}$; and
  5 to 6 membered heterocycle containing 1 to 4 heteroatoms selected from nitrogen, oxygen, and sulphur, wherein said 5 to 6 membered heterocycle is substituted with 0-3 $R^{1b}$;
$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, $C_1$-$C_2$ haloalkoxy, (methyl)OC(=O)—, (ethyl)OC(=O)—, (propyl)OC(=O)—, and (butyl)OC(=O)—;
$R^2$ is H or methyl;
$R^5$ is H, $OR^{14}$;
  $C_1$-$C_4$ alkyl substituted with 0-1 $R^{5b}$;
  $C_2$-$C_4$ alkenyl substituted with 0-1 $R^{5b}$; or
  $C_2$-$C_4$ alkynyl substituted with 0-1 $R^{5b}$;
$R^{5a}$ is H, methyl, ethyl, propyl, or butyl;
alternatively, $R^5$ and $R^{5a}$ may be combined to form a cyclobutyl, cyclopentyl, cyclohexyl, or cycloheptyl ring;
$R^{5b}$, at each occurrence, is independently selected from:
  H, methyl, ethyl, propyl, butyl, $CF_3$, $OR^{14}$, Cl, F, =O, $NR^{15}R^{16}$,
  $C_3$-$C_7$ cycloalkyl substituted with 0-3 $R^{5c}$;
  $C_3$-$C_7$ carbocycle substituted with 0-3 $R^{5c}$;
  phenyl substituted with 0-3 $R^{5c}$; and
  5 to 7 membered heterocycle containing 1 to 4 heteroatoms selected from nitrogen, oxygen, and sulphur, wherein said 5 to 7 membered heterocycle is substituted with 0-3 $R^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
W is a bond;
X is a bond;
Y is a bond;
Z is H,
  $C_1$-$C_4$ alkyl substituted with 0-2 $R^{12}$;
  $C_2$-$C_4$ alkenyl substituted with 0-2 $R^{12}$;
  $C_2$-$C_4$ alkynyl substituted with 0-2 $R^{12}$;
  aryl substituted with 0-4 $R^{12b}$;
  $C_3$-$C_6$ carbocycle substituted with 0-4 $R^{12b}$; or
  5 to 6 membered heterocycle containing 1 to 4 heteroatoms selected from nitrogen, oxygen, and sulphur, wherein said 5 to 6 membered heterocycle is substituted with 0-3 $R^{12b}$;
$R^{11}$ is selected from
  H, $NR^{18}R^{19}$, $CF_3$;
  $C_1$-$C_4$ alkyl substituted with 0-1 $R^{11a}$;
  phenyl substituted with 0-3 $R^{11b}$;
  $C_3$-$C_6$ carbocycle substituted with 0-3 $R^{11b}$; or
  5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;
$R^{11a}$, at each occurrence, is independently selected from H, methyl, ethyl, propyl, butyl, methoxy, ethoxy, propoxy, Cl, F, =O, $NR^{15}R^{16}$, $CF_3$;
  phenyl substituted with 0-3 $R^{11b}$;
  $C_3$-$C_6$ carbocycle substituted with 0-3 $R^{11b}$; or
  5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;
$R^{12}$ at each occurrence, is independently selected from H, OH, Cl, F, Br, $NR^{15}R^{16}$, —C(=O)$NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
  phenyl substituted with 0-4 $R^{12b}$;
  $C_3$-$C_6$ carbocycle substituted with 0-4 $R^{12b}$; or
  5 to 6 membered heterocycle containing 1 to 4 heteroatoms selected from nitrogen, oxygen, and sulphur, wherein said 5 to 6 membered heterocycle is substituted with 0-3 $R^{12b}$;
$R^{12b}$, at each occurrence, is independently selected from H, OH, Cl, F, Br, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;
$R^{13}$, at each occurrence, is independently selected from H, OH, methyl, ethyl, propyl, butyl, methoxy, ethoxy, propoxy, Cl, F, Br, CN, $NR^{15}R^{16}$, and $CF_3$;
$R^{14}$, at each occurrence, is independently selected from H, phenyl, benzyl, methyl, ethyl, propyl, and butyl;

R$^{15}$, at each occurrence, is independently selected from H, methyl, ethyl, propyl, or butyl;

R$^{16}$, at each occurrence, is independently selected from H, OH, methyl, ethyl, propyl, butyl, phenyl, benzyl, and phenethyl;

R$^{18}$, at each occurrence, is independently selected from H, methyl, ethyl, propyl, butyl, phenyl, benzyl and, phenethyl; and R$^{19}$, at each occurrence, is independently selected from H, OH, methyl, ethyl, propyl, butyl, phenyl, benzyl and, phenethyl.

5. A process according to claim 1, for preparing a compound of formula (Id)

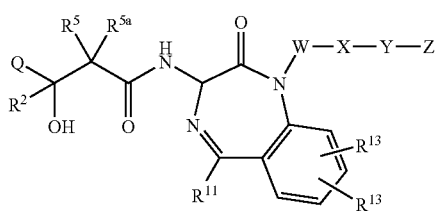

(Id)

or a stereoisomer or pharmaceutically acceptable salt forms thereof, wherein:

Q is —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH(CH$_3$)$_2$, —CH(CH$_3$)CH$_2$CH$_3$, —CH$_2$CH(CH$_3$)$_2$, —CH$_2$C(CH$_3$)$_3$, —CF$_3$, —CH$_2$CF$_3$, —CH$_2$CH$_2$CF$_3$, —CH$_2$CH$_2$CH$_2$CF$_3$,

—CH═CH$_2$, —CH$_2$CH═CH$_2$, —CH$_2$C(CH$_3$)═CH$_2$, —CH$_2$CH═C(CH$_3$)$_2$, —CH$_2$CH$_2$CH═CH$_2$, —CH$_2$CH$_2$C(CH$_3$)═CH$_2$, —CH$_2$CH$_2$CH═C(CH$_3$)$_2$, cis-CH$_2$CH═CH(CH$_3$), cis-CH$_2$CH$_2$CH═CH(CH$_3$), trans-CH$_2$CH═CH(CH$_3$), trans-CH$_2$CH$_2$CH═CH(CH$_3$);

—C≡CH, —CH$_2$C≡CH, —CH$_2$C≡C(CH$_3$), cyclopropyl-, cyclobutyl-, cyclopentyl-, cyclohexyl-, cyclopropyl-CH$_2$—, cyclobutyl-CH$_2$—, cyclopentyl-CH$_2$—, cyclohexyl-CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, phenyl-, 2-F-phenyl-, 3-F-phenyl-, 4-F-phenyl-, 4-methoxyphenyl-, 4-ethoxyphenyl-, 4-propoxyphenyl-, phenyl-CH$_2$—, (2-F-phenyl)CH$_2$—, (3-F-phenyl)CH$_2$—, (4-F-phenyl)CH$_2$—, (2-Cl-yl)CH$_2$—, (3-Cl-yl)CH$_2$—, (4-Cl-yl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-yl)CH$_2$—, (3-F-5-Cl-yl)CH$_2$—, (3-Cl-4-F-phenyl)CH$_2$—, 2-furanyl-CH$_2$—, 3-furanyl-CH$_2$—, 2-thienyl-CH$_2$—, 3-thienyl-CH$_2$—, 2-pyridyl-CH$_2$—, 3-pyridyl-CH$_2$—, 4-pyridyl-CH$_2$—, 1-imidazolyl-CH$_2$—, 2-oxazolyl-CH$_2$—, 4-oxazolyl-CH$_2$—, 5-oxazolyl-CH$_2$—, 3-isoxazolyl-CH$_2$—, 4-isoxazolyl-CH$_2$—, 5-isoxazolyl-CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, (2-Cl-yl)CH$_2$CH$_2$—, (3-Cl-yl)CH$_2$CH$_2$—, (4-Cl-yl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-yl)CH$_2$CH$_2$—, (3-F-5-Cl-yl)CH$_2$CH$_2$—;

furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, isoxazolyl-CH$_2$CH$_2$—, 3,5-dimethyl-isoxazol-4-yl-CH$_2$CH$_2$—, phenyl-propyl-;

benzyl-CH(NH$_2$)—, benzyl-CH(NHC(═O)—O-tBu)-, benzyloxy-CH$_2$—, pyrrolidin-2-yl-, or 3-t-butoxycarbonylpyrrolidin-2-yl-;

R$^2$ is H or methyl;

R$^5$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —CH$_2$C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$,

—CF$_3$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$, CH═CH$_2$, —CH$_2$CH═CH$_2$, —CH$_2$CH$_2$CH═CH$_2$, —CH═CHCH$_3$, cis-CH$_2$CH═CH(CH$_3$), trans-CH$_2$CH═CH(CH$_3$), trans-CH$_2$CH═CH(C$_6$H$_5$), —CH$_2$CH═C(CH$_3$)$_2$, cis-CH$_2$CH═CHCH$_2$CH$_3$, trans-CH$_2$CH═CHCH$_2$CH$_3$, cis-CH$_2$CH$_2$CH═CH(CH$_3$), trans-CH$_2$CH$_2$CH═CH(CH$_3$), trans-CH$_2$CH═CHCH$_2$(C$_6$H$_5$), —C≡CH, —CH$_2$C≡CH, —CH$_2$C≡C(CH$_3$), —CH$_2$C≡C(C$_6$H$_5$), —CH$_2$CH$_2$C≡CH, —CH$_2$CH$_2$C≡C(CH$_3$), —CH$_2$CH$_2$C≡C(C$_6$H$_5$), —CH$_2$CH$_2$CH$_2$C≡CH, —CH$_2$CH$_2$CH$_2$C≡C(CH$_3$), —CH$_2$CH$_2$CH$_2$C≡C(C$_6$H$_5$), cyclopropyl-CH$_2$—, cyclobutyl-CH$_2$—, cyclopentyl-CH$_2$—, cyclohexyl-CH$_2$—, (2-CH$_3$-cyclopropyl)CH$_2$—, (3-CH$_3$-cyclobutyl)CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, (2-CH$_3$-cyclopropyl)CH$_2$CH$_2$—, (3-CH$_3$-cyclobutyl)CH$_2$CH$_2$—, phenyl-CH$_2$—, (2-F-phenyl)CH$_2$—, (3-F-phenyl)CH$_2$—, (4-F-phenyl)CH$_2$—, (3,5-diF-phenyl)CH$_2$—, 2-furanyl-CH$_2$—, 3-furanyl-CH$_2$—, 2-thienyl-CH$_2$—, 3-thienyl-CH$_2$—, 2-pyridyl-CH$_2$—, 3-pyridyl-CH$_2$—, 4-pyridyl-CH$_2$—, 1-imidazolyl-CH$_2$—, 2-oxazolyl-CH$_2$—, 4-oxazolyl-CH$_2$—, 5-oxazolyl-CH$_2$—, 3-isoxazolyl-CH$_2$—, 4-isoxazolyl-CH$_2$—, 5-isoxazolyl-CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, isoxazolyl-CH$_2$CH$_2$—;

methoxy, ethoxy, propoxy, or butoxy;

R$^{5a}$ is H;

alternatively, R$^5$ and R$^{5a}$ may be combined to form cyclopentyl, cyclohexyl, or cycloheptyl;

W is a bond;

X is a bond;

Y is a bond;

Z is H, methyl, ethyl, n-propyl, i-propyl, n-butyl, i-butyl, s-butyl, t-butyl, cyclopropyl, cyclobutyl, cyclopentyl, cyclohexyl, phenyl, 2-F-phenyl, 3-F-phenyl, 4-F-phenyl, 2-Cl-yl, 3-Cl-yl, 4-Cl-yl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-yl, 3-F-5-Cl-yl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-$CF_3$O-phenyl, 3-$CF_3$O-phenyl, 4-$CF_3$O-phenyl, furanyl, thienyl, pyridyl, N-oxide-pyridinyl, 2-Me-pyridyl, 3-Me-pyridyl, 4-Me-pyridyl, 1-imidazolyl, oxazolyl, isoxazolyl, 1-benzimidazolyl, morpholino, N-piperidyl, phenyl-$CH_2$—, (2-F-phenyl)$CH_2$—, (3-F-phenyl)$CH_2$—, (4-F-phenyl)$CH_2$—, (2-Cl-yl)$CH_2$—, (3-Cl-yl)$CH_2$—, (4-Cl-yl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-yl)$CH_2$—, (3-F-5-Cl-yl)$CH_2$—, (3-Cl-4-F-phenyl)$CH_2$—, (2-MeO-phenyl)$CH_2$—, (3-MeO-phenyl)$CH_2$—, (4-MeO-phenyl)$CH_2$—, (2-PhO-phenyl)$CH_2$—, (3-PhO-phenyl)$CH_2$—, (4-PhO-phenyl)$CH_2$—, (2-Me-phenyl)$CH_2$—, (3-Me-phenyl)$CH_2$—, (4-Me-phenyl)$CH_2$—, (2-MeS-phenyl)$CH_2$—, (3-MeS-phenyl)$CH_2$—, 4-MeS-phenyl)$CH_2$—, (2-$CF_3$O-phenyl)$CH_2$—, (3-$CF_3$O-phenyl)$CH_2$—, (4-$CF_3$O-phenyl)$CH_2$—, (furanyl)$CH_2$—, (thienyl)$CH_2$—, (pyridyl)$CH_2$—, (2-Me-pyridyl)$CH_2$—, (3-Me-pyridyl)$CH_2$—, (4-Me-pyridyl)$CH_2$—, (1-imidazolyl)$CH_2$—, (oxazolyl)$CH_2$—, (isoxazolyl)$CH_2$—, (1-benzimidazolyl)$CH_2$—, (cyclopropyl)$CH_2$—, (cyclobutyl)$CH_2$—, (cyclopentyl)$CH_2$—, (cyclohexyl)$CH_2$—, (morpholino)$CH_2$—, (N-piperidinyl)$CH_2$—, phenyl-$CH_2CH_2$—, (phenyl)$_2$CH$CH_2$—, (2-F-phenyl)$CH_2CH_2$—, (3-F-phenyl)$CH_2CH_2$—, (4-F-phenyl)$CH_2CH_2$—, (2-Cl-yl)$CH_2CH_2$—, (3-Cl-yl)$CH_2CH_2$—, (4-Cl-yl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-yl)$CH_2CH_2$—, (3-F-5-Cl-yl)$CH_2CH_2$—, (3-Cl-4-F-phenyl)$CH_2CH_2$—, (2-MeO-phenyl)$CH_2CH_2$—, (3-MeO-phenyl)$CH_2CH_2$—, (4-MeO-phenyl)$CH_2CH_2$—, (2-Me-phenyl)$CH_2CH_2$—, (3-Me-phenyl)$CH_2CH_2$—, (4-Me-phenyl)$CH_2CH_2$—, (2-MeS-phenyl)$CH_2CH_2$—, (3-MeS-phenyl)$CH_2CH_2$—, (4-MeS-phenyl)$CH_2CH_2$—, (2-$CF_3$O-phenyl)$CH_2CH_2$—, (furanyl)$CH_2CH_2$—, (thienyl)$CH_2CH_2$—, (pyridyl)$CH_2CH_2$—, (2-Me-pyridyl)$CH_2CH_2$—, (3-Me-pyridyl)$CH_2CH_2$—, (4-Me-pyridyl)$CH_2CH_2$—, (imidazolyl)$CH_2CH_2$—, (oxazolyl)$CH_2CH_2$—, (isoxazolyl)$CH_2CH_2$—, (benzimidazolyl)$CH_2CH_2$, (cyclopropyl)$CH_2CH_2$—, (cyclobutyl)$CH_2CH_2$—, (cyclopentyl)$CH_2CH_2$—, (cyclohexyl)$CH_2CH_2$—, (morpholino)$CH_2CH_2$—, or (N-piperidinyl)$CH_2CH_2$—, $R^{11}$, at each occurrence, is independently selected from H, methyl, ethyl, n-propyl, i-propyl, n-butyl, i-butyl, s-butyl, phenyl, benzyl, phenethyl, cyclopropyl, cyclobutyl, cyclopentyl, cyclohexyl, cycloheptyl, cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, 2-F-phenyl, 3-F-phenyl, 4-F-phenyl, 4-Cl-yl, 4-$CH_3$-phenyl, 4-MeO-phenyl, 4-$CF_3$-phenyl, (4-F-phenyl)$CH_2$—, (4-Cl-yl)$CH_2$—, (4-$CH_3$-phenyl)$CH_2$—, (4-$CF_3$-phenyl)$CH_2$—, (4-F-phenyl)$CH_2CH_2$—, (4-Cl-yl)$CH_2CH_2$—, (4-$CH_3$-phenyl)$CH_2CH_2$—, (4-$CF_3$-phenyl)$CH_2CH_2$—, pyridin-2-yl-, pyridin-3-yl-, 4-$CF_3$-pyridin-2-yl-, 4-$CH_3$-pyridin-2-yl-, thiazol-2-yl-, azapan-1-yl, N,N-dimethylamino, N,N-diethylamino, N,N-dipropylamino, and N,N-dibutylamino; and $R^{13}$, at each occurrence, is independently selected from H, MeO, F, and Cl.

6. A process according to claim 1, for preparing a compound of formula (Ik)

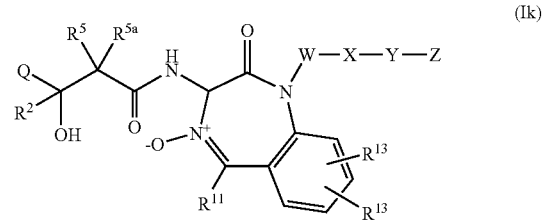

(Ik)

or a pharmaceutically acceptable salt form thereof, wherein

Q is $Q^1$, $Q^1$ is $C_1$-$C_6$ alkyl substituted with 0-3 $R^{1a}$;
  $C_2$-$C_6$ alkenyl substituted with 0-3 $R^{1a}$;
  $C_2$-$C_6$ alkynyl substituted with 0-3 $R^{1a}$;
  $C_3$-$C_6$ cycloalkyl substituted with 0-3 $R^{1b}$;
  phenyl substituted with 0-3 $R^{1b}$; or
  5 to 6 membered heterocycle containing 1 to 4 heteroatoms selected from nitrogen, oxygen, and sulphur, wherein said 5 to 6 membered heterocycle is substituted with 0-3 $R^{1b}$;

$R^{1a}$, at each occurrence, is independently selected from
  H, methyl, ethyl, propyl, butyl, $OR^{14}$, Cl, F, Br, I, $NR^{15}R^{16}$, $CF_3$;
  $C_3$-$C_6$ carbocycle substituted with 0-3 $R^{1b}$;
  phenyl substituted with 0-3 $R^{1b}$; and
  5 to 6 membered heterocycle containing 1 to 4 heteroatoms selected from nitrogen, oxygen, and sulphur, wherein said 5 to 6 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$-$C_2$ haloalkyl, $C_1$-$C_2$ haloalkoxy, (methyl)OC(=O)—, (ethyl)OC(=O)—, (propyl)OC(=O)—, and (butyl)OC(=O)—;

$R^2$ is H or methyl;

$R^5$ is H, $OR^{14}$;
  $C_1$-$C_4$ alkyl substituted with 0-1 $R^{5b}$;
  $C_2$-$C_4$ alkenyl substituted with 0-1 $R^{5b}$; or
  $C_2$-$C_4$ alkynyl substituted with 0-1 $R^{5b}$;

$R^{5a}$ is H, methyl, ethyl, propyl, or butyl;

alternatively, $R^5$ and $R^{5a}$ may be combined to form a cyclobutyl, cyclopentyl, cyclohexyl, or cycloheptyl ring;

$R^{5b}$, at each occurrence, is independently selected from:
H, methyl, ethyl, propyl, butyl, $CF_3$, $OR^{14}$, Cl, F, =O, $NR^{15}R^{16}$,
$C_3$-$C_7$ cycloalkyl substituted with 0-3 $R^{5c}$;
$C_3$-$C_7$ carbocycle substituted with 0-3 $R^{5c}$;
phenyl substituted with 0-3 $R^{5c}$; and
5 to 7 membered heterocycle containing 1 to 4 heteroatoms selected from nitrogen, oxygen, and sulphur, wherein said 5 to 7 membered heterocycle is substituted with 0-3 $R^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

W is a bond;
X is a bond;
Y is a bond;
Z is H,
$C_1$-$C_4$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
aryl substituted with 0-4 $R^{12b}$;
$C_3$-$C_6$ carbocycle substituted with 0-4 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{11}$ is selected from
H, $NR^{18}R^{19}$, $CF_3$;
$C_1$-$C_4$ alkyl substituted with 0-1 $R^{11a}$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein 5 to 7 membered heterocycle is substituted with 0-3 $R^{11b}$; wherein 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, =O, $NR^{15}R^{16}$, $CF_3$;
phenyl substituted with 0-3 $R^{11b}$;
$C_3$-$C_6$ carbocycle substituted with 0-3 $R^{11b}$;
5 to 7 membered heterocycle containing 1 to 4 heteroatoms selected from nitrogen, oxygen, and sulphur, wherein 5 to 7 membered heterocycle is substituted with 0-3 $R^{11b}$; wherein 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

$R^{12}$, at each occurrence, is independently selected from H, OH, Cl, F, Br, $NR^{15}R^{16}$, $-C(=O)NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

phenyl substituted with 0-4 $R^{12b}$;
$C_3$-$C_6$ carbocycle substituted with 0-4 $R^{12b}$; or
5 to 7 membered heterocycle containing 1 to 4 heteroatoms selected from nitrogen, oxygen, and sulphur, wherein 5 to 7 membered heterocycle is substituted with 0-3 $R^{12b}$;

$R^{12b}$, at each occurrence, is independently selected from H, OH, Cl, F, Br, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

$R^{13}$, at each occurrence, is independently selected from H, OH, methyl, ethyl, propyl, butyl, methoxy, ethoxy, propoxy, Cl, F, Br, CN, $NR^{15}R^{16}$, and $CF_3$;

$R^{14}$, at each occurrence, is independently selected from H, phenyl, benzyl, methyl, ethyl, propyl, and butyl;

$R^{15}$, at each occurrence, is independently selected from H, methyl, ethyl, propyl, or butyl;

$R^{16}$, at each occurrence, is independently selected from H, OH, methyl, ethyl, propyl, butyl, phenyl, benzyl, and phenethyl;

$R^{18}$, at each occurrence, is independently selected from H, methyl, ethyl, propyl, butyl, phenyl, benzyl and, phenethyl; and $R^{19}$, at each occurrence, is independently selected from H, OH, methyl, ethyl, propyl, butyl, phenyl, benzyl and, phenethyl.

7. A process according to claim 1, for preparing a compound of formula (Ig),

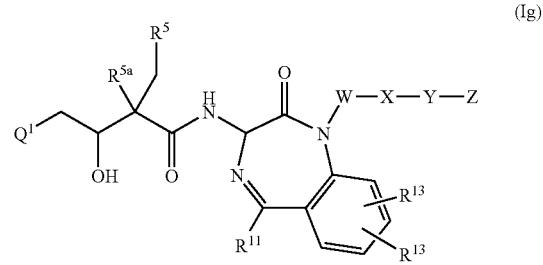

(Ig)

or a stereoisomer or pharmaceutically acceptable salt forms thereof, comprising a step of coupling

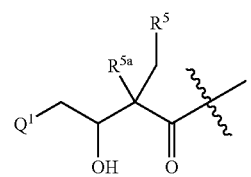

with lactam ring B structure selected from

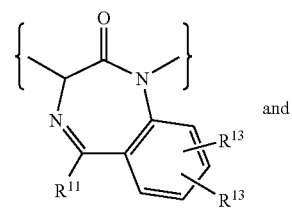

and

-continued

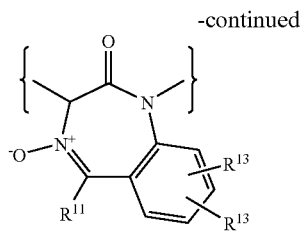

wherein:
Q$^1$ is C$_1$-C$_6$ alkyl substituted with 0-3 R$^{1a}$;
C$_2$-C$_6$ alkenyl substituted with 0-3 R$^{1a}$;
C$_2$-C$_6$ alkynyl substituted with 0-3 R$^{1a}$;
C$_3$-C$_{10}$ cycloalkyl substituted with 0-3 R$^{1b}$;
C$_3$-C$_{10}$ carbocycle substituted with 0-3 R$^{1b}$;
aryl substituted with 0-3 R$^{1b}$; or
5 to 10 membered heterocycle containing 1 to 4 heteroatoms selected from nitrogen, oxygen, and sulphur, wherein said 5 to 10 membered heterocycle is substituted with 0-3 R$^{1b}$;
R$^{1a}$, at each occurrence, is independently selected from H, C$_1$-C$_6$ alkyl, OR$^{14}$, Cl, F, Br, I, NR$^{15}$R$^{16}$, CF$_3$;
C$_3$-C$_{10}$ carbocycle substituted with 0-3 R$^{1b}$;
aryl substituted with 0-3 R$^{1b}$; and
5 to 10 membered heterocycle containing 1 to 4 heteroatoms selected from nitrogen, oxygen, and sulphur, wherein said 5 to 10 membered heterocycle is substituted with 0-3 R$^{1b}$;
R$^{1b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, C$_1$-C$_4$ haloalkyl-S—, and (C$_1$-C$_6$ alkyl)-O—C(=O)—;
R$^2$ is H, methyl, or ethyl;
R$^5$ is H, OR$^{14}$;
C$_1$-C$_6$ alkyl substituted with 0-3 R$^{5b}$;
C$_2$-C$_6$ alkenyl substituted with 0-3 R$^{5b}$;
C$_2$-C$_6$ alkynyl substituted with 0-3 R$^{5b}$;
C$_3$-C$_6$ cycloalkyl substituted with 0-3 R$^{5c}$;
C$_3$-C$_6$ carbocycle substituted with 0-3 R$^{5c}$;
phenyl substituted with 0-3 R$^{5c}$; or
5 to 7 membered heterocycle containing 1 to 4 heteroatoms selected from nitrogen, oxygen, and sulphur, wherein said 5 to 7 membered heterocycle is substituted with 0-3R$^{5c}$;
R$^{5a}$ is H, C$_1$-C$_4$ alkyl, or C$_2$-C$_4$ alkenyl;
alternatively, R$^5$ and R$^{5a}$ may be combined to form a C$_4$-C$_7$ cycloalkyl ring;
R$^{5b}$, at each occurrence, is independently selected from:
H, C$_1$-C$_6$ alkyl, CF$_3$, OR$^{14}$, Cl, F, Br, I, =O, CN, NO$_2$, NR$^{15}$R$^{16}$, acetyl, SCH$_3$, S(=O)CH$_3$, S(=O)$_2$CH$_3$, C$_2$-C$_6$ alkenyl, C$_2$-C$_6$ alkynyl, C$_1$-C$_4$ alkoxy, C$_1$-C$_4$ haloalkyl, C$_1$-C$_4$ haloalkoxy, and C$_1$-C$_4$ haloalkyl-S—,
C$_3$-C$_{10}$ cycloalkyl substituted with 0-3 R$^{5c}$;
C$_3$-C$_{10}$ carbocycle substituted with 0-3 R$^{5c}$;
aryl substituted with 0-3 R$^{5c}$; and
5 to 10 membered heterocycle containing 1 to 4 heteroatoms selected from nitrogen, oxygen, and sulphur, wherein said 5 to 10 membered heterocycle is substituted with 0-3 R$^{5c}$;
R$^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;
W is a bond;
X is a bond;
Y is a bond;
Z is H,
C$_1$-C$_4$ alkyl substituted with 0-2 R$^{12}$;
C$_2$-C$_4$ alkenyl substituted with 0-2 R$^{12}$;
C$_2$-C$_4$ alkynyl substituted with 0-2 R$^{12}$;
aryl substituted with 0-4 R$^{12b}$;
C$_3$-C$_6$ carbocycle substituted with 0-4 R$^{12b}$; or
5 to 6 membered heterocycle containing 1 to 4 heteroatoms selected from nitrogen, oxygen, and sulphur, wherein said 5 to 6 membered heterocycle is substituted with 0-3 R$^{12b}$;
R$^{11}$ is selected from
H, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$-C$_6$ alkyl substituted with 0-1 R$^{11a}$;
phenyl substituted with 0-3 R$^{11b}$;
C$_3$-C$_6$ carbocycle substituted with 0-3 R$^{11b}$; or
5 to 7 membered heterocycle containing 1 to 4 heteroatoms selected from nitrogen, oxygen, and sulphur, wherein said 5 to 7 membered heterocycle is substituted with 0-3 R$^{11b}$;
R$^{11a}$, at each occurrence, is independently selected from H, C$_1$-C$_4$ alkyl, OR$^{14}$, Cl, F, Br, =O, CN, NO$_2$, NR$^{15}$R$^{16}$, CF$_3$;
phenyl substituted with 0-3 R$^{11b}$;
C$_3$-C$_6$ carbocycle substituted with 0-3 R$^{11b}$; or
5 to 7 membered heterocycle containing 1 to 4 heteroatoms selected from nitrogen, oxygen, and sulphur, wherein said 5 to 7 membered heterocycle is substituted with 0-3 R$^{11b}$;
R$^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, C$_1$-C$_4$ haloalkyl-S—, benzyl, benzoyl, C(=O)CH$_3$, t-butoxycarbonyl, and 3,5-dimethyl-isoxazole-S(=O)$_2$—;
R$^{12}$ at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;
aryl substituted with 0-4 R$^{12b}$;
C$_3$-C$_{10}$ carbocycle substituted with 0-4 R$^{12b}$; or
5 to 10 membered heterocycle containing 1 to 4 heteroatoms selected from nitrogen, oxygen, and sulphur, wherein said 5 to 10 membered heterocycle is substituted with 0-3 R$^{12b}$;
R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;
R$^{13}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, and CF$_3$;
R$^{14}$, at each occurrence, is independently selected from H, phenyl, benzyl, C$_1$-C$_6$ alkyl, and C$_2$-C$_6$ alkoxyalkyl;
R$^{15}$, at each occurrence, is independently selected from H, C$_1$-C$_6$ alkyl, phenyl, benzyl, phenethyl, (C$_1$-C$_6$ alkyl)-C(=O)—, (C$_1$-C$_6$ alkyl)-O—C(=O)— and (C$_1$-C$_6$ alkyl)-S(=O)$_2$—;

R$^{16}$, at each occurrence, is independently selected from H, OH, C$_1$-C$_6$ alkyl, phenyl, benzyl, phenethyl, (C$_1$-C$_6$ alkyl)-C(=O)—, (C$_1$-C$_6$ alkyl)-O—C(=O)— and (C$_1$-C$_6$ alkyl)-S(=O)$_2$—;

alternatively, —NR$^{15}$R$^{16}$ may be a heterocyclic ring selected from the group piperidinyl, morpholinyl, thiomorpholinyl, pyrrolidinyl, homopiperidinyl, piperazinyl, and N-methylpiperazinyl; and R$^{17}$ is H, C$_1$-C$_6$ alkyl, or C$_2$-C$_6$ alkoxyalkyl,
aryl substituted by 0-4 R$^{17a}$, or
aryl-CH$_2$— wherein said aryl is substituted by 0-4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(=O)CH$_3$, S(=O)$_2$CH$_3$, —NH$_2$, —N(CH$_3$)$_2$, or C$_1$-C$_4$ haloalkyl;

R$^{18}$, at each occurrence, is independently selected from H, C$_1$-C$_6$ alkyl, phenyl, benzyl, phenethyl, (C$_1$-C$_6$ alkyl)-C(=O)— and (C$_1$-C$_6$ alkyl)-S(=O)$_2$—;

R$^{19}$, at each occurrence, is independently selected from H, OH, methyl, ethyl, propyl, butyl, phenyl, benzyl, and phenethyl; and alternatively, —NR$^{18}$R$^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 R$^{11b}$—.

8. A process according to claim 7, for preparing a compound of formula (Ig)

(Ig)

or a stereoisomer or pharmaceutically acceptable salt forms thereof,
wherein:

Q$^1$ is C$_1$-C$_6$ alkyl substituted with 0-3 R$^{1a}$;
C$_2$-C$_6$ alkenyl substituted with 0-3 R$^{1a}$;
C$_2$-C$_6$ alkynyl substituted with 0-3 R$^{1a}$;
C$_3$-C$_{10}$ cycloalkyl substituted with 0-3 R$^{1b}$;
C$_3$-C$_{10}$ carbocycle substituted with 0-3 R$^{1b}$;
aryl substituted with 0-3 R$^{1b}$; or
5 to 10 membered heterocycle containing 1 to 4 heteroatoms selected from nitrogen, oxygen, and sulphur, wherein said 5 to 10 membered heterocycle is substituted with 0-3 R$^{1b}$;

R$^{1a}$, at each occurrence, is independently selected from H, C$_1$-C$_6$ alkyl, OR$^{14}$, Cl, F, Br, I, NR$^{15}$R$^{16}$, CF$_3$;
C$_3$-C$_{10}$ carbocycle substituted with 0-3 R$^{1b}$;
aryl substituted with 0-3 R$^{1b}$; and
5 to 10 membered heterocycle containing 1 to 4 heteroatoms selected from nitrogen, oxygen, and sulphur, wherein said 5 to 10 membered heterocycle is substituted with 0-3 R$^{1b}$;

R$^{1b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, C$_1$-C$_4$ haloalkyl-S—, and (C$_1$-C$_6$ alkyl)-O—C(=O)—;

R$^2$ is H, methyl, or ethyl;

R$^5$ is H, OR$^{14}$,
C$_1$-C$_6$ alkyl substituted with 0-3 R$^{5b}$;
C$_1$-C$_6$ alkoxy substituted with 0-3 R$^{5b}$;
C$_2$-C$_6$ alkenyl substituted with 0-3 R$^{5b}$;
C$_2$-C$_6$ alkynyl substituted with 0-3 R$^{5b}$;
C$_3$-C$_{10}$ cycloalkyl substituted with 0-3 R$^{5c}$;
C$_3$-C$_{10}$ carbocycle substituted with 0-3 R$^{5c}$;
aryl substituted with 0-3 R$^{5c}$; or
5 to 10 membered heterocycle containing 1 to 4 heteroatoms selected from nitrogen, oxygen, and sulphur, wherein said 5 to 10 membered heterocycle is substituted with 0-3 R$^{5c}$;

R$^{5a}$ is H, C$_1$-C$_4$ alkyl, or C$_2$-C$_4$ alkenyl;

alternatively, R$^5$ and R$^{5a}$ may be combined to form a 3-7 membered cycloalkyl ring substituted with 0-3 R$^{5c}$;

R$^{5b}$, at each occurrence, is independently selected from:
H, C$_1$-C$_6$ alkyl, CF$_3$, OR$^{14}$, Cl, F, Br, I, =O, CN, NO$_2$, NR$^{15}$R$^{16}$, acetyl, SCH$_3$, S(=O)CH$_3$, S(=O)$_2$CH$_3$, C$_2$-C$_6$ alkenyl, C$_2$-C$_6$ alkynyl, C$_1$-C$_4$ alkoxy, C$_1$-C$_4$ haloalkyl, C$_1$-C$_4$ haloalkoxy, and C$_1$-C$_4$ haloalkyl-S—,
C$_3$-C$_{10}$ cycloalkyl substituted with 0-3 R$^{5c}$;
C$_3$-C$_{10}$ carbocycle substituted with 0-3 R$^{5c}$;
aryl substituted with 0-3 R$^{5c}$; and
5 to 10 membered heterocycle containing 1 to 4 heteroatoms selected from nitrogen, oxygen, and sulphur, wherein said 5 to 10 membered heterocycle is substituted with 0-3 R$^{5c}$;

R$^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

W is —(CR$^8$R$^{8a}$)$_p$—;

p is 0, 1, or 2;

R$^8$ and R$^{8a}$, at each occurrence, are independently selected from H, F, methyl, and ethyl;

X is a bond;

; or

-continued

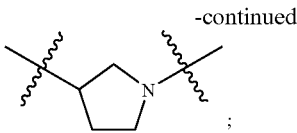

Y is a bond or —(CR$^9$R$^{9a}$)$_t$—V—(CR$^9$R$^{9a}$)$_u$—;
t is 0, 1, or 2;
u is 0, 1, or 2;
R$^9$ and R$^{9a}$, at each occurrence, are independently selected from H, F, methyl, and ethyl;
V is a bond, —C(=O)—, —O—, —S—, —S(=O)—, —S(=O)$_2$—, —N(R$^{19}$)—, —C(=O)NH—, or —NHC(=O)—;
C$_1$-C$_4$ alkyl substituted with 0-2 R$^{12}$;
C$_2$-C$_4$ alkenyl substituted with 0-2 R$^{12}$;
C$_2$-C$_4$ alkynyl substituted with 0-2 R$^{12}$;
aryl substituted with 0-4 R$^{12b}$;
C$_3$-C$_6$ carbocycle substituted with 0-4 R$^{12b}$; or
5 to 6 membered heterocycle containing 1 to 4 heteroatoms selected from nitrogen, oxygen, and sulphur, wherein said 5 to 6 membered heterocycle is substituted with 0-3 R$^{12b}$;
R$^{11}$ is selected from H,
C$_1$-C$_4$ alkoxy, Cl, F, Br, I, CN, NO$_2$, NR$^{18}$R$^{19}$, C(=O)R$^{17}$, C(=O)OR$^7$, C(=O)NR$^{18}$R$^{19}$, S(=O)$_2$NR$^{18}$R$^{19}$, CF$_3$;
C$_1$-C$_6$ alkyl substituted with 0-1 R$^{11a}$;
aryl substituted with 0-3 R$^{11b}$;
C$_3$-C$_{10}$ carbocycle substituted with 0-3 R$^{11b}$; or
5 to 10 membered heterocycle containing 1 to 4 heteroatoms selected from nitrogen, oxygen, and sulphur, wherein said 5 to 10 membered heterocycle is substituted with 0-3 R$^{11b}$;
R$^{11a}$, at each occurrence, is independently selected from H, C$_1$-C$_6$ alkyl, OR$^{14}$, Cl, F, Br, I, =O, CN, NO$_2$, NR$^{15}$R$^{16}$, CF$_3$;
phenyl substituted with 0-3 R$^{11b}$;
C$_3$-C$_{10}$ carbocycle substituted with 0-3 R$^{11b}$; or
5 to 10 membered heterocycle containing 1 to 4 heteroatoms selected from nitrogen, oxygen, and sulphur, wherein said 5 to 10 membered heterocycle is substituted with 0-3 R$^{11b}$;
R$^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, C$_1$-C$_4$ haloalkyl-S—, benzyl, benzoyl, C(=O)CH$_3$, t-butoxycarbonyl, and 3,5-dimethyl-isoxazole-S(=O)$_2$—;
R$^{12}$ at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;
aryl substituted with 0-4 R$^{12b}$;
C$_3$-C$_{10}$ carbocycle substituted with 0-4 R$^{12b}$; or
5 to 10 membered heterocycle containing 1 to 4 heteroatoms selected from nitrogen, oxygen, and sulphur, wherein said 5 to 10 membered heterocycle is substituted with 0-3 R$^{12b}$;
R$^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;
R$^{13}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, and CF$_3$;

R$^{14}$, at each occurrence, is independently selected from H, phenyl, benzyl, C$_1$-C$_6$ alkyl, and C$_2$-C$_6$ alkoxyalkyl;
R$^{15}$, at each occurrence, is independently selected from H, C$_1$-C$_6$ alkyl, phenyl, benzyl, phenethyl, (C$_1$-C$_6$ alkyl)-C(=O)—, (C$_1$-C$_6$ alkyl)-O—C(=O)— and (C$_1$-C$_6$ alkyl)-S(=O)$_2$—;
R$^{16}$, at each occurrence, is independently selected from H, OH, C$_1$-C$_6$ alkyl, phenyl, benzyl, phenethyl, (C$_1$-C$_6$ alkyl)-C(=O)—, (C$_1$-C$_6$ alkyl)-O—C(=O)— and (C$_1$-C$_6$ alkyl)-S(=O)$_2$—;
alternatively, —NR$^{15}$R$^{16}$ may be a heterocyclic ring selected from the group piperidinyl, morpholinyl, thiomorpholinyl, pyrrolidinyl, homopiperidinyl, piperazinyl, and N-methylpiperazinyl;
R$^{17}$ is H, C$_1$-C$_6$ alkyl, or C$_2$-C$_6$ alkoxyalkyl,
aryl substituted by 0-4 R$^{17a}$, or
aryl-CH$_2$— wherein said aryl is substituted by 0-4 R$^{17a}$;
R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(=O)CH$_3$, S(=O)$_2$CH$_3$, —NH$_2$, —N(CH$_3$)$_2$, or C$_1$-C$_4$ haloalkyl;
R$^{18}$, at each occurrence, is independently selected from H, C$_1$-C$_6$ alkyl, phenyl, benzyl, phenethyl, (C$_1$-C$_6$ alkyl)-C(=O)— and (C$_1$-C$_6$ alkyl)-S(=O)$_2$—;
R$^{19}$, at each occurrence, is independently selected from H, OH, C$_1$-C$_6$ alkyl, phenyl, benzyl, phenethyl, (C$_1$-C$_6$ alkyl)-C(=O)— and (C$_1$-C$_6$ alkyl)-S(=O)$_2$—;
alternatively, —NR$^{18}$R$^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 R$^{11b}$; and
R$^{20}$ is H, OH, C$_1$-C$_4$ alkyl, phenyl, benzyl, or phenethyl.

9. A process according to claim 7, for preparing a compound of formula (Ig)

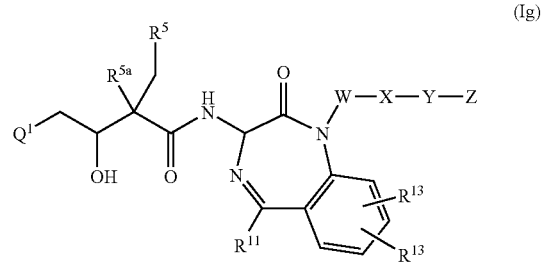

or a stereoisomer or pharmaceutically acceptable salt forms thereof,
wherein:
Q$^1$ is C$_1$-C$_6$ alkyl substituted with 0-3 R$^{1a}$;
C$_2$-C$_6$ alkenyl substituted with 0-3 R$^{1a}$;
C$_2$-C$_6$ alkynyl substituted with 0-3 R$^{1a}$;
C$_3$-C$_{10}$ cycloalkyl substituted with 0-3 R$^{1b}$;
C$_3$-C$_{10}$ carbocycle substituted with 0-3 R$^{1b}$;
aryl substituted with 0-3 R$^{1b}$; or
5 to 10 membered heterocycle containing 1 to 4 heteroatoms selected from nitrogen, oxygen, and sulphur, wherein said 5 to 10 membered heterocycle is substituted with 0-3 R$^{1b}$;
R$^{1a}$, at each occurrence, is independently selected from H, C$_1$-C$_6$ alkyl, OR$^{14}$, Cl, F, Br, I, NR$^{15}$R$^{16}$, CF$_3$;
C$_3$-C$_{10}$ carbocycle substituted with 0-3 R$^{1b}$;
aryl substituted with 0-3 R$^{1b}$; and
5 to 10 membered heterocycle containing 1 to 4 heteroatoms selected from nitrogen, oxygen, and sulphur, wherein said 5 to 10 membered heterocycle is substituted with 0-3 R$^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;

$R^2$ is H, methyl, or ethyl;

$R^5$ is H, $OR^{14}$;
- $C_1$-$C_6$ alkyl substituted with 0-3 $R^{5b}$;
- $C_1$-$C_6$ alkoxy substituted with 0-3 $R^{5b}$;
- $C_2$-$C_6$ alkenyl substituted with 0-3 $R^{5b}$;
- $C_2$-$C_6$ alkynyl substituted with 0-3 $R^{5b}$;
- $C_3$-$C_{10}$ cycloalkyl substituted with 0-3 $R^{5c}$;
- $C_3$-$C_{10}$ carbocycle substituted with 0-3 $R^{5c}$;
- aryl substituted with 0-3 $R^{5c}$; or
- 5 to 7 membered heterocycle containing 1 to 4 heteroatoms selected from nitrogen, oxygen, and sulphur, wherein said 5 to 7 membered heterocycle is substituted with 0-3$R^{5c}$;

$R^{5a}$ is H, $C_1$-$C_4$ alkyl, or $C_2$-$C_4$ alkenyl;

alternatively, $R^5$ and $R^{5a}$ may be combined to form a 3-7 membered cycloalkyl ring substituted with 0-3 $R^{5c}$;

$R^{5b}$, at each occurrence, is independently selected from:
- H, $C_1$-$C_6$ alkyl, $CF_3$, $OR^{14}$, Cl, F, Br, I, =O, CN, $NO_2$, $NR^{15}R^{16}$, acetyl, $SCH_3$, $S(=O)CH_3$, $S(=O)_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, and
- H, $C_1$-$C_6$ alkyl, $CF_3$, $OR^{14}$, Cl, F, Br, I, =O, CN, $NO_2$, $NR^{15}R^{16}$, acetyl, $SCH_3$, $S(=O)CH_3$, $S(=O)_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, and $C_1$-$C_4$ haloalkyl-S—,
- $C_3$-$C_{10}$ cycloalkyl substituted with 0-3 $R^{5c}$;
- $C_3$-$C_{10}$ carbocycle substituted with 0-3 $R^{5c}$;
- aryl substituted with 0-3 $R^{5c}$; and
- 5 to 10 membered heterocycle containing 1 to 4 heteroatoms selected from nitrogen, oxygen, and sulphur, wherein said 5 to 10 membered heterocycle is substituted with 0-3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

W is —$(CR^8R^{8a})_p$—;

p is 0, 1, or 2;

$R^8$ and $R^{8a}$, at each occurrence, are independently selected from H, F, methyl, and ethyl;

X is a bond;

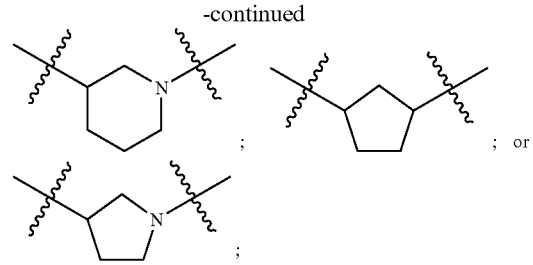

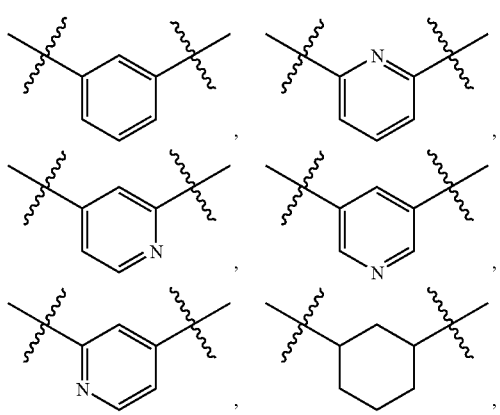

t is 0, 1, or 2;

u is 0, 1, or 2;

$R^9$ and $R^{9a}$, at each occurrence, are independently selected from H, F, methyl, and ethyl;

V is a bond, —C(=O)—, —O—, —S—, —S(=O)—, —S(=O)$_2$—, —N($R^{19}$)—, —C(=O)NH—, or —NHC(=O)—;

Z is H,
- $C_1$-$C_4$ alkyl substituted with 0-2 $R^{12}$;
- $C_2$-$C_4$ alkenyl substituted with 0-2 $R^{12}$;
- $C_2$-$C_4$ alkynyl substituted with 0-2 $R^{12}$;
- aryl substituted with 0-4 $R^{12b}$;
- $C_3$-$C_6$ carbocycle substituted with 0-4 $R^{12b}$; or
- 5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{11}$ is selected from H,
- $C_1$-$C_4$ alkoxy, Cl, F, Br, I, CN, $NO_2$, $NR^{18}R^{19}$, C(=O)$R^{17}$, C(=O)$OR^{17}$, C(=O)$NR^{18}R^{19}$, $S(=O)_2 NR^{18}R^{19}$, $CF_3$;
- $C_1$-$C_6$ alkyl substituted with 0-1 $R^{11a}$;
- aryl substituted with 0-3 $R^{11b}$;
- $C_3$-$C_{10}$ carbocycle substituted with 0-3 $R^{11b}$; or
- 5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, $OR^{14}$, Cl, F, Br, I, =O, CN, $NO_2$, $NR^{15}R^{16}$, $CF_3$;
- phenyl substituted with 0-3 $R^{11b}$;
- $C_3$-$C_{10}$ carbocycle substituted with 0-3 $R^{11b}$; or
- 5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, benzyl, benzoyl, C(=O)$CH_3$, t-butoxycarbonyl, and 3,5-dimethyl-isoxazole-$S(=O)_2$—;

$R^{12}$ at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
- aryl substituted with 0-4 $R^{12b}$;
- $C_3$-$C_{10}$ carbocycle substituted with 0-4 $R^{12b}$; or
- 5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)CH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, and C$_1$-C$_4$ haloalkyl-S—;

R$^{13}$, at each occurrence, is independently selected from H, OH, C$_1$-C$_6$ alkyl, C$_1$-C$_4$ alkoxy, Cl, F, Br, I, CN, NO$_2$, NR$^{15}$R$^{16}$, and CF$_3$;

R$^{14}$, at each occurrence, is independently selected from H, phenyl, benzyl, C$_1$-C$_6$ alkyl, and C$_2$-C$_6$ alkoxyalkyl;

R$^{15}$, at each occurrence, is independently selected from H, C$_1$-C$_6$ alkyl, phenyl, benzyl, phenethyl, (C$_1$-C$_6$ alkyl)-C(=O)—, (C$_1$-C$_6$ alkyl)-O—C(=O)— and (C$_1$-C$_6$ alkyl)-S(=O)$_2$—;

R$^{16}$, at each occurrence, is independently selected from H, OH, C$_1$-C$_6$ alkyl, phenyl, benzyl, phenethyl, (C$_1$-C$_6$ alkyl)-C(=O)—, (C$_1$-C$_6$ alkyl)-O—C(=O)— and (C$_1$-C$_6$ alkyl)-S(=O)$_2$—;

alternatively, —NR$^{15}$R$^{16}$ may be a heterocyclic ring selected from the group piperidinyl, morpholinyl, thiomorpholinyl, pyrrolidinyl, homopiperidinyl, piperazinyl, and N-methylpiperazinyl;

R$^{17}$ is H, C$_1$-C$_6$ alkyl, or C$_2$-C$_6$ alkoxyalkyl,
aryl substituted by 0-4 R$^{17a}$, or
aryl-CH$_2$— wherein said aryl is substituted by 0-4 R$^{17a}$;

R$^{17a}$ is H, methyl, ethyl, propyl, butyl, methoxy, ethoxy, propoxy, butoxy, —OH, F, Cl, Br, I, CF$_3$, OCF$_3$, SCH$_3$, S(=O)CH$_3$, S(=O)$_2$CH$_3$, —NH$_2$, —N(CH$_3$)$_2$, or C$_1$-C$_4$ haloalkyl;

R$^{18}$, at each occurrence, is independently selected from H, C$_1$-C$_6$ alkyl, phenyl, benzyl, phenethyl, (C$_1$-C$_6$ alkyl)-C(=O)— and (C$_1$-C$_6$ alkyl)-S(=O)$_2$—;

R$^{19}$, at each occurrence, is independently selected from H, OH, C$_1$-C$_6$ alkyl, phenyl, benzyl, phenethyl, (C$_1$-C$_6$ alkyl)-C(=O)— and (C$_1$-C$_6$ alkyl)-S(=O)$_2$—;

alternatively, —NR$^{18}$R$^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 R$^{11b}$—; and R$^{20}$ is H, OH, C$_1$-C$_4$ alkyl, phenyl, benzyl, or phenethyl.

10. A process according to claim 7, for preparing compound of Formula (Ig)

(Ig)

or a stereoisomer or pharmaceutically acceptable salt forms thereof,
wherein:

Q$^1$ is C$_1$-C$_6$ alkyl substituted with 0-3 R$^{1a}$;
C$_2$-C$_6$ alkenyl substituted with 0-3 R$^{1a}$;
C$_2$-C$_6$ alkynyl substituted with 0-3 R$^{1a}$;
C$_3$-C$_{10}$ cycloalkyl substituted with 0-3 R$^{1b}$;
C$_3$-C$_{10}$ carbocycle substituted with 0-3 R$^{1b}$;
aryl substituted with 0-3 R$^{1b}$; or
5 to 10 membered heterocycle containing 1 to 4 heteroatoms selected from nitrogen, oxygen, and sulphur, wherein 5 to 10 membered heterocycle is substituted with 0-3 R$^{1b}$;

R$^{1a}$, at each occurrence, is independently selected from H, C$_1$-C$_6$ alkyl, OR$^{14}$, Cl, F, Br, I, NR$^{15}$R$^{16}$, CF$_3$;
C$_3$-C$_{10}$ carbocycle substituted with 0-3 R$^{1b}$;
aryl substituted with 0-3 R$^{1b}$;
5 to 10 membered heterocycle containing 1 to 4 heteroatoms selected from nitrogen, oxygen, and sulphur, wherein 5 to 10 membered heterocycle is substituted with 0-3 R$^{1b}$;

R$^{1b}$, at each occurrence, is independently selected from H, OH, Cl, F, Br, I, CN, NO$_2$, NR$^{15}$R$^{16}$, CF$_3$, acetyl, SCH$_3$, S(=O)$_2$CH$_3$, C$_1$-C$_6$ alkyl, C$_1$-C$_4$ alkoxy, C$_1$-C$_4$ haloalkyl, C$_1$-C$_4$ haloalkoxy, C$_1$-C$_4$ haloalkyl-S—, and (C$_1$-C$_6$ alkyl)-O—C(=O)—;

R$^5$ is OR$^{14}$;
C$_1$-C$_6$ alkyl substituted with 0-3 R$^{5b}$;
C$_2$-C$_6$ alkenyl substituted with 0-3 R$^{5b}$; or
C$_2$-C$_6$ alkynyl substituted with 0-3 R$^{5b}$;

R$^{5a}$ is H, methyl, ethyl, propyl, butyl, or C$_2$-C$_6$ alkenyl,
alternatively, R$^5$ and R$^{5a}$ may be combined to form a C$_4$-C$_7$ cycloalkyl ring;

R$^{5b}$, at each occurrence, is independently selected from:
H, methyl, ethyl, propyl, butyl, CF$_3$, OR$^{14}$, Cl, F, Br, I, =O, NR$^{15}$R$^{16}$,
C$_3$-C$_7$ cycloalkyl substituted with 0-3 R$^{5c}$;
C$_3$-C$_7$ carbocycle substituted with 0-3 R$^{5c}$;
phenyl substituted with 0-3 R$^{5c}$; and
5 to 7 membered heterocycle containing 1 to 4 heteroatoms selected from nitrogen, oxygen, and sulphur, wherein said 5 to 7 membered heterocycle is substituted with 0-3 R$^{5c}$;

R$^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$-C$_4$ alkyl, C$_1$-C$_3$ alkoxy, C$_1$-C$_2$ haloalkyl, and C$_1$-C$_2$ haloalkoxy;

W is a bond;
X is a bond;
Y is a bond;
Z is H,
C$_1$-C$_4$ alkyl substituted with 0-2 R$^{12}$;
C$_2$-C$_4$ alkenyl substituted with 0-2 R$^{12}$;
C$_2$-C$_4$ alkynyl substituted with 0-2 R$^{12}$;
aryl substituted with 0-4 R$^{12b}$;
C$_3$-C$_6$ carbocycle substituted with 0-4 R$^{12b}$; or
5 to 6 membered heterocycle containing 1 to 4 heteroatoms selected from nitrogen, oxygen, and sulphur, wherein said 5 to 6 membered heterocycle is substituted with 0-3 R$^{12b}$;

R$^{11}$ is selected from
H, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
C$_1$-C$_6$ alkyl substituted with 0-1 R$^{11a}$;
phenyl substituted with 0-3 R$^{11b}$;
C$_3$-C$_6$ carbocycle substituted with 0-3 R$^{11b}$; or
5 to 7 membered heterocycle containing 1 to 4 heteroatoms selected from nitrogen, oxygen, and sulphur, wherein said 5 to 7 membered heterocycle is substituted with 0-3 R$^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

R$^{11a}$, at each occurrence, is independently selected from H, methyl, ethyl, propyl, butyl, methoxy, ethoxy, propoxy, Cl, F, =O, NR$^{15}$R$^{16}$, CF$_3$;
phenyl substituted with 0-3 R$^{11b}$;
C$_3$-C$_6$ carbocycle substituted with 0-3 R$^{11b}$; or
5 to 7 membered heterocycle containing 1 to 4 heteroatoms selected from nitrogen, oxygen, and sulphur, wherein said 5 to 7 membered heterocycle is substituted with 0-3 R$^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

$R^{12}$ at each occurrence, is independently selected from H, OH, Cl, F, Br, I, CN, $NO_2$, $NR^{15}R^{16}$, $—C(=O)NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$, at each occurrence, is independently selected from H, OH, $C_1$-$C_6$ alkyl, $C_1$-$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$-$C_4$ alkyl, and $C_2$-$C_4$ alkoxyalkyl;

$R^{15}$, at each occurrence, is independently selected from H, methyl, ethyl, propyl, butyl, phenyl, benzyl, and phenethyl;

$R^{16}$, at each occurrence, is independently selected from H, OH, methyl, ethyl, propyl, butyl, phenyl, benzyl, phenethyl, $CH_3CH_2C(=O)—$, $CH_3C(=O)—$, $CH_3CH_2OC(=O)—$, $CH_3OC(=O)—$, $CH_3CH_2S(=O)_2—$ and $CH_3S(=O)_2—$;

$R^{17}$ is H, phenyl, benzyl, $C_1$-$C_4$ alkyl, or $C_2$-$C_4$ alkoxyalkyl;

$R^{18}$, at each occurrence, is independently selected from H, methyl, ethyl, propyl, butyl, phenyl, benzyl, and phenethyl; and $R^{19}$, at each occurrence, is independently selected from H, OH, methyl, ethyl, propyl, and butyl.

11. A process according to claim 7, for preparing a compound of Formula (Ig),

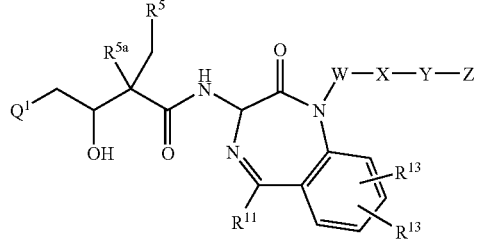

(Ig)

or a stereoisomer or pharmaceutically acceptable salt forms thereof,
wherein:
$Q^1$ is $C_1$-$C_6$ alkyl substituted with 0-3 $R^{1a}$;
$C_2$-$C_6$ alkenyl substituted with 0-3 $R^{1a}$;
$C_2$-$C_6$ alkynyl substituted with 0-3 $R^{1a}$;
$C_3$-$C_6$ cycloalkyl substituted with 0-3 $R^{1b}$;
phenyl substituted with 0-3 $R^{1b}$; or
5 to 6 membered heterocycle containing 1 to 4 heteroatoms selected from nitrogen, oxygen, and sulphur, wherein said 5 to 6 membered heterocycle is substituted with 0-3 $R^{1b}$;

$R^{1a}$, at each occurrence, is independently selected from H, methyl, ethyl, propyl, butyl, $OR^{14}$, Cl, F, Br, I, $NR^{15}R^{16}$, $CF_3$;

$C_3$-$C_6$ carbocycle substituted with 0-3 $R^{1b}$;
phenyl substituted with 0-3 $R^{1b}$; and
5 to 6 membered heterocycle containing 1 to 4 heteroatoms selected from nitrogen, oxygen, and sulphur, wherein said 5 to 6 membered heterocycle is substituted with 0-3 $R^{1b}$;

$R^{1b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, $C_1$-$C_2$ haloalkoxy, (methyl)OC(=O)—, (ethyl)OC(=O)—, (propyl)OC(=O)—, and (butyl)OC(=O)—;

$R^5$ is $OR^{14}$;
$C_1$-$C_4$ alkyl substituted with 0-1 $R^{5b}$;
$C_2$-$C_4$ alkenyl substituted with 0-1 $R^{5b}$; or
$C_2$-$C_4$ alkynyl substituted with 0-1 $R^{5b}$;

$R^{5a}$ is H, methyl, ethyl, propyl, or butyl;
alternatively, $R^5$ and $R^{5a}$ may be combined to form a cyclobutyl, cyclopentyl, cyclohexyl, or cycloheptyl ring;

$R^{5b}$, at each occurrence, is independently selected from:
H, methyl, ethyl, propyl, butyl, $CF_3$, $OR^{14}$, Cl, F, =O, $NR^{15}R^{16}$,
$C_3$-$C_7$ cycloalkyl substituted with 0-3 $R^{5c}$;
$C_3$-$C_7$ carbocycle substituted with 0-3 $R^{5c}$;
phenyl substituted with 0-3 $R^{5c}$; and
5 to 7 membered heterocycle containing 1 to 4 heteroatoms selected from nitrogen, oxygen, and sulphur, wherein said 5 to 7 membered heterocycle is substituted with 0-3 $R^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$-$C_2$ haloalkyl, and $C_1$-$C_2$ haloalkoxy;

W is a bond;
X is a bond;
Y is a bond;
Z is H,
$C_1$-$C_4$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
aryl substituted with 0-4 $R^{12b}$;
$C_3$-$C_6$ carbocycle substituted with 0-4 $R^{12b}$; or
5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{11}$ is selected from
H, $NR^{18}R^{19}$, $CF_3$;
$C_1$-$C_4$ alkyl substituted with 0-1 $R^{11a}$;
phenyl substituted with 0-3 $R^{11b}$;
$C_3$-$C_6$ carbocycle substituted with 0-3 $R^{11b}$; or
5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, =O, $NR^{15}R^{16}$, $CF_3$;

phenyl substituted with 0-3 $R^{11b}$;

$C_3$-$C_6$ carbocycle substituted with 0-3 $R^{11b}$; or 5 to 7 membered heterocycle containing 1 to 4 heteroatoms selected from nitrogen, oxygen, and sulphur, wherein said 5 to 7 membered heterocycle is substituted with 0-3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$-$C_2$ haloalkyl, and $C_1$-$C_2$ haloalkoxy;

$R^{12}$ at each occurrence, is independently selected from H, OH, Cl, F, Br, $NR^{15}R^{16}$, —C(=O)$NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$-$C_2$ haloalkyl, and $C_1$-$C_2$ haloalkoxy;

phenyl substituted with 0-4 $R^{12b}$;

$C_3$-$C_6$ carbocycle substituted with 0-4 $R^{12b}$; or 5 to 6 membered heterocycle containing 1 to 4 heteroatoms selected from nitrogen, oxygen, and sulphur, wherein said 5 to 6 membered heterocycle is substituted with 0-3 $R^{12b}$;

$R^{12b}$, at each occurrence, is independently selected from H, OH, Cl, F, Br, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$-$C_2$ haloalkyl, and $C_1$-$C_2$ haloalkoxy;

$R^{13}$, at each occurrence, is independently selected from H, OH, methyl, ethyl, propyl, butyl, methoxy, ethoxy, propoxy, Cl, F, Br, CN, $NR^{15}R^{16}$, and $CF_3$;

$R^{14}$, at each occurrence, is independently selected from H, phenyl, benzyl, methyl, ethyl, propyl, and butyl;

$R^{15}$, at each occurrence, is independently selected from H, methyl, ethyl, propyl, or butyl;

$R^{16}$, at each occurrence, is independently selected from H, OH, methyl, ethyl, propyl, butyl, phenyl, benzyl, and phenethyl;

$R^{18}$, at each occurrence, is independently selected from H, methyl, ethyl, propyl, butyl, phenyl, benzyl and, phenethyl; and $R^{19}$, at each occurrence, is independently selected from H, OH, methyl, ethyl, propyl, butyl, phenyl, benzyl and, phenethyl.

12. A process according to claim 7, for preparing compound of Formula (Ig)

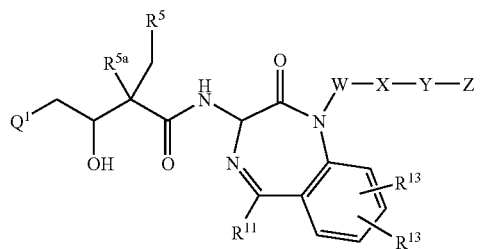

(Ig)

or a stereoisomer or pharmaceutically acceptable salt forms thereof, wherein:

$Q^1$ is —$CH_3$, —$CH_2CH_3$, —$CH_2CH_2CH_3$, —$CH_2CH_2CH_2CH_3$, —$CH_2CH_2CH_2CH_2CH_3$, —$CH_2CH_2CH_2CH_2CH_2CH_3$, —CH($CH_3$)$_2$, —CH($CH_3$)$CH_2CH_3$, —$CH_2CH(CH_3$)$_2$, —$CH_2C(CH_3$)$_3$,

—$CF_3$, —$CH_2CF_3$, —$CH_2CH_2CF_3$, —$CH_2CH_2CH_2CF_3$,

—CH=$CH_2$, —$CH_2$CH=$CH_2$, —$CH_2CH_2$C($CH_3$)=$CH_2$, —$CH_2$CH=C($CH_3$)$_2$, —$CH_2CH_2$CH=$CH_2$, —$CH_2CH_2$C($CH_3$)=$CH_2$, —$CH_2CH_2$CH=C($CH_3$)$_2$, cis-$CH_2$CH=CH($CH_3$), cis-$CH_2CH_2$CH=CH($CH_3$), trans-$CH_2$CH=CH($CH_3$), trans-$CH_2CH_2$CH=CH($CH_3$);

—C≡CH, —$CH_2$C≡CH, —$CH_2$C≡C($CH_3$), cyclopropyl-, cyclobutyl-, cyclopentyl-, cyclohexyl-, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—, phenyl-, 2-F-phenyl-, 3-F-phenyl-, 4-F-phenyl-, 4-methoxyphenyl-, 4-ethoxyphenyl-, 4-propoxyphenyl-, phenyl-$CH_2$—, (2-F-phenyl)$CH_2$—, (3-F-phenyl)$CH_2$—, (4-F-phenyl)$CH_2$—, (2-Cl-yl)$CH_2$—, (3-Cl-yl)$CH_2$—, (4-Cl-yl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-yl)$CH_2$—, (3-F-5-Cl-yl)$CH_2$—, (3-Cl-4-F-phenyl)$CH_2$—, 2-furanyl-$CH_2$—, 3-furanyl-$CH_2$—, 2-thienyl-$CH_2$—, 3-thienyl-$CH_2$—, 2-pyridyl-$CH_2$—, 3-pyridyl-$CH_2$—, 4-pyridyl-$CH_2$—, 1-imidazolyl-$CH_2$—, 2-oxazolyl-$CH_2$—, 4-oxazolyl-$CH_2$—, 5-oxazolyl-$CH_2$—, 3-isoxazolyl-$CH_2$—, 4-isoxazolyl-$CH_2$—, 5-isoxazolyl-$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, (2-Cl-yl)$CH_2CH_2$—, (3-Cl-yl)$CH_2CH_2$—, (4-Cl-yl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-yl)$CH_2CH_2$—, (3-F-5-Cl-yl)$CH_2CH_2$—;

furanyl-$CH_2CH_2$—, thienyl-$CH_2CH_2$—, pyridyl-$CH_2CH_2$—, 1-imidazolyl-$CH_2CH_2$—, oxazolyl-$CH_2CH_2$—, isoxazolyl-$CH_2CH_2$—, 3,5-dimethyl-isoxazol-4-yl-$CH_2CH_2$—, phenyl-propyl-;

benzyl-CH($NH_2$)—, benzyl-CH(NHC(=O)—O-tBu)-, benzyloxy-$CH_2$—, pyrrolidin-2-yl-, or 3-t-butoxycarbonylpyrrolidin-2-yl-;

$R^5$ is —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2$CH($CH_3$)$_2$, —$CH_2$C($CH_3$)$_3$, —$CH_2CH_2CH_2CH_2CH_3$, —CH($CH_3$)$CH_2CH_2CH_3$, —$CH_2$CH($CH_3$)$CH_2CH_3$, —$CH_2CH_2$CH($CH_3$)$_2$, —CH($CH_2CH_3$)$_2$,

—$CF_3$, —$CH_2CF_3$, —$CH_2CH_2CF_3$, —$CH_2CH_2CH_2CF_3$, —$CH_2CH_2CH_2CH_2CF_3$,

—CH=$CH_2$, —$CH_2$CH=$CH_2$, —$CH_2CH_2$CH=$CH_2$, —CH=$CHCH_3$, cis-$CH_2$CH=CH($CH_3$), trans-$CH_2$CH=CH($CH_3$), trans-$CH_2$CH=CH($C_6H_5$), —$CH_2$CH=C($CH_3$)$_2$, cis-$CH_2$CH=$CHCH_2CH_3$, trans-$CH_2$CH=$CHCH_2CH_3$, cis-$CH_2CH_2$CH=CH($CH_3$), trans-$CH_2CH_2$CH=CH($CH_3$), trans-$CH_2$CH=$CHCH_2$($C_6H_5$), —C≡CH, —$CH_2$C≡CH, —$CH_2$C≡C($CH_3$), —$CH_2$C≡C($C_6H_5$), —$CH_2CH_2$C≡CH, —$CH_2CH_2$C≡C($CH_3$), —$CH_2CH_2$C≡C($C_6H_5$), —CH₂CH₂CH₂C≡CH, —CH₂CH₂CH₂C≡C(CH₃), —CH₂CH₂CH₂C≡C(C₆H₅),
cyclopropyl-CH₂—, cyclobutyl-CH₂—, cyclopentyl-CH₂—, cyclohexyl-CH₂—, (2-CH₃-cyclopropyl)CH₂—, (3-CH₃-cyclobutyl)CH₂—, cyclopropyl-CH₂CH₂—, cyclobutyl-CH₂CH₂—, cyclopentyl-CH₂CH₂—, cyclohexyl-CH₂CH₂—, (2-CH₃-cyclopropyl)CH₂CH₂—, (3-CH₃-cyclobutyl)CH₂CH₂—,
phenyl-CH₂—, (2-F-phenyl)CH₂—, (3-F-phenyl)CH₂—, (4-F-phenyl)CH₂—, (3,5-diF-phenyl)CH₂—, 2-furanyl-CH₂—, 3-furanyl-CH₂—, 2-thienyl-CH₂—, 3-thienyl-CH₂—,
2-pyridyl-CH₂—, 3-pyridyl-CH₂—, 4-pyridyl-CH₂—, 1-imidazolyl-CH₂—, 2-oxazolyl-CH₂—, 4-oxazolyl-CH₂—, 5-oxazolyl-CH₂—, 3-isoxazolyl-CH₂—, 4-isoxazolyl-CH₂—, 5-isoxazolyl-CH₂—,
phenyl-CH₂CH₂—, (2-F-phenyl)CH₂CH₂—, (3-F-phenyl)CH₂CH₂—, (4-F-phenyl)CH₂CH₂—, furanyl-CH₂CH₂—, thienyl-CH₂CH₂—, pyridyl-CH₂CH₂—, 1-imidazolyl-CH₂CH₂—, oxazolyl-CH₂CH₂—, isoxazolyl-CH₂CH₂—;
methoxy, ethoxy, propoxy, or butoxy;
R⁵ᵃ is H;
alternatively, R⁵ and R⁵ᵃ may be combined to form cyclopentyl, cyclohexyl, or cycloheptyl;
W is a bond;
X is a bond;
Y is a bond;
Z is H, methyl, ethyl, n-propyl, i-propyl, n-butyl, i-butyl, s-butyl, t-butyl,
cyclopropyl, cyclobutyl, cyclopentyl, cyclohexyl,
phenyl, 2-F-phenyl, 3-F-phenyl, 4-F-phenyl, 2-Cl-yl, 3-Cl-yl, 4-Cl-yl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-yl, 3-F-5-Cl-yl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl,
furanyl, thienyl, pyridyl, 2-Me-pyridyl, 3-Me-pyridyl, 4-Me-pyridyl, 1-imidazolyl, oxazolyl, isoxazolyl, 1-benzimidazolyl, morpholino, N-piperidyl,
phenyl-CH₂—, (2-F-phenyl)CH₂—, (3-F-phenyl)CH₂—, (4-F-phenyl)CH₂—, (2-Cl-yl)CH₂—, (3-Cl-yl)CH₂—, (4-Cl-yl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-yl)CH₂—, (3-F-5-Cl-yl)CH₂—, (3-Cl-4-F-phenyl)CH₂—, (2-MeO-phenyl)CH₂—, (3-MeO-phenyl)CH₂—, (4-MeO-phenyl)CH₂—, (2-PhO-phenyl)CH₂—, (3-PhO-phenyl)CH₂—, (4-PhO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl)CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl)CH₂—, (1-benzimidazolyl)CH₂—, (cyclopropyl)CH₂—, (cyclobutyl)CH₂—, (cyclopentyl)CH₂—, (cyclohexyl)CH₂—, (morpholino)CH₂—, (N-piperidinyl)CH₂—,
phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-yl)CH₂CH₂—, (3-Cl-yl)CH₂CH₂—, (4-Cl-yl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-yl)CH₂CH₂—, (3-F-5-Cl-yl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-piperidinyl)CH₂CH₂—;

R¹¹, at each occurrence, is independently selected from H, methyl, ethyl, n-propyl, i-propyl, n-butyl, i-butyl, s-butyl, t-butyl, phenyl, benzyl, phenethyl, cyclopropyl, cyclobutyl, cyclopentyl, cyclohexyl, cycloheptyl, cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, 2-F-phenyl-, 3-F-phenyl, 4-F-phenyl, 4-Cl-yl, 4-CH₃-phenyl, 4-MeO-phenyl-, 4-CF₃-phenyl, (4-F-phenyl)CH₂—, (4-Cl-yl)CH₂—, (4-CH₃-phenyl)CH₂—, (4-CF₃-phenyl)CH₂—, (4-F-phenyl)CH₂CH₂—, (4-Cl-yl)CH₂CH₂—, (4-CH₃-phenyl)CH₂CH₂—, (4-CF₃-phenyl)CH₂CH₂—, pyridin-2-yl-, pyridin-3-yl-, 4-CF₃-pyridin-2-yl-, 4-CH₃-pyridin-2-yl-, thiazol-2-yl-, azapan-1-yl, N,N-dimethylamino, N,N-diethylamino, N,N-dipropylamino, and N,N-dibutylamino; and R¹³, at each occurrence, is independently selected from H, MeO, F, and Cl.

13. A process according to claim 1, for preparing a compound of formula (I″) of S or R configuration,

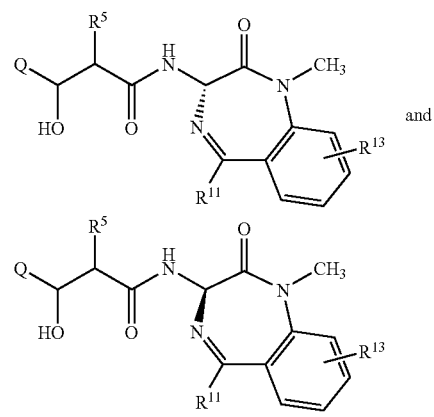

and comprising the steps of Scheme 1:

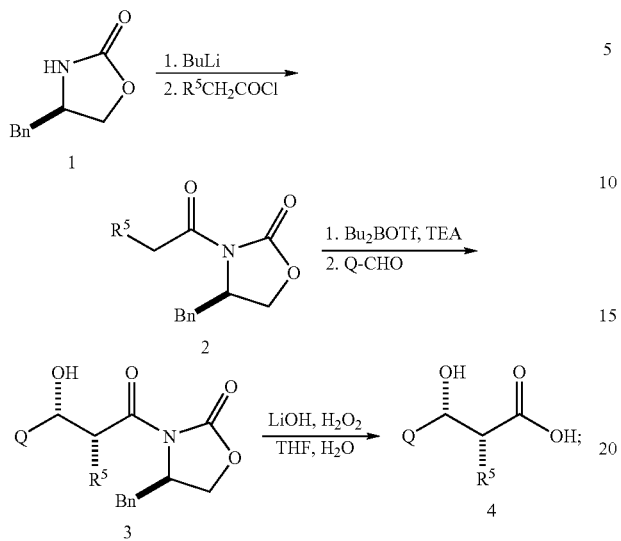

wherein acylation of oxazolidinone with an acid chloride provides structure 2 and an asymmetric aldol reaction forms intermediate 3 which upon cleavage yields □-hydroxycarboxylic acid;
followed by the steps of Scheme 2:

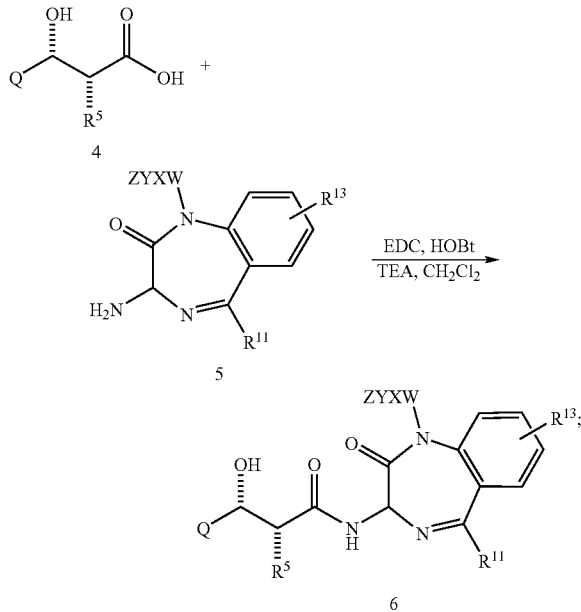

wherein carboxylic intermediate can be coupled to a lactam structure such as a 3-amino-1,4-benzodiazepin-2-one 5 to form compound 6;
wherein
Q is $Q^1$,
-($C_1$-$C_3$ alkylene)-O-$Q^1$,
-($C_1$-$C_3$ alkylene)-S-$Q^1$,
-($C_1$-$C_3$ alkylene)-S(=O)-$Q^1$,
-($C_1$-$C_3$ alkylene)-S(=O)$_2$-$Q^1$, or
-($C_1$-$C_3$ alkylene)-N($R^{20}$)-$Q^1$;
$Q^1$ is $C_1$-$C_8$ alkyl substituted with 0-3 $R^{1a}$;
$C_2$-$C_8$ alkenyl substituted with 0-3 $R^{1a}$;
$C_2$-$C_8$ alkynyl substituted with 0-3 $R^{1a}$;
$C_3$-$C_{10}$ cycloalkyl substituted with 0-3 $R^{1b}$;
$C_3$-$C_{10}$ carbocycle substituted with 0-3 $R^{1b}$;
aryl substituted with 0-3 $R^{1b}$; or
5 to 10 membered heterocycle containing 1 to 4 heteroatoms selected from nitrogen, oxygen, and sulphur, wherein said 5 to 10 membered heterocycle is substituted with 0-3 $R^{1b}$;
$R^{1a}$, at each occurrence, is independently selected from H, $C_1$-$C_6$ alkyl, $OR^{14}$, Cl, F, Br, I, $NR^{15}R^{16}$, $CF_3$;
$C_3$-$C_{10}$ carbocycle substituted with 0-3 $R^{1b}$;
aryl substituted with 0-3 $R^{1b}$; and
5 to 10 membered heterocycle containing 1 to 4 heteroatoms selected from nitrogen, oxygen, and sulphur, wherein said 5 to 10 membered heterocycle is substituted with 0-3 $R^{1b}$;
$R^{1b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, and ($C_1$-$C_6$ alkyl)-O—C(=O)—;
$R^5$ is H, $OR^{14}$;
$C_1$-$C_6$ alkyl substituted with 0-3 $R^{5b}$;
$C_1$-$C_6$ alkoxy substituted with 0-3 $R^{5b}$;
$C_2$-$C_6$ alkenyl substituted with 0-3 $R^{5b}$;
$C_2$-$C_6$ alkynyl substituted with 0-3 $R^{5b}$;
$C_3$-$C_{10}$ cycloalkyl substituted with 0-3 $R^{5c}$;
$C_3$-$C_{10}$ carbocycle substituted with 0-3 $R^{5c}$;
aryl substituted with 0-3 $R^{5c}$; or
5 to 10 membered heterocycle containing 1 to 4 heteroatoms selected from nitrogen, oxygen, and sulphur, wherein said 5 to 10 membered heterocycle is substituted with 0-3$R^{5c}$;
$R^{5b}$, at each occurrence, is independently selected from:
H, $C_1$-$C_6$ alkyl, $CF_3$, $OR^{14}$, Cl, F, Br, I, =O, CN, $NO_2$, $NR^{15}R^{16}$, acetyl, $SCH_3$, S(=O)$CH_3$, S(=O)$_2CH_3$, $C_2$-$C_6$ alkenyl, $C_2$-$C_6$ alkynyl, $C_1$-$C_4$ alkoxy, $C_1$-$C_4$ haloalkyl, $C_1$-$C_4$ haloalkoxy, $C_1$-$C_4$ haloalkyl-S—,
$C_3$-$C_{10}$ cycloalkyl substituted with 0-3 $R^{5c}$;
$C_3$-$C_{10}$ carbocycle substituted with 0-3 $R^{5c}$;
aryl substituted with 0-3 $R^{5c}$; and
5 to 7 membered heterocycle containing 1 to 4 heteroatoms selected from nitrogen, oxygen, and sulphur, wherein said 5 to 7 membered heterocycle is substituted with 0-3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
W is —($CR^8R^{8a}$)$_p$—;
p is 0, 1, 2, 3, or 4;
$R^8$ and $R^{8a}$, at each occurrence, are independently selected from H, F, $C_1$-$C_4$ alkyl, $C_2$-$C_4$ alkenyl, $C_2$-$C_4$ alkynyl and $C_3$-$C_8$ cycloalkyl;
X is a bond;
aryl substituted with 0-3 $R^{Xb}$;
$C_3$-$C_{10}$ cycloalkyl substituted with 0-3 $R^{Xb}$;
$C_3$-$C_{10}$ carbocycle substituted with 0-3 $R^{Xb}$; or
5 to 10 membered heterocycle substituted with 0-2 $R^{Xb}$;
$R^{Xb}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
Y is a bond or —($CR^9R^{9a}$)$_t$—V—($CR^9R^{9a}$)$_u$—;
t is 0, 1, 2, or 3;
u is 0, 1, 2, or 3;

$R^9$ and $R^{9a}$, at each occurrence, are independently selected from H, F, $C_1$-$C_6$ alkyl or $C_3$-$C_8$ cycloalkyl;

V is a bond, —C(=O)—, —O—, —S—, —S(=O)—, —S(=O)$_2$—, —N($R^{19}$)—, —C(=O)N$R^{19b}$—, —N$R^{19b}$C(=O)—, —N$R^{19b}$S(=O)$_2$—, —S(=O)$_2$N$R^{19b}$—, —C(=O)O—, or —OC(=O)—;

Z is H;
$C_1$-$C_8$ alkyl substituted with 0-2 $R^{12}$;
$C_2$-$C_4$ alkenyl substituted with 0-2 $R^{12}$;
$C_2$-$C_4$ alkynyl substituted with 0-2 $R^{12}$;
aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{11}$ is selected from H,
$C_1$-$C_4$ alkoxy, Cl, F, Br, I, CN, NO$_2$, N$R^{18}R^{19}$, C(=O)$R^{17}$, C(=O)O$R^{17}$, C(=O)N$R^{18}R^{19}$, S(=O)$_2$N$R^{18}R^{19}$, CF$_3$;
$C_1$-$C_6$ alkyl substituted with 0-1 $R^{11a}$;
aryl substituted with 0-3 $R^{11b}$;
$C_3$-$C_{10}$ carbocycle substituted with 0-3 $R^{11b}$; or
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11a}$, at each occurrence, is independently selected from H, $C_1$-$C_6$ alkyl, O$R^{14}$, Cl, F, Br, I, =O, CN, NO$_2$, N$R^{15}R^{16}$, CF$_3$;
phenyl substituted with 0-3 $R^{11b}$;
$C_3$-$C_{10}$ carbocycle substituted with 0-3 $R^{11b}$; or
5 to 10 membered heterocycle containing 1 to 4 heteroatoms selected from nitrogen, oxygen, and sulphur, wherein said 5 to 10 membered heterocycle is substituted with 0-3 $R^{11b}$;

$R^{11b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, $C_1$-$C_4$ haloalkyl-S—, benzyl, benzoyl, C(=O)CH$_3$, t-butoxycarbonyl, and 3,5-dimethyl-isoxazole-S(=O)$_2$—;

$R^{12}$ at each occurrence, is independently selected from H, OH, Cl, F, Br, I, CN, NO$_2$, N$R^{15}R^{16}$, —C(=O)N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;
aryl substituted with 0-4 $R^{12b}$;
$C_3$-$C_{10}$ carbocycle substituted with 0-4 $R^{12b}$; or
5 to 10 membered heterocycle containing 1 to 4 heteroatoms selected from nitrogen, oxygen, and sulphur, wherein said 5 to 10 membered heterocycle is substituted with 0-3 $R^{12b}$;

$R^{12b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$-$C_6$ alkyl, $C_1$-$C_4$ alkoxy, $C_1$-$C_4$ haloalkyl, $C_1$-$C_4$ haloalkoxy, and $C_1$-$C_4$ haloalkyl-S—;

$R^{13}$ is selected from H, OH, $C_1$-$C_6$ alkyl, $C_1$-$C_4$ alkoxy, Cl, F, Br, I, CN, NO$_2$, N$R^{15}R^{16}$, and CF$_3$;

$R^{14}$, at each occurrence, is independently selected from H, phenyl, benzyl, $C_1$-$C_6$ alkyl, and $C_2$-$C_6$ alkoxyalkyl;

$R^{14a}$ is H, phenyl, benzyl, or $C_1$-$C_6$ alkyl;

$R^{15}$, at each occurrence, is independently selected from H, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

$R^{16}$, at each occurrence, is independently selected from H, OH, $C_1$-$C_6$ alkyl, phenyl, benzyl, phenethyl, ($C_1$-$C_6$ alkyl)-C(=O)—, ($C_1$-$C_6$ alkyl)-O—C(=O)— and ($C_1$-$C_6$ alkyl)-S(=O)$_2$—;

alternatively, —N$R^{15}R^{16}$ may be a heterocyclic ring selected from the group piperidinyl, morpholinyl, thiomorpholinyl, pyrrolidinyl, homopiperidinyl, piperazinyl, and N-methylpiperazinyl;

$R^{17}$ is H, $C_1$-$C_6$ alkyl, or $C_2$-$C_6$ alkoxyalkyl,
aryl substituted by 0-4 $R^{17a}$, or
aryl-CH$_2$— wherein said aryl is substituted by 0-4 $R^{17a}$;

$R^{17a}$ is H, methyl, ethyl, propyl, butyl, methoxy, ethoxy, propoxy, butoxy, —OH, F, Cl, Br, I, CF$_3$, OCF$_3$, SCH$_3$, S(=O)CH$_3$, S(=O)$_2$CH$_3$, —NH$_2$, —N(CH$_3$)$_2$, or $C_1$-$C_4$ haloalkyl;

$R^{18}$, at each occurrence, is independently selected from H, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

alternatively, —N$R^{18}R^{19}$ may be a heterocyclic ring selected from the group: piperidinyl, morpholinyl, thiomorpholinyl, pyrrolidinyl, homopiperidinyl, piperazinyl, and N-methylpiperazinyl; wherein said heterocyclic ring is substituted with 0-3 $R^{11b}$—;

$R^{19}$, at each occurrence, is independently selected from H, OH, $C_1$-$C_6$ alkyl, phenyl, benzyl, phenethyl, ($C_1$-$C_6$ alkyl)-C(=O)— and ($C_1$-$C_6$ alkyl)-S(=O)$_2$—;

$R^{19b}$, at each occurrence, is independently selected from H and $C_1$-$C_6$ alkyl;

$R^{20}$ is H, OH, $C_1$-$C_4$ alkyl, phenyl, benzyl, or phenethyl;

$R^{21}$ at each occurrence, is independently selected from H, $C_1$-$C_6$ alkyl, phenyl, benzyl, and phenethyl; and $R^{22}$, at each occurrence, is independently selected from H, $C_1$-$C_6$ alkyl, phenyl, benzyl, and phenethyl.

14. A process according to claim 1, for preparing a compound of formula (I), 3-(2(R)-Cyclopentylmethyl-3(S)-hydroxyl-1-oxo-5-phenylpentyl)amino-1-methyl-5-phenyl-2,3-dihydro-1H-1,4-benzodiazepin-2-one, comprising the steps of, as illustrated in the following scheme, (i) Step 1,

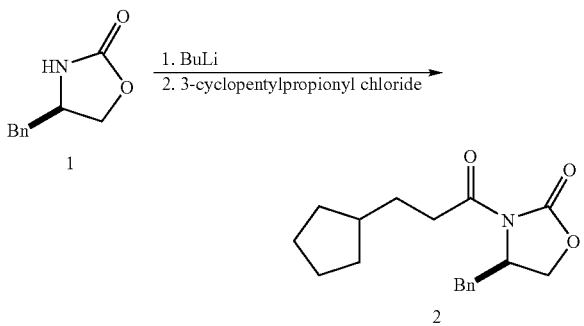

cooling a solution of (R)-4-(phenylmethyl)-2-oxazolidinone (1, 17.7 g, 0.100 mol), anhydrous tetrahydrofuran (300 mL) to −78° C.; adding butyllithium (42.0 mL, 0.105 mol, 2.50 M in hexane) to the reaction flask over a 10-min period; adding 3-Cyclopentylpropionyl chloride (16.8 mL, 0.110 mol), stirring for 30 min at −78° C., warming to ambient temperature over a 30-min period; quenching 3-cyclopentylpropionyl chloride by the addition of 60 mL of saturated aqueous ammonium chloride; remove the bulk of the tetrahydrofuran and hexane on a rotary evaporator, and extricate the slurry with two 80 mL portion of dichloromethane; washing combined organic layers with 75 mL of 1 M sodium hydroxide and 75 mL of brine, drying over anhydrous magnesium sulfate, and filtering and removing the solvent under reduced pressure; and triturating the residue with hexane to provide 16.5 g of desired product 2 as a white solid; ¹H NMR (300 MHz, CDCl₃) δ 7.18-7.40 (5 H, m), 4.67 (1 H, m), 4.12-4.22 (2 H, m), 3.30 (1 H, dd, J=13.4, 3.1 Hz), 2.84-3.06 (2 H, m), 2.76 (1 H, dd, J=13.4, 9.6 Hz), 1.42-1.96 (9 H, m), 1.15 (2 H, br, m);

(ii) synthetic Step 2:
3-(2(R)-cyclopentylmethyl-3(S)-hydroxyl-5-phenyl-1-oxopentyl)-4(R)-(phenylmethyl)-2-oxazolidinone (3),

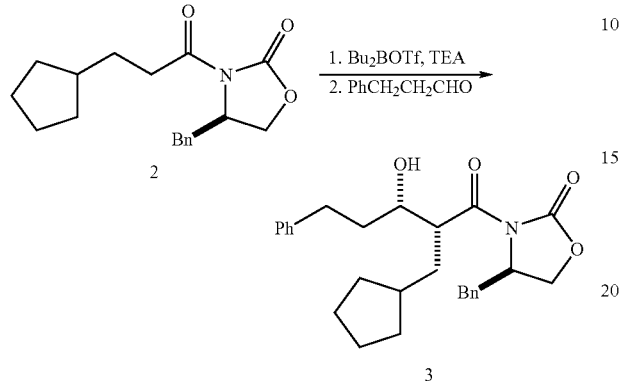

create a solution of acyloxazolidinone 2 (1.57 g, 5.00 mmol) in 20 mL of dichloromethane, cooled to −78° C. under nitrogen atmosphere, adding dibutylboron triflate (1.40 mL, 5.50 mmol) dropwise, followed by the addition of triethylamine; warming the mixture slowly to 0° C. and stirring at 0° C. for an additional hour; cooling resultant boryl enolate solution to −78° C., and adding 3-phenylpropanal (0.80 mL, 5.5 mmol) over a 5-min period time; stirring the solution for 1 h at −78° C., then for 1 h at 0° C.; quenching the reaction mixture by the addition of 4 mL of a pH 7 aqueous phosphate buffer and 12 mL of methanol; adding 8 mL of methanol and 10 mL of 30% aqueous hydrogen peroxide at such a rate as to keep the internal temperature below 110° C. an additional hour, and remove the volatile material in a rotary evaporator; extract the resulting slurry with three 20 mL portions of diethyl ether; washing the combined organic layers with 20 mL of 5% aqueous sodium bicarbonate and 20 mL of brine, drying over anhydrous magnesium sulfate, filtering and concentrating under reduced pressure; followed by purification by flash column chromatography (25% ethyl acetate-hexane) provided 1.11 g (56%) of aldol 3 as a colorless oil. ¹H NMR (300 MHz, CDCl₃) δ 7.15-7.38 (m, 10 H), 4.72 (m, 1 H), 4.12-4.28 (m, 3 H), 3.85 (m, 1 H), 3.34 (1 H, dd, J=13.4, 3.1 Hz), 2.80-2.95 (1 H, m), 2.60-2.78 (2 H, m), 1.95-2.05 (1 H, m), 1.40-1.90 (10 H, m), 1.10 (2 H, m);

(iii) step 3,
2(R)-cyclopentylmethyl-3(S)-hydroxyl-5-phenylpentanoic acid (4),

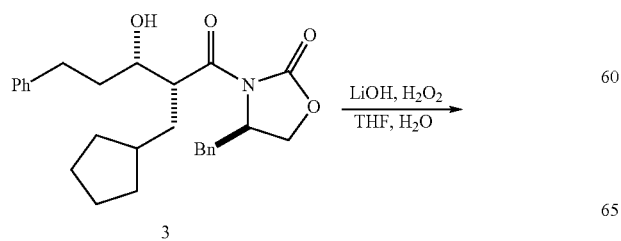

-continued

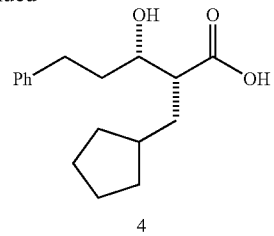

dissolve acyloxazolidinone 3 (226 mg, 0.500 mmol) was dissolved in 3 mL of THF and 1 mL of distilled water; cooling the resulting solution to 0° C.; adding to this solution 30% aqueous hydrogen peroxide (0.40 mL, 4.0 mmol), and a solution of lithium hydroxide (19 mg, 0.80 mmol) in 0.5 mL of distilled water; stirring the solution for 16 h, and adding sodium sulfite (567 mg, 4.50 mmol) in 3 mL of distilled water; removing most of tetrahydrofuran under reduced pressure; extracting the resulting mixture (pH 12~13) with three 20 mL portion of methylene chloride to remove the oxazolidinone auxiliary; cooling the aqueous layer in an ice bath to acidify to pH 1 with 6 M aqueous hydrochloric acid; extracting the resulting cloudy solution with five portion of 30 mL ethyl acetate; and whereupon the combined organic layers are dried over anhydrous magnesium sulfate, filtered and concentrated under reduced pressure to yield 230 mg (81%) of the desired acid 4 as a white solid. ¹H NMR (300 MHz, CDCl₃) δ 7.18-7.35 (5 H, m), 3.87 (1 H, m), 2.81-2.87 (1 H, m), 2.60-2.76 (1 H, m); 2.54-2.60 (1 H, m), 1.00-1.95 (m, 13H);

(iv) step (4):
3-(2(R)-Cyclopentylmethyl-3(S)-hydroxyl-1-oxo-5-phenylpentyl)amino-1-methyl-5-phenyl-2,3-dihydro-1H-1,4-benzodiazepin-2-one (6),

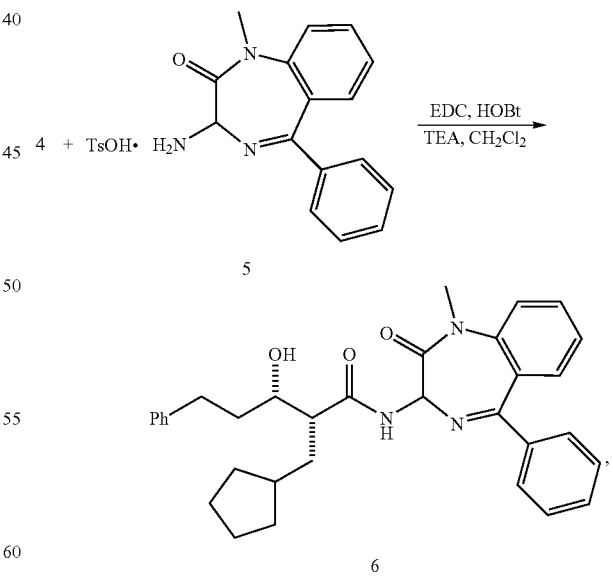

stirring a mixture of acid 4 (250 mg, 0.900 mmol) and 3-amino-1-methyl-5-phenyl-2,3-dihydro-1H-1,4-benzodiazepin-2-one p-toluenesulfonate salt (364 mg, 0.820 mmol) in 4 mL of methylene chloride at 0° C. and adding 1-Hydroxy-benzotriazole hydrate (133 mg, 0.980 mmol), 1-[3-(dimethylamine)propyl]-3-ethylcarbodiimide hydrochloride (314 mg, 1.64 mmol) and triethylamine (0.51 mL, 3.7 mmol) sequentially; stirring the mixture was stirred for 16 h, and adding 30 mL of ethyl acetate; washing the organic layer with 1 M HCl (15 mL), 5% NaHCO$_3$ (30 mL) and brine (30 mL), drying the same over anhydrous magnesium sulfate and concentrating the same under reduced pressure; further purifying by chromatotron (30% ethyl acetate-hexane) afforded two diastereomers A and B: A: 120 mg (25%); $^1$H NMR (300 MHz, CDCl$_3$) δ 7.20-7.70 (15 H, m), 5.54 (1 H, d, J=8.0 Hz), 4.02 (1 H, m), 3.48 (3 H, s), 2.83-3.00 (1 H, m), 2.62-2.74 (1 H, m), 2.40-2.48 (1 H, m), 1.00-2.00 (13 H, m); MS (ESI): 524 (M+H), 546 (M+Na), 522 (M−H), 558 (M+Cl). B: 120 mg (25%); $^1$H NMR (300 MHz, CDCl$_3$) δ 7.60 (1 H, d, J=6.9 Hz), 7.20-7.45 (14 H, m), 5.56 (1 H, d, J=8.4 Hz), 3.84 (1 H, m), 3.48 (3 H, s), 2.83-3.00 (1 H, m), 2.62-2.74 (1 H, m), 2.50-2.60 (1 H, m), 1.00-1.95 (13 H, m); MS (ESI): 524 (M+H), 546 (M+Na), 522 (M−H).

15. A process as claimed in claim 13, for preparing a compound of Formula (I), or a stereoisomer or pharmaceutically acceptable salt forms thereof, selected from:

3-(2(R)-Cyclopentylmethyl-3 (S)-hydroxyl-1-oxo-5-phenylpentyl)amino-1-methyl-5-(4-fluoro-phenyl)-2,3-dihydro-1H-1,4-benzodiazepin-2-one;

3-(2(R)-Benzyl-3(S)-hydroxyl-1-oxo-5-phenylpentyl)amino-1-methyl-5-phenyl-2,3-dihydro-1H-1,4-benzodiazepin-2-one;

3-(2(R)-Isopropyl-3(S)-hydroxyl-1-oxo-5-phenylpentyl)amino-1-methyl-5-phenyl-2,3-dihydro-1H-1,4-benzodiazepin-2-one;

3-(2(R)-Cyclopentylmethyl-3(S)-hydroxyl-1-oxo-4-(3,5-difluorophenoxy)butyl)amino-1-methyl-5-phenyl-2,3-dihydro-1H-1,4-benzodiazepin-2-one;

3-(2(R)-Isobutyl-3(S)-hydroxyl-1-oxo-4-(3,5-difluorophenoxy)butyl)amino-1-methyl-5-phenyl-2,3-dihydro-1H-1,4-benzodiazepin-2-one;

3-(2(R)-Cyclopentylmethyl-3(S)-hydroxyl-1-oxo-4-phenoxybutyl)amino-7-chloro-1-methyl-5-phenyl-2,3-dihydro-1H-1,4-benzodiazepin-2-one;

3-(2(R)-Isobutyl-3(S)-hydroxyl-1-oxo-4-phenoxybutyl)amino-7-chloro-1-methyl-5-(4-fluorophenyl)-2,3-dihydro-1H-1,4-benzodiazepin-2-one;

3-(2(R)-Methyl-3(S)-hydroxyl-1-oxo-4-cyclohexyloxybutyl)amino-1-methyl-5-phenyl-2,3-dihydro-1H-1,4-benzodiazepin-2-one;

3-(2(R)-Isobutyl-3(S)-hydroxyl-1-oxo-4-cyclohexyloxybutyl)amino-1-methyl-5-phenyl-2,3-dihydro-1H-1,4-benzodiazepin-2-one;

3-(2(R)-Methyl-3(S)-hydroxyl-1-oxo-4-phenoxybutyl)amino-7-chloro-1-methyl-5-phenyl-2,3-dihydro-1H-1,4-benzodiazepin-2-one;

3-(2(R)-Isobutyl-3(S)-hydroxyl-1-oxo-4-phenoxybutyl)amino-7-chloro-1-methyl-5-phenyl-2,3-dihydro-1H-1,4-benzodiazepin-2-one;

3-(2(R)-Benzyl-3(S)-hydroxyl-1-oxo-4-cyclohexyloxybutyl)amino-7-chloro-1-methyl-5-phenyl-2,3-dihydro-1H-1,4-benzodiazepin-2-one;

3-(2(R)-Cyclopentylmethyl-3(S)-hydroxyl-1-oxo-4-cyclohexyloxybutyl)amino-7-chloro-1-methyl-5-phenyl-2,3-dihydro-1H-1,4-benzodiazepin-2-one;

3-(2(R)-Isobutyl-3(S)-hydroxyl-1-oxo-4-cyclohexyloxybutyl)amino-7-chloro-1-methyl-5-phenyl-2,3-dihydro-1H-1,4-benzodiazepin-2-one;

3-(2(R)-Isopropyl-3(S)-hydroxyl-1-oxo-4-cyclohexyloxybutyl)amino-7-chloro-1-methyl-5-phenyl-2,3-dihydro-1H-1,4-benzodiazepin-2-one;

3-(2(R)-Methoxy-3(S)-hydroxyl-1-oxo-4-(4-trifluoromethylbenzyloxy)butyl)amino-7-chloro-1-methyl-5-phenyl-2,3-dihydro-1H-1,4-benzodiazepin-2-one;

3-(2(R)-Methyl-3(S)-hydroxyl-1-oxo-4-(2,4-difluorobenzyloxy)butyl)amino-7-chloro-1-methyl-5-phenyl-2,3-dihydro-1H-1,4-benzodiazepin-2-one;

3-(2(R)-Vinyl-3(S)-hydroxyl-1-oxo-4-benzyloxybutyl)amino-7-chloro-1-methyl-5-phenyl-2,3-dihydro-1H-1,4-benzodiazepin-2-one;

3-(2(R)-Methyl-3(S)-hydroxyl-1-oxo-4-cyclohexyloxybutyl)amino-7-chloro-1-methyl-5-phenyl-2,3-dihydro-1H-1,4-benzodiazepin-2-one;

3-(2(R)-Isobutyl-3(S)-hydroxyl-1-oxo-5-phenylpentyl)amino-1-methyl-5-phenyl-2,3-dihydro-1H-1,4-benzodiazepin-2-one;

3-(2(R)-Isobutyl-3(S)-hydroxyl-1-oxo-3-cyclopropylpropyl)amino-1-methyl-5-phenyl-2,3-dihydro-1H-1,4-benzodiazepin-2-one;

3-(2(R)-Isobutyl-3(S)-hydroxyl-1-oxo-heptyl)amino-1-methyl-5-phenyl-2,3-dihydro-1H-1,4-benzodiazepin-2-one;

3-(R)-(2(R)-Isobutyl-3(S)-hydroxyl-1-oxo-heptyl)amino-1-methyl-5-phenyl-2,3-dihydro-1H-1,4-benzodiazepin-2-one;

3-(S)-(2(R)-Isobutyl-3(S)-hydroxyl-1-oxo-heptyl)amino-1-methyl-5-phenyl-2,3-dihydro-1H-1,4-benzodiazepin-2-one;

3-(2(R)-Isobutyl-3(S)-hydroxyl-1-oxo-nonyl)amino-1-methyl-5-phenyl-2,3-dihydro-1H-1,4-benzodiazepin-2-one;

3-(2(R)-Isobutyl-3(S)-hydroxyl-1-oxo-hexyl)amino-1-methyl-5-phenyl-2,3-dihydro-1H-1,4-benzodiazepin-2-one;

3-(2(R)-Isobutyl-3(S)-hydroxyl-1-oxo-4-phenylbutyl)amino-1-methyl-5-phenyl-2,3-dihydro-1H-1,4-benzodiazepin-2-one;

3-(2(R)-Methyl-3 (S)-hydroxyl-1-oxo-5-phenylpentyl)amino-1-methyl-5-phenyl-2,3-dihydro-1H-1,4-benzodiazepin-2-one;

3-(2(R)-Methyl-3(S)-hydroxyl-1-oxo-6-phenylhexyl)amino-1-methyl-5-phenyl-2,3-dihydro-1H-1,4-benzodiazepin-2-one;

3-(2(R)-Isobutyl-3 (S)-hydroxyl-1-oxo-butyl)amino-1-methyl-5-phenyl-2,3-dihydro-1H-1,4-benzodiazepin-2-one;

3-(2(R)-Isobutyl-3(S)-hydroxyl-1-oxo-octyl)amino-1-methyl-5-phenyl-2,3-dihydro-1H-1,4-benzodiazepin-2-one;

3-(2(R)-Methyl-3(S)-hydroxyl-1-oxo-heptyl)amino-1-methyl-5-phenyl-2,3-dihydro-1H-1,4-benzodiazepin-2-one;

3-(2(R)-Methyl-3(s)-hydroxyl-1-oxo-3-phenylpropyl)amino-1-methyl-5-phenyl-2,3-dihydro-1H-1,4-benzodiazepin-2-one;

3-(2(R)-Methyl-3(S)-hydroxyl-1-oxo-5,5-dimethylhexyl)amino-1-methyl-5-phenyl-2,3-dihydro-1H-1,4-benzodiazepin-2-one;

3-(2(R)-Methyl-3(S)-hydroxyl-1-oxo-hexyl)amino-1-methyl-5-phenyl-2,3-dihydro-1H-1,4-benzodiazepin-2-one;

3-(2(R)-Methyl-3(S)-hydroxyl-1-oxo-3-(4-propoxyphenyl)propyl)amino-1-methyl-5-phenyl-2,3-dihydro-1H-1,4-benzodiazepin-2-one;

3-(2-(R)-cyclopropylmethyl-3-(S)-hydroxyl-1-oxoheptyl)amino-5-(2-fluorophenyl)-1-methyl-2,3-dihydro-1H-1,4-benzodiazepin-2-one;

3-(2-(R)-cyclopropylmethyl-3-(S)-hydroxyl-1-oxoheptyl)amino-5-(azapan-1-yl)-1-methyl-2,3-dihydro-1H-1,4-benzodiazepin-2-one;

3-(2-(R)-cyclopropylmethyl-5-(3,5-difluorophenyl)-3(S)-hydroxyl-1-oxopentyl)amino-1-methyl-5-(pyridin-2-yl)-2,3-dihydro-1H-1,4-benzodiazepin-2-one;

3-(2-(R)-cyclopropylmethyl-3-(S)-hydroxyl-1-oxopentyl)amino-1-methyl-5-(4-chlorophenyl)-2,3-dihydro-1H-1,4-benzodiazepin-2-one;

3-(2-(R)-cyclopropylmethyl-3-(S)-hydroxyl-1-oxoheptyl)amino-5-(4-methoxyphenyl)1-methyl-2,3-dihydro-1H-1,4-benzodiazepin-2-one;

3-(2-(R)-cyclopropylmethyl-3-(S)-hydroxyl-1-oxoheptyl)amino-5-(4-methoxyphenyl)-1-methyl-2,3-dihydro-1H-1,4-benzodiazepin-2-one;

3-(S)-(4-cyclopentyl-2-(R)-cyclopropylmethyl-3-(S)-hydroxyl-1-oxobutyl)amino-1-methyl-5-phenyl-2,3-dihydro-1H-1,4-benzodiazepin-2-one;

3-(S)-(2-(R)-cyclopropylmethyl-3-(S)-hydroxyl-1-oxohept-6-enyl)amino-1-methyl-5-phenyl-2,3-dihydro-1H-1,4-benzodiazepin-2-one;

3-(2-(R)-cyclopropylmethyl-3-(S)-hydroxyl-1-oxohept-6-enyl)amino-1-methyl-5-(4-trifluoromethyl-phenyl)-2,3-dihydro-1H-1,4-benzodiazepin-2-one;

3-(S)-(2-(R)-cyclopropylmethyl-5-(3,5-dimethylisoxazol-4-yl)-3-(S)-hydroxyl-1-oxopentyl)amino-1-methyl-5-phenyl-2,3-dihydro-1H-1,4-benzodiazepin-2-one;

3-(2-(R)-cyclopropylmethyl-3-(S)-hydroxyl-1-oxoheptyl)amino-7-chloro-1-methyl-5-phenyl-2,3-dihydro-1H-1,4-benzodiazepin-2-one;

3-(2-(R)-cyclopropylmethyl-3-(S)-hydroxyl-1-oxoheptyl)amino-1-methyl-(pyridin-2-yl)-2,3-dihydro-1H-1,4-benzodiazepin-2-one;

3-(2-(R)-cyclopropylmethyl-3-(S)-hydroxyl-1-oxoheptyl)amino-5-(4-fluorophenyl)-1-methyl-2,3-dihydro-1H-1,4-benzodiazepin-2-one;

3-(2-(R)-cyclopropylmethyl-3-(S)-hydroxyl-1-oxoheptyl)amino-1-methyl-5-(4-trifluoromethylphenyl)-2,3-dihydro-1H-1,4-benzodiazepin-2-one;

3-(5-cyclopentyl-2-(R)-cyclopropylmethyl-3-(S)-hydroxyl-1-oxopentyl)amino-1-methyl-5-(pyridin-2-yl)-2,3-dihydro-1H-1,4-benzodiazepin-2-one;

3-(2-(R)-iso-butyl-3-(S)-hydroxyl-1-oxoheptyl)amino-1-methyl-5-(4-trifluoromethylphenyl)-2,3-dihydro-1H-1,4-benzodiazepin-2-one;

3-(S)-(2-(R)-cyclopropylmethyl-3-(S)-hydroxyl-1-oxo-5-(thiophen-2-yl)amino-1-methyl-5-phenyl-2,3-dihydro-1H-1,4-benzodiazepin-2-one;

3-(S)-(2-(R)-cyclopropylmethyl-5-(furan-2-yl)3-(S)-hydroxyl-1-oxopentyl)amino-1-methyl-5-phenyl-2,3-dihydro-1H-1,4-benzodiazepin-2-one;

3-(5-cyclopentyl-2-(R)-cyclopropylmethyl-3-(S)-hydroxyl-1-oxopentyl)amino-5-(4-fluorophenyl)-1-methyl-2,3-dihydro-1H-1,4-benzodiazepin-2-one;

3-(S)-(2-(R)-cyclopropylmethyl-5-(3,5-difluorophenyl)-3-(S)-hydroxy-1-oxopentyl)amino-1-methyl-5-phenyl-2,3-dihydro-1H-1,4-benzodiazepin-2-one;

3-(S)-(3-(S)-hydroxyl-2-(R)-(thiophen-2-yl)methyl-1-oxoheptyl)amino-1-methyl-5-phenyl-2,3-dihydro-1H-1,4-benzodiazepin-2-one;

3-(S)-(2-(R)-cyclopropylmethyl-3-(S)-hydroxyl-1-oxoheptyl)amino-7-methyl-5-phenyl-2,3-dihydro-1H-1,4-benzodiazepin-2-one;

3-(2-(R)-cyclopropylmethyl-3-(S)-hydroxyl-1-oxoheptyl)amino-7-methoxy-1-methyl-5-phenyl-2,3-dihydro-1H-1,4-benzodiazepin-2-one;

3-(S)-(2-(R)-cyclobutylmethyl-3-(S)-hydroxyl-1-oxoheptyl)amino-1-methyl-5-phenyl-2,3-dihydro-1H-1,4-benzodiazepin-2-one;

3-(S)-(2-(R)-(3,5-difluorobenzyl)-3-(S)-hydroxyl-1-oxoheptyl)amino-1-methyl-5-phenyl-2,3-dihydro-1H-1,4-benzodiazepin-2-one;

3-(S)-(2-(R)-(furan-2-yl)methyl-3-(S)-hydroxyl-1-oxoheptyl)amino-1-methyl-5-phenyl-2,3-dihydro-1H-1,4-benzodiazepin-2-one;

3-(2-(R)-cyclopropylmethyl-3-(S)-hydroxyl-1-oxo-5-phenylpentyl)amino-1-methyl-5-(pyridin-2-yl)-2,3-dihydro-1H-1,4-benzodiazepin-2-one;

3-(2-(R)-iso-butyl-3-(S)-hydroxyl-1-oxoheptyl)amino-5-(4-fluorophenyl)-1-methyl-2,3-dihydro-1H-1,4-benzodiazepin-2-one;

3-(2-(R)-iso-butyl-3-(S)-hydroxyl-1-oxoheptyl)amino-5-(4-fluorophenyl)-1-methyl-2,3-dihydro-1H-1,4-benzodiazepin-2-one;

3-(2-(R)-cyclopropylmethyl-3-(S)-hydroxyl-1-oxo-5-phenylpentyl)amino-1-methyl-5-phenyl-2,3-dihydro-1H-1,4-benzodiazepin-2-one;

3-(2-(R)-cyclopropylmethyl-5-(furan-2-yl)-3-(S)-hydroxyl-oxopentyl)amino-1-methyl-5-(4-trifluoromethylphenyl)-2,3-dihydro-1H-1,4-benzodiazepin-2-one;

3-(5-cyclopentyl-2-(R)-cyclopropylmethyl-3-(S)-hydroxyl-1-oxopentyl)amino-1-methyl-5-(4-trifluoromethylphenyl)-2,3-dihydro-1H-1,4-benzodiazepin-2-one;

3-(2-(R)-cyclopropylmethyl-3-(S)-hydroxyl-1-oxooctyl)amino-1-methyl-5-(4-trifluoromethylphenyl)-2,3-dihydro-1H-1,4-benzodiazepin-2-one;

3-(2-(R)-cyclopropylmethyl-3-(S)-hydroxyl-1-oxononyl)amino-1-methyl-5-(4-trifluoromethylphenyl)-2,3-dihydro-1H-1,4-benzodiazepin-2-one;

3-(2-(R)-cyclopropylmethyl-3-(S)-hydroxyl-1-oxoheptyl)amino-1-methyl-5-(4-trifluoromethyl(pyridin-2-yl))-2,3-dihydro-1H-1,4-benzodiazepin-2-one;

3-(2-(R)-cyclobutylmethyl-3-(S)-hydroxyl-1-oxoheptyl)amino-1-methyl-5-(40-trifluoromethylphenyl)-2,3-dihydro-1H-1,4-benzodiazepin-2-one;

3-(2-(R)-cyclopentylmethyl-3-(S)-hydroxyl-1-oxoheptyl)amino-1-methyl-5-(4-trifluoromethylphenyl)-2,3-dihydro-1H-1,4-benzodiazepin-2-one;

3-(2-(R)-cyclopropylmethyl-3-(S)-hydroxyl-1-oxoheptyl)amino-1-methyl-5-(4-methyl-2-pyridyl)-2,3-dihydro-1H-1,4-benzodiazepin-2-one;

3-(2-(R)-cyclopropylmethyl-3-(S)-hydroxyl-1-oxoheptyl)amino-1-methyl-5-(4-methyl-2-pyridyl)-2,3-dihydro-1H-1,4-benzodiazepin-2-one;

3-(2-(R)-cyclopropylmethyl-3-(S)-hydroxyl-1-oxobutyl)amino-1-methyl-5-(4-trifluoromethylphenyl)-2,3-dihydro-1H-1,4-benzodiazepin-2-one;

3-(S)-(2-(R)-(3-butenyl)-3-(S)-hydroxyl-1-oxoheptyl)amino-1-methyl-5-phenyl-2,3-dihydro-1H-1,4-benzodiazepin-2-one;

3-(S)-(2-(R)-(3-methylbutyl)3-(S)-hydroxyl-1-oxoheptyl)amino-1-methyl-5-phenyl-2,3-dihydro-1H-1,4-benzodiazepin-2-one;

3-(S)-(2-(R)-ethyl-3-(S)-hydroxyl-1-oxoheptyl)amino-1-methyl-5-phenyl-2,3-dihydro-1H-1,4-benzodiazepin-2-one;

3-(S)-(2-(R)-propyl-3-(S)-hydroxyl-1-oxoheptyl)amino-1-methyl-5-phenyl-2,3-dihydro-1,4-benzodiazepin-2-one;

3-(S)-(2-(R)-butyl-3-(S)-hydroxyl-1-oxoheptyl)amino-1-methyl-5-phenyl-2,3-dihydro-1H-1,4-benzodiazepin-2-one;

3-(4-(S)-amino-3-(R)-hydroxyl-2-(R)-methyl-1-oxo-5-phenylpentyl)amino-7-chloro-5-(2-fluorophenyl)-1-methyl-2,3-dihydro-1H-1,4-benzodiazepin-2-one;

3-(4-(S)-(tert-butoxycarbonylamino-3-(R)-hydroxyl-2-(R)-methyl-1-oxo-5-phenylpentyl)amino-7-chloro-5-(2-fluorophenyl)-1-methyl-2,3-dihydro-1H-1,4-benzodiazepin-2-one;

3-(3-(tert-butoxycarbonylpyrrolidin-2-(R)-yl)-3-(R)-hydroxyl-2-(R)-methyl-1-oxopropyl)amino-7-chloro-5-(2-fluorophenyl)-1-methyl-2,3-dihydro-1H-1,4-benzodiazepin-2-one;

3-(3(R)-hydroxyl-2(R)-methyl-1-oxo-3-(pyrrolidin-2-(R)-yl)propyl)amino-7-chloro-5-(2-fluorophenyl)-1-methyl-2,3-dihydro-1H-1,4-benzodiazepin-2-one;

3-(4-benzyloxy-3(R)-hydroxyl-2(R)-iso-propyl-1-oxobutyl-amino-7-chloro-1-methyl-5-phenyl-2,3-dihydro-1H-1,4-benzodiazepin-2-one;

2-(4-(S)-amino-3-(S)-hydroxyl-2(S)-methyl-1-oxo-5-phenylpentyl)amino-7-chloro-5-(2-fluorophenyl)-1-methyl-2,3-dihydro-1H-1,4-benzodiazepin-2-one;

2-(4(S)-(tert-butoxycarbonylamino-3-(S)hydroxyl-2(S)-methyl-1-oxo-5-phenylpentyl)amino-7-chloro-5-(2-fluorophenyl)-1-methyl-2,3-dihydro-1H-1,4-benzodiazepin-2-one;

3-(2(R)-cyclopropylmethyl-3-(S)-hydroxyl-1-oxoheptyl)amino-1-methyl-5-(thiazol-2-yl)-2,3-dihydro-1H-1,4-benzodiazepin-2-one;

3-(2(R)-cyclopropylmethyl-3-(S)-hydroxyl-1-oxoheptyl)amino-1-cyclopropylmethyl-5-(thiazol-2-yl)-2,3-dihydro-1H-1,4-benzodiazepin-2-one;

3-(2(R)-cyclopropylmethyl-3-(S)-hydroxyl-1-oxoheptyl)amino-1-cyclopropylmethyl-5-(4-trifluoromethylphenyl)-2,3-dihydro-1H-1,4-benzodiazepin-2-one;

3-(2(R)-cyclopropylmethyl-3-(S)-hydroxyl-1-oxoheptyl)amino-1-benzyl-5-(4-trifluoromethylphenyl)-2,3-dihydro-1H-1,4-benzodiazepin-2-one;

3-(2(R)-cyclopropylmethyl-3-(S)-hydroxyl-1-oxoheptyl)amino-1-(3-phenoxybenzyl)-5-(4-trifluoromethyl-phenyl)-2,3-dihydro-1H-1,4-benzodiazepin-2-one;

3-(2(R)-cyclopropylmethyl-3-(S)-hydroxyl-1-oxoheptyl)amino-1-(3-pyridinylmethyl)-5-(4-trifluoromethyl-phenyl)-2,3-dihydro-1H-1,4-benzodiazepin-2-one;

3-(2-(S)-cyclopropylmethyl-3-(R)-hydroxyl-1-oxoheptyl)amino-1-methyl-5-(4-trifluoromethyl-phenyl)-2,3-dihydro-1H-1,4-benzodiazepin-2-one;

3-(2-(S)-cyclopropylmethyl-3-(R)-hydroxyl-1-oxoheptyl)amino-1-methyl-5-(4-trifluoromethylphenyl)-2,3-dihydro-1H-1,4-benzodiazepin-2-one;

3-(2-(R)-cyclopropylmethyl-3-(R)-hydroxyl-1-oxoheptyl)amino-1-methyl-5-(4-trifluoromethylphenyl)-2,3-dihydro-1H-1,4-benzodiazepin-2-one;

3-(2-(S)-cyclopropylmethyl-3-(S)-hydroxyl-1-oxoheptyl)amino-1-methyl-5-(4-trifluoromethylphenyl)-2,3-dihydro-1H-1,4-benzodiazepin-2-one;

3-(2-(S)-cyclopropylmethyl-3-(S)-hydroxyl-1-oxoheptyl)amino-1-methyl-5-(4-trifluoromethylphenyl)-2,3-dihydro-1H-1,4-benzodiazepin-2-one;

3-(2-(R)-cyclopropylmethyl-3-(S)-hydroxyl-3-(S)-methyl-1-oxoheptyl)amino-1-methyl-5-(4-trifluoromethyl-phenyl)-2,3-dihydro-1H-1,4-benzodiazepin-2-one;

3-(2-(R)-cyclopropylmethyl-3-(S)-hydroxyl-1-oxoheptyl)amino-1-(3-phenoxybenzyl)-5-methyl-2,3-dihydro-1H-1,4-benzodiazepin-2-one;

3-(2-(R)-cyclopropylmethyl-3-(S)-hydroxyl-1-oxoheptyl)amino-1-benzyl-5-methyl-2,3-dihydro-1H-1,4-benzodiazepin-2-one;

3-(3-(S)-acetoxy-2-(R)-iso-butyl-1-oxoheptyl)amino-5-(4-fluorophenyl)-1-methyl-2,3-dihydro-1H-1,4-benzodiazepin-2-one;

3-(S)-(5-cyclopentyl-2-(R)-cyclopropylmethyl-3-(S)-methoxy-1-oxopentyl)amino-1-methyl-5-phenyl-2,3-dihydro-1H-1,4-benzodiazepin-2-one;

1-(1-hydroxypentyl)cyclohexanecarboxylic acid(5-(4-fluorophenyl)-1-methyl-2-oxo-2,3-dihydro-1H-1,4-benzodiazepin-3-yl)amide;

3-(2-(R)-cyclopropylmethyl-3-(S)-hydroxyl-1-oxoheptyl)amino-5-cyclopentyl-1-methyl-2,3-dihydro-1H-1,4-benzodiazepin-2-one;

3-(2-(R)-cyclopropylmethyl-3-(S)-hydroxyl-1-oxoheptyl)amino-5-benzyl-1-methyl-2,3-dihydro-1H-1,4-benzodiazepin-2-one;

3-(2-(R)-cyclopropylmethyl-3-(S)-hydroxyl-1-oxoheptyl)amino-5-benzyl-1-butyl-2,3-dihydro-1H-1,4-benzodiazepin-2-one;

3-(2-(R)-cyclopropylmethyl-3-(S)-hydroxyl-1-oxoheptyl)amino-5-cycloheptyl-1-methyl-2,3-dihydro-1H-1,4-benzodiazepin-2-one;

3-(2-(R)-cyclopropylmethyl-3-(S)-hydroxyl-1-oxoheptyl)amino-1-benzyl-5-cycloheptyl-2,3-dihydro-1H-1,4-benzodiazepin-2-one;

3-(2-(R)-cyclopropylmethyl-3-(S)-hydroxyl-1-oxoheptyl)amino-1-butyl-5-cycloheptyl-2,3-dihydro-1H-1,4-benzodiazepin-2-one;

3-(2-(R)-cyclopropylmethyl-3-(S)-hydroxyl-1-oxoheptyl)amino-1-(2-pyridinylmethyl)-5-(4-trifluoromethylphenyl)-2,3-dihydro-1H-1,4-benzodiazepin-2-one;

3-(2-(R)-cyclopropylmethyl-3-(S)-hydroxyl-1-oxoheptyl)amino-1-(3-pyridinylmethyl)-5-(2-fluorophenyl)-2,3-dihydro-1H-1,4-benzodiazepin-2-one;

3-(2-(S)-cyclopropylmethyl-3-(S)-hydroxyl-1-oxopentyl)amino-1-(3-pyridinylmethyl)-5-(4-trifluoromethylphenyl)-2,3-dihydro-1H-1,4-benzodiazepin-2-one;

3-(2-1(R)-Cyclopropylmethyl-3-(S)-hydroxyl-1-oxoheptyl)amino-1-methyl-5-(N,N-dibutylamino)-2,3-dihydro-1H-1,4-benzodiazepin-2-one;

3-(2-(R)-Cyclopropylmethyl-3-(S)-hydroxyl-1-oxoheptyl)amino-1-n-butyl-5-t-butyl-2,3-dihydro-1H-1,4-benzodiazepin-2-one;

3-(2-(R)-Cyclopropylmethyl-3-(S)-hydroxyl-1-oxoheptyl)amino-1-(2-oxo-3,3-dimethylbutyl)-5-n-butyl-2,3-dihydro-1H-1,4-benzodiazepin-2-one;

3-(2-(R)-Cyclopropylmethyl-3-(S)-hydroxyl-1-oxoheptyl)amino-1-benzyl-5-t-butyl-2,3-dihydro-1H-1,4-benzodiazepin-2-one;

3-(2-(R)-Cyclopropylmethyl-3-(S)-hydroxyl-1-oxoheptyl)amino-1-(2-picolyl)-5-n-butyl-2,3-dihydro-1H-1,4-benzodiazepin-2-one;

3-(2-(R)-Isobutyl-3-(S)-hydroxyl-1-oxoheptyl)amino-1-methyl-5-homopiperidino-2,3-dihydro-1H-1,4-benzodiazepin-2-one;

3-(2-(R)-cyclopropylmethyl-1,3-dioxoheptyl)amino-1-methyl-5-(4-trifluoromethylphenyl)-2,3-dihydro-1H-1,4-benzodiazepin-2-one; and 1-pentyrylcyclohexanecarboxylic acid (5-(4-fluorophenyl)-1-methyl-2-oxo-2,3-dihydro-1H-1,4-benzodiazepin-3-yl)amide.

16. A process as claimed in claim 1 for preparing a compound, or pharmaceutically acceptable salt forms thereof, selected from:

3-(R,S)-(2-(R)-Cyclopropylmethyl-3-(S)-hydroxyl-1-oxoheptyl)amino-1-methyl-5-t-butyl-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-piperazinyl-2,3-dihydro-1H-1,4-benzodiazepin-2-one;

3-(R,S)-(2-(R)-Cyclopropylmethyl-3-(S)-hydroxyl-1-oxoheptyl)amino-1-(benzyl-5-(2,2-dimethylpropyl)-2,3-dihydro-1H-1,4-benzodiazepin-2-one;

3-(R,S)-(2-(R)-Cyclopropylmethyl-3-(S)-hydroxyl-1-oxoheptyl)amino-1-n-butyl-5-n-butyl-2,3-dihydro-1H-1,4-benzodiazepin-2-one;

3-(R,S)-(2-(R)-Cyclopropylmethyl-3-(S)-hydroxyl-1-oxoheptyl)amino-1-benzyl-5-n-butyl-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-(3,4-dihydro-1H-isoquinolin-2-yl)-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-(2,2-dimethylpropyl)-2,3-dihydro-1H-1,4-benzodiazepin-2-one;

3-(R,S)-(2-(R)-Cyclopropylmethyl-3-(S)-hydroxyl-1-oxoheptyl)amino-1-(2-ethylbutyl)-5-n-butyl-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-pyrrolidin-1-yl-2,3-dihydro-1H-1,4-benzodiazepin-2-one;

3-(R,S)-(2-(R)-Cyclopropylmethyl-3-(S)-hydroxyl-1-oxoheptyl)amino-1-(3-hydroxypropyl)-5-t-butyl-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-ethoxy-2,3-dihydro-1H-1,4-benzodiazepin-2-one;

3-(R,S)-(2-(R)-Cyclopropylmethyl-3-(S)-hydroxyl-1-oxoheptyl)amino-1-butyl-5-(2,2-dimethylpropyl)-2,3-dihydro-1H-1,4-benzodiazepin-2-one;

3-(2-(R)-cyclopropylmethyl-3-(S)-hydroxyl-1-oxoheptyl)amino-1-(2-pyridinylmethyl N-oxide)-5-(4-trifluoromethyl)phenyl-2,3-dihydro-1H-1,4-benzodiazepin-2-one;

3-(2-(R)-cyclopropylmethyl-3-(S)-hydroxyl-1-oxoheptyl)amino-1-(3-pyridinylmethyl N-oxide)-5-(4-trifluoromethyl)phenyl-2,3-dihydro-1H-1,4-benzodiazepin-2-one;

3-(2-(S)-cyclopropylmethyl-3-(S)-hydroxyl-1-oxopentyl)amino-1-(3-pyridinylmethyl)-5-phenyl-2,3-dihydro-1H-1,4-benzodiazepin-2-one;

3-(2-(R)-cyclopropylmethyl-3-(S)-hydroxyl-1-oxoheptyl)amino-1-(2-(diethylamino)ethyl)-5-(4-trifluoromethylphenyl)-2,3-dihydro-1H-1,4-benzodiazepin-2-one;

3-(2-(R)-cyclopropylmethyl-3-(S)-hydroxyl-1-oxopentyl)amino-1-(3-pyridinylmethyl N-oxide)-5-phenyl-2,3-dihydro-1H-1,4-benzodiazepin-2-one;

(2R,3S)—N-(8-bromo-1,5-dimethyl-2-oxo-2,3-dihydro-1H-1,4-benzodiazepin-3-yl)-2-(cyclopropylmethyl)-3-hydroxyheptanamide;

3-(R,S)-(2-(R)-Cyclopropylmethyl-3-(S)-hydroxyl-1-oxoheptyl)amino-1-methyl-5-(4-benzylpiperazin-1-yl)-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-(4-methanesulfonyl-piperazin-1-yl)-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-(4-methylpiperazin-1-yl)-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-(4-acetylpiperazin-1-yl)-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-([4-(3,5-dimethyl-isoxazole-4-sulfonyl)-piperazin-1-yl]-2,3-dihydro-1H-1,4-benzodiazepin-2-one;

3-(R,S)-(2-(R)-Cyclopropylmethyl-3-(S)-hydroxyl-1-oxoheptyl)amino-1-methyl-5-(4-benzoylpiperazin-1-yl)-2,3-dihydro-1H-1,4-benzodiazepin-2-one;

4-[3-(2-(R)-Cyclopropylmethyl-3-(S)-hydroxy-heptanoylamino)-1-methyl-2-oxo-2,3-dihydro-1H-benzo[e][1,4]diazepin-5-yl]-piperazine-1-carboxylic acid tert-butyl ester; and 3-(2-(R)-cyclopropylmethyl-3-(S)-hydroxyl-1-oxoheptyl)amino-1-(3-pyridinylmethyl N-oxide)-5-(4-trifluoromethyl)phenyl-2,3-dihydro-1H-1,4-benzodiazepin-2-one-4-N-oxide.

17. A method for preparing a pharmaceutical composition comprising combining a compound prepared according to the process of claim 1; and a pharmaceutically acceptable carrier.

18. A method for preparing a pharmaceutical composition comprising combining a compound prepared according to the process of claim 2; and a pharmaceutically acceptable carrier.

19. A method for preparing a pharmaceutical composition comprising combining a compound prepared according to the process of claim 3; and a pharmaceutically acceptable carrier.

20. A method for preparing a pharmaceutical composition comprising combining a compound prepared according to the process of claim 4; and a pharmaceutically acceptable carrier.

21. A method for preparing a pharmaceutical composition comprising combining a compound prepared according to the process of claim 5; and a pharmaceutically acceptable carrier.

22. A method for preparing a pharmaceutical composition comprising combining a compound prepared according to the process of claim 6; and a pharmaceutically acceptable carrier.

23. A method for preparing a pharmaceutical composition comprising combining a compound prepared according to the process of claim 7; and a pharmaceutically acceptable carrier.

24. A method for preparing a pharmaceutical composition comprising combining a compound prepared according to the process of claim 8; and a pharmaceutically acceptable carrier.

25. A method for preparing a pharmaceutical composition comprising combining a compound prepared according to the process of claim 9; and a pharmaceutically acceptable carrier.

26. A method for preparing a pharmaceutical composition comprising combining a compound prepared according to the process of claim 10; and a pharmaceutically acceptable carrier.

27. A method for preparing a pharmaceutical composition comprising combining a compound prepared according to the process of claim 11; and a pharmaceutically acceptable carrier.

28. A method for preparing a pharmaceutical composition comprising combining a compound prepared according to the process of claim 12; and a pharmaceutically acceptable carrier.

29. A method for preparing a pharmaceutical composition comprising combining a compound prepared according to the process of claim 13; and a pharmaceutically acceptable carrier.

30. A method for preparing a pharmaceutical composition comprising combining a compound prepared according to the process of claim 14; and a pharmaceutically acceptable carrier.

31. A method for preparing a pharmaceutical composition comprising combining a compound prepared according to the process of claim 15; and a pharmaceutically acceptable carrier.

32. A method for preparing a pharmaceutical composition comprising combining a compound prepared according to the process of claim 16; and a pharmaceutically acceptable carrier.

* * * * *